(12) United States Patent
Armani et al.

(10) Patent No.: US 9,944,612 B2
(45) Date of Patent: Apr. 17, 2018

(54) 1-PHENYL-2-PYRIDINYL ALKYL ALCOHOL DERIVATIVES AS PHOSPHODIESTERASE INHIBITORS

(71) Applicant: CHIESI FARMACEUTICI S.p.A., Parma (IT)

(72) Inventors: Elisabetta Armani, Parma (IT); Gabriele Amari, Parma (IT); Oriana Esposito, Parma (IT); Laura Carzaniga, Parma (IT); Carmelida Capaldi, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 9 days.

(21) Appl. No.: 14/097,445

(22) Filed: Dec. 5, 2013

(65) Prior Publication Data

US 2014/0155391 A1    Jun. 5, 2014

(30) Foreign Application Priority Data

Dec. 5, 2012  (EP) .................................... 12195738

(51) Int. Cl.

| | | |
|---|---|---|
| *A61K 31/44* | (2006.01) |
| *A61K 31/435* | (2006.01) |
| *A61K 31/425* | (2006.01) |
| *C07D 295/155* | (2006.01) |
| *A61M 15/00* | (2006.01) |
| *A61M 16/14* | (2006.01) |
| *C07D 213/89* | (2006.01) |
| *C07D 401/12* | (2006.01) |
| *C07D 407/12* | (2006.01) |
| *C07D 417/12* | (2006.01) |
| *C07D 213/61* | (2006.01) |

(52) U.S. Cl.
CPC ....... *C07D 295/155* (2013.01); *A61M 15/009* (2013.01); *A61M 15/0065* (2013.01); *A61M 16/14* (2013.01); *C07D 213/61* (2013.01); *C07D 213/89* (2013.01); *C07D 401/12* (2013.01); *C07D 407/12* (2013.01); *C07D 417/12* (2013.01)

(58) Field of Classification Search
CPC .............. C07D 295/155; C07D 213/89; C07D 213/30; A61K 31/4409; A61K 31/4439; A61K 31/4427; A61K 31/444; A61M 15/0065; A61M 15/009; A61M 16/14

USPC ..... 546/344, 194, 276.4, 335; 544/124, 360, 544/58.2; 514/277, 357, 358, 372
See application file for complete search history.

(56) References Cited

U.S. PATENT DOCUMENTS

| | | |
|---|---|---|
| 7,820,698 B2 | 10/2010 | Rizzi et al. |
| 7,923,565 B2 * | 4/2011 | Delcanale ............ C07D 213/61 546/301 |
| 7,968,724 B2 | 6/2011 | Armani et al. |
| 8,203,000 B2 | 6/2012 | Delcanale et al. |
| 8,383,826 B2 | 2/2013 | Delcanale et al. |
| 8,440,834 B2 | 5/2013 | Amari et al. |
| 8,648,204 B2 | 2/2014 | Amari et al. |
| 2011/0144075 A1 | 6/2011 | Delcanale et al. |
| 2013/0005716 A1 | 1/2013 | Armani et al. |
| 2013/0012487 A1 | 1/2013 | Amari et al. |
| 2013/0079313 A1 | 3/2013 | Armani et al. |
| 2013/0137648 A1 | 5/2013 | Delcanale et al. |
| 2013/0324501 A1 | 12/2013 | Armani et al. |

FOREIGN PATENT DOCUMENTS

| | | | |
|---|---|---|---|
| WO | WO 2001/032163 A1 * | 5/2001 |
| WO | WO 2009/018909 A1 * | 2/2009 |
| WO | WO 2009/019909 A2 * | 2/2009 |
| WO | WO 2010/089107 A1 * | 8/2010 |

OTHER PUBLICATIONS

Lehner, MD. et al. PDE4 inhibitors: a review of current developments (2005-2009). Expert Opinion, 2009, p. 1501.*
Spina, D. PDE4 inhibitors: current status. Brittish Journal of Pharmacology, 2008, p. 308.*
NLHEP. Strategies in Preserving Lung Health and Preventing COPD and Associated Diseases. CHEST, 1998, p. 123S.*
U.S. Appl. No. 14/161,285, filed Jan. 22, 2014, Delcanale, et al.
U.S. Appl. No. 14/164,527, filed Jan. 27, 2014, Armani, et al.
U.S. Appl. No. 14/482,287, filed Sep. 10, 2014, Amari, et al.
U.S. Appl. No. 14/097,693, filed Dec. 5, 2013, Armani, et al.
U.S. Appl. No. 14/097,397, filed Dec. 5, 2013, Armani, et al.
U.S. Appl. No. 14/097,586, filed Dec. 5, 2013, Armani, et al.
U.S. Appl. No. 14/048,651, filed Oct. 8, 2013, Armani, et al.
U.S. Appl. No. 14/108,731, filed Dec. 17, 2013, Amari, et al.

* cited by examiner

*Primary Examiner* — Taylor V Oh
(74) *Attorney, Agent, or Firm* — Oblon, McClelland, Maier & Neustadt, L.L.P.

(57) ABSTRACT

Compounds of formula (I) described herein are inhibitors of the phosphodiesterase 4 (PDE4) enzyme and are useful for the prevention and/or treatment of an allergic disease state or a disease of the respiratory tract characterized by airway obstruction.

21 Claims, No Drawings

1-PHENYL-2-PYRIDINYL ALKYL ALCOHOL DERIVATIVES AS PHOSPHODIESTERASE INHIBITORS

CROSS REFERENCES TO RELATED APPLICATIONS

This application claims priority to European Patent Application No. 12195738.5 filed on Dec. 5, 2012, which is incorporated herein by reference in its entirety.

BACKGROUND OF THE INVENTION

Field of the Invention

The present invention relates to inhibitors of the phosphodiesterase 4 (PDE4) enzyme. More particularly, the invention relates to compounds that are derivatives of 1-phenyl-2-pyridinyl alkyl alcohols, methods of preparing such a compound, compositions which contain such a compound, and therapeutic uses of such a compound.

Discussion of the Background

Airway obstruction characterizes a number of severe respiratory diseases including asthma and chronic obstructive pulmonary disease (COPD). Events leading to airway obstruction include oedema of airway walls, increased mucous production and inflammation.

Drugs for treating respiratory diseases such as asthma and COPD are currently administered through inhalation. One of the advantages of the inhalatory route over the systemic one is the possibility of delivering the drug directly at site of action, reducing systemic side-effects, thus resulting in a more rapid clinical response and a higher therapeutic ratio.

Inhaled corticosteroids are the current maintenance therapy of choice for asthma and, together with bronchodilator beta$_2$-agonists for acute symptom relief, they form the mainstay of current therapy for the disease. The current management of COPD is largely symptomatic by means of bronchodilating therapy with inhaled anticholinergics and inhaled beta$_2$-adrenoceptor agonists. However, corticosteroids do not reduce the inflammatory response in COPD as they do in asthma.

Another class of therapeutic agents which has been widely investigated in view of its anti-inflammatory effects for the treatment of inflammatory respiratory diseases such as asthma and COPD is represented by the inhibitors of the enzymes phosphodiesterases (PDEs), in particular of the phosphodiesterase type 4 (hereinafter referred to as PDE4). Various compounds acting as PDE4 inhibitors have been disclosed in the prior art.

However, the usefulness of several PDE4 inhibitors of the first-generation such as rolipram and piclamilast has been limited due to their undesirable side effects. Said effects include nausea and emesis due to their action on PDE4 in the central nervous system and gastric acid secretion due to the action on PDE4 in parietal cells in the gut.

The cause of said side effects has been widely investigated.

It has been found that PDE4 exists in two distinct forms representing different conformations, that were designated as high affinity rolipram binding site or HPDE4, especially present in the central nervous system and in parietal cells, and low affinity rolipram binding site or LPDE4 (see Jacobitz, S et al Mol. Pharmacol, 1996, 50, 891-899, which is incorporated herein by reference in its entirety), which is found in the immune and inflammatory cells. While both forms appear to exhibit catalytic activity, they differ with respect to their sensitivity to inhibitors. In particular compounds with higher affinity for LPDE4 appear less prone to induce side-effects such as nausea, emesis and increased gastric secretion.

The effort of targeting LPDE4 has resulted in a slight improvement in the selectivity for the second-generation PDE4 inhibitors such as roflumilast. Nonetheless, roflumilast is under dosed in order to achieve an acceptable side effect profile.

Other classes of compounds acting as PDE4 inhibitors have been disclosed in the prior art.

For example, EP 1 634 606, which is incorporated herein by reference in its entirety, discloses, among others, ketone derivatives like benzofuran or 1,3-benzodioxole derivatives.

WO 94/02465, which is incorporated herein by reference in its entirety, discloses, among others, ketone derivatives of general formula

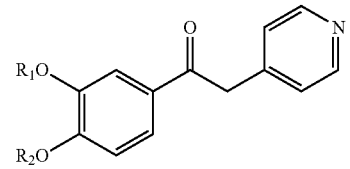

wherein R$_1$ is lower alkyl and R$_2$ may be alkyl, alkenyl, cycloalkyl, cycloalkyl, cycloalkenyl, cyclothioalkyl or cyclothioalkenyl.

WO 95/35281, which is incorporated herein by reference in its entirety, in the name of Celltech Therapeutics concerns tri-substituted phenyl derivatives.

WO2009/018909, which is incorporated herein by reference in its entirety, discloses derivatives of 1-phenyl-2-pyridinyl alkyl alcohols which have general formula below reported

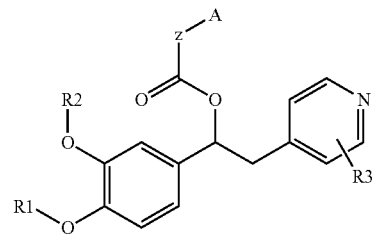

as inhibitors of phosphodiesterase 4 (PDE4) enzyme.

WO2009/077068, which is incorporated herein by reference in its entirety, discloses further derivatives of 1-phenyl-2-pyridinyl alkyl alcohols which have general formula below reported

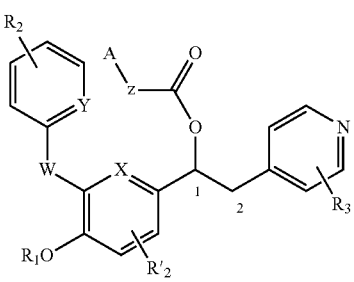

as inhibitors of phosphodiesterase 4 (PDE4) enzyme.

WO2010/089107, which is incorporated herein by reference in its entirety, discloses further derivatives of 1-phenyl-2-pyridinyl alkyl alcohols which have general formula below reported

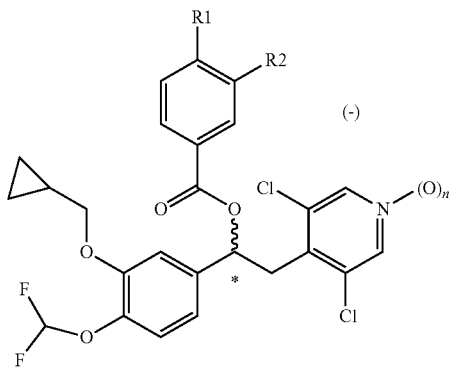

as inhibitors of phosphodiesterase 4 (PDE4) enzyme.

Although several PDE4 inhibitors have been disclosed so far as above reported, there is still a need for further PDE4 inhibitors. Particularly, there is still a need for further PDE4 inhibitors endowed with a high affinity for PDE4 enzyme.

Particularly advantageous would also be the identification of further PDE4 inhibitors endowed both with a high affinity for PDE4 enzyme and good solubility in water and/or in aqueous system.

As such, besides of being used by inhalable preparations in form of dry powder inhaler, pressurized metered dosed inhaler, or propellant-free nebulized formulation, the said compounds, due to their absorbability and formulability, could also be administered by other routes such as oral or transdermal but also in any other pharmaceutical solutions such as, for instance, those for injectable, infusion or ocular administration.

SUMMARY OF THE INVENTION

Accordingly, it is one object of the present invention to provide novel inhibitors of the phosphodiesterase 4 (PDE4) enzyme.

It is another object of the present invention to provide novel processes for the preparation of such a compound.

It is another object of the present invention to provide novel compositions which contain such a compound.

It is another object of the present invention to provide novel therapeutic uses of such a compound.

It is another object of the present invention to provide novel combinations of such a compound with other pharmaceutical active ingredients among which are, for instance, those currently used in the treatment of respiratory disorders, e.g. beta2-agonists, corticosteroids, P38 MAP kinase inhibitors, IKK2, HNE inhibitors, M3 antagonists, leukotriene modulators, NSAIDs and mucus regulators.

These and other objects, which will become apparent during the following detailed description, have been achieved by the inventors' discovery of compounds of general formula (I), described below, which acting as inhibitors of the phosphodiesterase 4 (PDE4) enzyme.

DETAILED DESCRIPTION OF THE PREFERRED EMBODIMENTS

The invention is directed to compounds of general formula (I), which act as inhibitors of the phosphodiesterase 4 (PDE4) enzyme, to processes for the preparation thereof, compositions comprising them and therapeutic uses thereof.

Thus, the present invention provides compounds of formula (I):

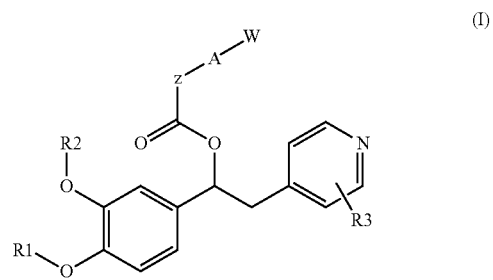

wherein:

$R_1$ and $R_2$ are different or the same and are independently selected from the group consisting of:

H;

linear or branched ($C_1$-$C_6$) alkyl, optionally substituted by one or more substituents selected from ($C_3$-$C_7$) cycloalkyl and ($C_5$-$C_7$) cycloalkenyl;

($C_1$-$C_6$) haloalkyl;

($C_3$-$C_7$) cycloalkyl;

($C_5$-$C_7$) cycloalkenyl;

linear or branched ($C_2$-$C_6$) alkenyl; and linear or branched ($C_2$-$C_6$) alkynyl.

$R_3$ is H or represents one or more substituents independently selected from the group consisting of CN, $NO_2$, $CF_3$ and a halogen atom;

Z is a group $(CH_2)_m$ wherein m=0 or 1;

A is a phenyl ring, which is optionally substituted by one or more substituents $R_4$, which may be the same or different and are independently selected from the group consisting of:

linear or branched ($C_1$-$C_6$) alkyl optionally substituted by one or more ($C_3$-$C_7$) cycloalkyl or ($C_3$-$C_7$)heterocycloalkyl;

($C_1$-$C_6$) haloalkyl;

($C_1$-$C_6$) alkylthio;

halogen;

$NH_2$; and $OR_7$ wherein $R_7$ is selected from the group consisting of H;

($C_1$-$C_{10}$) alkyl optionally substituted by a radical selected from ($C_3$-$C_7$) cycloalkyl, ($C_3$-$C_7$) heterocycloalkyl, aryl and heteroaryl;

($C_1$-$C_{10}$) alkyl substituted by one group OH;

($C_1$-$C_6$) haloalkyl;

($C_3$-$C_7$) cycloalkyl;

($C_1$-$C_4$)alkylaminocarbonyl;

($C_1$-$C_4$)alkyloxycarbonyl;

($C_3$-$C_7$) heterocycloalkyl optionally substituted by ($C_1$-$C_4$) alkyl; and $R_5R_6N$—($C_1$-$C_{10}$)alkylene wherein $R_5$ and $R_6$ are independently selected from the group consisting of H and linear or branched ($C_1$-$C_6$) alkyl or, together with the nitrogen atom to which they are linked, they form a saturated, partially saturated or unsaturated ring, wherein these rings are optionally substituted by ($C_1$-$C_4$) alkyl, halogen atoms or $R_7R_8N$—($C_1$-$C_4$)alkylene wherein $R_7$ and $R_8$ are different or the same and are independently selected from the group consisting of H and linear or branched ($C_1$-$C_6$) alkyl or, together with the nitrogen atom to which they are linked, they form a saturated or partially saturated ring;

W is selected in the group consisting of:
—$NR_9SO_2R_{10}$ wherein
$R_9$ is selected from the group consisting of
  ($C_1$-$C_{10}$) alkyl optionally substituted by ($C_3$-$C_7$) cycloalkyl, ($C_3$-$C_7$) heterocycloalkyl, or ($C_3$-$C_7$) heterocycloalkylcarbonyl, wherein any such ring may be optionally substituted by one or more ($C_1$-$C_4$) alkyl or OH; and
  $R_{11}R_{12}N$—($C_1$-$C_{10}$)alkylene wherein $R_{11}$ and $R_{12}$ are independently H or ($C_1$-$C_6$) alkyl, each of which may optionally be substituted by a group OH; and
$R_{10}$ is selected from the group consisting of
  ($C_1$-$C_4$) alkyl optionally substituted by ($C_3$-$C_7$) cycloalkyl;
  ($C_3$-$C_7$)cycloalkyl; and
  phenyl, any of which may be optionally substituted with one or more halogen atoms or ($C_1$-$C_4$) alkyl group;
—$CH_2NR_{13}SO_2R_{14}$ wherein
$R_{13}$ is selected from the group consisting of:
  H;
  ($C_3$-$C_7$) cycloalkyl;
  ($C_1$-$C_{10}$) alkyl optionally substituted by ($C_3$-$C_7$) cycloalkyl, ($C_3$-$C_7$) heterocycloalkyl, where any such ring may be optionally substituted by ($C_1$-$C_4$) alkyl; and
  $R_{11}R_{12}N$—($C_1$-$C_{10}$)alkylene wherein $R_{11}$ and $R_{12}$ are independently H or ($C_1$-$C_6$) alkyl, each of which may optionally be substituted by a group OH;
$R_{14}$ is selected from the group consisting of:
  ($C_1$-$C_4$) alkyl;
  ($C_3$-$C_7$) heterocycloalkyl-($C_1$-$C_4$)alkylene; and
  phenyl, any of which may be optionally substituted with one or more halogen atom or ($C_1$-$C_4$) alkyl group;
—($C_1$-$C_4$)alkylene-($C_3$-$C_7$)heterocycloalkyl, which may be optionally substituted by one or more groups selected from: oxo, OH, SH, ($C_1$-$C_4$) alkyl and hydroxy(C1-C6)alkylene;
—($C_3$-$C_7$) heterocycloalkyl ring, which may be optionally substituted by one or more groups selected from: oxo, OH, SH, ($C_1$-$C_4$) alkyl and hydroxy(C1-C6)alkylene;
—($C_1$-$C_4$)alkylene-amino-($C_3$-$C_7$)heterocycloalkyl, which may be optionally substituted by one or more groups selected from: oxo, OH, SH, ($C_1$-$C_4$) alkyl and hydroxy(C1-C6)alkylene
  —$SO_2NR_{15}R_{16}$ wherein
  $R_{15}$ is selected from the group consisting of H and ($C_1$-$C_{10}$) alkyl; and
  $R_{16}$ is selected from the group consisting of:
    ($C_1$-$C_{10}$) alkyl which is optionally substituted by ($C_3$-$C_7$) cycloalkyl or ($C_3$-$C_7$) heterocycloalkyl, where any such ring may be optionally substituted by ($C_1$-$C_4$) alkyl; and
    $R_{11}R_{12}N$—($C_1$-$C_{10}$)alkylene wherein $R_{11}$ and $R_{12}$ are independently H or ($C_1$-$C_6$) alkyl, each of which may optionally be substituted by a group OH; or
  $R_{15}$ and $R_{16}$, together with the nitrogen atom to which they are linked, form a ($C_3$-$C_7$) heterocycloalkyl ring optionally substituted by one or more ($C_1$-$C_4$) alkyl;
—$NHSO_2R_{17}$ wherein
$R_{17}$ is selected from the group consisting of:
  ($C_1$-$C_{10}$) alkyl which is optionally substituted by ($C_3$-$C_7$)cycloalkyl, ($C_3$-$C_7$) heterocycloalkyl, aryl and heteroaryl ring, where any such ring may be optionally substituted by ($C_1$-$C_4$) alkyl;
  $R_{11}R_{12}N$—($C_1$-$C_{10}$)alkylene wherein $R_{11}$ and $R_{12}$ are independently H or ($C_1$-$C_6$) alkyl, each of which may optionally be substituted by a group OH;
—$OSO_2R_{18}$ wherein
$R_{18}$ is selected from the group consisting of:
  ($C_1$-$C_{10}$) alkyl which is optionally substituted by halogen, OH, ($C_1$-$C_4$) alkoxyl, ($C_3$-$C_7$) cycloalkyl, ($C_3$-$C_7$) heterocycloalkyl, aryl or heteroaryl, where any such ring may be optionally substituted by ($C_1$-$C_4$) alkyl; and
  $R_{11}R_{12}N$—($C_1$-$C_{10}$)alkylene wherein $R_{11}$ and $R_{12}$ are independently H or ($C_1$-$C_6$) alkyl, each of which may optionally be substituted by a group OH;
—$OC(O)R_{19}$ wherein
$R_{19}$ is selected from the group consisting of:
  ($C_3$-$C_7$) cycloalkyl, ($C_3$-$C_7$) heterocycloalkyl, where any such ring may be optionally substituted by ($C_1$-$C_4$) alkyl;
  ($C_1$-$C_{10}$) alkyl which is optionally substituted by one or more halogen, OH, $NH_2$, ($C_3$-$C_7$) cycloalkyl, ($C_3$-$C_7$) heterocycloalkyl, where any such ring may be optionally substituted by ($C_1$-$C_4$) alkyl; and
  $R_{11}R_{12}N$—($C_1$-$C_{10}$)alkylene wherein $R_{11}$ and $R_{12}$ are independently H or ($C_1$-$C_6$) alkyl, each of which may optionally be substituted by a group OH;
—$C(O)R_{20}$ wherein
$R_{20}$ is selected from the group consisting of:
  —$NR_{21}R_{22}$ wherein $R_{21}$ and $R_{22}$ are independently selected from: H, ($C_1$-$C_6$) alkyl, ($C_3$-$C_7$) cycloalkyl and ($C_3$-$C_7$)heterocycloalkyl($C_1$-$C_4$)alkylene, each of which may optionally be substituted by ($C_1$-$C_4$) alkyl, OH, $NH_2$ or, together with the nitrogen atom to which they are linked, they form a saturated or partially saturated heterocyclic ring which may be optionally substituted by ($C_1$-$C_4$) alkyl, OH or $NH_2$;
  —$OR_{23}$ wherein $R_{23}$ is ($C_1$-$C_{10}$) alkyl which is substituted by one or more halogen, OH, ($C_3$-$C_7$)cycloalkyl, ($C_3$-$C_7$)heterocycloalkyl, where any such ring may be optionally substituted by ($C_1$-$C_4$) alkyl;
—NH—($C_1$-$C_4$)alkylene-$NR_{24}R_{25}$ wherein
$R_{24}$ and $R_{25}$, the same or different, are independently selected from H and ($C_1$-$C_6$) alkyl or, with the nitrogen atom to which they are linked, they form a saturated or partially saturated ring, which is optionally substituted by one ore more ($C_1$-$C_4$) alkyl groups;
—$NHCOR_{26}$ wherein
$R_{26}$ is selected from the group consisting of:
  $R_{27}R_{28}N$—($C_1$-$C_6$)alkylene wherein $R_{27}$ and $R_{28}$, the same or different, are independently selected from H, ($C_1$-$C_6$) alkyl optionally substituted by OH or $NH_2$ or, together with the nitrogen atom to which they are linked, they form a saturated or partially saturated ring, which is optionally substituted by one or more ($C_1$-$C_4$) alkyl, OH or NH2 groups;
  $R_{27}R_{28}$N-carbonyl-($C_1$-$C_6$)alkylene wherein $R_{27}$ and $R_{28}$, the same or different, are independently selected from H, ($C_1$-$C_6$) alkyl optionally substituted by OH or $NH_2$ or, together with the nitrogen atom to which they are linked, they form a saturated or partially saturated ring, which is optionally substituted by one or more ($C_1$-$C_4$) alkyl, OH or NH2 groups; and
  ($C_3$-$C_7$) heterocycloalkyl ring, which may be optionally substituted by one or more groups selected from: oxo, OH, SH or hydroxy($C_1$-$C_6$)alkylene;
—NH—($C_1$-$C_4$)alkylene-$OR_{29}$ wherein $R_{29}$ is H or ($C_1$-$C_6$) alkyl;

—CH2OC(O)R$_{30}$ wherein R$_{30}$ is selected from
(C$_3$-C$_7$) cycloalkyl,
(C$_3$-C$_7$) heterocycloalkyl where any such ring may be optionally substituted by (C$_1$-C$_4$) alkyl;
(C$_1$-C$_{10}$) alkyl which is substituted by one or more halogen, OH, (C$_3$-C$_7$) cycloalkyl, (C$_3$-C$_7$) heterocycloalkyl where any such ring may be optionally substituted by OH or (C$_1$-C$_4$) alkyl; and
R$_{11}$R$_{12}$N—(C$_1$-C$_{10}$)alkylene wherein R$_{11}$ and R$_{12}$ are independently H or (C$_1$-C$_6$) alkyl, each of which may optionally be substituted by a group OH their N-oxides on the pyridine ring, and pharmaceutically acceptable salts thereof.

The present invention further provides the corresponding N-oxides on the pyridine ring of compounds of formula (I) which are represented by the formula (Ia)

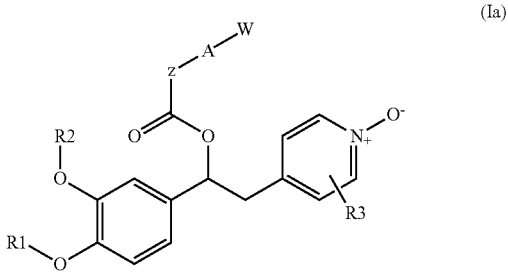

(Ia)

wherein R1, R2, R3, z, A and W are as described above for compounds of formula (I).

The present invention also encompasses the pharmaceutically acceptable salts and/or solvates thereof.

The term "pharmaceutically acceptable salts," as used herein, refers to derivatives of compounds of formula (I) or of their corresponding N-oxides on the pyridine ring wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic acid residues such as carboxylic groups.

Cations of inorganic bases which can be suitably used to prepare salts within the invention comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, sulfuric acid, phosphoric acid, methane sulfonic acid, camphor sulfonic acid, oxalic acid, maleic acid, succinic acid and citric acid.

Those skilled in the art of organic chemistry will appreciate that many organic compounds can form complexes with solvents in which they are reacted or from which they are precipitated or crystallized. These complexes are known as "solvates." Pharmaceutically acceptable solvates of compound of the invention are within the scope of the invention.

Included within the scope of the present invention are also polymorphs and crystalline forms of compounds of formula (I), of their N-oxides on the pyridine ring, or of pharmaceutically acceptable salts, or solvates thereof.

Hereinafter, compounds of formula (I), corresponding N-oxides on the pyridine ring, embodiments, enantiomers, diastereoisomers thereof, their pharmaceutically acceptable salts and solvates, and polymorphs or crystalline forms thereof defined in any aspect of the invention (except intermediate compounds described in the chemical processes) are referred to as "compounds of the invention".

The invention further comprises a process for the preparation of compounds of the invention.

The present invention also provides pharmaceutical compositions of compounds of the invention either alone or in combination, in admixture with one or more pharmaceutically acceptable carriers.

In a further aspect, the present invention provides the use of the compounds of the invention as a medicament.

In one aspect, the present invention provides the use of the compounds of the invention for the manufacture of a medicament.

In particular, the present invention provides the use of the compounds of the invention for the prevention and/or treatment of any disease characterized by phosphodiesterase 4 (PDE4) overactivity and/or wherein an inhibition of PDE4 activity is desirable.

In particular, the compounds of the invention alone or combined with other active ingredients may be administered for the prevention and/or treatment of a disease the respiratory tract characterized by airway obstruction such as asthma and COPD.

In a further aspect, the present invention provides the use of compounds of the invention for the preparation of a medicament for the prevention and/or treatment of any disease characterized by phosphodiesterase 4 (PDE4) overactivity and/or wherein an inhibition of PDE4 activity is desirable.

Moreover, the present invention provides a method for prevention and/or treatment of any disease wherein PDE4 inhibition is desirable, said method comprising administering to a patient in need of such treatment a therapeutically effective amount of a compound of the invention.

The term "halogen atoms" as used herein includes fluorine, chlorine, bromine, and iodine, preferably chlorine.

As used herein, the term "(C$_1$-C$_x$) alkyl" where x is an integer greater than 1, refers to straight-chained and branched alkyl groups wherein the number of constituent carbon atoms is in the range 1 to x. Particular alkyl groups are methyl, ethyl, n-propyl, isopropyl, and t-butyl.

By analogy, the term "(C$_1$-C$_x$)alkylene", refers to a divalent (C$_1$-C$_x$)alkyl radical, wherein (C$_1$-C$_x$)alkyl is as above defined.

The term "(C$_1$-C$_x$) alkoxyl" where x is an integer greater than 1 refers to straight-chained and branched alkoxy groups wherein the number of constituent carbon atoms is in the range 1 to x. Particular alkoxyl groups are methoxyl, ethoxyl, n-propoxyl, isopropoxyl, and t-butoxyl.

The expression "(C$_1$-C$_x$)haloalkyl" refers to the above defined "(C$_1$-C$_x$)alkyl" groups wherein one or more hydrogen atoms are replaced by one or more halogen atoms, which can be the same or different from each other. Examples of said (C$_1$-C$_6$)haloalkyl groups may thus include halogenated, poly-halogenated and fully halogenated alkyl groups wherein all of the hydrogen atoms are replaced by halogen atoms, e.g. trifluoromethyl or difluoro methyl groups.

The term "(C$_1$-C$_x$) alkylthio" where x is an integer greater than 1 refers to straight-chained and branched alkyl-S— groups wherein the number of constituent carbon atoms is in the range 1 to x. Particular alkylthio groups are methylthio, ethylthio, n-propylthio, isopropylthyio, and t-butylthio.

The term "$(C_3-C_y)$ cycloalkyl" where y is an integer greater than or equal to 3 refers to saturated cyclic hydrocarbon groups containing from 3 to y ring carbon atoms. Examples include cyclopropyl, cyclobutyl, cyclopentyl, cyclohexyl, and cycloheptyl.

The derived expression "$(C_3-C_y)$heterocycloalkyl" refers to monocyclic $(C_3-C_y)$cycloalkyl groups, in which at least one ring carbon atom is replaced by a heteroatom (e.g. N, NH, S or O). Non-limiting examples of $(C_3-C_y)$heterocycloalkyl are represented by: pyrrolidinyl, imidazolidine, thiazolidinyl, piperazinyl, piperidinyl, morpholinyl, thiomorpholinyl, azetidinyl and monoxide or dioxide thereof.

By analogy, the term "$(C_3-C_y)$heterocycloalkylene" refers to a divalent $(C_3-C_y)$heterocycloalkyl radical, wherein $(C_3-C_y)$heterocycloalkyl is as above defined.

The expression "$(C_3-C_y)$cycloalkylcarbonyl" refers to $(C_3-C_y)$cycloalkylCO— groups wherein the group "$(C_3-C_y)$cycloalkyl" has the meaning above defined.

The term "$(C_2-C_z)$alkenyl" refers to straight or branched, conjugated or non-conjugated, carbon chains with one or more double bonds, in cis or trans configuration, wherein the number atoms is in the range 2 to 6.

The term "$(C_5-C_z)$ cycloalkenyl" where z is an integer greater than or equal to 5 refers to cyclic hydrocarbon groups containing from 5 to z ring carbon atoms and one or more double bonds.

The term "$(C_2-C_6)$alkynyl" refers to straight or branched carbon chains with one or more triple bonds wherein the number atoms is in the range 2 to 6.

The term "$(C_3-C_y)$heterocycloalkyl$(C_1-C_x)$alkylene" refers to the above "$(C_1-C_x)$alkylene" group wherein one terminal carbon atom is linked to a "$(C_3-C_y)$heterocycloalkyl" group.

As used herein, the expression "ring system" refers to mono- or bicyclic ring systems which may be saturated, partially unsaturated or unsaturated, such as aryl, $(C_3-C_8)$ cycloalkyl, $(C_3-C_7)$ heterocycloalkyl or heteroaryl, having 5 to 11 ring atoms in which at least one ring atom is a heteroatom (e.g. N, S or O).

The expression "aryl" refers to mono or bi-ring systems which have 6 to 10 ring atoms, wherein at least one ring is aromatic.

The expression "heteroaryl" refers to mono or bi-ring systems with 5 to 11 ring atoms, in which at least one ring is aromatic and in which at least one ring atom is a heteroatom (e.g. N, NH, S or O).

Examples of suitable aryl or 5 and 6-membered heteroaryl monocyclic systems include, for instance, benzene (phenyl), thiophene (thiophenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), furan (furanyl) derived radicals and the like.

Examples of suitable aryl or heteroaryl bicyclic systems include naphthalene (naphthyl), biphenylene (biphenylenyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, dihydrobenzo dioxepin, benzo oxazin radicals and the like.

In the present description, unless otherwise provided, $R_3$ represents a H atom or, alternatively, one or more substituents as previously indicated. If more than one of said substituents on the pyridyl ring are present, they may be in any free position.

It will be apparent to those skilled in the art that compounds of general formula (I) at least contain one stereogenic center, namely represented by the carbon atom (1) with an asterisk below, and therefore exist as optical stereoisomers.

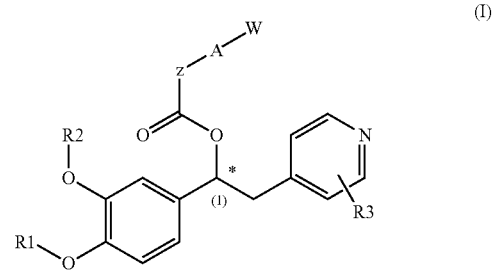

(I)

When the compounds according to the invention have at least one stereogenic center, they may accordingly exist as enantiomers. When the compounds according to the invention possess two or more stereogenic centers, they may additionally exist as diastereoisomers.

It is to be understood that all such isomers and mixtures thereof in any proportion are encompassed within the scope of the present invention.

In a preferred embodiment, the present invention is directed to compounds of formula (I)', which are compounds of formula (I), their N-oxides on the pyridine ring, and pharmaceutically acceptable salts thereof as above defined where the absolute configuration of carbon (1) is that shown below:

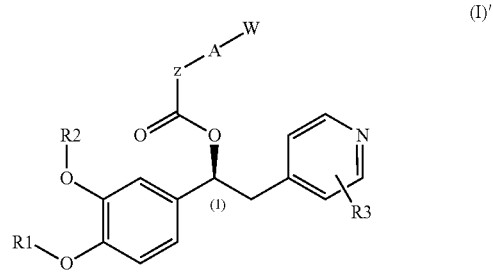

(I)'

The absolute configuration for carbon (1) is assigned on the basis of Cahn-Ingold-Prelog nomenclature based on groups' priorities.

In one preferred embodiment, for compounds of formula (I), absolute configuration at carbon (1) is (S).

In a preferred embodiment the invention provides compounds of formula (I) wherein R1 and R2 are different or the same and are independently selected from the group consisting of:

H;

linear or branched $(C_1-C_6)$ alkyl, optionally substituted by one or more substituents selected from $(C_3-C_7)$ cycloalkyl;

$(C_1-C_6)$ haloalkyl;

$R_3$ is one or more substituents selected from $CF_3$ and halogen atoms;

Z is a group $(CH_2)_m$, wherein m=0 or 1;

A is a phenyl ring, which is optionally substituted by one or more substituents $R_4$, which may be the same or different and are independently selected from the group consisting of:

linear or branched $(C_1-C_6)$ alkyl optionally substituted by one or more $(C_3-C_7)$ cycloalkyl or $(C_3-C_7)$heterocycloalkyl;

($C_1$-$C_6$) haloalkyl;
($C_1$-$C_6$) alkylthio;
halogen; and
$NH_2$; and
$OR_7$ wherein $R_7$ is selected from the group consisting of
H;
($C_1$-$C_{10}$) alkyl optionally substituted by a radical selected from ($C_3$-$C_7$) cycloalkyl, ($C_3$-$C_7$) heterocycloalkyl, aryl and heteroaryl;
$C_1$-$C_{10}$) alkyl substituted by one group OH;
($C_1$-$C_6$) haloalkyl;
($C_3$-$C_7$) cycloalkyl; and
$R_5R_6N$—($C_1$-$C_{10}$)alkylene wherein $R_5$ and $R_6$ are independently selected from the group consisting of H, linear or branched ($C_1$-$C_6$) alkyl or, with the nitrogen atom to which they are linked, they form a saturated, partially saturated or unsaturated ring, wherein these rings are optionally substituted by ($C_1$-$C_4$) alkyl, halogen atoms or $R_7R_8N$—($C_1$-$C_4$)alkylene wherein $R_7$ and $R_8$ are different or the same and are independently selected from the group consisting of H, linear or branched ($C_1$-$C_6$) alkyl or, with the nitrogen atom to which they are linked, they form a saturated or partially saturated ring;

W is selected in the group consisting of:
—$NR_9SO_2R_{10}$ wherein
$R_9$ is selected from the group consisting of
($C_1$-$C_{10}$) alkyl optionally substituted by ($C_3$-$C_7$) heterocycloalkyl, ($C_3$-$C_7$) heterocycloalkylcarbonyl, wherein any such ring may be optionally substituted by one or more ($C_1$-$C_4$) alkyl or OH; and
$R_{11}R_{12}N$—($C_1$-$C_{10}$)alkylene wherein $R_{11}$ and $R_{12}$ are independently H or ($C_1$-$C_6$) alkyl, each of which may optionally be substituted by a group OH; and
$R_{10}$ is selected in the group consisting of
($C_1$-$C_4$) alkyl optionally substituted by ($C_3$-$C_7$) cycloalkyl;
($C_3$-$C_7$)cycloalkyl; and
phenyl, any of which may be optionally substituted with one or more halogen atoms or ($C_1$-$C_4$) alkyl group;
—$CH_2NR_{13}SO_2R_{14}$ wherein
$R_{13}$ is selected from the group consisting of:
H; and
($C_1$-$C_{10}$) alkyl optionally substituted by ($C_3$-$C_7$) cycloalkyl, ($C_3$-$C_7$) heterocycloalkyl, where any such ring may be optionally substituted by ($C_1$-$C_4$) alkyl;
$R_{14}$ is selected in the group consisting of:
($C_1$-$C_4$) alkyl;
($C_3$-$C_7$) heterocycloalkyl-($C_1$-$C_4$)alkylene; and
phenyl, any of which may be optionally substituted with one or more halogen atom or ($C_1$-$C_4$) alkyl group;
—($C_1$-$C_4$)alkylene-($C_3$-$C_7$)heterocycloalkyl, which may be optionally substituted by one or more groups selected from: oxo, OH, ($C_1$-$C_4$) alkyl and hydroxy(C1-C6)alkylene;
—($C_3$-$C_7$) heterocycloalkyl ring, which may be optionally substituted by one or more groups selected from: oxo, OH, ($C_1$-$C_4$) alkyl and hydroxy(C1-C6)alkylene;
—($C_1$-$C_4$)alkylene-amino-($C_3$-$C_7$)heterocycloalkyl, which may be optionally substituted by one or more groups selected from: oxo, OH, ($C_1$-$C_4$) alkyl and hydroxy(C1-C6) alkylene
—$SO_2NR_{15}R_{16}$ wherein
$R_{15}$ is H; and
$R_{16}$ is selected from the group consisting of:
($C_1$-$C_{10}$) alkyl which is optionally substituted by ($C_3$-$C_7$) heterocycloalkyl, which may be optionally substituted by ($C_1$-$C_4$) alkyl; and
$R_{11}R_{12}N$—($C_1$-$C_{10}$)alkylene wherein $R_{11}$ and $R_{12}$ are independently H, methyl, ethyl, hydroxymethyl, hydroxyethyl; or
$R_{15}$ and $R_{16}$, together with the nitrogen atom to which they are linked, form a ($C_3$-$C_7$) heterocycloalkyl ring optionally substituted by one or more ($C_1$-$C_4$) alkyl;
—$NHSO_2R_{17}$ wherein
$R_{17}$ is selected from the group consisting of:
($C_1$-$C_{10}$) alkyl which is optionally substituted by ($C_3$-$C_7$) cycloalkyl, ($C_3$-$C_7$) heterocycloalkyl, aryl and heteroaryl ring, where any such ring may be optionally substituted by ($C_1$-$C_4$) alkyl; and
$R_{11}R_{12}N$—($C_1$-$C_{10}$)alkylene wherein $R_{11}$ and $R_{12}$ are independently H or ($C_1$-$C_6$) alkyl, each of which may optionally be substituted by a group OH;
—$OSO_2R_{18}$ wherein
$R_{18}$ is selected from the group consisting of:
($C_1$-$C_{10}$) alkyl which is optionally substituted by halogen, OH, ($C_1$-$C_4$) alkoxyl; and
$R_{11}R_{12}N$—($C_1$-$C_{10}$)alkylene wherein $R_{11}$ and $R_{12}$ are independently H or ($C_1$-$C_6$) alkyl, each of which may optionally be substituted by a group OH;
—$OC(O)R_{19}$ wherein
$R_{19}$ is ($C_1$-$C_{10}$) alkyl which is optionally substituted by one or more halogen, OH, $NH_2$, ($C_3$-$C_7$) cycloalkyl, ($C_3$-$C_7$) heterocycloalkyl, where any such ring may be optionally substituted by ($C_1$-$C_4$) alkyl;
—$C(O)R_{20}$ wherein
$R_{20}$ is selected from the group consisting of:
—$NR_{21}R_{22}$ wherein $R_{21}$ and $R_{22}$ are independently selected from: H, ($C_1$-$C_6$) alkyl, ($C_3$-$C_7$) cycloalkyl and ($C_3$-$C_7$)heterocycloalkyl($C_1$-$C_4$)alkylene, each of which may optionally be substituted by ($C_1$-$C_4$) alkyl, OH, $NH_2$ or, with the nitrogen atom to which they are linked, they form a saturated or partially saturated heterocyclic ring which may be optionally substituted by ($C_1$-$C_4$) alkyl, OH or $NH_2$; and
—$OR_{23}$ wherein $R_{23}$ is ($C_1$-$C_{10}$) alkyl which is substituted by one or more halogen, OH, ($C_3$-$C_7$)cycloalkyl, ($C_3$-$C_7$)heterocycloalkyl, where any such ring may be optionally substituted by ($C_1$-$C_4$) alkyl;
—NH—($C_1$-$C_4$)alkylene-$NR_{24}R_{25}$ wherein
$R_{24}$ and $R_{25}$, the same or different, are independently selected from H and ($C_1$-$C_6$) alkyl or, with the nitrogen atom to which they are linked, they form a saturated or partially saturated ring, which is optionally substituted by one ore more ($C_1$-$C_4$) alkyl groups;
—$NHCOR_{26}$ wherein
$R_{26}$ is selected from the group consisting of:
$R_{27}R_{28}N$—($C_1$-$C_6$)alkylene wherein $R_{27}$ and $R_{28}$, the same or different, are independently selected from H, ($C_1$-$C_6$) alkyl optionally substituted by OH or $NH_2$ or, with the nitrogen atom to which they are linked, they form a saturated or partially saturated ring, which is optionally substituted by one or more ($C_1$-$C_4$) alkyl, OH or NH2 groups;
$R_{27}R_{28}N$-carbonyl-($C_1$-$C_6$)alkylene wherein $R_{27}$ and $R_{28}$, the same or different, are independently selected from H, ($C_1$-$C_6$) alkyl optionally substituted by OH or $NH_2$ or, with the nitrogen atom to which they are linked, they form a saturated or partially saturated ring, which is optionally substituted by one or more ($C_1$-$C_4$) alkyl, OH or NH2 groups; and ($C_3$-$C_7$) heterocycloalkyl ring, which may be optionally substituted by one or more groups selected from: oxo, OH, SH or hydroxy($C_1$-$C_6$)alkylene;

—NH—($C_1$-$C_4$)alkylene-$OR_{29}$ wherein $R_{29}$ is H or ($C_1$-$C_6$) alkyl; and —CH2OC(O)$R_{30}$ wherein $R_{30}$ is selected from a ($C_1$-$C_{10}$) alkyl which is substituted by one or more halogen, OH, ($C_3$-$C_7$) heterocycloalkyl optionally substituted by OH or ($C_1$-$C_4$) alkyl their N-oxides on the pyridine ring, and pharmaceutically acceptable salts thereof.

In a more preferred embodiment the invention provides compounds of formula (I) wherein R1 and R2 are different or the same and are independently selected from the group consisting of hydrogen, methyl, ethyl, difluoromethyl or cyclopropylmethyl and cyclopropyl $R_3$ is one or more substituents selected from $CF_3$, fluorine and chlorine atoms, preferably they are the same two substituents in position 3 and 5 of the pyridyl ring;

Z is a group $(CH_2)_m$, wherein m=0;

A is a phenyl ring, which is optionally substituted by one or more substituents $R_4$, which may be the same or different and are independently selected from the group consisting of:
linear or branched ($C_1$-$C_2$) alkyl optionally substituted by one or more ($C_3$-$C_7$)heterocycloalkyl and preferably 4-morpholinyl;
trifluoromethyl;
methylthio;
halogen selected from fluoro or chloro; and
$OR_7$ wherein $R_7$ is selected from the group consisting of H;
  ($C_1$-$C_4$) alkyl optionally substituted by a radical selected from OH, cyclopropyl, 4-moprpholinyl, 1- or 4-piperidinyl, 4-pyridinyl and phenyl; an trifluoromethyl or difluoromethyl; and W is selected in the group consisting of:
—$NR_9SO_2R_{10}$ wherein
$R_9$ is selected from the group consisting of
  ($C_1$-$C_4$) alkyl optionally substituted by 4-morpholinyl, 1-piperidinyl, 1-pyrrolidinyl, piperazinyl, 1,2-thiazolidin-3-yl, piperazin-1-ylcarbonyl wherein any such ring may be optionally substituted by one or more methyl, ethyl or OH; and
  $R_{11}R_{12}N$—($C_1$-$C_3$)alkylene wherein $R_{11}$ and $R_{12}$ are independently H or methyl optionally substituted by a group OH; and
$R_{10}$ is selected from the group consisting of cyclopropylmethyl and cyclopropyl;
—$CH_2NR_{13}SO_2R_{14}$ wherein
$R_{13}$ is selected from the group consisting of H, 4-morpholinomethyl and 4-morpholinoethyl;
$R_{14}$ is selected from the group consisting of methyl, ethyl and phenyl optionally substituted with one or more halogen atom or ($C_1$-$C_4$) alkyl group;
—($C_1$-$C_2$)alkylene-($C_3$-$C_7$)heterocycloalkyl, which may be optionally substituted by one or more groups selected from: oxo, OH, methyl, hydroxymethyl and 2-hydroxyethyl;
—($C_3$-$C_7$) heterocycloalkyl ring, which may be optionally substituted by one or more groups selected from: oxo, OH, methyl, hydroxymethyl and 2-hydroxyethyl;
—($C_1$-$C_4$)alkylene-amino-($C_3$-$C_7$)heterocycloalkyl which may be for instance a 4-pyranylaminomethyl group
—$SO_2NR_{15}R_{16}$ wherein
$R_{15}$ is H; and
$R_{16}$ is selected from the group consisting of
  4-morpholinomethyl,
  2-(4-morpholino)ethyl,
  4-methylpiperazinomethyl,
  2-(4-methylpiperaziono)ethyl; and
  $R_{11}R_{12}N$—($C_1$-$C_2$)alkylene wherein $R_{11}$ and $R_{12}$ are independently H, methyl, ethyl, hydroxymethyl, hydroxyethyl; or
$R_{15}$ and $R_{16}$, together with the nitrogen atom to which they are linked, form piperazinyl, morpholinyl or piperidinyl ring optionally substituted by one or more methyl group;
—$NHSO_2R_{17}$ wherein
$R_{17}$ is selected from the group consisting of
  piperazinyl, morpholinyl and piperidinyl ring each optionally substituted by one or more methyl group; and
  aminoethyl, methylaminoethyl, dimethylaminoethyl, hydroxymethylaminoethyl and bis(hydroxymethyl) aminoethyl groups
—$OSO_2R_{18}$ wherein
$R_{18}$ is selected from the group consisting of:
  methoxymethyl,
  ethoxymethyl and
  $R_{11}R_{12}N$—($C_1$-$C_{10}$)alkylene wherein $R_{11}$ and $R_{12}$ are independently H, methyl, ethyl, hydroxymethyl or 2-hydroxyethyl;
—$OC(O)R_{19}$ wherein
$R_{19}$ is ($C_1$-$C_{10}$) alkyl which is optionally substituted by one or more $NH_2$;
—$C(O)R_{20}$ wherein
$R_{20}$ is selected from the group consisting of:
  —$NR_{21}R_{22}$ wherein $R_{21}$ is H; $R_{22}$ is selected from a ($C_3$-$C_6$) cycloalkyl and ($C_3$-$C_7$)heterocycloalkyl($C_1$-$C_2$)alkylene, each of which may optionally be substituted by ($C_1$-$C_4$) alkyl or $NH_2$ or, with the nitrogen atom to which they are linked, they form a piperazinyl or a piperidinyl ring which may be optionally substituted by methyl; and
  —$OR_{23}$ wherein $R_{23}$ is ($C_1$-$C_3$) alkyl which is substituted by a ($C_3$-$C_6$)heterocycloalkyl, optionally substituted by methyl;
—$NHCOR_{26}$ wherein
$R_{26}$ is selected from the group consisting of:
  $R_{27}R_{28}N$—($C_1$-$C_6$)alkylene wherein $R_{27}$ and $R_{28}$, the same or different, are independently selected from H, methyl, hydroxymethyl, ethyl or 2-hydroxyethyl or, with the nitrogen atom to which they are linked, they form a saturated ring, optionally substituted by one or more methyl, OH or NH2 groups;
  $R_{27}R_{28}N$-carbonyl-($C_1$-$C_6$)alkylene wherein $R_{27}$ and $R_{28}$, are ($C_1$-$C_6$)alkyl and with the nitrogen atom to which they are linked, they form a saturated ring substituted by one or more methyl; and
  ($C_3$-$C_7$) heterocycloalkyl ring, which may be optionally substituted by one or more groups selected from: oxo, OH, SH or hydroxy($C_1$-$C_6$)alkylene;
—NH—($C_1$-$C_4$)alkylene-$OR_{29}$ wherein $R_{29}$ is H or ($C_1$-$C_6$) alkyl; and
—CH2OC(O)$R_{30}$ wherein $R_{30}$ is selected from 1-piperidinylmethyl, 2-(1-piperidinyl)ethyl, 1-pyrrolidinylmethyl, 2-(1-pyrrolidinyl)ethyl, piperazinylmethyl, and 2-(piperazinyl)ethyl, whose rings are all optionally substituted by OH or methyl their N-oxides on the pyridine ring, and pharmaceutically acceptable salts thereof.

The compounds of the invention are endowed both with a high affinity for PDE4 enzyme and a good solubility in water and/or in aqueous system which may provide them with favorable oral or transdermal absorbability and/or formulability in any pharmaceutical solutions such as those for injectable, infusion or ocular administration.

Compounds of the invention may be prepared according to appropriate adaptation of synthetic approaches herebelow described in the Examples, in particular Examples 1 to 39.

Processes described below should not be viewed as limiting the scope of the synthetic methods available for the preparation of the compounds of the invention.

The process described is particularly advantageous as it is susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form. In particular, functional groups present in the compounds of the invention or intermediates thereof which could generate unwanted side reaction and by-products, need to be properly protected before the alkylation, acylation, coupling, oxidation or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art (see, for a general reference, T. W. Green; Protective Groups in Organic Synthesis (Wiley, N.Y. 1999), which is incorporated herein by reference in its entirety).

Likewise, selective protection and deprotection of any of the said groups, for instance including carbonyl, hydroxyl or amino groups, may be accomplished according to very well-known methods commonly employed in organic synthetic chemistry.

The N-oxides on the 4-pyridinyl ring of the compounds of general formula (I) and embodiments thereof may be prepared according to methods available in the literature and well known to the skilled person. For instance they may be prepared by dissolving the compound of general formula (I) or embodiments thereof in $CH_2Cl_2$ or $CHCl_3$, then adding an oxidizing agent such as m-chloro perbenzoic acid (mCPBA) to the resulting solution. Other oxidizing agents which may be used are hydrogen peroxide, perbenzoic acid and peracetic acid.

Alternatively, in particular for those compounds comprising functional groups sensitive to oxidation, the corresponding N-oxides are prepared by carrying out the oxidation step before further functional groups are introduced.

In one embodiment, the process for preparation of compounds of formula (I) or embodiments thereof is performed starting from N-oxide on the pyridine ring of intermediate compounds, thus allowing the preparation of compound of formula (I) or embodiments thereof in the form of N-oxides on the pyridine ring.

Optional salification of the compounds of formula (I) or N-oxides on the pyridine ring thereof may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear to the skilled person that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

The present invention also provides pharmaceutical compositions of compounds of the invention in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering compounds of the invention including such solid forms as tablets, gelcaps, capsules, caplets, granules, lozenges and bulk powders. The compounds of the present invention or compounds of formula (II) may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention or compounds of formula (II).

Various liquid oral dosage forms may also be used for administering compounds of the invention including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention or compounds of formula (II). The compounds of the present invention may be injected, for example, intravenously, in the form of an isotonic sterile solution. Other preparations are also possible.

Suppositories for rectal administration of the compounds of the present invention may be prepared by mixing the compound with a suitable excipient such as cocoa butter, salicylates and polyethylene glycols.

Formulations for vaginal administration may be in the form of cream, gel, paste, foam, or spray formula containing, in addition to the active ingredient, such suitable carriers as are known in the art.

For topical administration the pharmaceutical composition may be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation. Inhalable preparations include inhalable powders, propellant-containing metered aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in form of dispersed or suspended micronized particles. The propellant-containing formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs), and mucus regulators.

Thus, the present invention also provides combinations of a compound of the invention, with a β2-agonist selected from the group consisting of carmoterol, vilanterol (GSK-642444), indacaterol, milveterol, arformoterol, formoterol, salbutamol, levalbuterol, terbutaline, AZD-3199, olodaterol (BI-1744-CL), abediterol (LAS-100977), bambuterol, isoproterenol, procaterol, clenbuterol, reproterol, fenoterol, and ASF-1020 and salts thereof.

The present invention also provides combinations of a compound of the invention, with a corticosteroid selected from the group consisting of fluticasone propionate, fluticasone furoate, mometasone furoate, beclometasone dipropionate, ciclesonide, budesonide, GSK 685698, and SK 870086.

The present invention also provides combinations of a compound of the invention, with an antimuscarinic agent selected from the group consisting of aclidinium, tiotropium, ipratropium, trospium, glycopyrronium and oxitropium salts.

The present invention also provides combinations of a compound of the invention, with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414, and RPL-554.

The present invention also provides combinations of a compound of the invention, with a P38 MAP kinase inhibitor selected from the group consisting of semapimod, talmapimod, pirfenidone, PH-797804, GSK-725, minokine, and losmapimod and salts thereof.

In a preferred embodiment, the present invention provides combinations of a compound of the invention with an IKK2 inhibitor.

The invention also provides combinations of a compound of the invention, with a FINE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled.

The invention also provides combinations of a compound of the invention, with a leukotriene modulator selected from the group consisting of montelukast, zafirlukast, and pranlukast.

The invention also provides combinations of a compound of the invention, with a NSAID selected from the group consisting of ibuprofen and ketoprofen.

The invention also provides combinations of a compound of the invention, with a mucus regulator selected from the group consisting of INS-37217, diquafosol, sibenadet, CS-003, talnetant, DNK-333, MSI-1956, and gefitinib.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of the invention may be administered for example, at a dosage comprised between 0.001 and 1000 mg/day, preferably between 0.1 and 500 mg/day.

When they are administered by inhalation route, the dosage of the compounds of the invention is advantageously comprised between 0.01 and 20 mg/day, preferably between 0.1 and 10 mg/day.

Preferably, the compounds of the invention alone or combined with other active ingredients may be administered for the prevention and/or treatment of any obstructive respiratory disease such as asthma, chronic bronchitis and chronic obstructive pulmonary disease (COPD).

However the compounds of the invention may be administered for the prevention and/or treatment of any disease wherein PDE4 inhibition is required. Said disease include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia areata, hypertrophic scars, discoid lupus erythematosus, systemic lupus erythematosus, follicular and wide-area pyodermias, endogenous and exogenous acne, acne rosacea, Behçet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Chemical Names of the compounds were generated with Structure To Name Enterprise 10.0 Cambridge Software.

Purification by prepacked SCX cartridge refers to Isolute SCX, a strong cation exchange sorbent.

Procedures for Salt Formation:

Unless otherwise stated, trifluoroacetate salts and formic acid salts described in the experimental section were obtained according to the following procedure: Compounds containing one or more basic centres and purified by preparative HPLC were obtained as formic acid salt (Method 1) or trifluoroacetic acid salt (Method 2), once clean fractions collected from chromatography were evaporated under reduced pressure without any further basic treatment. If not otherwise indicated, any other salt was obtained by treating the base with a solution of the corresponding acid under conditions known to the skilled person. The salt stoichiometry was determined, if required, by NMR.

NMR Characterization:

NMR spectra were recorder either with:

$^1$H-NMR spectra were recorded on a 400 MHz Varian AS400 spectrometer. Chemical shift are reported as δ values in ppm relative to trimethyl silane (TMS) as an internal standard. Coupling constants (J values) are given in hertz (Hz) and multiplicities are reported using the following abbreviation (s=singlet, d=doublet, t=triplet, q=quartet, m=multiplet, br=broad, nd=not determined).

Or

1H-NMR spectra were recorded on a Bruker ARX300 Spectrometer at 300.13 MHz (1H) using deuterated solvents, such as deuterated dimethylsulfoxide (DMSO-d6) or deuterated chloroform (CDCl3). The instrument was equipped with a multinuclear inverse probe and temperature controller. Chemical shifts are expressed in parts per million (ppm) downfield of tetramethylsilane (d units). Multiplicity is indicated as follow: (s) singlet, (d) doublet, (dd) double doublet, (ddd) triple doublet, (t) triplet, (dt) double triplet, (q) quartet, (m) multiplet, (br s) broad signal. Coupling constants J are expressed in units of hertz (Hz).

Preparative HPLC—Method 1:
Column: Waters Symmetry Prep C18 17 um 19×300
Flow: 20 ml/min
Mobile phase: 90% $H_2O$, 10% acetonitrile, 0.05% TFA (A), 10% $H_2O$, 90% acetonitrile, 0.05% TFA (B)
Gradient:

| Time (min) | % A | % B |
|---|---|---|
| 0.00 | 95 | 5 |
| 5 | 95 | 5 |
| 28 | 0 | 100 |
| 30 | 0 | 100 |

The same gradient without TFA in mobile phase was used for preparative HPLC under neutral conditions.

Preparative HPLC—Method 2:
Waters Micromass ZQ; Sample manager 2767; Photodiode array detector 2996;
Column XTerra Prep MS C18 Column (5 µm, 19×150 mm, Waters); flow rate of 20 ml/min with MS detection or UV set at 254 nm.
Gradient:

| Time (min) | % A | % B |
|---|---|---|
| 0.00 | 100.0 | 0.00 |
| 1.00 | 100 | 0.00 |
| 10.00 | 0.00 | 100.0 |
| 11.00 | 0.00 | 100.0 |
| 12.00 | 100.0 | 0.00 |

Eluent
Solvent A (water:MeCN:HCOOH 95:5:0.05)
Solvent B (water:MeCN:HCOOH 5:95:0.05)
Preparative HPLC—Method 3
Waters Micromass ZQ/sample manager 2767
Photodiode array detector: 2996
Column: XTERRA Prep MS C18 10 um 19×300
Flow: 20 ml/min
Mobile phases: $H_2O$, 0.1% TFA (A); acetonitrile, 0.1% TFA (B)
Gradient:

| Time (min) | % A | % B |
|---|---|---|
| 0.00 | 90 | 10 |
| 2 | 90 | 10 |
| 23 | 0 | 100 |
| 30 | 0 | 100 |

Conditioning:

| Time (min) | % A | % B |
|---|---|---|
| 30.5 | 90 | 10 |
| 32 | 90 | 10 |

Chiral HLPC:

The enantiomeric purity was determined on Hewlett Packard 1050 HPLC system using Chiracel OD column (5µ 4.6×250 mm), eluting using isocratic mixture of hexane and isopropanol in different ratios as indicated in each specific example.
Flow=0.8 ml/min
UV detection=230 nm.

Optical Rotation (Activity) Determination:

Specific rotations of compounds were measured with a Polarimeter Perkin Elmer model 241 or 341.

| Temperature (° C.) | 25 |
|---|---|
| Path Length (dm) | 1 |
| Wavelength | Sodium D-line (589 nm) |

The MS/ESI$^+$ [MH]$^+$ values reported in the text below may be obtained or by MS instrument Waters ZQ (or equivalent) or by UPLC Waters instrument:
MS instrument: Waters ZQ (or equivalent)

| Polarity ES+ | |
|---|---|
| Capillary (kV) | 3.00 |
| Cone (V) | 20.00 |
| Extractor (V) | 3.00 |
| RF Lens (V) | 1.0 |
| Polarity ES− | |
| Capillary (kV) | 3.00 |
| Cone (V) | 20.00 |
| Extractor (V) | 3.00 |
| RF Lens (V) | 1.0 |

-continued

| | |
|---|---|
| Source Temperature (° C.) | 110 |
| Desolvation Temperature (° C.) | 210 |
| Cone Gas Flow (L/Hr) | 150 |
| Desolvation Gas Flow (L/Hr) | 650 |
| Mass range: | 100 to 950 |
| Scan time (sec): | 0.32 |
| Inter-Scan delay (sec): | 0.03 |

LC instrument: Acquity Waters UPLC:
Instrument: UPLC Waters coupled with ZQ micromass and interfaced with 2996 PDA detector
Column: Acquity UPLC BEH C18 1.7 um 50×2.1 mm
Method: TFA long
Conditions: ESI+, 3.2 KV, 25V, 350° C.
Wavelength: PBI

| Time (sec) | % B | Flow (mL/min) | A | B |
|---|---|---|---|---|
| 0.00 | 5.0 | 0.6 | 95:5 H2O:ACN (0.1% TFA) | 5:95 H2O:ACN (0.1% TFA) |
| 0.50 | 5.0 | 0.6 | | |
| 6.00 | 100.0 | 0.6 | | |
| 7.00 | 100.0 | 0.6 | | |
| 7.10 | 5.0 | 0.6 | | |
| 8.50 | 5.0 | 0.6 | | |

Detailed synthetic pathways and procedures for specific examples are outlined in Examples 1 to 39.

In the procedures that follow, after each starting material, reference to a compound number is sometimes provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Some compounds or intermediates mentioned in the present application and used for the synthesis of compounds of the present invention have been described in previous patent applications, all of which are incorporated herein by reference in their entireties, as listed in Table 1.

TABLE 1

| | Structure | Reference |
|---|---|---|
| 3 | 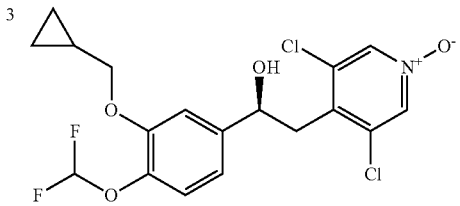 | Compound 7, WO2010/089107 |
| 4 | 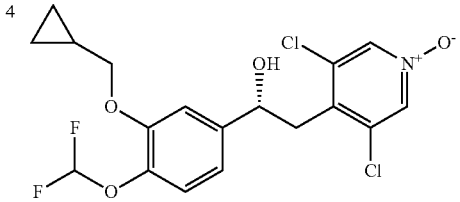 | Compound 9, WO2010/089107 |
| 5 | 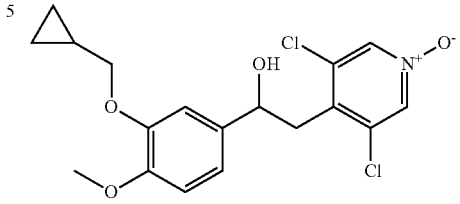 | Compound 19, WO2009/18909 |
| 6 | 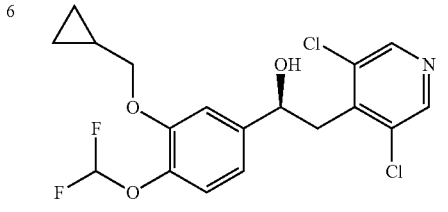 | Compound 14, WO2010/089107 |

TABLE 1-continued
| | Structure | Reference |
|---|---|---|
| 7 | 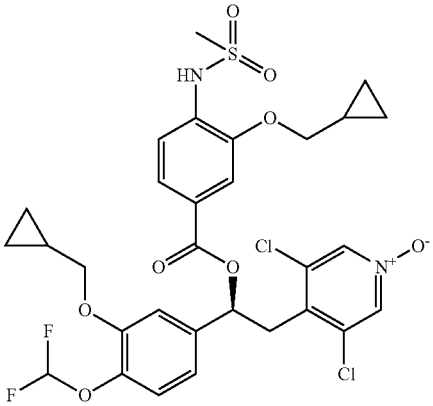 [SMILES: CS(=O)(=O)Nc1ccc(C(=O)O[C@@H](Cc2c(Cl)c[n+]([O-])cc2Cl)c2ccc(OC(F)F)c(OCC3CC3)c2)cc1OCC1CC1] | Compound C2, WO2010/089107 |
| 8 | 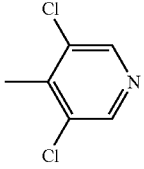 | Compound 4, WO2009/18909 |
| 9 | 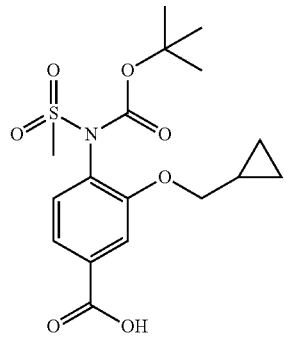 [SMILES: CC(C)(C)OC(=O)N(c1ccc(C(=O)O)cc1OCC1CC1)S(C)(=O)=O] | Example 18, Scheme 2 WO2010/089107 |

Example 1
Synthesis of (S)-3,5-dichloro-4-(2-(3,4-dimethoxyphenyl)-2-hydroxyethyl)pyridine 1-oxide (Compound 1)
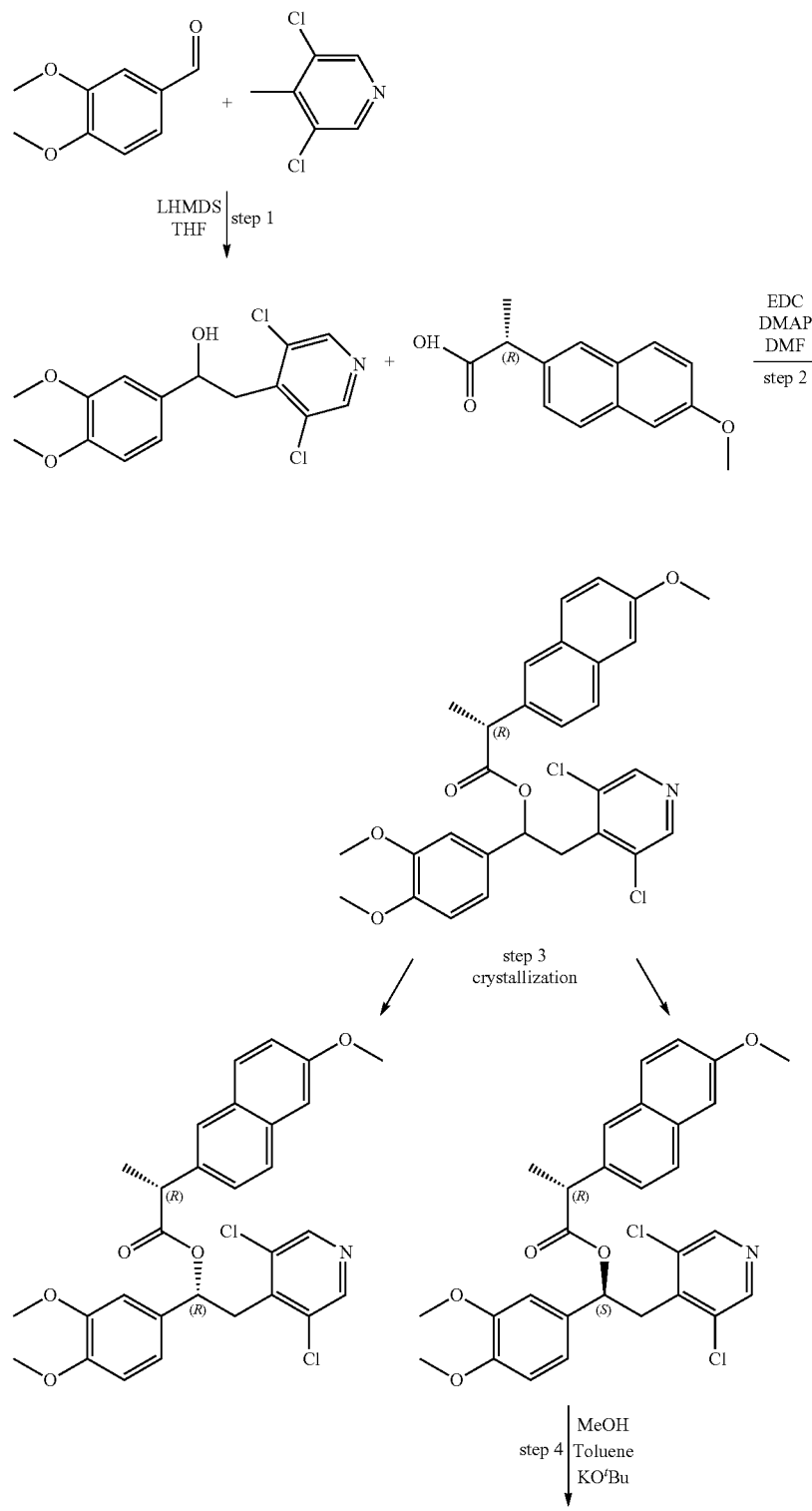
Scheme 1

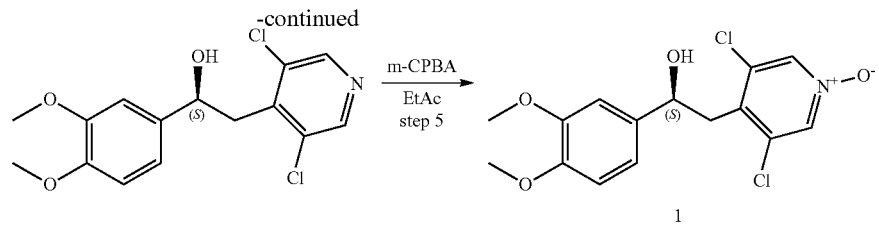

Step 1: Synthesis of 2-(3,5-dichloropyridin-4-yl)-1-(3,4-dimethoxyphenyl)ethanol (2)

3,5-dichloro-4-methylpyridine (54 g, 331 mmol) was dissolved in dry THF (480 mL) under argon atmosphere and it was cooled at −78° C. in dry-ice/acetone bath. LHMDS 1N THF solution (331 ml, 331 mmol) was added drop-wise by keeping the temperature at −78°. The mixture was stirred at −78° for 1 hour. After that, a solution of 3,4-dimethoxybenzaldehyde (50 g, 301 mmol) in dry THF (120 ml) was added drop-wise by keeping the temperature at −78° C. When the addition was completed, the mixture was allowed to warm at RT.

The reaction was poured in ice and water (1 L) and the mixture was stirred until a copious precipitate formed. The solid was filtered, and dissolved in Ethyl Acetate (500 ml), dried over $Na_2SO_4$ and the solvent evaporated under vacuum. The crude was crystallized in $CHCl_3$/hexane. The precipitate was filtered, washed with hexane and dried under vacuum at 40° C. for 8 h to give 55 g (yield 45%). The mother liquor solution was evaporated under vacuum at 40° C., dissolved in ethyl acetate (200 ml) and extracted with 200 ml of water. The organic solution was dried over $Na_2SO_4$ and the solvent evaporated under vacuum at 40° C. The crude was crystallized in $CHCl_3$/hexane, and additional 15 g of the desired product were obtained (overall yield 70%).

Step 2: Synthesis of ((S)-2-(3,5-dichloropyridin-4-yl)-1-(3,4-dimethoxyphenyl)ethyl) 2-(6-methoxynaphthalen-2-yl)propanoate (11)

2-(3,5-dichloropyridin-4-yl)-1-(3,4-dimethoxyphenyl) ethanol (compound 2, 50 g, 152 mmol) and commercially available (R)-2-(6methoxynaphthalen-2-yl)propanoic acid (compound 10, 38.6 g, 168 mmol), DMAP (20.5 g, 168 mmol), and EDC (43.8 g, 229 mmol) were dissolved in DMF (300 ml) and the reaction mixture was stirred at RT for 2 hours. After that time water (500 ml) was added, and the solution stirred upon precipitation occurs. The solid was filtered and dissolved in DCM (500 ml). The organic solution was washed with aqueous HCl 1N (2×500 ml), saturated aqueous $NaHCO_3$ solution (500 ml) and dried over $Na_2SO_4$. The solvent was evaporated under vacuum and the solid residue sonicated in EtOH (300 ml) and triturated for 1 hour. The resulting precipitate was collected by filtration and dried under vacuum at 40° C. for 4 h to give the title compound (79 g; yield 99%) as diastereoisomeric mixture.

Step 3: Synthesis of (R)-((S)-2-(3,5-dichloropyridin-4-yl)-1-(3,4-dimethoxyphenyl)ethyl) 2-(6-methoxynaphthalen-2-yl)propanoate (12)

((S)-2-(3,5-dichloropyridin-4-yl)-1-(3,4-dimethoxyphenyl)ethyl) 2-(6-methoxy naphthalen-2-yl)propanoate (79 g, 146 mmol) was dissolved in $CHCl_3$ (100 ml) and MeOH (30 ml) was slowly added up to persistent opalescence and the mixture left at RT for 2 hours. The solid formed was collected by filtration and re-crystallized by $CHCl_3$/MeOH (70 ml/20 ml) solvent system to obtain 35 g of the desired compound (yield 88%, ee 98%).

Chiral HPLC analysis $R_t$=42.33 min (fast isomer); eluent: hexane:isopropanol 97:3

$^1$H NMR (600 MHz, CHLOROFORM-d) δ ppm 8.04 (s, 2 H), 7.67 (d, J=8.79 Hz, 1 H), 7.58 (d, J=8.52 Hz, 1 H), 7.53 (m, 1 H), 7.12-7.20 (m, 3 H), 6.95 (dd, J=8.24, 1.92 Hz, 1 H), 6.78-6.88 (m, 2 H), 6.14 (dd, J=10.44, 4.12 Hz, 1 H), 3.95 (s, 3H), 3.88 (s, 3 H), 3.78-3.81 (m, 4 H), 3.55 (dd, J=13.73, 10.44 Hz, 1 H), 3.14 (dd, J=13.60, 4.26 Hz, 1 H), 1.44 (d, J=7.14 Hz, 3 H).

Step 4: Synthesis of (S)-2-(3,5-dichloropyridin-4-yl)-1-(3,4-dimethoxyphenyl)ethanol (13)

(R)-((S)-2-(3,5-dichloropyridin-4-yl)-1-(3,4-dimethoxyphenyl)ethyl) 2-(6-methoxynaphthalen-2-yl)propanoate (30 g, 56 mmol) was dissolved in MeOH, and toluene was slowly added. Potassium tert-butoxide was slowly added to the suspension. The mixture was stirred for 24 hours at RT. The reaction was diluted with water (500 ml) and the aqueous mixture was extracted with $CHCl_3$ (500 ml). The organic layer was dried over $Na_2SO_4$ and the solvent was evaporated under vacuum. The residue was crystallized from $CHCl_3$ (100 ml) and Hexane (20 ml, till persistent opalescence). The mother liquor was concentrated and recrystallized in the same way giving a second crop of desired compound. Totally 16 g of desired compound (yield 87%) were obtained.

Chiral HPLC analysis $R_t$=58.03 min; eluent: hexane: isopropanol 95:5. $[\alpha]_D^{20}$=+10.21 (c=0.506, Methanol)

$^1$H NMR (400 MHz, acetone) δ ppm 8.47 (s, 2 H), 6.96-7.15 (m, 1 H), 6.87 (m, 2 H), 4.93-5.21 (m, 1 H), 4.50 (d, J=3.97 Hz, 1 H), 3.78 (s, 6 H), 3.44 (dd, J=12.79, 8.38 Hz, 1 H), 3.22 (dd, J=13.01, 5.51 Hz, 1 H).

MS/ESI$^+$ [MH]$^+$: 328.19

Step 5: Synthesis of (S)-3,5-dichloro-4-(2-(3,4-dimethoxyphenyl)-2-hydroxyethyl)pyridine 1-oxide (1)

(S)-2-(3,5-dichloropyridin-4-yl)-1-(3,4-dimethoxyphenyl)ethanol (4 g, 12 mmol) was dissolved in Ethyl Acetate, and m-CPB acid was added to the solution. The mixture was stirred at RT for 5 hours. The formed solid was collected by filtration, washed with ethyl acetate and dried under vacuum to give 1.72 g of title compound (yield 41%). Chiral HPLC analysis $R_t$=22.16 min; eluent: hexane:isopropanol 6:4. $[\alpha]_D^{20}$=+68.91 (c=0.253, Methanol/$CHCl_3$ 1:1). MS/ESI$^+$ [MH]$^+$: 344.19

$^1$H NMR (400 MHz, CHLOROFORM-d) δ ppm 8.15 (s, 2 H), 6.99 (m, 1 H), 6.79-6.88 (m, 2 H), 5.03 (dd, J=8.50, 5.32 Hz, 1 H), 3.75-3.98 (m, 6 H), 3.42 (dd, J=13.57, 8.56 Hz, 1 H), 3.19 (dd, J=13.51, 5.32 Hz, 1 H), 2.06-2.15 (m, 1 H).

Example 2

Synthesis of (S)-3,5-dichloro-4-(2-(3-(cyclopropylmethoxy)-4-(N-(2-morpholinoethyl)methylsulfonamido)benzoyloxy)-2-(3,4-dimethoxyphenyl)ethyl)pyridine 1-oxide hydrochloride (Compound 14)

Scheme 2

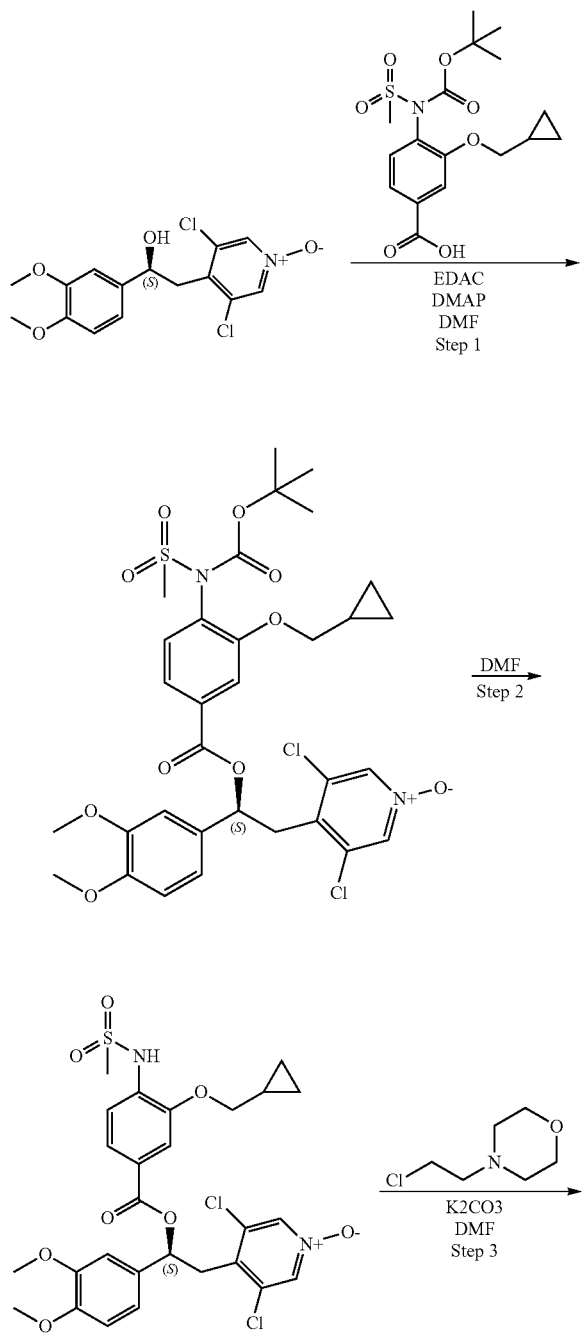

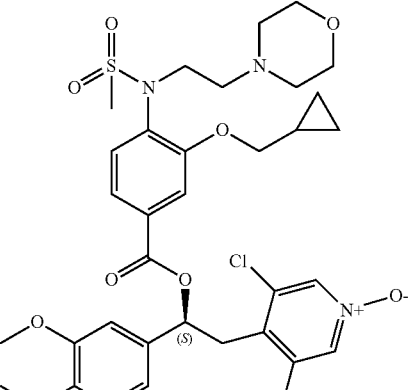

Step 1: Synthesis of (S)-4-(2-(4-(N-(tert-butoxycarbonyl)methylsulfonamido)-3-(cyclopropylmethoxy)benzoyloxy)-2-(3,4-dimethoxyphenyl)ethyl)-3,5-dichloropyridine 1-oxide (15)

(S)-3,5-dichloro-4-(2-(3,4-dimethoxyphenyl)-2-hydroxyethyl)pyridine 1-oxide (734 mg 2.13 mmol) was dissolved in DMF (5.5 ml). EDAC (840 mg, 4.36 mmol), DMAP (390 mg, 3.2 mmol) and compound 9 (1.23 g, 3.2 mmol) were added. The mixture was stirred at RT for 1 hour, then water was added and the aqueous phase was extracted with AcOEt twice. The combined organic phase was washed with HCl 1N, dried over Na2SO4 and evaporated to dryness. The crude was triturated with n-hexane to give 1.87 g of the desired compound (yield 90%). MS/ESI+ 710.15 [MH]+

Step 2: Synthesis of (S)-3,5-dichloro-4-(2-(3-(cyclopropylmethoxy)-4-(methylsulfonamido)benzoyloxy)-2-(3,4-dimethoxyphenyl)ethyl)pyridine 1-oxide (16)

(S)-4-(2-(4-(N-(tert-butoxycarbonyl)methylsulfonamido)-3-(cyclopropylmethoxy)benzoyloxy)-2-(3,4-dimethoxyphenyl)ethyl)-3,5-dichloropyridine 1-oxide (240 mg, 0.34 mmol) was dissolved in DMF (4.5 ml) and the solution stirred at 100 degrees for 5 days to get to completion. Then the mixture was allowed to cool to RT and water was added. The aqueous phase was extracted with EtOAc twice. The organic phase was dried over Na2SO4 and evaporated to dryness. The crude was triturated with Et2O to give the title compound (160 mg, 80% yield). MS/ESI+ 610.09 [MH]+

1H NMR (400 MHz, CHLOROFORM-d) δ ppm 8.15 (s, 2 H), 7.70 (dd, J=8.38, 1.65 Hz, 1 H), 7.59 (d, J=8.44 Hz, 1 H), 7.47 (d, J=1.59 Hz, 1 H), 7.21 (m, 1 H), 6.95-7.08 (m, 2 H), 6.87 (d, J=8.31 Hz, 1 H), 6.29 (dd, J=10.15, 4.28 Hz, 1 H), 3.82 and 4.02 (2s, 6 H, 3H each), 3.72 (dd, J=14.00, 10.09 Hz, 1 H), 3.34 (dd, J=14.06, 4.28 Hz, 1 H), 3.06 (s, 3 H), 1.22-1.36 (m, 1 H), 0.60-0.77 (m, 2 H), 0.35 (q, J=5.01 Hz, 2 H)

Step 3: Synthesis of (S)-3,5-dichloro-4-(2-(3-(cyclopropylmethoxy)-4-(N-(2-morpholinoethyl)methylsulfonamido)benzoyloxy)-2-(3,4-dimethoxyphenyl)ethyl)pyridine 1-oxide hydrochloride (14)

(S)-3,5-dichloro-4-(2-(3-(cyclopropylmethoxy)-4-(methylsulfonamido)-benzoyloxy)-2-(3,4-dimethoxyphenyl)

ethyl)pyridine 1-oxide (40 mg, 0.065 mmol) was dissolved in DMF (1 ml). $K_2CO_3$ (25 mg, 0.18 mmol) and 4-(2-chloroethyl)morpholine (20 mg, 0.133 mmol) were added and the mixture stirred at 45 degrees overnight. The reaction was then allowed to cool to RT and water was added. The aqueous phase was extracted with AcOEt twice and the organic layer was dried over $Na_2SO_4$. The solvent was evaporated under vacuum to give the crude product, that was purified by preparative HPLC (Method 2) and crystallized from Petroleum Ether/Diethyl Ether 1/1. Salification was achieved after treatment with HCl/AcOEt to give (S)-3,5-dichloro-4-(2-(3-(cyclopropylmethoxy)-4-(N-(2-morpholinoethyl)methylsulfonamido)benzoyloxy)-2-(3,4-dimethoxyphenyl)ethyl)pyridine 1-oxide hydrochloride (10 mg, 0.013 mmol, yield 20%). MS/ESI$^+$ 724.2 [MH]$^+$ $^1$H NMR (400 MHz, CHLOROFORM-d) δ ppm 8.16 (s, 2 H), 7.61-7.71 (m, 1 H), 7.53 (m, 1 H), 7.33-7.45 (m, 1 H), 6.92-7.06 (m, 2 H), 6.87 (d, J=8.38 Hz, 1 H), 6.22-6.32 (m, 1 H), 3.84-3.96 (m, 12 H), 3.65-3.78 (m, 1 H), 3.28-3.41 (m, 1 H), 3.00 (s, 3 H), 2.4-1.5 (m, 6 H), 1.25 (m, 1 H), 0.69 (d, J=7.94 Hz, 2 H), 0.37 (d, J=4.41 Hz, 2 H).

The compounds listed in Table 2 were prepared with analogous synthetic steps and procedures to those described in Example 2, by reacting the appropriate precursors (commercially available or synthesized by a person skilled in the art) with suitable reagents. Specific variations in the experimentals or purification methods are indicated in the table.

Carboxylic acid were synthesized following analogous procedures as for compound 9 (WO2010/089107 (which is incorporated herein by reference in its entirety Example 18, step 1-6).

TABLE 2

| Structure | Compound | NMR characterization and MS/ESI+ [MH]+ | Experimental procedure | Salification | Alkylating agent | Alcohol (Comp.) | Carboxylic acid (Comp.) |
|---|---|---|---|---|---|---|---|
| (structure shown) | 17 | 1H NMR (400 MHz, CHLOROFORM-d) δ ppm 8.15 (s, 2 H), 7.65 (dd, J = 7.94, 1.76 Hz, 1 H), 7.50 (d, J = 1.32 Hz, 1 H), 7.39 (d, J = 8.38 Hz, 1 H), 6.92-7.07 (m, 2 H), 6.86 (d, J = 8.38 Hz, 1 H), 6.27 (dd, J = 10.14, 4.41 Hz, 1 H), 3.67-3.94 (m, 15 H), 3.34 (dd, J = 14.11, 4.41 Hz, 1 H), 2.99 (s, 3 H), 2.62-2.74 (m, 6 H), 1.80 (ddd, J = 13.89, 6.84, 6.62 Hz, 2 H), 1.20-1.32 (m, 1 H), 0.63-0.72 (m, 2H), 0.34 (q, J = 5.29 Hz, 2 H). [MH]+: 738.3 | | No Salt | (structure shown) | 1 (structure shown) | 9 (structure shown) |

TABLE 2-continued

| Compound | NMR characterization and MS/ESI+ [MH]+ | Experimental procedure | Salification | Alkylating agent | Alcohol (Comp.) | Carboxylic acid (Comp.) |
|---|---|---|---|---|---|---|
| 18 | 1H NMR (400 MHz, acetone) δ ppm 13.01 (bs, 1 H), 8.31 (s, 2 H), 7.56-7.74 (m, 2 H), 7.43 (d, J = 8.82 Hz, 1 H), 7.18 (d, J = 2.21 Hz, 1 H), 7.10 (dd, J = 8.16, 1.98 Hz, 1 H), 6.97 (d, J = 7.94 Hz, 1 H), 6.33 (dd, J = 9.70, 4.41 Hz, 1 H), 4.26-4.45 (m, 2 H), 3.98-4.18 (m, 2 H), 3.73-3.90 (m, 7 H), 3.36-3.52 (m, 3 H), 3.04-3.20 (m, 6 H), 2.77-2.99 (m, 5 H), 1.39-1.53 (m, 1 H), 0.61-0.77 (m, 2 H), 0.51 (q, J = 4.85 Hz, 2 H). [MH]+: 722.3 | | Hydrochloride | | 1 | 9 |

Structure:

| Structure | Compound | NMR characterization and MS/ESI⁺ [MH]⁺ | Experimental procedure | Salification | Alkylating agent | Alcohol (Comp.) | Carboxylic acid (Comp.) |
|---|---|---|---|---|---|---|---|
| [structure shown] | 19 | ¹H NMR (400 MHz, acetone) δ ppm 12.84-13.34 (bs, 1 H), 8.26 (s, 2 H), 7.53-7.69 (m, 2 H), 7.45 (d, J = 8.29 Hz, 1 H), 7.14 (d, J = 1.66 Hz, 1 H), 7.06 (dd, J = 8.29, 2.21 Hz, 1 H), 6.94 (d, J = 8.29 Hz, 1 H), 6.29 (dd, J = 9.95, 4.42 Hz, 1 H), 4.14-4.31 (m, 2 H), 4.04 (d, J = 7.19 Hz, 2 H), 3.68-3.84 (m, 7 H), 3.56 (d, J = 4.98 Hz, 2 H), 3.38 (dd, J = 13.82, 4.42 Hz, 1 H), 3.26 (d, J = 6.08 Hz, 2 H), 3.08 (s, 3 H), 2.96 (m 2 H), 1.95-1.80 (m, 4H), 1.37 (d, J = 6.08 Hz, 1 H), 0.58-0.68 (m, 2 H), 0.47 (d, J = 4.98 Hz, 2 H). [MH]⁺: 708.1 | | Hydro-chloride | [structure shown] | 1 | 9 |

TABLE 2-continued

| Compound | NMR characterization and MS/ESI+ [MH]+ | Experimental procedure | Salification | Alkylating agent | Alcohol (Comp.) | Carboxylic acid (Comp.) |
|---|---|---|---|---|---|---|
| 20 | 1H NMR (400 MHz, acetone) δ ppm 13.06-13.40 (bs, 1 H), 8.30 (s, 2 H), 7.60-7.70 (m, 2 H), 7.50 (d, J = 7.94 Hz, 1 H), 7.18 (d, J = 2.21 Hz, 1 H), 7.10 (dd, J = 8.16, 1.98 Hz, 1 H), 6.97 (d, J = 8.38 Hz, 1 H), 6.33 (dd, J = 9.70, 4.41 Hz, 1 H), 4.23-4.36 (m, 2 H), 4.08 (d, J = 7.50 Hz, 2 H), 3.72-3.86 (m, 7 H), 3.42 (dd, J = 14.11, 4.41 Hz, 1 H), 3.17-3.27 (m, 2 H), 3.10-3.15 (m, 3 H), 2.79 (s, 6 H), 1.38-1.57 (m, 1 H), 0.60-0.72 (m, 2 H), 0.44-0.57 (m, 2 H). [MH]+: 682.2 | | Hydrochloride | | 1 | 9 |

Structure: (compound 20 structure shown)

TABLE 2-continued

| Structure | Compound | NMR characterization and MS/ESI+ [MH]+ | Experimental procedure | Salification | Alkylating agent | Alcohol (Comp.) | Carboxylic acid (Comp.) |
|---|---|---|---|---|---|---|---|
| [structure] | 21 | 1H NMR (400 MHz, acetone) δ ppm 8.64 (s, 2 H), 7.64 (m, 2 H), 7.49 (m, 1 H), 7.36 (d, J = 1.76 Hz, 1 H), 7.18-7.27 (m, 2 H), 6.94 (t, J = 75.00 Hz, 1 H), 6.33-6.41 (m, 1 H), 4.32-4.45 (m, 2 H), 4.10 (d, J = 7.06 Hz, 4 H), 4.01 (d, J = 7.06 Hz, 2 H), 3.81-3.97 (m, 3 H), 3.44-3.58 (m, 3 H), 3.23-3.35 (m, 2 H), 3.14 (s, 5 H), 1.39-1.53 (m, 1 H), 1.23-1.36 (m, 1 H), 0.60-0.69 (m, 2 H), 0.47-0.57 (m, 2 H), 0.40 (d, J = 6.17 Hz, 2 H). [MH]+: 800.7 | | Hydrochloride | [structure] | 3 | 9 |

TABLE 2-continued

| Com- pound | Structure | NMR characterization and MS/ESI+ [MH]+ | Experimental procedure | Salif- ication | Alkylating agent | Alcohol (Comp.) | Carboxylic acid (Comp.) |
|---|---|---|---|---|---|---|---|
| 22 | 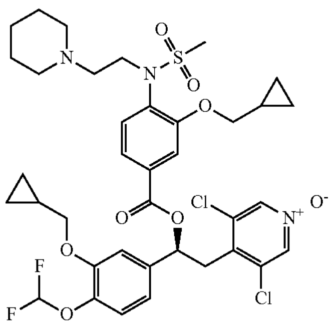 | 1H NMR (400 MHz, acetone) δ ppm 12.75-12.99 (bs, 1 H), 8.41 (m, 2 H), 7.56-7.70 (m, 2 H), 7.43 (d, J = 8.38 Hz, 1 H), 7.32 (d, J = 1.76 Hz, 1 H), 7.13-7.26 (m, 2 H), 6.91 (t, J = 75.00 Hz, 1 H), 6.25-6.37 (m, 1 H), 4.27-4.44 (m, 2 H), 4.07 (d, J = 7.06 Hz, 2 H), 3.98 (d, J = 6.62 Hz, 2 H), 3.74-3.86 (m, 1 H), 3.46 (d, J = 14.11 Hz, 3 H), 3.10-3.19 (m, 5 H), 2.80-3.00 (m, 2 H), 2.09-2.16 (m, 2 H), 1.68-1.84 (m, 3 H), 1.38-1.55 (m, 2 H), 1.16-1.34 (m, 1 H), 0.56-0.75 (m, 4 H), 0.50 (d, J = 5.29 Hz, 2 H), 0.33-0.44 (m, 2 H). [MH]+: 798.4 | | Hydro- chloride | | 3 | 9 |

TABLE 2-continued

| Structure | Compound | NMR characterization and MS/ESI+ [MH]+ | Experimental procedure | Salification | Alkylating agent | Alcohol (Comp.) | Carboxylic acid (Comp.) |
|---|---|---|---|---|---|---|---|
| (structure shown) | 23 | 1H NMR (400 MHz, CHLOROFORM-d) δ ppm 12.16-12.50 (bs, 1 H), 8.16 (s, 2 H), 7.96-8.04 (m, 1 H), 7.88 (d, J = 1.17 Hz, 1 H), 7.17 (m, 1 H), 7.03 (m, 3 H), 6.62 (t, 1 H, CHF₂), 6.14-6.29 (m, 1 H), 4.17-4.38 (m, 2 H), 3.90 (d, J = 7.04 Hz, 2 H), 3.62-3.77 (m, 1 H), 3.37-3.60 (m, 2 H), 3.25-3.36 (m, 1 H), 3.02-3.22 (m, 2 H), 2.99 (s, 3 H), 2.65-2.79 (m, 2 H), 2.13-2.33 (m, 2 H), 1.75-1.95 (m, 6 H), 1.26 (m, 2 H), 0.67 (dd, J = 18.59, 8.02 Hz, 4 H), 0.32-0.49 (m, 4 H). [MH]+: 798.2 | Step 2: Deprotection of amine was performed with HCl/Dioxane (4 eq.) at RT for 4 hrs instead of DMF at 100 degrees | Hydrochloride | (structure shown) | (structure shown) 3 | (structure shown) |

TABLE 2-continued
| Compound | Structure | NMR characterization and MS/ESI+ [MH]+ | Experimental procedure | Salification | Alkylating agent | Alcohol (Comp.) | Carboxylic acid (Comp.) |
|---|---|---|---|---|---|---|---|
| 24 | 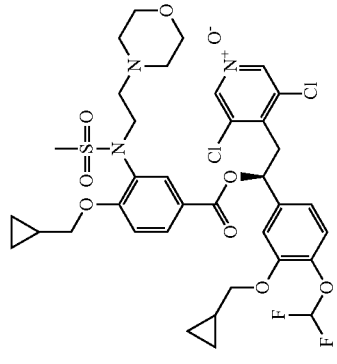 | 1H NMR (400 MHz, acetone) δ ppm 8.25 (s, 2 H), 8.06-8.13 (m, 1 H), 7.98-8.04 (m, 1 H), 7.26-7.39 (m, 1 H), 7.05-7.24 (m, 3 H), 6.89 (t, J = 75.00 Hz, 1 H), 6.17-6.45 (m, 1 H), 4.08-3.97 (m, 4 H), 3.66-3.87 (m, 3 H), 3.48-3.41 (m, 5 H), 3.06 (s, 3 H), 2.23-2.59 (m, 6 H), 1.22-1.46 (m, 2 H), 0.53-0.77 (m, 4 H), 0.33-0.49 (m, 4 H). [MH]+: 800.2 | Step 2: Deprotection of amine was performed with HCl/Dioxane (4 eq.) at RT for 4 hrs instead of DMF at 100 degrees | No Salt | 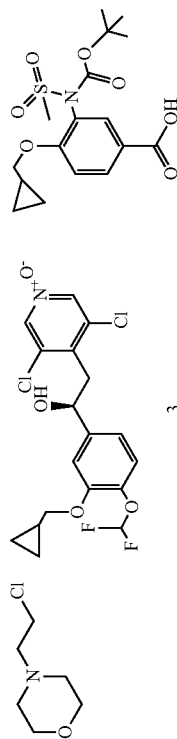 | 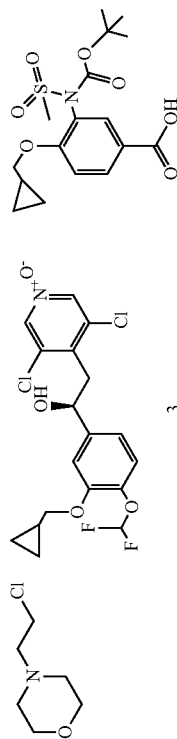 3 | 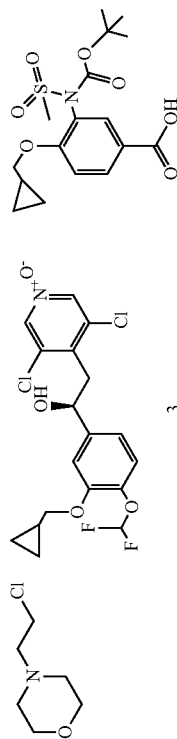 |

TABLE 2-continued

| Structure | Compound | NMR characterization and MS/ESI+ [MH]+ | Experimental procedure | Salification | Alkylating agent | Alcohol (Comp.) | Carboxylic acid (Comp.) |
|---|---|---|---|---|---|---|---|
| [structure shown] | 25 | 1H NMR (400 MHz, DMSO-d6) δ ppm 8.56 (s, 2 H), 7.48-7.63 (m, 2 H), 7.41 (d, J = 7.94 Hz, 1 H), 7.16-7.30 (m, 5 H), 7.00-7.14 (m, 2 H), 6.18 (dd, J = 9.26, 3.97 Hz, 1 H), 3.95 (dd, J = 17.64, 5.73 Hz, 4 H), 3.54-3.77 (m, 3 H), 3.43 (m, 4 H), 3.36 (d, J = 3.53 Hz, 1 H), 3.11 (s, 3 H), 2.20-2.39 (m, 6 H), 1.23 (dd, J = 13.23, 7.06 Hz, 2 H), 0.58 (dd, J = 12.35, 7.94 Hz, 4 H), 0.28-0.44 (m, 4 H). [MH]+: 799.9 | | No Salt | Br~~Br followed by nucleophilic substitution via procedure described in step 2, scheme 9, example 9 with [N-methylpiperazine structure] | 4 | 9 |

TABLE 2-continued

| Structure | Compound | NMR characterization and MS/ESI+ [MH]+ | Experimental procedure | Salification | Alkylating agent | Alcohol (Comp.) | Carboxylic acid (Comp.) |
|---|---|---|---|---|---|---|---|
| [structure] | 26 | 1H NMR (400 MHz, acetone) δ ppm 13.64-13.97 (bs, 1 H), 8.31 (s, 2 H), 7.75 (m, 1 H), 7.33-7.57 (m, 3 H), 6.89 (t, J = 75.00 Hz, 1 H), 6.23-6.33 (m, 1 H), 4.25-4.50 (m, 2 H), 4.07-4.22 (m, 2 H), 3.99 (dd, J = 12.57, 6.84 Hz, 6 H), 3.68-3.83 (m, 1 H), 3.44 (d, J = 14.11 Hz, 3 H), 3.11 (m, 7H), 1.28 (m, 2 H), 0.61 (t, J = 5.95 Hz, 4 H), 0.39 (m, 4 H). [MH]+: 800.0 | Step 2: Deprotection of amine was performed with HCl/Dioxane (4 eq.) at RT for 4 hrs instead of DMF at 100 degrees | Hydrochloride | [structure] | [structure] 3 | [structure] |

TABLE 2-continued

| Structure | Compound | NMR characterization and MS/ESI+ [MH]+ | Experimental procedure | Salification | Alkylating agent | Alcohol (Comp.) | Carboxylic acid (Comp.) |
|---|---|---|---|---|---|---|---|
| [structure] | 27 | 1H NMR (400 MHz, acetone) δ ppm 12.79-13.32 (bs, 1 H), 8.31 (s, 2 H), 7.81 (m, 1 H), 7.50 (m, 2 H), 7.38 (m, 1 H), 7.21 (m, 2 H), 6.92 (t, J = 75.00 Hz, 1 H), 6.31 (dd, J = 9.70, 3.97 Hz, 1 H), 4.30 (d, J = 7.06 Hz, 2 H), 4.00 (dd, J = 15.66, 6.84 Hz, 4 H), 3.52-3.86 (m, 3 H), 3.44 (dd, J = 14.55, 4.41 Hz, 1 H), 3.31 (d, J = 5.73 Hz, 2 H), 2.96-3.18 (m, 5 H), 1.90-2.15 (m, 4 H), 1.28 (m, 2 H), 0.60 (t, J = 5.95 Hz, 4 H), 0.39 (m, 4 H). [MH]+: 784.0 | Step 2: Deprotection of amine was performed with HCl/Dioxane (4 eq.) at RT for 4 hrs instead of DMF at 100 degrees | Hydrochloride | [structure] | [structure] 3 | [structure] |

TABLE 2-continued

| Compound | NMR characterization and MS/ESI+ [MH]+ | Experimental procedure | Salification | Alkylating agent | Alcohol (Comp.) | Carboxylic acid (Comp.) |
|---|---|---|---|---|---|---|
| 28 | 1H NMR (400 MHz, DMSO-d6) δ ppm 8.55 (s, 2 H), 7.49-7.53 (m, 1 H), 7.38-7.45 (m, 1 H), 7.13-7.34 (m, 3 H), 7.03-7.11 (m, 2 H), 6.12-6.22 (m, 1 H), 3.86-3.97 (m, 4 H), 3.68-3.78 (m, 2 H), 3.51-3.67 (m, 1 H), 3.14-3.21 (m, 1 H), 3.03 (s, 3 H), 2.54-2.60 (m, 2 H), 2.13-2.42 (m, 8 H), 2.07 (s, 3 H), 1.12-1.34 (m, 1 H), 0.50-0.65 (m, 4 H), 0.35 (m, 4 H) [MH]+: 813.3 | Step 2: Deprotection of amine was performed with HCl/Dioxane (4 eq.) at RT for 4 hrs instead of DMF at 100 degrees | No Salt | Br∼∼Br followed by nucleophilic substitution via procedure described in step 2, scheme 9, example 9 with N-methylpiperazine | (alcohol structure) | (carboxylic acid structure) |

Structure: (compound 28 structure)

TABLE 2-continued

| Structure | Compound | NMR characterization and MS/ESI+ [MH]+ | Experimental procedure | Salification | Alkylating agent | Alcohol (Comp.) | Carboxylic acid (Comp.) |
|---|---|---|---|---|---|---|---|
| 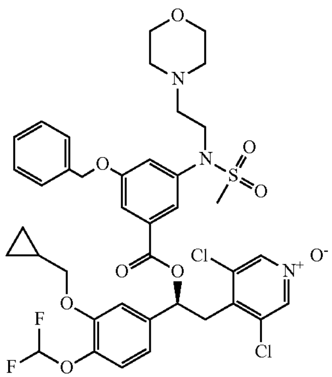 | 29 | 1H NMR (400 MHz, acetone) δ ppm 8.28 (s, 2 H), 7.69-7.76 (m, 1 H), 7.59-7.65 (m, 1 H), 7.49-7.57 (m, 2 H), 7.30-7.48 (m, 5 H), 7.14-7.25 (m, 2 H), 6.91 (t, J = 75.00 Hz, 1 H), 6.26-6.39 (m, 1 H), 5.24 (s, 2 H), 3.93-4.06 (m, 2 H), 3.81-3.90 (m, 2 H), 3.65-3.80 (m, 1 H), 3.50 (m, 4 H), 3.32-3.46 (m, 1 H), 3.02 (s, 3 H), 2.39-2.46 (m, 2 H), 2.28-2.38 (m, 4 H), 1.22-1.36 (m, 1 H), 0.52-0.68 (m, 2 H), 0.29-0.46 (m, 2 H) [MH]+: 836.4 | Step 2 In the synthesis of carboxylic acid step (described in WO2010/ 089107 Example 18, step 1-6): alkylation with benzyl bromide, instead of cyclopropyl bromide, was performed. | No Salt | | | |

TABLE 2-continued

| Structure | Compound | NMR characterization and MS/ESI+ [MH]+ | Experimental procedure | Salification | Alkylating agent | Alcohol (Comp.) | Carboxylic acid (Comp.) |
|---|---|---|---|---|---|---|---|
| 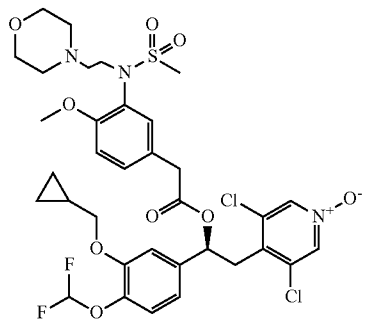 [SMILES: COc1ccc(CC(=O)O[C@@H](Cc2c(Cl)c[n+]([O-])cc2Cl)c2ccc(OC(F)F)c(OCC3CC3)c2)cc1N(CCN1CCOCC1)S(C)(=O)=O] | 30 | 1H NMR (400 MHz, acetone) δ ppm 8.20 (s, 2 H), 7.26 (d, J = 2.21 Hz, 1 H), 7.17 (d, J = 7.94 Hz, 2 H), 7.12 (m, 1 H), 6.98-7.06 (m, 2 H), 6.90 (t, J = 75.00 Hz, 1 H), 6.06 (dd, J = 9.70, 4.41 Hz, 1 H), 3.86-3.99 (m, 5 H), 3.66 (d, J = 16.76 Hz, 2 H), 3.60 (d, J = 3.09 Hz, 2 H), 3.44-3.54 (m, 5 H), 3.26 (dd, J = 14.11, 4.41 Hz, 1 H), 3.01 (s, 3 H), 2.23-2.38 (m, 6 H), 1.27 (m, 1 H), 0.52-0.67 (m, 2 H), 0.34-0.47 (m, 2 H). [MH]+: 774.3 | Step 1-3 In the synthesis of carboxylic acid (described in WO2010/089107 Example 18, step 1-6) were not performed. Starting material commercially available: 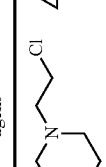 | No salt |  |  |  |

The compounds listed in Table 3 were prepared with analogous synthetic steps and procedures to those described in Example 2, by reacting the appropriate precursors (commercially available or synthesized by a person skilled in the art) with suitable reagents. Specific variations in the experimental or purification methods are indicated in the table.

References to the procedures for syntheses of different alcohols are listed in Table 1.

Carboxylic acid where synthesized following the same procedure as for compound 9 (WO2010/089107 (which is incorporated herein by reference in its entirety) Example 18, Scheme 2, step 4-6).

TABLE 3

| Structure | CHD | NMR characterization and MS/ESI+ [MH]+ | Experimental procedure | Salification | Alkylating agent | Alcohol (Comp. 3) | Carboxylic acid |
|---|---|---|---|---|---|---|---|
| (structure) | 31 | ¹H NMR (400 MHz, acetone) δ ppm 8.43 (d, J = 1.76 Hz, 2 H), 8.03 (d, J = 1.76 Hz, 2 H), 7.34 (m, 1 H), 7.15-7.27 (m, 3 H), 6.73-6.92-7.11 (t, 1 H, CHF₂), 6.26-6.34 (m, 1 H), 4.10-4.25 (m, 2 H), 3.96-4.08 (m, 5 H), 3.69-3.95 (m, 5 H), 3.34-3.51 (m, 3 H), 3.21 (m, 2 H), 3.01 (m, 5 H), 1.19-1.36 (m, 1 H), 0.60 (d, J = 7.94 Hz, 2 H), 0.40 (d, J = 4.41 Hz, 2 H). [MH]+ 774.3 | Step 6 (in WO2010/089107 Example 18, Scheme 2): Instead of ester hydrolysis, debenzylation with Pd/C 5% in MeOH was performed | Hydrochloride | (structure) | (structure) | (structure) |
| (structure) | 32 | ¹H NMR (400 MHz, acetone) δ ppm 13.07-13.30 (m, 1 H), 8.30 (s, 2 H), 7.96-8.16 (m, 2 H), 7.14-7.41 (m, 4 H), 6.66-6.91-7.12 (t, 1 H, CHF₂), 6.30 (dd, J = 9.70, 3.97 Hz, 1 H), 4.20 (t, J = 7.50 Hz, 2 H), 3.90-4.10 (m, 5 H), 3.74 (dd, J = 13.89, 9.92 Hz, 1 H), 3.42 (dd, J = 14.11, 4.41 Hz, 1 H), 3.17-3.32 (m, 2 H), 3.08 (s, 3 H), 2.81 (s, 6 H), 1.28 (d, J = 7.50 Hz, 1 H), 0.60 (d, J = 7.50 Hz, 2 H), 0.40 (d, J = 3.97 Hz, 2 H). [MH]+ 718.2 | Step 6 (in WO2010/089107 Example 18): Instead of ester hydrolysis, debenzylation with Pd/C 5% in MeOH was performed | Hydrochloride | (structure) | (structure) | (structure) |

TABLE 3-continued

| Structure | CHD | NMR characterization and MS/ESI+ [MH]+ | Experimental procedure | Salification | Alkylating agent | Alcohol (Comp. 3) | Carboxylic acid |
|---|---|---|---|---|---|---|---|
| (structure) | 33 | ¹H NMR (400 MHz, acetone) δ ppm 8.32 (s, 2 H), 8.07 (d, J = 8.82 Hz, 1 H), 8.01 (d, J = 1.76 Hz, 1 H), 7.32 (d, J = 1.76 Hz, 1 H), 7.14-7.28 (m, 3 H), 6.71-6.92-7.12 (t, 1 H, CHF₂), 6.25-6.36 (m, 1 H), 4.27 (t, J = 7.72 Hz, 2 H), 4.05 (s, 3 H), 3.99 (dd, J = 6.84, 2.87 Hz, 2 H), 3.68-3.80 (m, 1 H), 3.44 (d, J = 4.41 Hz, 3 H), 3.09-3.27 (m, 2 H), 3.06 (s, 3 H), 2.87-3.00 (m, 2 H), 2.07-2.19 (m, 2 H), 1.78 (d, J = 11.03 Hz, 3 H), 1.38-1.55 (m, 1 H), 1.12-1.35 (m, 1 H), 0.60 (dd, J = 8.16, 1.54 Hz, 2 H), 0.40 (d, J = 4.41 Hz, 2 H). [MH]+ 758.3 | Step 6 (in WO2010/ 089107 Example 18): Instead of ester hydrolysis, debenzylation with Pd/C 5% in MeOH was performed | Hydro-chloride | (structure) | (structure) | (structure) |
| (structure) | 34 | ¹H NMR (400 MHz, acetone) δ ppm 8.33 (s, 2 H), 7.98-8.10 (m, 2 H), 7.34 (m, 1 H), 7.15-7.29 (m, 3 H), 6.73-6.927.11 (t, 1 H, CHF₂), 6.25-6.35 (m, 1 H), 3.94-4.13 (m, 5 H), 3.80 (d, J = 6.62 Hz, 3 H), 3.43 (d, J = 4.41 Hz, 3 H), 3.11-3.13 (m, 2 H), 3.01 (s, 3 H), 2.83-2.86 (m, 2 H), 2.12-2.27 (m, 2 H), 2.06-2.08 (m, 2H), 1.78 (m, 3 H), 1.38-1.53 (m, 1 H), 1.21-1.32 (m, 1 H), 0.60 (dd, J = 7.94, 1.32 Hz, 2 H), 0.40 (d, J = 4.41 Hz, 2 H). [MH]+ 772.3 | Step 6 (in WO2010/ 089107 Example 18): Instead of ester hydrolysis, debenzylation with Pd/C 5% in MeOH was performed | Hydro-chloride | (structure) | (structure) | (structure) |

TABLE 3-continued

| Structure | CHD | NMR characterization and MS/ESI+ [MH]+ | Experimental procedure | Salification | Alkylating agent | Alcohol (Comp. 3) | Carboxylic acid |
|---|---|---|---|---|---|---|---|
| (structure shown) | 35 | 1H NMR (400 MHz, acetone) δ ppm 13.59-14.10 (bs, 1 H), 8.32 (s, 2 H), 7.77 (m, 1 H), 7.53 (m, 1 H), 7.39-7.46 (m, 2 H), 7.21 (m, 2 H), 6.92 (t, J = 75.00 Hz, 1 H), 6.25-6.37 (m, 1 H), 4.27-4.59 (m, 2 H), 4.07-4.26 (m, 2 H), 3.87-4.05 (m, 7 H), 3.77 (dd, J = 14.11, 10.14 Hz, 1 H), 3.44 (dd, J = 14.33, 4.19 Hz, 4 H), 3.11 (m, 6 H), 2.29-2.51 (m, 1 H), 1.28 (m, 1 H), 0.60 (dd, J = 8.16, 1.54 Hz, 2 H), 0.40 (d, J = 4.85 Hz, 2 H). [MH]+ 760.0 | Step 6 (in WO2010/089107 Example 18): Instead of ester hydrolysis, debenzylation with Pd/C 5% in MeOH was performed | Hydrochloride | (structure shown) | (structure shown) | (structure shown) |
| (structure shown) | 36 | 1H NMR (400 MHz, acetone) δ ppm 8.29 (s, 2 H), 7.38-7.47 (m, 1 H), 7.27-7.32 (m, 1 H), 7.24-7.26 (m, 1 H), 7.19-7.23 (m, 1 H), 7.13-7.18 (m, 1 H), 6.87-6.93 (m, 2 H), 6.27-6.35 (m, 1 H), 4.74-4.86 (m, 1 H), 3.96-4.03 (m, 2 H), 3.92 (s, 3 H), 3.68-3.78 (m, 1 H), 3.65 (m, 2 H), 3.39-3.45 (m, 1 H), 3.37 (m, 5 H), 1.23-1.36 (m, 1 H), 0.57-0.65 (m, 2 H), 0.34-0.42 (m, 2 H) [MH]+ 626.14 | During preparation of carboxylic acid just step 5 (in WO2010/089107 Example 18) was performed | No Salt | (structure shown) | (structure shown) | (structure shown) |

Example 3

Synthesis of (S)-3,5-dichloro-4-(2-(3-(cyclopropylmethoxy)-4-(difluoromethoxy)phenyl)-2-(4-(1,1-dioxothiomorpholinylmethyl)benzoyloxy)-ethyl)pyridine 1-oxide (Compound 37)

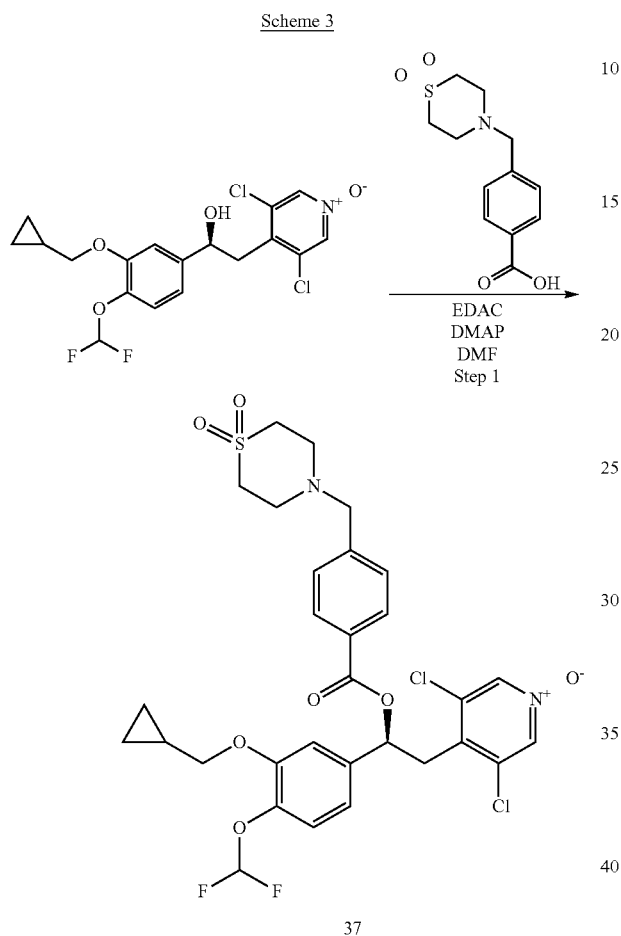

(S)-3,5-dichloro-4-(2-(3-(cyclopropylmethoxy)-4-(difluoromethoxy)phenyl)-2-hydroxyethyl)pyridine 1-oxide (compound 3, 40 mg, 0.095 mmol) was dissolved in DMF (1.5 ml). EDAC (55 mg, 0.285 mmol), DMAP (14 mg, 0.114 mmol), and 1,1-dioxothiomorpholinylmethyl)benzoic acid (39 mg, 0.143 mmol) were added. The mixture was stirred at RT for 1 hour, then water was added and the aqueous phase was extracted with AcOEt twice. The combined organic phase was washed with HCl 1N, dried over Na2SO4 and evaporated to dryness to give 40 mg of the desired compound (yield 65%). MS/ESI$^+$ 671.1 [MH]$^+$ $^1$H NMR (400 MHz, acetone) δ ppm 8.27 (s, 2 H), 8.05 (d, J=7.06 Hz, 2 H), 7.54 (d, J=7.94 Hz, 2 H), 7.31 (m, 1 H), 7.20 (q, J=8.38 Hz, 2 H), 6.92 (t, J=75.00 Hz, 1 H), 6.34 (dd, J=9.26, 4.41 Hz, 1 H), 3.98 (d, J=7.06 Hz, 2 H), 3.70-3.83 (m, 3 H), 3.41-3.50 (m, 1 H), 3.07 (d, J=3.97 Hz, 4 H), 2.99 (d, J=4.41 Hz, 4 H), 1.22-1.35 (m, 1 H), 1.11 (t, J=7.06 Hz, 1 H), 0.55-0.64 (m, 2 H), 0.33-0.42 (m, 2 H).

The compounds listed in Table 4 were prepared with analogous synthetic steps and procedures to those described in Example 3, by reacting the appropriate precursors (commercially available or synthesized by a person skilled in the art) with suitable reagents. Specific variations in the experimental or purification methods are indicated in the table.

TABLE 4
| Structure | Compound | NMR characterization | MS/ESI+ [MH]+ | Salification | Carboxylic acid |
|---|---|---|---|---|---|
| 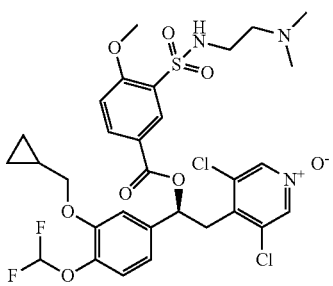 | 38 | 1H NMR (400 MHz, acetone) δ ppm 8.54 (d, J = 2.20 Hz, 1 H), 8.23-8.29 (m, 3 H), 8.13 (m, 1 H), 7.32-7.38 (m, 2 H), 7.19-7.25 (m, 1 H), 7.14-7.19 (m, 1 H), 6.92 (t, J = 75.00 Hz, 1 H), 6.32 (dd, J = 9.70, 4.41 Hz, 1 H), 6.14-6.26 (bs, 1 H), 4.09 (s, 3 H), 3.99 (dd, J = 6.62, 3.97 Hz, 2 H), 3.76 (dd, J = 14.11, 9.70 Hz, 1 H), 3.45 (dd, J = 14.11, 4.41 Hz, 1 H), 2.89-3.05 (m, 2 H), 2.38 (t, J = 6.17 Hz, 2 H), 2.11 (m, 6 H), 1.28 (m, 1 H), 0.55-0.66 (m, 2 H), 0.34-0.42 (m, 2 H). | 703.9 | No Salt | 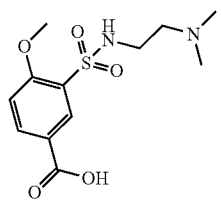 [SMILES: COc1ccc(C(=O)O)cc1S(=O)(=O)NCCN(C)C] |
| 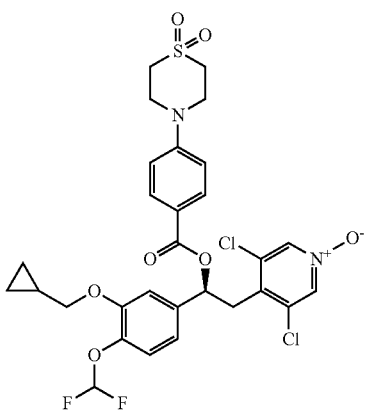 [SMILES: O=C(O[C@@H](Cc1c(Cl)c[n+]([O-])cc1Cl)c1ccc(OC(F)F)c(OCC2CC2)c1)c1ccc(N2CCS(=O)(=O)CC2)cc1] | 39 | 1H NMR (400 MHz, acetone) δ ppm 8.26 (s, 2 H), 7.95 (d, J = 8.82 Hz, 2 H), 7.28 (m, 1 H), 7.06-7.23 (m, 4 H), 6.91 (t, 1 H, CHF2), 6.31 (dd, J = 9.70, 4.41 Hz, 1 H), 4.05 (d, J = 4.85 Hz, 4 H), 3.97 (d, J = 7.06 Hz, 2 H), 3.71 (dd, J = 14.11, 9.70 Hz, 1 H), 3.41 (dd, J = 14.11, 4.85 Hz, 1 H), 3.12 (d, J = 4.41 Hz, 4 H), 1.23-1.35 (m, 1 H), 0.52-0.67 (m, 2 H), 0.31-0.44 (m, 2 H) | 657.51 | No Salt | 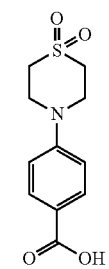 [SMILES: O=C(O)c1ccc(N2CCS(=O)(=O)CC2)cc1] |

TABLE 4-continued
| Structure | Com-pound | NMR characterization | MS/ESI+ [MH]+ | Salification | Carboxylic acid |
|---|---|---|---|---|---|
| 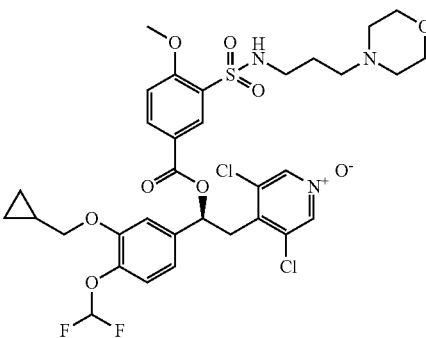 | 40 | $^1$H NMR (400 MHz, acetone) δ ppm 8.47-8.60 (m, 1 H), 8.28 (m, 3 H), 8.06-8.17 (m, 1 H), 7.15-7.44 (m, 4 H), 6.71-7.13 (m, 1 H), 6.23-6.41 (m, 1 H), 4.09-3.97 (m, 5 H), 3.68-3.82 (m, 1 H), 3.55 (m, 5 H), 2.95-3.02 (m, 2 H), 2.19-2.46 (m, 6 H), 1.56-1.74 (m, 2 H), 1.16-1.38 (m, 1 H), 0.52-0.70 (m, 2 H), 0.33-0.48 (m, 2 H). | 760.1 | No Salt | 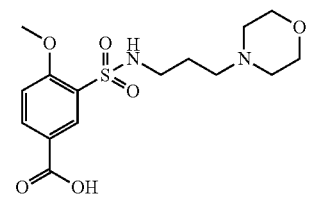 [SMILES: COc1ccc(C(=O)O)cc1S(=O)(=O)NCCCN1CCOCC1] |
| 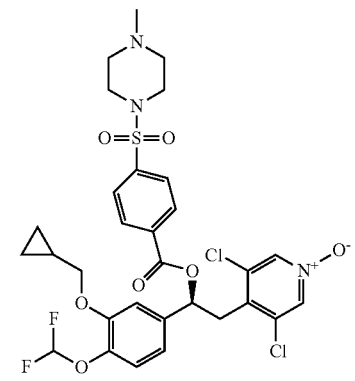 [SMILES: CN1CCN(S(=O)(=O)c2ccc(C(=O)O[C@@H](Cc3c(Cl)c[n+]([O-])cc3Cl)c3ccc(OC(F)F)c(OCC4CC4)c3)cc2)CC1] | 41 | $^1$H NMR (400 MHz, acetone) δ ppm 8.23-8.36 (m, 4 H), 7.90 (d, J = 8.38 Hz, 2 H), 7.33 (s, 1 H), 7.16-7.27 (m, 2 H), 6.68-6.91-7.12 (t, 1 H, CHF$_2$), 6.37 (dd, J = 9.48, 4.63 Hz, 1 H), 3.99 (d, J = 6.62 Hz, 2 H), 3.79 (dd, J = 14.33, 9.48 Hz, 1 H), 3.47 (dd, J = 14.11, 4.85 Hz, 1 H), 3.00 (d, J = 4.41 Hz, 4 H), 2.41 (t, J = 4.85 Hz, 4 H), 2.18 (s, 3 H), 1.22-1.35 (m, 1 H), 0.54-0.66 (m, 2 H), 0.37 (q, J = 5.00 Hz, 2 H). | 686.2 | No Salt | 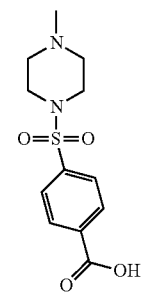 [SMILES: CN1CCN(S(=O)(=O)c2ccc(C(=O)O)cc2)CC1] |

Example 4
Synthesis of (S)-3,5-dichloro-4-(2-(3-(cyclopropyl-methoxy)-4-(difluoromethoxy)phenyl)-2-(4-hydroxy-3-(N-(2-morpholinoethyl)methylsulfonamido)benzoyloxy)ethyl)pyridine 1-oxide hydrochloride (Compound 42)
Scheme 4
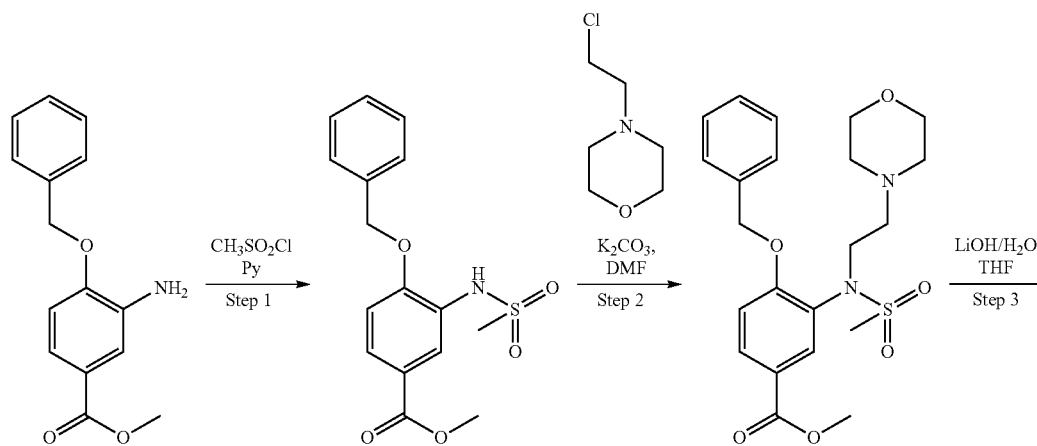
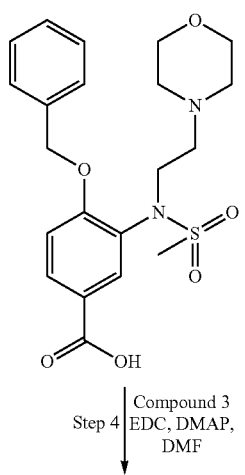

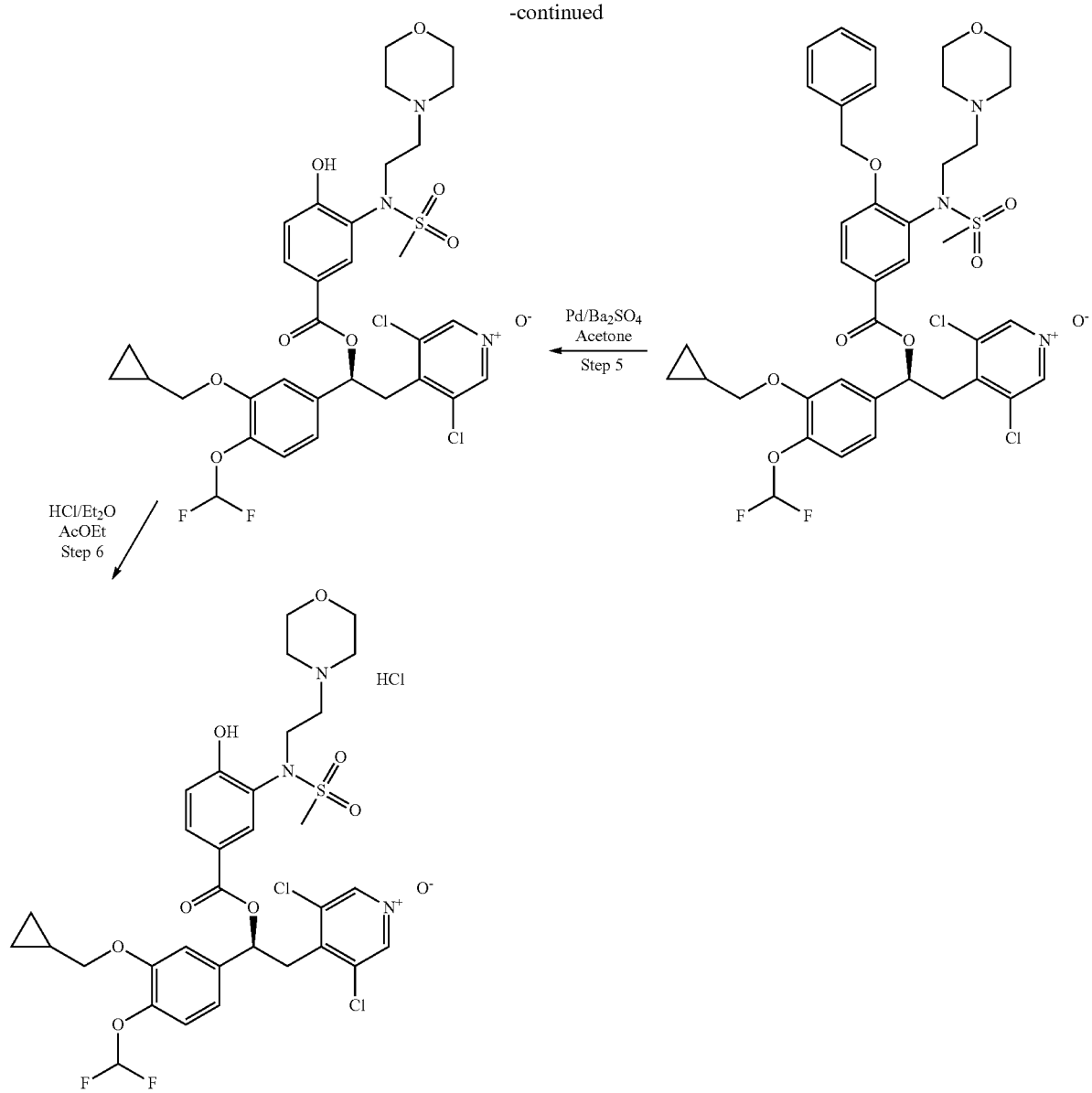

Step 1: Synthesis of methyl 4-(benzyloxy)-3-(methylsulfonamido)benzoate (47)

Methyl 3-amino-4-(benzyloxy)benzoate (1.7 g, 6.61 mmol) was dissolved in pyridine (5 ml), then methanesulfonyl chloride (0.62 ml, 7.93 mmol) was added at 0° C., and the mixture was stirred at RT for 2 hours. The reaction was quenched with HCl 1N, and the product was extracted with ethyl acetate. The organic phase was washed with HCl 1N (2×30 ml) and brine, then dried over $Na_2SO_4$. The solvent was removed to yield 1.7 g of the desired intermediate (Yield: 77%).

Step 2: Synthesis of methyl 4-(benzyloxy)-3-(N-(2-morpholinoethyl) methylsulfonamido)benzoate (46)

Methyl 4-(benzyloxy)-3-(methylsulfonamido)benzoate (700 mg, 2.1 mmol) was dissolved in DMF (5 ml). $K_2CO_3$ (580 mg, 4.2 mmol) and 4-(2 chloroethyl) morpholine (628 mg, 4.2 mmol) were added. The mixture was stirred at 60° C. for 3 hours. The reaction was quenched with water, and the product was extracted with ethyl acetate. The organic layer was washed with $H_2O$ (2×) and NaCl saturated solution, dried over $Na_2SO_4$ and evaporated under vacuum to yield 750 mg of the desired compound. (Yield 80%).

Step 3: Synthesis of 4-(benzyloxy)-3-(N-(2-morpholinoethyl) methylsulfonamido)benzoic acid (45)

Methyl 4-(benzyloxy)-3-(N-(2-morpholinoethyl)methylsulfonamido)benzoate (750 mg, 1.7 mmol) was dissolved in THF (10 ml). LiOH 1N (1.5 ml) was added and the resulting mixture was stirred at RT for 5 hours. The pH was adjusted to neutral by adding HCl 1N and then the volatiles were removed under vacuum to yield 650 mg of crude.

Step 4: Synthesis of (S)-4-(2-(4-(benzyloxy)-3-(N-(2-morpholinoethyl) methylsulfonamido)benzoyloxy)-2-(3-(cyclopropylmethoxy)-4-(difluoromethoxy) phenyl)ethyl)-3,5-dichloropyridine 1-oxide (44)

Compound 3 (200 mg, 0.5 mmol) and 4-(benzyloxy)-3-(N-(2-morpholinoethyl)methylsulfonamido)benzoic acid (652 mg, 1.5 mmol) were dissolved in DMF (5 ml), then EDC (767 mg, 4 mmol) and DMAP (122 mg, 1 mmol) were added. The mixture was stirred at RT for 24 hours, then quenched by adding water, and the product was extracted with ethyl acetate. The organic phase was washed with $K_2CO_3$ saturated solution (2×), water (2×) and brine, dried over $Na_2SO_4$ and evaporated under vacuum to yield 350 mg of crude that was used for the next step without any further purification.

$^1$H NMR (400 MHz, acetone) δ ppm 8.25 (s, 2 H), 8.00-8.14 (m, 2 H), 7.58 (d, J=7.06 Hz, 2 H), 7.27-7.48 (m, 5 H), 7.13-7.24 (m, 2 H), 6.69-6.91-7.11 (t, 1 H, $CHF_2$), 6.32 (dd, J=9.70, 4.85 Hz, 1 H), 5.35 (s, 2 H), 3.91-4.05 (m, 2 H), 3.74 (dd, J=14.11, 9.70 Hz, 3 H), 3.33-3.54 (m, 5 H), 2.91 (s, 3 H), 2.19-2.50 (m, 6 H), 1.18-1.36 (m, 1 H), 0.54-0.66 (m, 2 H), 0.39 (q, J=4.85 Hz, 2 H).

MS/ESI$^+$ 836.2 [MH]$^+$

Step 5: Synthesis of (S)-3,5-dichloro-4-(2-(3-(cyclopropylmethoxy)-4-(difluoromethoxy)phenyl)-2-(4-hydroxy-3-(N-(2-morpholinoethyl)methylsulfonamido)benzoyloxy)ethyl)pyridine 1-oxide (43)

(S)-4-(2-(4-(benzyloxy)-3-(N-(2-morpholinoethyl) methylsulfonamido)benzoyloxy)-2-(3-(cyclopropylmethoxy)-4-(difluoromethoxy) phenyl)ethyl)-3,5-dichloropyridine 1-oxide (120 mg, 0.14 mmol) was dissolved in acetone (10 ml), then 5% Pd/$Ba_2SO_4$ (149 mg, 0.07 mmol) was added, and the mixture was hydrogenated by shaking the mixture in a Parr apparatus ($H_2$: 30 psi) for 30 minutes. Additional 5% Pd/$Ba_2SO_4$ (149 mg, 0.07 mmol) was added and shaking continued for 30'. The catalyst was filtered over a celite pad, and the solvent was evaporated under vacuum. The crude was purified by preparative HPLC (Method 1) to yield 50 mg of the title compound.

MS/ESI$^+$ 712.15 [MH]$^+$ $^1$H NMR (400 MHz, acetone) δ ppm 8.22 (m, 1 H), 8.07 (d, J=2.21 Hz, 1 H), 7.98 (d, J=6.62 Hz, 2 H), 7.40 (d, J=6.62 Hz, 1 H), 7.28 (m, 1 H), 7.04-7.22 (m, 2 H), 6.65-7.04 (m, 2 H), 6.20-6.28 (m, 1 H), 3.95 (d, J=5.73 Hz, 2 H), 3.73 (t, J=4.41 Hz, 6 H), 3.48-3.60 (m, 1 H), 3.31-3.43 (m, 1 H), 3.04 (s, 3 H), 2.75-2.62 (m, 6 H), 1.19-1.37 (m, 1 H), 0.60 (d, J=7.06 Hz, 2 H), 0.37 (d, J=4.85 Hz, 2 H).

Step 6: Synthesis of (S)-3,5-dichloro-4-(2-(3-(cyclopropylmethoxy)-4-(difluoromethoxy)phenyl)-2-(4-hydroxy-3-(N-(2-morpholinoethyl) methylsulfonamido)benzoyloxy)ethyl)pyridine 1-oxide hydrochloride (42)

(S)-3,5-dichloro-4-(2-(3-(cyclopropylmethoxy)-4-(difluoromethoxy)phenyl)-2-(4-hydroxy-3-(N-(2-morpholinoethyl)methylsulfonamido)benzoyloxy)ethyl)pyridine 1-oxide (50 mg, 0.07 mmol) was dissolved in ethyl acetate (1.5 ml), and HCl/$Et_2O$ 2N (100 μl) was added. $Et_2O$ (5 ml) was added until a copious precipitate formed. The title compound (35 mg) was obtained by filtration (Yield 67%).

MS/ESI$^+$ 746.2 [MH]$^+$ $^1$H NMR (400 MHz, acetone) δ ppm 10.33-10.77 (m, bs H), 8.31 (s, 2 H), 7.99-8.12 (m, 1 H), 7.79-7.98 (m, 1 H), 7.27-7.36 (m, 1 H), 7.05-7.27 (m, 3 H), 6.90 (t, J=75.00 Hz, 1 H), 6.20-6.38 (m, 1 H), 5.60-5.90 (m, bs H), 3.85-4.41 (m, 8 H), 3.69-3.81 (m, 1 H), 3.22-3.63 (m, 7 H), 3.14 (s, 3 H), 1.16-1.39 (m, 1 H), 0.53-0.68 (m, 2 H), 0.29-0.48 (m, 2 H).

The compounds listed in Table 5 were prepared with analogous synthetic steps and procedures to those described in Example 4, step 1-4, by reacting the appropriate precursors (commercially available or synthesized by a person skilled in the art) with suitable reagents.

TABLE 5

| Structure | Comp. | NMR characterization and MS/ESI+ [MH]+ | Salification | Alkylating agent | Alcohol | Carboxylic acid |
|---|---|---|---|---|---|---|
| (structure shown) | 48 | ¹H NMR (400 MHz, acetone) δ ppm 8.24 (s, 2 H), 8.01-8.12 (m, 2 H), 7.30 (d, J = 1.76 Hz, 1 H), 7.18-7.25 (m, 2 H), 7.13-7.17 (m, 1 H), 6.90 (t, J = 75.00 Hz, 1 H), 6.32 (dd, J = 9.70, 4.85 Hz, 1 H), 3.89-4.07 (m, 5 H), 3.74 (dd, J = 14.11, 9.70 Hz, 3 H), 3.25-3.51 (m, 5 H), 3.00 (s, 3 H), 2.22-2.50 (m, 6 H), 1.16-1.35 (m, 1 H), 0.52-0.68 (m, 2 H), 0.33-0.46 (m, 2 H) [MH]+ 760.2 | No Salt | (morpholine alkylating agent) | (alcohol structure) | (carboxylic acid structure) |
| (structure shown) | 49 | ¹H NMR (400 MHz, acetone) δ ppm 12.99-13.11 (bs, 1 H), 8.33 (s, 2 H), 8.05-8.10 (m, 2 H), 7.30-7.39 (m, 1 H), 7.23-7.29 (m, 1 H), 7.13-7.23 (m, 2 H), 6.91 (t, J = 75.00 Hz, 1 H), 6.25-6.37 (m, 1 H), 4.12-4.25 (m, 2 H), 4.05 (m, 5 H), 3.70-3.81 (m, 1 H), 3.55-3.68 (m, 2 H), 3.39-3.49 (m, 1 H), 3.26-3.38 (m, 2 H), 3.07 (m, 5 H), 2.07-2.11 (m, 4 H), 1.20-1.36 (m, 1 H), 0.52-0.65 (m, 2 H), 0.33-0.48 (m, 2 H). [MH]+ 744.2 | Hydrochloride | (pyrrolidine alkylating agent) | (alcohol structure) | (carboxylic acid structure) |

TABLE 5-continued

| Structure | Comp. | NMR characterization and MS/ESI+ [MH]+ | Salification | Alkylating agent | Alcohol | Carboxylic acid |
|---|---|---|---|---|---|---|
| (structure) | 50 | 1H NMR (400 MHz, acetone) δ ppm 8.53 (s, 2 H), 8.07 (dd, J = 8.80, 2.02 Hz, 1 H), 8.00 (d, J = 2.02 Hz, 1 H), 7.13-7.35 (m, 4 H), 6.91 (t, J = 75.00 Hz, 1 H), 6.36 (dd, J = 10.00, 4.31 Hz, 1 H), 4.28 (t, J = 7.61 Hz, 2 H), 4.03-4.18 (m, 5 H), 3.88-4.02 (m, 4 H), 3.83 (dd, J = 13.76, 9.90 Hz, 1 H), 3.36-3.55 (m, 3 H), 3.09-3.34 (m, 4 H), 3.06 (s, 3 H), 1.27 (ddd, J = 12.20, 7.43, 4.77 Hz, 1 H), 0.51-0.68 (m, 2 H), 0.39 (q, J = 4.95 Hz, 2 H). [MH]+ 744.1 | Hydrochloride | (structure) | (structure) | (structure) |
| (structure) | 51 | 1H NMR (400 MHz, acetone) δ ppm 8.25 (s, 2 H), 7.96-8.10 (m, 2 H), 7.22 (d, J = 8.38 Hz, 1 H), 7.13 (d, J = 1.76 Hz, 2 H), 6.98 (d, J = 8.38 Hz, 1 H), 6.27-6.36 (m, 1 H), 3.96-4.10 (s, 3 H), 3.68-3.92 (m, 6 H), 3.46-3.61 (m, 4 H), 3.32-3.44 (m, 1 H), 3.01 (s, 3 H), 2.27-2.48 (m, 6 H), 1.18-1.36 (m, 1 H), 0.59 (dd, J = 7.94, 1.32 Hz, 2 H), 0.36 (d, J = 4.85 Hz, 2 H). [MH]+ 724.1 | No salt | (structure) | (structure) | (structure) |

TABLE 5-continued

| Structure | Comp. | NMR characterization and MS/ESI+ [MH]+ | Salification | Alkylating agent | Alcohol | Carboxylic acid |
|---|---|---|---|---|---|---|
| 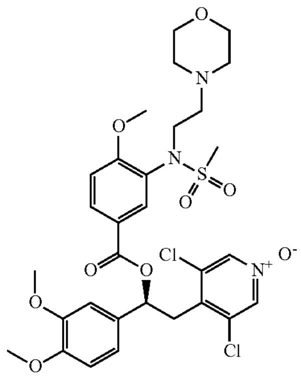 | 52 | ¹H NMR (400 MHz, acetone) δ ppm 8.37 (s, 2 H), 8.07 (dd, J = 8.66, 1.61 Hz, 1 H), 8.00 (d, J = 1.76 Hz, 1 H), 7.25 (d, J = 8.51 Hz, 1 H), 7.18 (m, 1 H), 7.10 (d, J = 8.22 Hz, 1 H), 6.97 (d, J = 8.22 Hz, 1 H), 6.31 (dd, J = 9.98, 4.11 Hz, 1 H), 4.27 (t, J = 7.34 Hz, 2 H), 4.06-4.16 (m, 2 H), 4.04 (s, 3 H), 3.93 (d, J = 12.33 Hz, 2 H), 3.83 (d, J = 13.79 Hz, 6 H), 3.72-3.78 (m, 1 H), 3.37-3.55 (m, 3 H), 3.11-3.31 (m, 4 H), 3.06 (s, 3 H). [MH]+ 684.2 | Hydrochloride | | | |

Example 5

Synthesis of (S)-3,5-dichloro-4-(2-(3-(cyclopropylmethoxy)-4-(difluoromethoxy)phenyl)-2-(4-fluoro-3-(N-(2-morpholinoethyl)methylsulfonamido)benzoyloxy)ethyl)pyridine 1-oxide (Compound 53)

Scheme 5

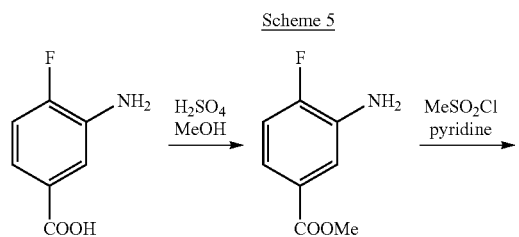

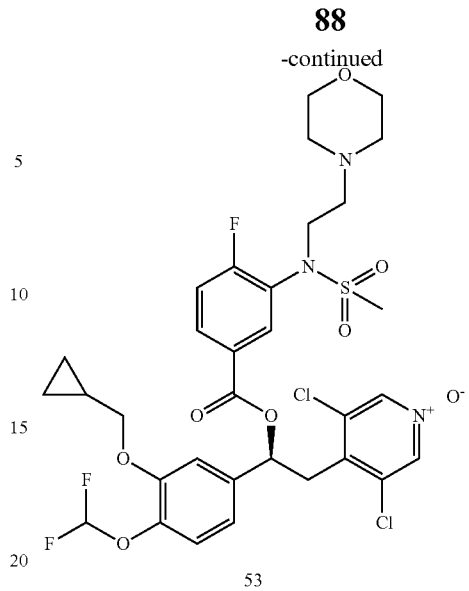

Step 1: Preparation of methyl 3-amino-4-fluorobenzoate (54)

To a mixture of 3-amino-4-fluorobenzoic acid (1 g, 6.45 mmol) in MeOH (20 ml), conc. $H_2SO_4$ (0.687 ml, 12.89 mmol) was added drop wise, and the reaction was refluxed for 20 hours. After cooling to room temperature the solvent was evaporated and the residue was partitioned between aq. $NaHCO_3$ sat. sol. and ethyl acetate; the organic phase was washed with brine, dried over $Na_2SO_4$ and evaporated to dryness affording methyl 3-amino-4-fluorobenzoate as a brown solid (0.970 g, 5.73 mmol, 89% yield, MS/ESI$^+$170.0 [MH]$^+$) (43)

Step 2: Preparation of methyl 4-fluoro-3-(methylsulfonamido)benzoate (55)

A solution of methyl 3-amino-4-fluorobenzoate (0.970 g, 5.73 mmol) in dry pyridine (12 ml), was cooled to 0° C. and methanesulfonyl chloride (0.577 ml, 7.45 mmol) was added drop wise. The resulting mixture was allowed to warm to room temperature and stirred for 3 hours. The solvent was evaporated and the residue was partitioned between DCM and aq. $NaHCO_3$ sat. sol. The organic layer was washed with brine and dried over $Na_2SO_4$; the solvent was evaporated and the residue was purified by flash chromatography on silica gel column (ethyl acetate:petroleum ether: 35:65) affording methyl 4-fluoro-3-(methylsulfonamido)benzoate as an off white powder (0.400 g, 1.618 mmol, 28.2% yield, MS/ESI$^+$ 248.1 [MH]$^+$).

Step 3: Preparation of methyl 4-fluoro-3-(N-(2-morpholinoethyl)methylsulfonamido)benzoate (56)

To a solution of Methyl 4-fluoro-3-(methylsulfonamido)benzoate (0.400 g, 1.618 mmol) in dry DMF (16.200 ml) under $N_2$ atmosphere, $K_2CO_3$ (0.492 g, 3.56 mmol) was added followed by 4-(2-chloroethyl)morpholine hydrochloride (0.361 g, 1.941 mmol). The resulting white suspension was heated to 70° C. for 1 hours, stirred at room temperature overnight and heated to 70° C. for additional 3.5 hours. Water (20 ml) was added and the mixture was extracted several times with ethyl ether (25 ml×5). The combined organic layers were dried over Na$_2$SO$_4$ and evaporated to dryness. The residue was purified by flash chromatography on silica gel column (ethyl acetate:petroleum ether=85:15) to give methyl 4-fluoro-3-(N-(2-morpholinoethyl)methylsulfonamido)-benzoate as a colorless oil (0.512 g, 1.421 mmol, 88% yield, MS/ESI$^+$ 361.0 [MH]$^+$).

Step 4: Preparation of 4-fluoro-3-(N-(2-morpholinoethyl)methylsulfonamido)benzoic acid hydrochloride (57)

Methyl 4-fluoro-3-(N-(2-morpholinoethyl)methylsulfonamido)benzoate (0.504 g, 1.398 mmol) was dissolved in dioxane (14.000 ml), and aq. 6N HCl (1.398 ml, 8.39 mmol) was added. The mixture was heated to 70° C. for 24 hours. Additional aq. 6N HCl (2.80 ml, 16.78 mmol) was added in three portions heating to 100° C. for 4 hours. The volatiles were removed under vacuum affording 4-fluoro-3-(N-(2-morpholinoethyl)methylsulfonamido)benzoic acid hydrochloride as a pale yellow solid (0.518 g, 1.353 mmol, 97% yield, MS/ESI$^+$ 347.0 [MH]$^+$). This product was used without any further purification.

Step 5: Preparation of (S)-3,5-dichloro-4-(2-(3-(cyclopropylmethoxy)-4-(difluoromethoxy)phenyl)-2-(4-fluoro-3-(N-(2-morpholinoethyl)methylsulfonamido)benzoyloxy)ethyl)pyridine 1-oxide (53)

4-Fluoro-3-(N-(2-morpholinoethyl)methylsulfonamido)benzoic acid hydrochloride (0.180 g, 0.470 mmol) was suspended in dry DCM (13.100 ml); (S)-3,5-dichloro-4-(2-(3-(cyclopropylmethoxy)-4-(difluoromethoxy)phenyl)-2-hydroxyethyl)pyridine 1-oxide (0.165 g, 0.392 mmol), EDC (0.225 g, 1.175 mmol), and DMAP (0.096 g, 0.784 mmol) were sequentially added, and the mixture was stirred at room temperature for 5 hours. A second portion of 4-fluoro-3-(N-(2-morpholinoethyl)methylsulfonamido)benzoic acid hydrochloride (0.030 g, 0.078 mmol) was added and the reaction was stirred at room temperature overnight. The mixture was diluted with DCM (20 ml) and washed with aq. 1N HCl (15 ml×3). The organic phase was dried over Na$_2$SO$_4$ and evaporated to dryness. The crude was purified by flash chromatography on silica gel column (DCM:MeOH=97:3) affording (S)-3,5-dichloro-4-(2-(3-(cyclopropylmethoxy)-4-(difluoromethoxy)phenyl)-2-(4-fluoro-3-(N-(2-morpholinoethyl) methylsulfonamido)benzoyloxy)ethyl)pyridine 1-oxide as a white spongy solid (0.202 g, 0.270 mmol, 69% yield, MS/ESI$^+$ 748.52 [MH]$^+$, [α$_D$]=−30.52, c=0.5, MeOH).

$^1$H NMR (300 MHz, DMSO-d$_6$) d ppm 8.53 (s, 2 H), 7.97-8.14 (m, 2 H), 7.49 (t, 1 H), 7.23 (d, 1 H), 7.20 (d, 1 H), 7.09 (dd, 1 H), 7.06 (t, 1 H), 6.19 (dd, 1 H), 3.95 (dd, 1 H), 3.90 (dd, 1 H), 3.66-3.81 (m, 2 H), 3.64 (dd, 1 H), 3.31-3.44 (m, 5 H), 3.13 (s, 3 H), 2.32-2.45 (m, 2 H), 2.11-2.31 (m, 4 H), 1.05-1.39 (m, 1 H), 0.46-0.67 (m, 2 H), 0.20-0.44 (m, 2 H)

The compounds listed in Table 6 were prepared with analogous synthetic steps and procedures to those described in Example 5 by reacting the appropriate precursors (commercially available or synthesized by a person skilled in the art) with suitable reagents.

Specific variations in the experimentals or purification methods are indicated in the table.

TABLE 6

| Structure | Comp | NMR characterization and MS/ESI+ [MH]+ | [α_D] | Salification | Alkylating agent | Experimental procedure | Carboxylic acid |
|---|---|---|---|---|---|---|---|
| (structure shown) | 58 | 1H NMR (300 MHz, DMSO-d6 + Na2CO3 353K) δ ppm 8.39 (s, 2 H), 8.17 (d, 1 H), 8.12 (s, 1 H), 7.95 (d, 1 H), 7.16-7.27 (m, 2 H), 7.06-7.15 (m, 1 H), 6.98 (t, 1 H), 6.30 (dd, 1 H), 3.96 (d, 2 H), 3.77-3.94 (m, 1 H), 3.53-3.76 (m, 2 H), 3.43 (dd, 1 H), 3.29-3.39 (m, 4 H), 3.17 (s, 3 H), 2.36-2.47 (m, 2 H), 2.10-2.36 (m, 4 H), 1.13-1.32 (m, 1 H), 0.50-0.67 (m, 2 H), 0.26-0.41 (m, 2 H) [MH]+ 798.52 | [α_D] = −28.36, c = 0.5, MeOH | •HCl | (2-chloroethyl morpholine) | | (3-amino-4-(trifluoromethyl)benzoic acid) |
| (structure shown) | 59 | 1H NMR (400 MHz, acetone) δ ppm 8.27 (s, 2 H), 7.97-8.09 (m, 2 H), 7.30 (d, J = 1.76 Hz, 1 H), 7.18-7.27 (m, 2 H), 7.16 (d, J = 1.76 Hz, 1 H), 6.91 (t, J = 75.00 Hz, 1 H), 6.28-6.35 (m, 1 H), 4.04 (s, 3 H), 3.98 (t, J = 6.84 Hz, 2 H), 3.74 (m, 1 H), 3.50-3.68 (m, 6 H), 3.37-3.47 (m, 1 H), 2.94 (s, 3 H), 2.16-2.35 (m, 6 H), 1.34-1.53 (m, 6 H), 1.20-1.32 (m, 1 H), 0.60 (dd, J = 7.94, 1.76 Hz, 2 H), 0.34-0.42 (m, 2 H). [MH]+ 802.1 | | No salt | Alkylation with 1,4-dibromobutane followed by nucleophilic substitution via procedure described in Step 1-2, Example 9, Scheme 9, with morpholine | Step 1: benzylation with BzOH, EDAC, DMAP. Step 4 debenzylation with PD/C 5% and H2. | (3-amino-4-(trifluoromethyl)benzoic acid) |

TABLE 6-continued

| Structure | Comp | NMR characterization and MS/ESI+ [MH]+ | [α_D] | Salification | Alkylating agent | Experimental procedure | Carboxylic acid |
|---|---|---|---|---|---|---|---|
| (structure with morpholine, methanesulfonamide, CF3-phenyl benzoate, cyclopropylmethoxy/difluoromethoxy phenyl, dichloropyridine N-oxide) | 60 | 1H NMR (300 MHz, DMSO-d6) δ ppm 8.53 (s, 2 H), 8.06-8.24 (m, 3 H), 7.27 (d, 1 H), 7.21 (d, 1 H), 7.10 (dd, 1 H), 7.07 (t, 1 H), 6.19 (dd, 1 H), 3.96 (dd, 1 H), 3.91 (dd, 1 H), 3.80-3.89 (m, 2 H), 3.68 (dd, 1 H), 3.39 (dd, 1 H), 3.30-3.36 (m, 4 H), 3.09 (s, 3 H), 2.31-2.42 (m, 2 H), 2.14-2.27 (m, 4 H), 1.11-1.31 (m, 1 H), 0.49-0.66 (m, 2 H), 0.28-0.40 (m, 2 H) [MH]+ 797.98 | [α_D] = −24.04 (c = 0.5; DCM) | No Salt | 4-(2-chloroethyl)morpholine | Step 2: MeSO2Cl 1.1 eq. 0° C. to r.t. 3 h Step 3: 4-(2-chloroethyl)-morpholine hydrochloride 1.5 eq, K2CO3 2.8 eq, 100° C., o.n. Step 4: 6M HCl 12 eq, 100° C., 6 h. Purification: Flash chromatography on silica gel (DCM/MeOH = 98/2 to 90/10) | 3-amino-5-(trifluoromethyl)benzoic acid |
| (structure with pyrrolidine, methanesulfonamide, CF3-phenyl benzoate, cyclopropylmethoxy/difluoromethoxy phenyl, dichloropyridine N-oxide) | 61 | 1H NMR (300 MHz, DMSO-d6) δ ppm 8.13-8.22 (m, 1 H), 8.11 (s, 1 H), 7.96 (dd, 1 H), 7.24 (d, 1 H), 7.21 (d, 1 H), 7.10 (dd, 1 H), 7.07 (t, 1 H), 6.15-6.31 (m, 1 H), 3.93 (d, 2 H), 3.31-3.90 (m, 4 H), 3.19 (s, 3 H), 2.12-2.42 (m, 6 H), 1.40-1.65 (m, 4 H), 1.00-1.30 (m, 1 H), 0.47-0.67 (m, 2 H), 0.22-0.42 (m, 2 H) [MH]+ 782.04 | [α_D] = −1.52 (c = 0.5, MeOH) | No Salt | 1-(2-chloroethyl)pyrrolidine HCl | | 3-amino-4-(trifluoromethyl)benzoic acid |

Example 6

Synthesis of (S)-3,5-dichloro-4-(2-(3-(cyclopropylmethoxy)-4-(difluoromethoxy)phenyl)-2-(5-(N-(cyclopropylmethyl)methylsulfonamido)-2-(2-morpholinoethoxy)benzoyloxy)ethyl)pyridine 1-oxide (62)

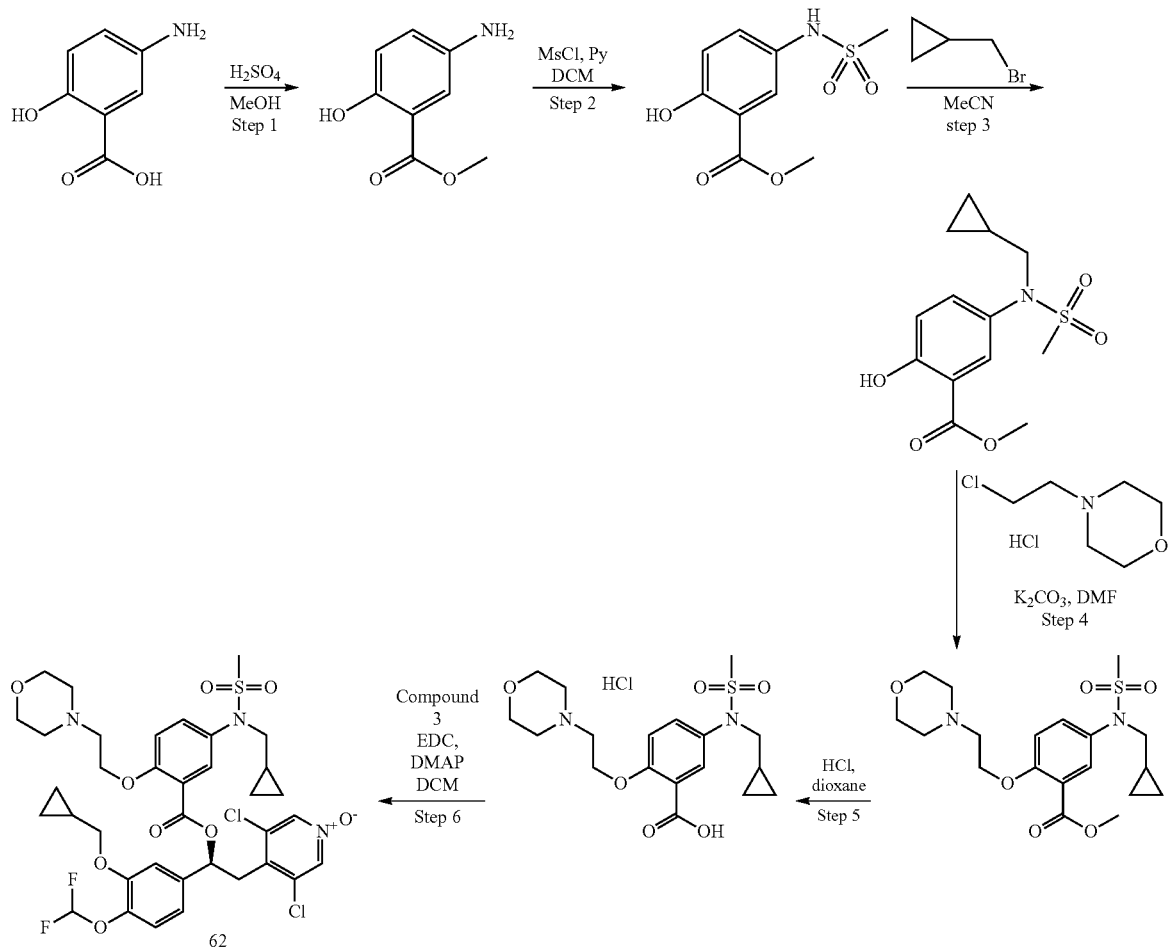

Step 1: Synthesis of methyl 5-amino-2-hydroxybenzoate (63)

5-Amino-2-hydroxybenzoic acid (10 g, 65.3 mmol) was suspended in MeOH (150 ml) and 96% sulfuric acid (12 ml, 225 mmol) was added dropwise. The mixture was heated at reflux for 96 h, then cooled to RT: part of the solvent was evaporated (90 ml left) and 5% solution of NaHCO₃ was added (pH basic). The mixture was extracted with AcOEt. The combined organic layers were washed with brine, dried over Na₂SO₄ and evaporated. The desired product was obtained as a solid (9.68 g, 89% yield) and was used in the following reaction without further purification.

MS/ESI⁺ 168 [MH]⁺

Step 2: Synthesis of methyl 2-hydroxy-5-(methylsulfonamido)benzoate (64)

Methyl 5-amino-2-hydroxybenzoate (9.58 g, 57.3 mmol) was dissolved in DCM (150 ml). Pyridine (9.27 ml, 115 mmol) and methanesulfonyl chloride (4.47 ml, 57.3 mmol) were added. The reaction mixture was stirred at RT for 4 hours, and then water (50 ml) and 6M HCl (15 ml) were added. A pink solid started to crystallize. The solid was recovered by filtration and washed with water. The title compound was obtained as a pink solid (13 g, 92% yield) and used in the following reaction without further purification.

MS/ESI⁺ 246 [MH]⁺

Step 3: Synthesis of methyl 5-(N-(cyclopropylmethyl)methylsulfonamido)-2-hydroxybenzoate (65)

Methyl 2-hydroxy-5-(methylsulfonamido)benzoate (5.565 g, 22.69 mmol) was dissolved in acetonitrile (250 ml). Bromomethyl cyclopropane (4.59 g, 34 mmol) and potassium carbonate (6.27 g, 45.4 mmol) were added, and the mixture was stirred at RT for 4 days. The reaction mixture was poured into ice-water (200 ml) and 36% HCl was added until pH=1. The mixture was then extracted with AcOEt, the organic layer was dried over Na₂SO₄ and the solvent was evaporated. The resulting crude was purified by flash chromatography on silica gel (petroleum ether:AcOEt 4:1) affording 4.75 g of the desired product (70% yield)
MS/ESI⁺ 300 [MH]⁺

Step 4: Synthesis of methyl 5-(N-(cyclopropylmethyl)methylsulfonamido)-2-(2-morpholinoethoxy)benzoate (66)

A mixture of methyl 5-(N-(cyclopropylmethyl)methylsulfonamido)-2-hydroxybenzoate (200 mg, 0.668 mmol), 4-(2-chloroethyl)morpholine hydrochloride (149 mg, 0.802 mmol) and K₂CO₃ (231 mg, 1.670 mmol) in 10 ml of DMF was stirred for 4 hours at 80° C. The mixture was poured into water and extracted twice with AcOEt, which was then washed with brine, dried and evaporated to obtain the desired product (259 mg, 94% yield) which was used in the next step without further purification.
MS/ESI⁺ 413.0 [MH]⁺

Step 5: Synthesis of 5-(N-(cyclopropylmethyl)methylsulfonamido)-2-(2-morpholinoethoxy)benzoic acid hydrochloride (67)

A mixture of methyl 5-(N-(cyclopropylmethyl)methylsulfonamido)-2-(2-morpholinoethoxy)benzoate (260 mg, 0.630 mmol) and conc. HCl (1.5 ml, 18.00 mmol) in 3 ml of dioxane was heated at 100° C. for 1 hour under microwave irradiation. The mixture was evaporated to obtain the title compound (303 mg, quantitative yield) which was used in the next step without further purification.
MS/ESI⁺ 434.9 [MH]⁺

Step 6: Synthesis of (S)-3,5-dichloro-4-(2-(3-(cyclopropylmethoxy)-4-(difluoromethoxy)phenyl)-2-(5-(N-(cyclopropylmethyl)methylsulfonamido)-2-(2-morpholinoethoxy)benzoyloxy)ethyl)pyridine 1-oxide (62)

A mixture of 5-(N-(cyclopropylmethyl)methylsulfonamido)-2-(2-morpholinoethoxy)benzoic acid hydrochloride (303 mg, 0.627 mmol), compound 3 (220 mg, 0.522 mmol), DMAP (128 mg, 1.045 mmol) and EDC (250 mg, 1.306 mmol) in 25 ml of dry DCM was stirred overnight at RT. The mixture was washed with diluted HCl and brine, then dried and evaporated. The crude was purified by prep. HPLC; the fractions containing the product were basified with NaHCO₃ and extracted with AcOEt, which was then washed with brine, dried and evaporated to obtain (S)-3,5-dichloro-4-(2-(3-(cyclopropylmethoxy)-4-(difluoromethoxy)phenyl)-2-(5-(N-(cyclopropylmethyl)methylsulfonamido)-2-(2-morpholinoethoxy)benzoyloxy)ethyl)pyridine 1-oxide (31 mg, 7.41% yield).
MS/ESI⁺ 800.27 [MH]⁺,
[α]_D^{20}=−25.21 (c=0.365, MeOH).

¹H NMR (300 MHz, DMSO-d6) δ ppm 8.53 (s, 2 H), 7.64 (d, 1 H), 7.58 (dd, 1 H), 7.21 (d, 1 H), 7.20 (d, 1 H), 7.16 (d, 1 H), 7.06 (dd, 1 H), 7.06 (t, 1 H), 6.17 (dd, 1 H), 4.15 (t, 2 H), 3.93 (dd, 1 H), 3.87 (dd, 1 H), 3.56 (dd, 1 H), 3.49-3.53 (m, 4 H), 3.47 (d, 2 H), 3.32 (dd, 1 H), 2.97 (s, 3 H), 2.56-2.69 (m, 2 H), 2.33-2.45 (m, 4 H), 1.11-1.23 (m, 1 H), 0.72-0.92 (m, 1 H), 0.48-0.63 (m, 2 H), 0.25-0.47 (m, 4 H), −0.07-0.19 (m, 2 H) MS/ESI⁺ 800.27 [MH]⁺

Example 7

Synthesis of (S)-3,5-dichloro-4-(2-(3-(cyclopropylmethoxy)-4-(difluoromethoxy)phenyl)-2-(4-methoxy-3-(N-(2-(4-methylpiperazin-1-yl)ethyl)methylsulfonamido)benzoyloxy)ethyl)pyridine 1-oxide trifluoroacetate (68)

Scheme 7

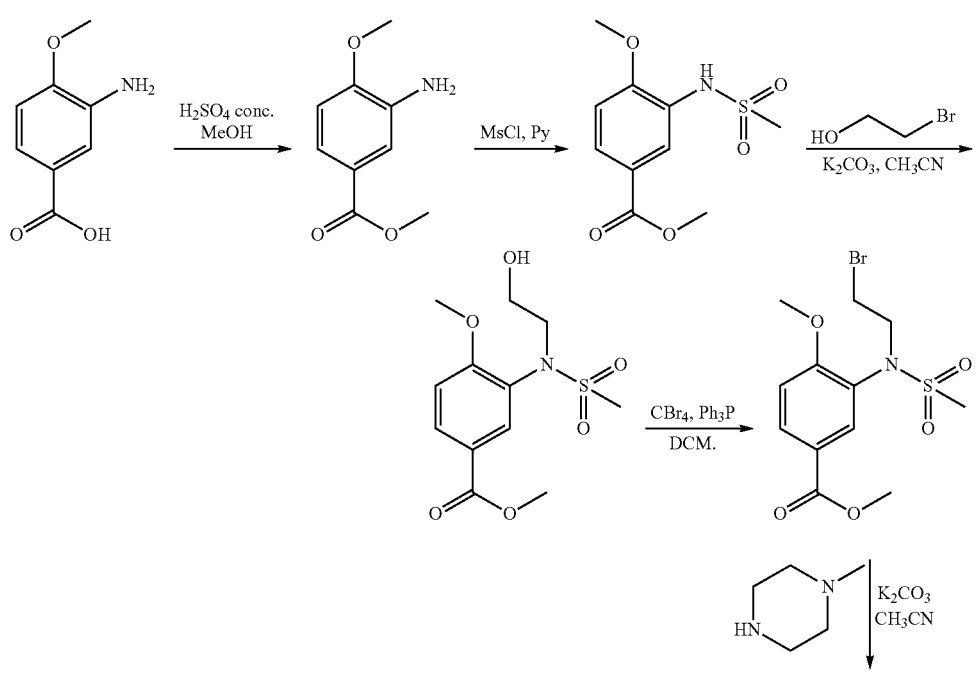

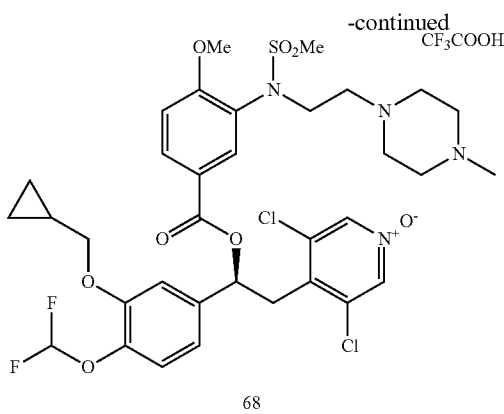

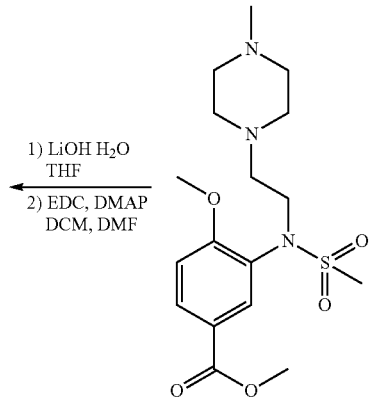

Step 1: Preparation of methyl 3-amino-4-methoxybenzoate (69)

A mixture of 3-amino-4-methoxybenzoic acid (2.00 g, 11.96 mmol) and sulfuric acid (1.275 ml, 23.93 mmol) in MeOH (25 ml) was heated to reflux for 24 hours. After cooling to room temperature the solvent was removed under vacuum and the residue was partitioned between aq. NaHCO$_3$ sat. sol. and ethyl acetate. The organic layer was dried over Na$_2$SO$_4$ and evaporated to dryness affording methyl 3-amino-4-methoxybenzoate as an off-white powder (2.00 g, 11.04 mmol, 92% yield, MS/ESI$^+$ 182.1 [MH]$^+$).

Step 2: Preparation of methyl 4-methoxy-3-(methylsulfonamido)benzoate (70)

A solution of methyl 3-amino-4-methoxybenzoate (2.00 g, 11.04 mmol) in dry pyridine (25 ml) was cooled to 0° C. and methanesulfonyl chloride (1.115 ml, 14.35 mmol) was added drop wise. The reaction was allowed to warm to room temperature and stirred for 3 hours. The solvent was evaporated to dryness and the residue was partitioned between DCM and aq. 2N HCl; the organic layer was washed with brine, dried over Na$_2$SO$_4$ and the solvent was removed under vacuum. The residue was triturated with iPr$_2$O and the resulting solid was collected by filtration to give methyl 4-methoxy-3-(methylsulfonamido)benzoate as an off-white powder (2.6 g, 10.03 mmol, 91% yield, MS/ESI$^+$ 260.1 [MH]$^+$).

Step 3: Preparation of methyl 3-(N-(2-hydroxyethyl)methylsulfonamido)-4-methoxybenzoate (71)

A mixture of methyl 4-methoxy-3-(methylsulfonamido)benzoate (0.300 g, 1.157 mmol), 2-bromoethanol (0.434 g, 3.47 mmol), and K$_2$CO$_3$ (0.320 g, 2.314 mmol) in acetonitrile (5 ml) was heated under microwave irradiation at 110° C. for 5 hours. The solvent was evaporated and the residue was treated with ethyl acetate. Inorganic salts were filtered off and the filtrate was evaporated to dryness. The crude was purified by flash chromatography on silica gel column (petroleum ether:ethyl acetate=1:9) affording methyl 3-(N-(2-hydroxyethyl) methylsulfonamido)-4-methoxybenzoate as a light brown oil (0.200 g, 0.659 mmol, 57.0% yield, MS/ESI$^+$ 326.3 [MNa]$^+$).

Step 4: Preparation of methyl 3-(N-(2-bromoethyl)methylsulfonamido)-4-methoxybenzoate (72)

To a solution of methyl 3-(N-(2-hydroxyethyl)methylsulfonamido)-4-methoxybenzoate (0.200 g, 0.659 mmol) and triphenylphosphine (0.173 g, 0.659 mmol) in dry DCM (3 ml), CBr$_4$ (219 mg, 0.659 mmol) was added portion wise at room temperature under nitrogen atmosphere and the mixture was stirred for 30 minutes. The solvent was removed under vacuum and the residue was purified by flash chromatography on silica gel column (ethyl acetate:petroleum ether=9:1) affording methyl 3-(N-(2-bromoethyl)methylsulfonamido)-4-methoxybenzoate as a white solid (0.150 g, 0.410 mmol, 62.1% yield, MS/ESI$^+$ 365.9-367.9 [MH]$^+$).

Step 5: Preparation of methyl 4-methoxy-3-(N-(2-(4-methylpiperazin-1-yl)ethyl) methylsulfonamido) benzoate (73)

A mixture of methyl 3-(N-(2-bromoethyl)methylsulfonamido)-4-methoxybenzoate (0.150 g, 0.410 mmol), 1-methylpiperazine (0.041 g, 0.410 mmol), and K$_2$CO$_3$ (0.085 g, 0.614 mmol) in acetonitrile (3 ml) was heated under microwave irradiation at 130° C. for 3 hours. The insoluble residue was filtered off and the filtrate was evaporated to dryness. The crude was purified by flash chromatography on silica gel column (DCM:MeOH:aq. 32% NH$_4$OH=95:5:0.5) affording methyl 4-methoxy-3-(N-(2-(4-methylpiperazin-1-yl)ethyl)methylsulfonamido)-benzoate as a light brown oil (0.140 g, 0.363 mmol, 89% yield, MS/ESI$^+$ 386.4 [MH]$^+$).

Step 6: Preparation of (S)-3,5-dichloro-4-(2-(3-(cyclopropylmethoxy)-4-(difluoromethoxy)phenyl)-2-(4-methoxy-3-(N-(2-(4-methylpiperazin-1-yl)ethyl) methylsulfonamido)benzoyloxy)ethyl)pyridine 1-oxide trifluoroacetate (68)

To a solution of methyl 4-methoxy-3-(N-(2-(4-methylpiperazin-1-yl)ethyl)methylsulfonamido)benzoate (0.140 g, 0.363 mmol) in THF (5 ml), a solution of LiOH*H$_2$O (0.183 g, 0.436 mmol) in water (0.5 ml) was added, and the mixture was stirred at room temperature for 24 hours. The solvent was evaporated under vacuum. The dry solid crude was suspended in DCM/DMF=1/1 with EDC (0.209 g, 1.089 mmol), (S)-3,5-dichloro-4-(2-(3-(cyclopropylmethoxy)-4-(difluoromethoxy)phenyl)-2-hydroxyethyl)pyridine 1-oxide (0.137 g, 0.327 mmol) and DMAP (0.44 g, 0.363 mmol), and the resulting solution was stirred at room temperature overnight. The solvent was evaporated and the residue was partitioned between ethyl acetate and aq. NaHCO$_3$ sat. sol. The organic phase was washed with brine and dried over Na$_2$SO$_4$; the solvent was removed under vacuum and the residue was purified by flash chromatography on silica gel column (DCM:MeOH:aq. 32% NH₄OH=95:5:0.5) affording 0.150 g of desired product. An additional purification by preparative HPLC (Method 3) was required to obtain (S)-3,5-dichloro-4-(2-(3-(cyclopropylmethoxy)-4-(difluoromethoxy)phenyl)-2-(4-methoxy-3-(N-(2-(4-methylpiperazin-1-yl)ethyl)methylsulfonamido)benzoyloxy)-ethyl)pyridine 1-oxide as trifluoroacetate salt (white powder) (0.068 g, 0.077 mmol, 21.10% yield, LC-MS purity (BPI): 99.2%, MS/ESI⁺ 773.36 [MH]⁺, [α$_D$]=−30.48, c=0.5, DCM).

Example 8

Synthesis of (3,5-dichloro-4-((S)-2-(3-(cyclopropylmethoxy)-4-(N-(3-((2S,5R)-2,5-dimethylpiperazin-1-yl)propyl)methylsulfonamido)benzoyloxy)-2-(3-(cyclopropylmethoxy)-4-(difluoromethoxy)phenyl)ethyl)pyridine 1-oxide (74)

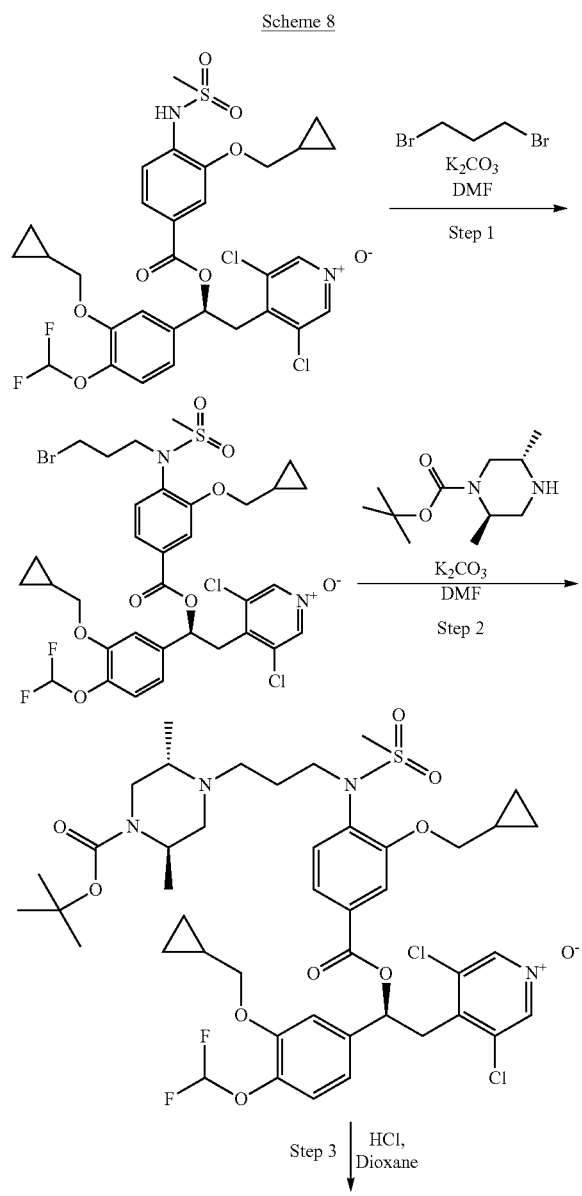

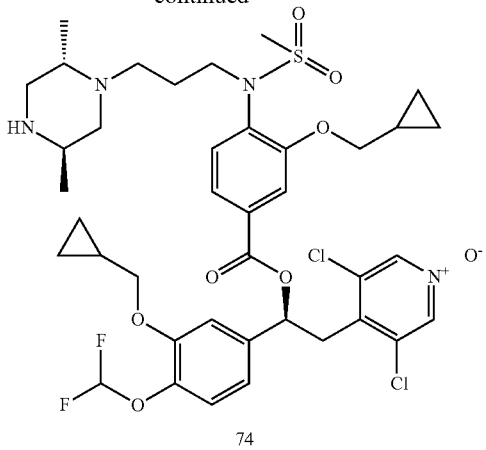

74

Step 1: Synthesis of (S)-4-(2-(4-(N-(3-bromopropyl)methylsulfonamido)-3-(cyclopropyl methoxy)benzoyloxy)-2-(3-(cyclopropylmethoxy)-4-(difluoromethoxy)phenyl)ethyl)-3,5-dichloropyridine 1-oxide (75)

To a solution of (S)-3,5-dichloro-4-(2-(3-(cyclopropylmethoxy)-4-(difluoromethoxy)phenyl)-2-(3-(cyclopropylmethoxy)-4-(methylsulfonamido)benzoyloxy)ethyl)pyridine 1-oxide, (comp. 7, 1 g, 1.5 mmol) dissolved in DMF (10 ml), 1,3-dibromopropane (1.52 ml, 15 mmol) and K₂CO₃ (414 mg, 3 mmol) were added, and the mixture was stirred at 40° C. for 6 hours. The reaction was diluted with water and then extracted with ethyl acetate. The organic phase was washed with water (3×30 ml), dried over Na₂SO₄ and evaporated to dryness. The solid was triturated with Petroleum Ether and filtered, to yield 700 mg of the desired product (Yield: 58%).

MS/ESI⁺ 808.51 [MH]⁺

¹H NMR (400 MHz, acetone) δ ppm 8.28 (s, 2 H), 7.68 (dd, J=7.94, 1.76 Hz, 1 H), 7.63 (d, J=1.76 Hz, 1 H), 7.44 (d, J=8.38 Hz, 1 H), 7.32 (d, J=1.76 Hz, 1 H), 7.15-7.25 (m, 2 H), 6.92 (t, J=75.00 Hz, 1 H), 6.31 (dd, J=9.92, 4.63 Hz, 1 H), 4.07 (d, J=7.06 Hz, 2 H), 3.99 (d, J=7.06 Hz, 2 H), 3.86 (t, J=6.62 Hz, 2 H), 3.77 (dd, J=14.33, 9.92 Hz, 1 H), 3.56 (t, J=6.62 Hz, 2 H), 3.44 (dd, J=14.11, 4.41 Hz, 1 H), 3.09 (s, 3 H), 1.96-2.03 (m, 2 H), 1.34-1.46 (m, 1 H), 1.21-1.33 (m, 1 H), 0.64-0.75 (m, 2 H), 0.54-0.63 (m, 2 H), 0.42-0.51 (m, 2 H), 0.34-0.41 (m, 2 H).

Step 2: Synthesis of 4-((S)-2-(4-(N-(3-((2S,5R)-4-(tert-butoxycarbonyl)-2,5-dimethyl piperazin-1-yl)propyl)methylsulfonamido)-3-(cyclopropylmethoxy)benzoyloxy)-2-(3-(cyclopropylmethoxy)-4-(difluoromethoxy)phenyl)ethyl)-3,5-dichloropyridine 1-oxide (76)

To a solution of (S)-4-(2-(4-(N-(3-bromopropyl)methylsulfonamido)-3-(cyclopropylmethoxy)benzoyloxy)-2-(3-(cyclopropylmethoxy)-4-(difluoromethoxy)phenyl)ethyl)-3,5-dichloropyridine1-oxide (200 mg, 0.21 mmol) in DMF (4 ml) (2R,5S)-tert-butyl 2,5-dimethylpiperazine-1-carboxylate (135 mg, 0.63 mmol) and K₂CO₃ (58 mg, 0.42 mmol) were added, and the mixture was stirred at RT over night. The reaction was diluted with water and extracted with ethyl acetate. The organic phase was washed with water, dried over Na₂SO₄ and evaporated to dryness, to yield 250 mg of crude that was used for the next step without any further purification.

Step 3: Synthesis of 3,5-dichloro-4-((S)-2-(3-(cyclopropylmethoxy)-4-(N-(3-((2S,5R)-2,5-dimethylpiperazin-1-yl)propyl)methylsulfonamido)benzoyloxy)-2-(3-(cyclopropylmethoxy)-4-(difluoromethoxy)phenyl)ethyl)pyridine 1-oxide (74)

4-((S)-2-(4-(N-(3-((2S,5R)-4-(tert-butoxycarbonyl)-2,5-dimethylpiperazin-1-yl)propyl)methylsulfonamido)-3-(cyclopropylmethoxy)benzoyloxy)-2-(3-(cyclopropylmethoxy)-4-(difluoromethoxy)phenyl)ethyl)-3,5-dichloropyridine 1-oxide (250 mg, 0.26 mmol) was dissolved in HCl/Dioxane 4M, and the reaction was stirred at RT for 6 hours. The solvent was evaporated under vacuum and the residue partitioned between NaHCO₃ saturated solution and ethyl acetate. The organic phase was dried over Na₂SO₄ and evaporated under vacuum. The obtained crude was purified by semi-preparative HPLC to yield 150 mg of the final compound (Yield: 68%)

MS/ESI⁺ 841.8 [MH]⁺

¹H NMR (400 MHz, acetone) δ ppm 8.23 (s, 2 H), 7.67 (d, J=7.94 Hz, 1 H), 7.61 (d, J=1.32 Hz, 1 H), 7.40 (d, J=7.94 Hz, 1 H), 7.32 (d, J=1.32 Hz, 1 H), 7.13-7.24 (m, 2 H), 6.91 (t, J=75.00 Hz, 1 H), 6.31 (dd, J=9.70, 4.41 Hz, 1 H), 4.05 (d, J=7.06 Hz, 2 H), 3.98 (d, J=6.62 Hz, 2 H), 3.65-3.87 (m, 4 H), 3.43 (dd, J=14.11, 4.41 Hz, 2 H), 2.93-3.07 (d, 3 H), 2.79 (d, J=12.79 Hz, 2 H), 2.39 (m, 1 H), 2.10 (s, 3 H), 1.72-1.84 (m, 1 H), 1.57 (m, 2 H), 1.32-1.47 (m, 1 H), 1.21-1.31 (m, 1 H), 1.11 (dd, J=6.84, 4.19 Hz, 1 H), 1.01 (d, J=6.62 Hz, 1 H), 0.91 (d, J=5.73 Hz, 3 H), 0.64-0.73 (m, 2 H), 0.55-0.63 (m, 2 H), 0.45 (d, J=4.41 Hz, 2 H), 0.37 (d, J=5.73 Hz, 2 H).

The compounds listed in Table 7 were prepared with analogous synthetic steps and procedures to those described in Example 8, Scheme 8, Step 1-2 by reacting the appropriate precursors (commercially available or synthesized by a person skilled in the art) with suitable reagents. Specific variations in the experimentals or purification methods are indicated in the table.

TABLE 8

| Structure | Compound | NMR characterization | MS/ESI⁺ [MH]⁺ | Salt Name | Nucleophilic agent |
|---|---|---|---|---|---|
| (structure) | 77 | ¹H NMR (400 MHz, DMSO-d₆) δ ppm 8.87 (d, J = 8.82 Hz, 2 H), 8.58 (s, 2 H), 7.93 (d, J = 7.06 Hz, 2 H), 7.56 (m, 2 H), 7.41 (m, 3 H), 7.18-7.28 (m, 2 H), 7.07 (m, 2 H), 6.01-6.26 (m, 1 H), 3.93 (d, J = 7.06 Hz, 4 H), 3.24-3.61 (m, 8 H), 3.08 (s, 3 H), 2.71-2.92 (m, 6 H), 2.51-2.53 (s, 3 H), 1.44-1.88 (m, 2 H), 1.11-1.35 (m, 2 H), 0.50-0.70 (m, 4 H), 0.27-0.45 (m, 4 H). | 827.8 | 1,5-Naphtalen disulphonic acid | (structure) |
| (structure) | 78 | ¹H NMR (400 MHz, acetone) δ ppm 10.97-11.42 (bs, 1 H), 8.29 (s, 2 H), 7.58-7.70 (m, 2 H), 7.44-7.53 (m, 1 H), 7.27-7.36 (m, 1 H), 7.14-7.23 (m, 2 H), 6.91 (t, J = 75.00 Hz, 1 H), 6.26-6.35 (m, 1 H), 3.90-4.08 (m, 12 H), 3.70-3.80 (m, 1 H), 3.24-3.49 (m, 7 H), 3.07 (s, 3 H), 1.34-1.51 (m, 1 H), 1.17-1.33 (m, 1 H), 0.55-0.73 (m, 4 H), 0.33-0.51 (m, 4 H). | 752.3 [M + Na]⁺ | Hydrochloride | (structure) |

TABLE 8-continued

| Structure | Compound | NMR characterization | MS/ESI+ [MH]+ | Salt Name | Nucleophilic agent |
|---|---|---|---|---|---|
| (structure 79) | 79 | ¹H NMR (400 MHz, DMSO-d₆) δ ppm 8.58 (s, 2 H), 7.58 (m, J = 8.16, 1.54 Hz, 1 H), 7.53 (d, J = 1.32 Hz, 1 H), 7.39 (d, J = 7.94 Hz, 1 H), 7.16-7.28 (m, 2 H), 7.03-7.12 (m, 2 H), 6.16 (dd, J = 9.70, 4.41 Hz, 1 H), 4.45-4.65 (bs, 1 H), 3.85-4.07 (m, 4 H), 3.52-3.70 (m, 3 H), 3.24-3.27 (m, 2 H), 3.08 (s, 3 H), 2.58 (d, J = 11.03 Hz, 2 H), 2.27 (t, J = 6.84 Hz, 2 H), 1.93 (t, J = 10.14 Hz, 2 H), 1.64 (d, J = 9.70 Hz, 2 H), 1.45 (t, J = 6.84 Hz, 2 H), 1.11-1.37 (m, 4 H), 0.49-0.66 (m, 4 H), 0.31-0.43 (m, 4 H) | 828.1 | No Salt | 4-hydroxypiperidine |
| (structure 80) | 80 | ¹H NMR (400 MHz, DMSO-d₆) δ ppm 8.57 (s, 2 H), 7.48-7.67 (m, 2 H), 7.40 (d, J = 7.94 Hz, 1 H), 7.12-7.29 (m, 2 H), 7.02-7.12 (m, 2 H), 6.17 (dd, J = 9.48, 4.19 Hz, 1 H), 3.84-4.04 (m, 6 H), 3.52-3.80 (m, 3 H), 3.35-3.42 (m, 1 H), 3.07 (s, 3 H), 2.83-2.94 (m, 2 H), 2.64-2.82 (m, 2 H), 2.29 (t, J = 6.84 Hz, 2 H), 1.47 (qd, J = 6.76, 6.62 Hz, 2 H), 1.13-1.38 (m, 2 H), 0.45-0.65 (m, 4 H), 0.27-0.44 (m, 4 H) | 816.0 | No Salt | thiazolidine |

Example 11

Synthesis of (S)-3,5-dichloro-4-(2-(3-(cyclopropylmethoxy)-4-(difluoromethoxy)phenyl)-2-(2-hydroxy-4-(N-(2-(morpholino-4-ium)ethyl)methylsulfonamido)benzoyloxy)ethyl)pyridine 1-oxide 2,2,2-trifluoroacetate (Compound 81)

Scheme 11

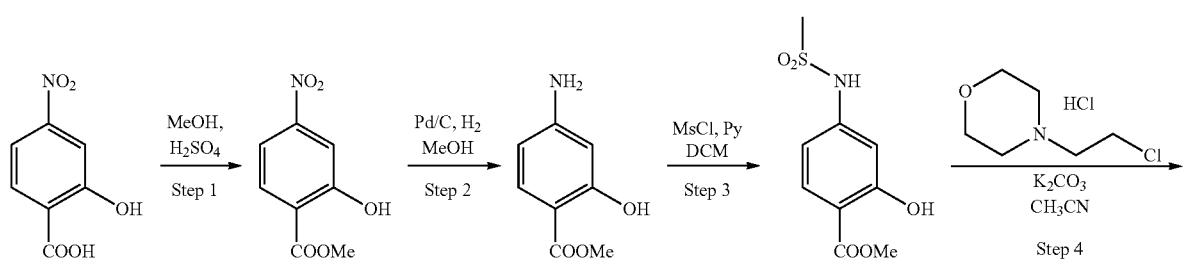

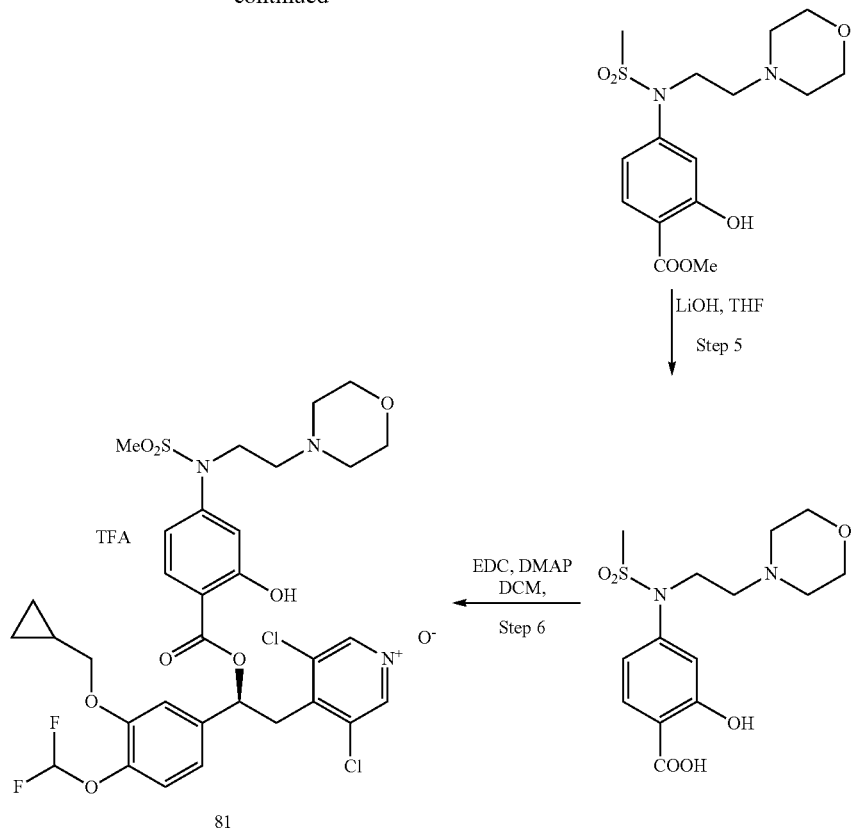

Step 1: Preparation of methyl 2-hydroxy-4-nitrobenzoate (82)

To a solution of 2-hydroxy-4-nitrobenzoic acid (3 g, 16.38 mmol) in MeOH (150 ml) cooled at 0° C. (ice/water bath), concentrated sulfuric acid (15 ml) was added dropwise. The reaction was warmed to room temperature then heated at 80° C. for 16 hours. MeOH was partially removed under vacuum, and water was added to the mixture. The pale yellow precipitate that formed was filtered and washed with plenty of water. Methyl 2-hydroxy-4-nitrobenzoate was obtained, after drying, as a pale yellow solid (3.03 g, 15.37 mmol, 94% yield, UPLC-MS purity: 98%, MS/ESI$^+$ not detectable [MH]$^+$).

Step 2: Preparation of methyl 4-amino-2-hydroxybenzoate (83)

In a 500 ml Parr bottle, methyl 2-hydroxy-4-nitrobenzoate (1.3 g, 6.59 mmol) was added to a suspension of 10% Pd/C (100 mg) in MeOH (40 ml). The reaction was shaken under H$_2$ atmosphere (30 psi) for 1 hour. Catalyst was filtered through a pad of celite and mother liquors were evaporated under vacuum. Methyl 4-amino-2-hydroxybenzoate was obtained as a yellow solid (1.08 g, 6.46 mmol, 98% yield, UPLC-MS purity: 100%, MS/ESI$^+$ 167.9 [MH]$^+$).

Step 3: Preparation of methyl 2-hydroxy-4-(methylsulfonamido)benzoate (84)

To a solution of methyl 4-amino-2-hydroxybenzoate (1.08 g, 6.46 mmol) in DCM (100 ml), pyridine (1.043 ml, 12.92 mmol) and methanesulfonyl chloride (0.600 ml, 7.75 mmol) were added at room temperature. The reaction was stirred at the same temperature for 48 hours. 2N HCl was added to the mixture, the organic phase was separated, dried (sodium sulfate), filtered and evaporated under vacuum. Methyl 2-hydroxy-4-(methylsulfonamido)benzoate was obtained as a pink solid (0.87 g, 3.55 mmol, 54.9% yield, UPLC-MS purity: 95%, MS/ESI$^+$ 245.8, 167.9 [MH]$^+$) and used as such in the following reaction without further purification.

Step 4: Preparation of methyl 2-hydroxy-4-(N-(2-morpholinoethyl)methylsulfonamido)-benzoate (85)

To a solution of methyl 2-hydroxy-4-(methylsulfonamido)benzoate (0.435 g, 1.774 mmol) in CH$_3$CN (50 ml), K$_2$CO$_3$ (0.368 g, 2.66 mmol) was added at room temperature. The reaction was stirred at the same temperature for 10 min, then 4-(2-chloroethyl)morpholine hydrochloride (0.330 g, 1.774 mmol) was added in one portion. The suspension was stirred at 80° C. overnight. CH$_3$CN was removed under vacuum and the remaining crude was portioned between a saturated aqueous solution of NH$_4$Cl and DCM. The organic phase was separated and the aqueous phase was neutralized and extracted with DCM. The combined organics were dried (sodium sulfate), filtered and evaporated under vacuum. Purification by flash chromatography on silica gel (DCM:MeOH 95:5) afforded methyl 2-hydroxy-4-(N-(2-morpholinoethyl)-methylsulfonamido) benzoate as a pale yellow oil (0.21 g, 0.586 mmol, 33.0% yield, UPLC-MS purity: 95%, MS/ESI$^+$ 358.9 [MH]$^+$).

Step 5: Preparation of 4-(2-(N-(4-carboxy-3-hydroxyphenyl)methylsulfonamido)-ethyl)morpholin-4-ium 2,2,2-trifluoroacetate (86)

1M lithium hydroxide (1.172 ml, 1.172 mmol) was added to a solution of methyl 2-hydroxy-4-(N-(2-morpholinoethyl)methylsulfonamido)benzoate (0.21 g, 0.586 mmol) in a THF:MeOH (4:1) mixture (20 ml). The reaction was stirred at 80° C. for 16 hours. Solvents were evaporated under vacuum. Purification by reverse phase preparative HPLC afforded 4-(2-(N-(4-carboxy-3-hydroxyphenyl)methylsulfonamido)-ethyl)morpholin-4-ium 2,2,2-trifluoroacetate as a white solid (0.1 g, 0.218 mmol, 37.2% yield, UPLC-MS purity: 100%, MS/ESI$^+$ 345.0 [MH]$^+$).

Step 6: Preparation of (S)-3,5-dichloro-4-(2-(3-(cyclopropylmethoxy)-4-(difluoromethoxy)phenyl)-2-(2-hydroxy-4-(N-(2-(morpholino-4-ium)ethyl)-methylsulfonamido)benzoyloxy)ethyl)pyridine 1-oxide 2,2,2-trifluoroacetate (81)

To a solution of 4-(2-(N-(4-carboxy-3-hydroxyphenyl)methylsulfonamido)-ethyl)morpholin-4-ium 2,2,2-trifluoroacetate (0.1 g, 0.218 mmol) in DCM (10 ml), Compound 3 (0.092 g, 0.218 mmol), EDC (0.042 g, 0.218 mmol) and DMAP (0.053 g, 0.436 mmol) were added at room temperature. The reaction was stirred at the same temperature overnight. 2N HCl was added to the reaction and the organic phase was separated, dried (sodium sulfate), filtered and evaporated under vacuum. The obtained crude was purified by reverse phase preparative HPLC. (S)-3,5-dichloro-4-(2-(3-(cyclopropylmethoxy)-4-(difluoromethoxy)phenyl)-2-(2-hydroxy-4-(N-(2-(morpholino-4-ium)ethyl)methylsulfonamido)benzoyloxy)ethyl)pyridine 1-oxide 2,2,2-trifluoroacetate was obtained as an off white solid (0.032 g, 0.037 mmol, 17.04% yield, LC-MS purity: 100%, MS/ESI$^+$ 746.22 [MH]$^+$, [$\alpha_D$]=−37.84, c=0.5, MeOH).

The compounds listed in Table 8 were prepared with analogous synthetic steps and procedures to those described in Example 9, Scheme 9 by reacting the appropriate precursors (commercially available or synthesized by a person skilled in the art) with suitable reagents.

TABLE 8

| Structure | Comp. | [α$_D$] NMR characterization And MS/ESI+ [MH]+ | Salt Name | Sulfonyl chloride | Carboxylic acid |
|---|---|---|---|---|---|
| (structure shown) | 87 | −16.65, $^1$H NMR (300 MHz, DMSO-d6) δ ppm 10.34 (s, 1 H) 8.52 (s, 2 H) c = 0.46, 7.79-7.87 (m, 1 H) 7.55 (ddd, 1 H) 7.23 (d, 1 H) 7.20 (d, 1 H) MeOH 7.07 (dd, 1 H) 6.99 (dd, 1 H) 7.07 (t, 1 H) 6.21 (dd, 1 H) 3.95 (dd, 1 H) 3.89 (dd, 1 H) 3.56-3.81 (m, 3 H) 3.49 (t, 4 H) 3.35 (dd, 1 H) 3.03 (s, 3 H) 2.22-2.41 (m, 6 H) 1.10-1.37 (m, 1 H) 0.48-0.70 (m, 2 H) 0.25-0.47 (m, 2 H) [MH]+ 746.16 | No Salt | MeSO$_2$Cl | (4-nitro-2-hydroxybenzoic acid structure) |
| (structure shown) | 88 | −39.63, $^1$H NMR (300 MHz, DMSO-d6) δ ppm 10.84 (br. s., 1 H), 9.65 c = 0.49, (br. s., 1 H), 8.58 (s, 2 H), 8.08 (dd, 1 H), 7.66 (dd, 1 H) 7.26 (d, 1 MeOH H), 7.22 (d, 1 H), 7.11 (dd, 1 H), 7.08 (t, 1 H), 7.07 (t, 1 H) 6.22 (dd, 1 H), 3.94 (d, 2 H), 3.82-3.92 (m, 4 H), 3.69 (dd, 1 H) 3.37 (dd, 1 H), 3.12-3.64 (m, 8 H), 3.09 (s, 3 H), 1.17-1.30 (m, 1 H), 0.46-0.65 (m, 2 H), 0.25-0.45 (m, 2 H) [MH]+ 746.16 | Trifluoroacetate | MeSO$_2$Cl | (3-nitro-2-hydroxybenzoic acid structure) |

TABLE 8-continued

| Structure | Comp. | NMR characterization And MS/ESI+ [MH]+ | [α_D] | Salt Name | Sulfonyl chloride | Carboxylic acid |
|---|---|---|---|---|---|---|
| (structure) | 89 | 1H NMR (400 MHz, DMSO-d6) δ ppm 10.33 (s, 1 H), 8.53 (s, 2 H), 7.82 (d, J = 2.65 Hz, 1 H), 7.54 (dd, J = 8.82, 2.65 Hz, 1 H), 7.17-7.24 (m, 2 H), 7.03-7.11 (m, 2 H), 6.97 (d, J = 8.82 Hz, 1 H), 6.20 (dd, J = 9.26, 4.41 Hz, 1 H), 3.85-3.97 (m, 2 H), 3.68-3.82 (m, 2 H), 3.62 (dd, J = 14.11, 9.26 Hz, 1 H), 3.46 (t, J = 4.41 Hz, 4 H), 3.36 (d, J = 4.41 Hz, 1 H), 3.12 (dd, J = 7.06, 4.85 Hz, 2 H), 2.23-2.39 (m, 6 H), 1.21-1.27 (m, 1 H), 1.08 (d, J = 7.50 Hz, 1 H), 0.51-0.65 (m, 4 H), 0.28-0.41 (m, 4 H) [MH]+ 786.0 | | Formate | (cyclopropylmethyl-SO2Cl) | (4-amino-2-COOMe-phenol) |
| (structure) | 90 | 1H NMR (400 MHz, DMSO-d6) δ ppm 10.41 (s, 1 H), 8.55 (s, 2 H), 7.79-7.94 (m, 1 H), 7.40-7.64 (m, 1 H), 7.22 (m, 2 H), 7.03-7.10 (m, 2 H), 6.93-7.01 (m, 1 H), 6.09-6.27 (m, 1 H), 3.84-3.98 (m, 2 H), 3.67-3.83 (m, 2 H), 3.58-3.66 (m, 1 H), 3.48 (t, J = 4.41 Hz, 4 H), 3.29 (m, 1 H), 2.72-2.86 (m, 1 H), 2.32 (m, 6 H), 1.16-1.33 (m, 1 H), 0.92-1.01 (m, 2 H), 0.73-0.82 (m, 2 H), 0.52-0.61 (m, 2 H), 0.24-0.40 (m, 2 H) [MH]+ 771.9 | | No Salt | (cyclopropyl-SO2Cl) | (4-amino-2-COOMe-phenol) |

Example 10

Preparation of (S)-3,5-dichloro-4-(2-(2-(cyclopropylmethoxy)-4-(N-(2-(morpholino-4-ium)ethyl)methylsulfonamido)benzoyloxy)-2-(3-(cyclopropylmethoxy)-4-(difluoromethoxy)phenyl)ethyl)pyridine 1-oxide (Compound 91)

Scheme 10

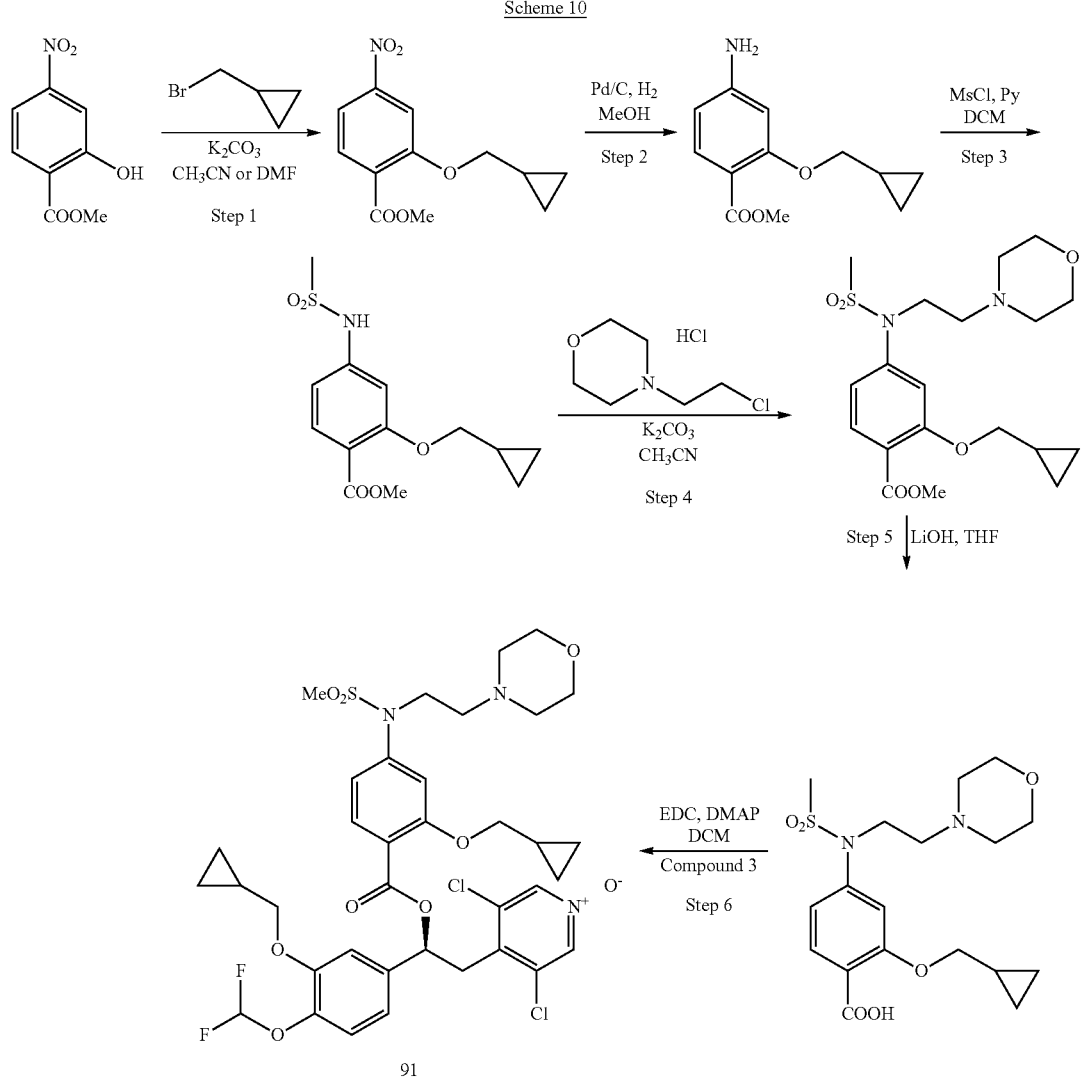

91

Step 1: Preparation of methyl 2-(cyclopropylmethoxy)-4-nitrobenzoate (92)

To a solution of methyl 2-hydroxy-4-nitrobenzoate (0.5 g, 2.54 mmol) in CH$_3$CN (30 ml), K$_2$CO$_3$ (0.701 g, 5.07 mmol) was added at room temperature. The reaction was stirred at the same temperature for 15 minutes then (bromomethyl)cyclopropane (0.372 ml, 3.80 mmol) was added. The reaction was heated to 80° C. and stirred for 48 hours. The solvent was removed under vacuum and the crude was portioned between a saturated solution of NH$_4$Cl and DCM. The organic phase was separated, dried (sodium sulfate), filtered and evaporated under vacuum. Methyl 2-(cyclopropylmethoxy)-4-nitrobenzoate was obtained as a pale yellow solid (0.49 g, 1.950 mmol, 77% yield, MS/ESI$^+$ not detectable [MH]$^+$) and used in the next step without further purification.

Step 2: Preparation of methyl 4-amino-2-(cyclopropylmethoxy)benzoate (93)

In a 250 ml Parr bottle, methyl 2-(cyclopropylmethoxy)-4-nitrobenzoate (0.49 g, 1.950 mmol) was added to a suspension of 10% Pd/C (0.05 g, 2.070 mmol) in MeOH (40 ml). The reaction was shaken under hydrogen atmosphere (30 psi) for 1 hour. Catalyst was removed by filtration and the solution was evaporated under vacuum. Methyl 4-amino-2-(cyclopropylmethoxy)benzoate was obtained as a colorless oil (0.27 g, 1.220 mmol, 62.6% yield, MS/ESI$^+$ 221.9, 243.9 [MH]$^+$) and used in the next step without further purification.

Step 3: Preparation of methyl 2-(cyclopropylmethoxy)-4-(methylsulfonamido)benzoate (94)

To a solution of methyl 4-amino-2-(cyclopropylmethoxy)benzoate (0.27 g, 1.220 mmol) in DCM (20 ml), pyridine (0.197 ml, 2.441 mmol) and methanesulfonyl chloride (0.113 ml, 1.464 mmol) were added at room temperature. The reaction was stirred at the same temperature and under nitrogen for 3 days. 2N HCl was added to the mixture, the organic phase was separated, dried (sodium sulfate), filtered and evaporated to dryness. Methyl 2-(cyclopropylmethoxy)-4-(methylsulfonamido)benzoate was obtained as a pale yellow oil (0.35 g, 1.169 mmol, 96% yield, MS/ESI$^+$ 300.0 [MH]$^+$) and used in the next step without further purification.

Step 4: Preparation of methyl 2-(cyclopropylmethoxy)-4-(N-(2-morpholinoethyl)methylsulfonamido)benzoate (95)

To a solution of methyl 2-(cyclopropylmethoxy)-4-(methylsulfonamido)benzoate (0.35 g, 1.169 mmol) in CH$_3$CN (20 ml), K$_2$CO$_3$ (0.323 g, 2.338 mmol) was added at room temperature, and the suspension thus obtained was stirred at the same temperature for 10 minutes. 4-(2-chloroethyl)morpholine hydrochloride (0.326 g, 1.754 mmol) was added, and the mixture was heated at 80° C. for 20 hours. The solvent was removed under reduced pressure and the crude compound was partitioned between water and DCM. The organic layer was separated, dried (sodium sulfate), filtered and evaporated to dryness. Methyl 2-(cyclopropylmethoxy)-4-(N-(2-morpholinoethyl)methylsulfonamido)benzoate was obtained as a pale yellow oil (0.42 g, 1.018 mmol, 87% yield, MS/ESI$^+$ 412.9 [MH]$^+$) and used in the next step without further purification.

Step 5: Preparation of 4-(2-(N-(4-carboxy-3-(cyclopropylmethoxy)phenyl)-methylsulfonamido)ethyl)morpholin-4-ium 2,2,2-trifluoroacetate (96)

To a solution of methyl 2-(cyclopropylmethoxy)-4-(N-(2-morpholinoethyl)-methylsulfonamido)benzoate (0.42 g, 1.018 mmol) in THF (30 ml), 1M lithium hydroxide (2.036 ml, 2.036 mmol) was added. The reaction was stirred at room temperature overnight. Solvents were removed under vacuum and the remaining crude was purified by reverse phase preparative HPLC. 4-(2-(N-(4-carboxy-3-(cyclopropylmethoxy)phenyl)methylsulfonamido)ethyl)morpholin-4-ium 2,2,2-trifluoroacetate was obtained as a colorless sticky oil (0.19 g, 0.371 mmol, 36.4% yield, MS/ESI$^+$ 398.9 [MH]$^+$).

Step 6: Preparation of (S)-3,5-dichloro-4-(2-(2-(cyclopropylmethoxy)-4-(N-(2-(morpholino-4-ium)ethyl)methylsulfonamido)benzoyloxy)-2-(3-(cyclopropylmethoxy)-4-(difluoromethoxy)phenyl)ethyl)pyridine 1-oxide (91)

To a solution of 4-(2-(N-(4-carboxy-3-(cyclopropylmethoxy)phenyl)-methylsulfonamido)ethyl)morpholin-4-ium 2,2,2-trifluoroacetate (0.19 g, 0.371 mmol) in DCM (20 ml) (S)-3,5-dichloro-4-(2-(3-(cyclopropylmethoxy)-4-(difluoromethoxy)-phenyl)-2-hydroxyethyl)pyridine 1-oxide (0.171 g, 0.408 mmol), EDC (0.071 g, 0.371 mmol) and DMAP (0.091 g, 0.741 mmol) were added at room temperature. The reaction was stirred at the same temperature for 16 hours. 2N HCl was added, the organic phase was separated, dried (sodium sulfate), filtered and evaporated under vacuum. The crude was purified by preparative HPLC. (Method 1) (S)-3,5-dichloro-4-(2-(2-(cyclopropylmethoxy)-4-(N-(2-(morpholino-4-ium)ethyl)methylsulfonamido)-benzoyloxy)-2-(3-(cyclopropylmethoxy)-4-(difluoromethoxy)phenyl)ethyl)pyridine 1-oxide 2,2,2-trifluoroacetate was obtained as an off-white solid (0.04 g, 0.044 mmol, 11.80% yield, MS/ESI$^+$ 800.23 [MH]$^+$, [α$_D$]=−8.8, c=0.5, MeOH).

The compounds listed in Table 9 were prepared with analogous synthetic steps and procedures to those described in Example 10, Scheme 10 by reacting the appropriate precursors (commercially available or synthesized by a person skilled in the art) with suitable reagents.

TABLE 9

| Structure | Comp. | [α$_D$] | NMR characterization | MS/ESI$^+$ [MH]$^+$ | Salt Name | Carboxylic acid |
|---|---|---|---|---|---|---|
| (structure shown) | 97 | −11.44, c = 0.50, MeOH | $^1$H NMR (300 MHz, DMSO-d6) δ ppm 9.65 (br. s., 1 H), 8.55 (s, 2 H), 7.67 (d, 1 H), 7.63 (dd, 1 H), 7.09-7.25 (m, 4 H), 7.06 (t, 1 H), 6.18 (dd, 1 H), 3.79-4.10 (m, 8 H), 3.40-3.76 (m, 6 H), 3.09-3.26 (m, 4 H), 3.04 (s, 3 H), 1.04-1.31 (m, 2 H), 0.49-0.68 (m, 4 H), 0.21-0.46 (m, 4 H) | 800.34 | Trifluoroacetate | (structure: O$_2$N-phenyl with OH and COOH) |

TABLE 9-continued

| Structure | Comp. | [α_D] | NMR characterization | MS/ESI+ [MH]+ | Salt Name | Carboxylic acid |
|---|---|---|---|---|---|---|
| 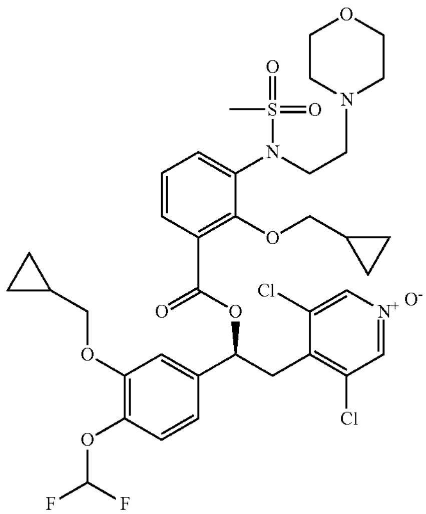 | 98 | −18.20, c = 0.42, DCM | $^1$H NMR (300 MHz, DMSO-d6) δ ppm 9.68 (br. s., 1 H) 8.58 (s, 2 H) 7.71 (dd, 1 H) 7.67 (dd, 1 H) 7.27 (t, 1 H) 7.20-7.24 (m, 2 H) 7.09 (dd, 1 H) 7.08 (t, 1 H) 6.19 (dd, 1 H) 3.86-3.99 (m, 8 H) 3.48-3.70 (m, 5 H) 3.34 (dd, 1 H) 3.25 (s, 3 H) 2.94-3.29 (m, 4 H) 1.14-1.23 (m, 1 H) 0.98-1.14 (m, 1 H) 0.53-0.67 (m, 2 H) 0.40-0.53 (m, 2 H) 0.26-0.40 (m, 2 H) −0.03-0.19 (m, 2 H) | 800.27 | Tri-fluoro-acetate |  |

Example 11

Synthesis (S)-4-(2-(3-(2-(bis(2-hydroxyethyl)amino)ethylsulfonyloxy)-4-methoxybenzoyloxy)-2-(3-(cyclopropylmethoxy)-4-(difluoromethoxy)phenyl)ethyl)-3,5-dichloropyridine 1-oxide (99)

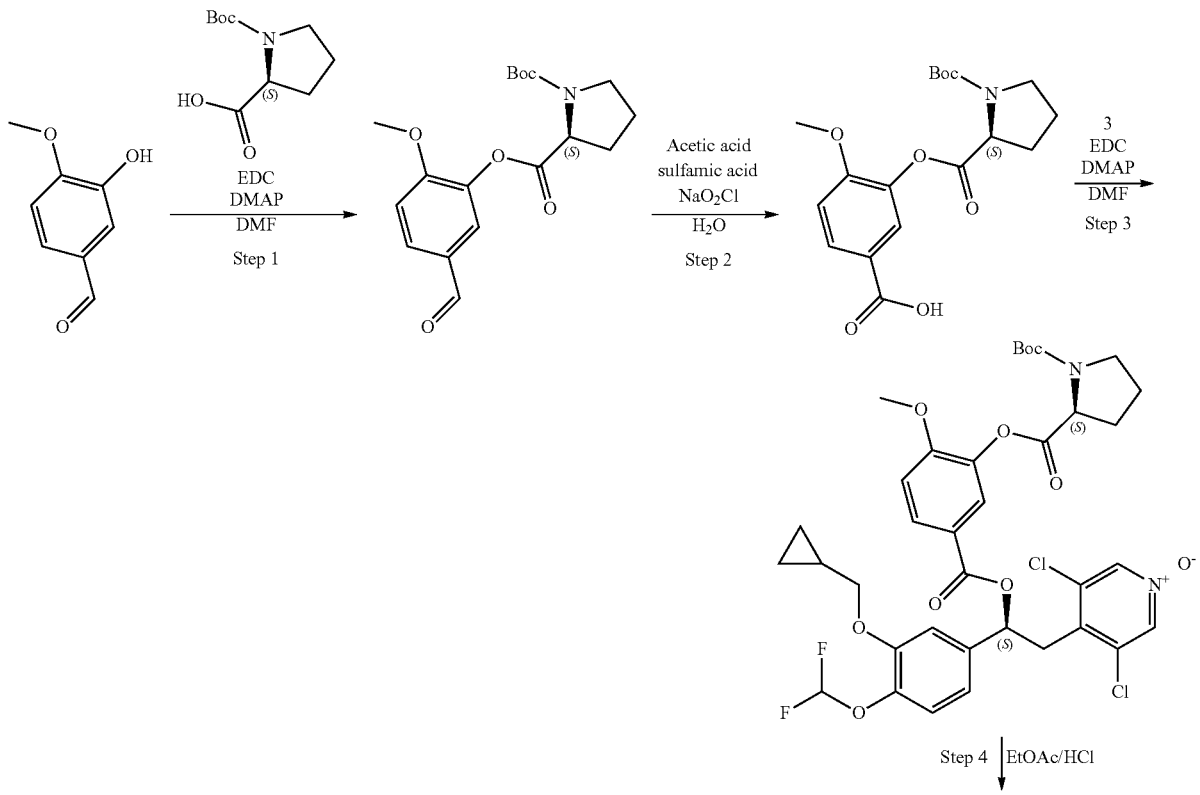

Scheme 11

-continued

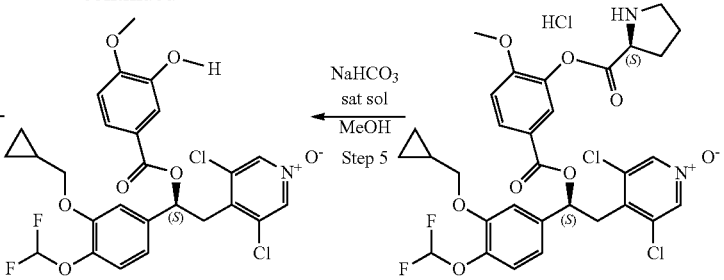

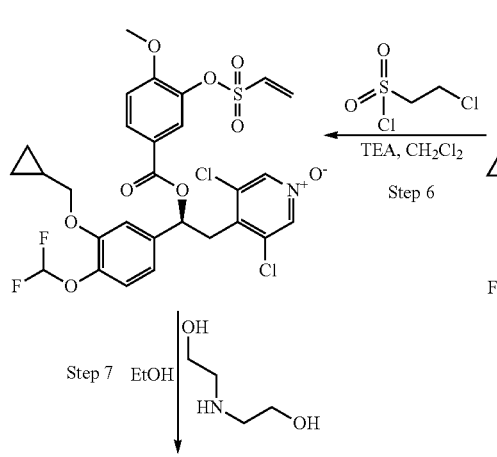

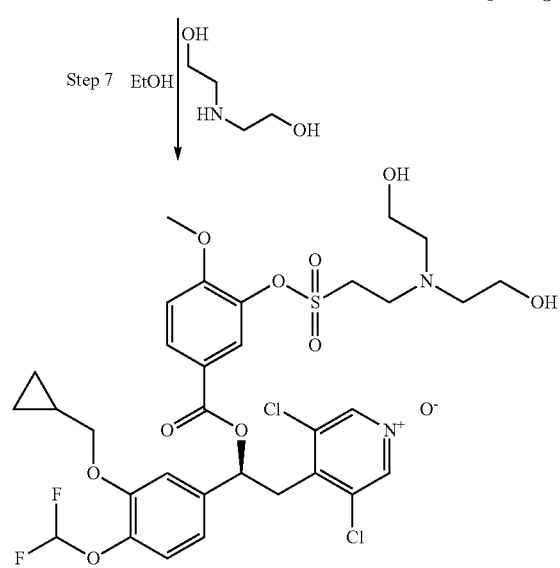

99

Step 1: Synthesis of (S)-1-tert-butyl 2-(5-formyl-2-methoxyphenyl) pyrrolidine-1,2-dicarboxylate (105)

3-hydroxy-4-methoxybenzaldehyde (200 mg, 1.315 mmol) was dissolved in DMF (5 ml) followed by (S)-1-(tert-butoxycarbonyl)pyrrolidine-2-carboxylic acid (290 mg, 1.347 mmol), and DMAP (50 mg, 0.410 mmol). The reaction was sonicated for 30 minutes and stirred for about 2 hours at RT. After that time, the reaction was diluted with $K_2CO_3$ (50 ml) and extracted with diisopropyl ether (50 ml). The organic extract was washed with $K_2CO_3$ conc. sol. (6×50 ml). The solution was dried over $Na_2SO_4$ and the solvent removed under reduced pressure to afford 400 mg of desired product (yield=87%).

Step 2: Synthesis of (S)-3-(1-(tert-butoxycarbonyl) pyrrolidine-2-carbonyloxy)-4-methoxybenzoic acid (104)

(S)-1-tert-butyl 2-(5-formyl-2-methoxyphenyl) pyrrolidine-1,2-dicarboxylate (380 mg, 1.088 mmol) was dissolved in acetic acid and cooled down to 0° C. by ice bath. Sulfamic acid (106 mg, 1.088 mmol) was added followed by dropwise addition of sodium chlorite (180 mg, 1.990 mmol) pre-dissolved in water (0.5 mL). The reaction was stirred at RT overnight, diluted with water (30 mL) and extracted with ethyl acetate (40 mL). Solvent was removed under reduced pressure and the oily residue was triturated with chloroform and hexane (10:90) solvent system leading to a white solid. The solid was filtered and washed with water (100 mL) before being dried in a vacuum oven overnight to give 300 mg of the title compound (yield 75%).

Step 3: Synthesis of 4-((S)-2-(3-((S)-1-(tert-butoxycarbonyl)pyrrolidine-2-carbonyloxy)-4-methoxybenzoyloxy)-2-(3-(cyclopropylmethoxy)-4-(difluoromethoxy)phenyl)ethyl)-3,5-dichloropyridine 1-oxide (103)

Coupling of 3 to (S)-3-(1-(tert-butoxycarbonyl)pyrrolidine-2-carbonyloxy)-4-methoxybenzoic acid, under the same conditions and experimental procedure shown in Example 4, Scheme4, Step 4, gave the corresponding ester derivative in quantitative yield.

Step 4: Synthesis of 3,5-dichloro-4-((S)-2-(3-(cyclopropylmethoxy)-4-(difluoromethoxy)phenyl)-2-(4-methoxy-3-((S)-pyrrolidine-2-carbonyloxy)benzoyloxy)ethyl)pyridine 1-oxide hydrochloride (102)

4-((S)-2-(3-((S)-1-(tert-butoxycarbonyl)pyrrolidine-2-carbonyloxy)-4-methoxybenzoyloxy)-2-(3-(cyclopropylmethoxy)-4-(difluoromethoxy)phenyl)ethyl)-3,5 dichloropyridine 1-oxide (620 mg; 0.808 mmol) was dissolved in HCl/AcOEt 4M (2.0 ml) and stirred for 2 hours at RT. Solvent was removed under reduced pressure to give the crude that was recrystallized from AcOEt:hexane (1:2). The solid was filtered to obtain the title compound (480 mg; yield=89%). MS/ESI$^+$ 667.1 [MH]$^+$.

$^1$H NMR (400 MHz, CHLOROFORM-d) δ ppm 8.29 (s, 2 H), 7.90 (d, J=9.00 Hz, 1 H), 7.73 (m, 1 H), 7.12-7.23 (m, 1 H), 6.93-7.10 (m, 3H), 6.39-6.85 (m, 1 H, CHF$_2$), 6.20 (dd, J=9.78, 3.91 Hz, 1 H), 4.83 (br. s., 1 H), 3.77-3.96 (m, 5 H), 3.53-3.76 (m, 2H), 3.34 (d, J=11.35 Hz, 1 H), 1.80-2.70 (m, 6 H), 1.27 (d, J=4.30 Hz, 1H), 0.58-0.75 (m, 2 H), 0.37 (q, J=5.09 Hz, 2 H).

Step 5: Synthesis of (S)-3,5-dichloro-4-(2-(3-(cyclopropylmethoxy)-4-(difluoromethoxy)-phenyl)-2-(3-hydroxy-4-methoxybenzoyloxy)ethyl)pyridine 1-oxide (101)

3,5-dichloro-4-((S)-2-(3-(cyclopropylmethoxy)-4-(difluoromethoxy)phenyl)-2-(4-methoxy-3-((S)-pyrrolidine-2-carbonyloxy)benzoyloxy)ethyl)pyridine 1-oxide hydrochloride (150.0 mg; 0.2 mmol) was dissolved in MeOH (2.0 ml) followed by addition of NaHCO$_3$ sat. sol. (2.0 ml). The solution was stirred at RT for 5 hours. MeOH was evaporated under vacuum, and the aqueous phase was acidified with HCl 1M (50 ml) and then extracted with AcOEt (50 ml; ×3). The organic extract was dried over Na$_2$SO$_4$ (1.0 g) and the solvent removed under reduced pressure to yield 100.0 mg of desired product as white powder (yield=78.0%).
MS/ESI$^+$ 570.366 [MH]$^+$ Step 6: Synthesis of (S)-3,5-dichloro-4-(2-(3-(cyclopropylmethoxy)-4-(difluoromethoxy)-phenyl)-2-(4-methoxy-3-(vinylsulfonyloxy)benzoyloxy)ethyl) pyridine 1-oxide (100)

(S)-3,5-dichloro-4-(2-(3-(cyclopropylmethoxy)-4-(difluoromethoxy)phenyl)-2-(3-hydroxy-4-methoxybenzoyloxy)ethyl)pyridine 1-oxide (30 mg, 0.05 mmol) was dissolved in DCM (2.5 ml), then TEA (8.4 µl, 0.06 mmol) and 2-chloroethanesulfonyl chloride (6.3 µl, 0.06 mmol) were added, and the mixture was stirred at RT for 30'. The reaction was diluted with DCM and washed with HCl 1N (2×10 ml). The organic phase was dried over Na$_2$SO$_4$ and evaporated under vacuum to yield 30 mg of crude that was used for the next step without any further purification.

Step 7: Synthesis of (S)-4-(2-(3-(2-(bis(2-hydroxyethyl)amino)ethylsulfonyloxy)-4-methoxybenzoyloxy)-2-(3-(cyclopropylmethoxy)-4-(difluoromethoxy)phenyl)ethyl)-3,5-dichloropyridine 1-oxide (99)

(S)-3,5-dichloro-4-(2-(3-(cyclopropylmethoxy)-4-(difluoromethoxy)phenyl)-2-(4-methoxy-3-(vinylsulfonyloxy)benzoyloxy)ethyl)pyridine 1-oxide (30 mg, 0.045 mmol) was dissolved in EtOH (1.5 ml), then diethanolamine (9.5 µl, 0.09 mmol) was added, and the reaction was stirred at RT for 30'. The solvent was evaporated, and the crude was purified by semi-preparative HPLC to yield 20 mg of the final product. (Yield=59%)
MS/ESI$^+$ 765.3 [MH]$^+$, 787.2 [MNa]$^+$
$^1$H NMR (400 MHz, acetone) δ ppm 8.27 (s, 2 H), 7.93-8.07 (m, 2 H), 7.27-7.35 (m, 2 H), 7.18-7.24 (m, 1 H), 7.13-7.18 (m, 1 H), 6.91 (t, J=75.00 Hz, 1 H), 6.31 (dd, J=9.70, 4.41 Hz, 1 H), 4.03 (s, 3 H), 3.98 (dd, J=6.62, 3.97 Hz, 2 H), 3.65-3.82 (m, 3 H), 3.53-3.62 (m, 4 H), 3.43 (dd, J=14.11, 4.41 Hz, 1 H), 3.20-3.29 (m, 2 H), 2.72-2.78 (m, 4H), 1.27 (m, 1 H), 0.60 (d, J=6.62 Hz, 2 H), 0.34-0.42 (m, 2 H).

The compounds listed in Table 10 were prepared with analogous synthetic steps and procedures to those described in Example 11, Scheme 11, Steps 1-3, 5-7 by reacting the appropriate precursors (commercially available or synthesized by a person skilled in the art) with suitable reagents. Specific variations in the experimentals or purification methods are indicated in the table.

TABLE 10

| Structure | Comp. | NMR characterization and MS/ESI+ [MH]+ | Salification | Nucleophilic agent | Carboxylic acid | Alcohol |
|---|---|---|---|---|---|---|
| 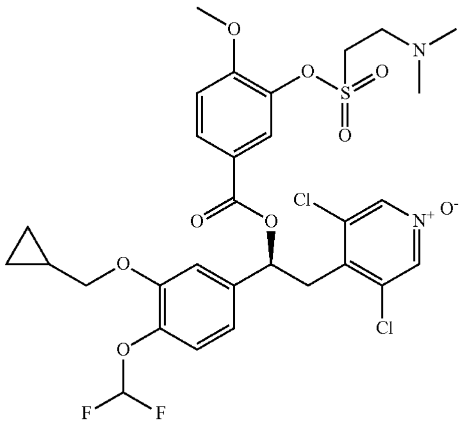 | 106 | 1H NMR (400 MHz, acetone) δ ppm 13.28-13.72 (m, 1 H), 8.28 (s, 2 H), 7.97-8.08 (m, 2 H), 7.27-7.39 (m, 2 H), 7.12-7.25 (m, 2 H), 6.68-6.91-7.11 (t, 1 H, CHF2), 6.31 (dd, J = 9.30, 4.74 Hz, 1 H), 4.24-4.41 (m, 2 H), 4.11 (s, 3 H), 4.00 (dq, J = 6.93, 3.51 Hz, 2 H), 3.65-3.80 (m, 3 H), 3.46 (dd, J = 14.04, 4.56 Hz, 1 H), 1.10-1.34 (m, 1 H), 0.50-0.65 (m, 2 H), 0.38 (q, J = 4.81 Hz, 2 H). [MH]+ 705.2 | Hydrochloride | | Step 1: As carboxylic acid, was used | |
| 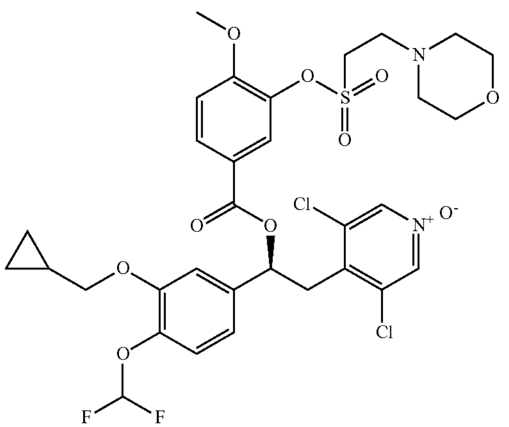 | 107 | 1H NMR (400 MHz, acetone) δ ppm 8.31 (s, 2 H), 7.99-8.10 (m, 2 H), 7.35-7.39 (m, 1 H), 7.26-7.34 (m, 1 H), 7.14-7.25 (m, 2 H), 6.91 (t, J = 75.00 Hz, 1 H), 6.26-6.34 (m, 1 H), 4.33-4.45 (m, 2 H), 3.94-4.20 (m, 9 H), 3.69-3.83 (m, 3 H), 3.56-3.66 (m, 2 H), 3.40 (m, 3 H), 1.24-1.34 (m, 1 H), 0.52-0.67 (m, 2 H), 0.32-0.48 (m, 2 H). [MH]+ 747.2 | Hydrochloride | | Step 1: As carboxylic acid, was used | |

TABLE 10-continued

| Structure | Comp. | NMR characterization and MS/ESI+ [MH]+ | Salification | Nucleophilic agent | Carboxylic acid | Alcohol |
|---|---|---|---|---|---|---|
| [structure with morpholine-ethyl-sulfonyl group, methoxyphenyl benzoate ester, and dichloropyridine N-oxide] | 108 | 1H NMR (400 MHz, acetone) δ ppm 8.51 (s, 2 H), 7.90-8.06 (m, 2 H), 7.30 (dd, J = 5.07, 3.31 Hz, 2 H), 7.13-7.25 (m, 2 H), 6.71-7.11 (t, 1 H, CHF2), 6.38 (dd, J = 9.92, 4.19 Hz, 1 H), 3.91-4.11 (m, 5 H), 3.84 (dd, J = 13.89, 9.92 Hz, 1 H), 3.57-3.70 (m, 6 H), 3.51 (dd, J = 13.67, 4.41 Hz, 1 H), 2.91-3.02 (m, 2 H), 2.47-2.55 (m, 4 H), 1.22-1.38 (m, 1 H), 0.60 (dd, J = 8.16, 1.54 Hz, 2 H), 0.32-0.45 (m, 2 H). [MH]+ 731.2 | No Salt | morpholine (NH) | Step 1: As carboxylic acid, BocN-piperazine-COOH was used | [chiral alcohol with cyclopropylmethoxy-difluoromethoxy phenyl and dichloropyridine] |

Example 12

Synthesis of 4-((S)-2-(3-((S)-2-amino-3-methylbutanoyloxy)-4-methoxybenzoyloxy)-2-(3-(cyclopropylmethoxy)-4-(difluoromethoxy)phenyl)ethyl)-3,5-dichloropyridine 1-oxide hydrochloride (Compound 109)

Scheme 12

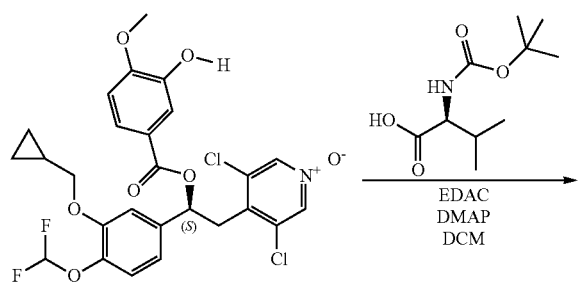

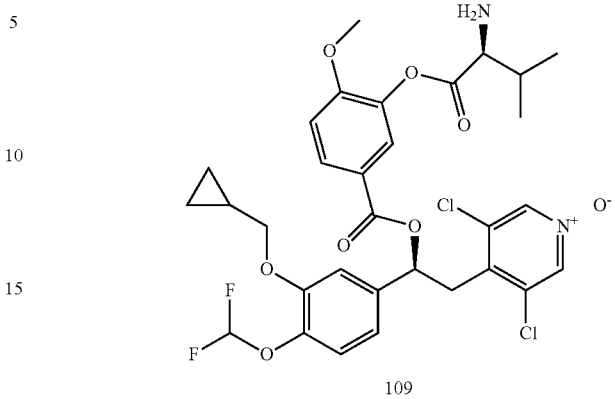

Step 1: Synthesis of 4-((S)-2-(3-((S)-2-(tert-butoxycarbonylamino)-3-methylbutanoyloxy)-4-methoxybenzoyloxy)-2-(3-(cyclopropylmethoxy)-4-(difluoromethoxy)phenyl)ethyl)-3,5-dichloropyridine 1-oxide (110)

Coupling of (S)-3,5-dichloro-4-(2-(3-(cyclopropylmethoxy)-4-(difluoromethoxy)phenyl)-2-(3-hydroxy-4-methoxybenzoyloxy)ethyl)pyridine 1-oxide (20 mg, 0.035 mmol) (comp. 101, obtained as described in Example 11, Scheme 11, Steps 1-5) to (S)-Boc-Valine (20 mg, 0.092 mmol), under the same conditions and experimental procedure shown in Example 10, Scheme 10, Step 6, gave the corresponding ester derivative in quantitative yield. MS/ESI$^+$ 768.2 [MH]$^+$ Step 2: Synthesis of 4-((S)-2-(3-((S)-2-amino-3-methylbutanoyloxy)-4-methoxybenzoyloxy)-2-(3-(cyclopropylmethoxy)-4-(difluoromethoxy)phenyl)ethyl)-3,5-dichloropyridine 1-oxide hydrochloride (109)

4-((S)-2-(3-((S)-2-(tert-butoxycarbonylamino)-3-methylbutanoyloxy)-4-methoxybenzoyloxy)-2-(3-(cyclopropylmethoxy)-4-(difluoromethoxy)phenyl)ethyl)-3,5-dichloropyridine 1-oxide (20 mg, 0.026 mmol) underwent deprotection reaction (as described in Example 11, Scheme 11, Steps 4), to give the desired product (15 mg, 0.021 mmol, yield 81%). MS/ESI$^+$ 669.07 [MH]$^+$.

$^1$H NMR (400 MHz, CHLOROFORM-d) δ ppm 9.22 (br. s., 3 H), 8.40 (s, 2 H), 7.73-7.93 (m, 2 H), 7.15 (d, J=7.83 Hz, 1 H), 7.03-7.10 (m, 1 H), 7.01 (m, 1 H), 6.93 (d, J=8.61 Hz, 1 H), 6.38-6.61-6.83 (t, 1 H, CHF$_2$), 6.20 (dd, J=9.20, 4.50 Hz, 1 H), 4.27 (br. s., 1 H), 3.80-3.98 (m, 5 H), 3.62 (d, J=4.30 Hz, 1 H), 3.33 (d, J=10.17 Hz, 1 H), 2.51-2.75 (m, 1 H), 1.13-1.34 (m, 7 H), 0.53-0.71 (m, 2 H), 0.29-0.45 (m, 2 H).

Example 13
Synthesis of (S)-3,5-dichloro-4-(2-(3-(cyclopropyl-methoxy)-4-(2-(dimethylamino)ethylsulfonyloxy) benzoyloxy)-2-(3-(cyclopropylmethoxy)-4-(difluoromethoxy)phenyl)ethyl)pyridine 1-oxide hydrochloride (111)
Scheme 13
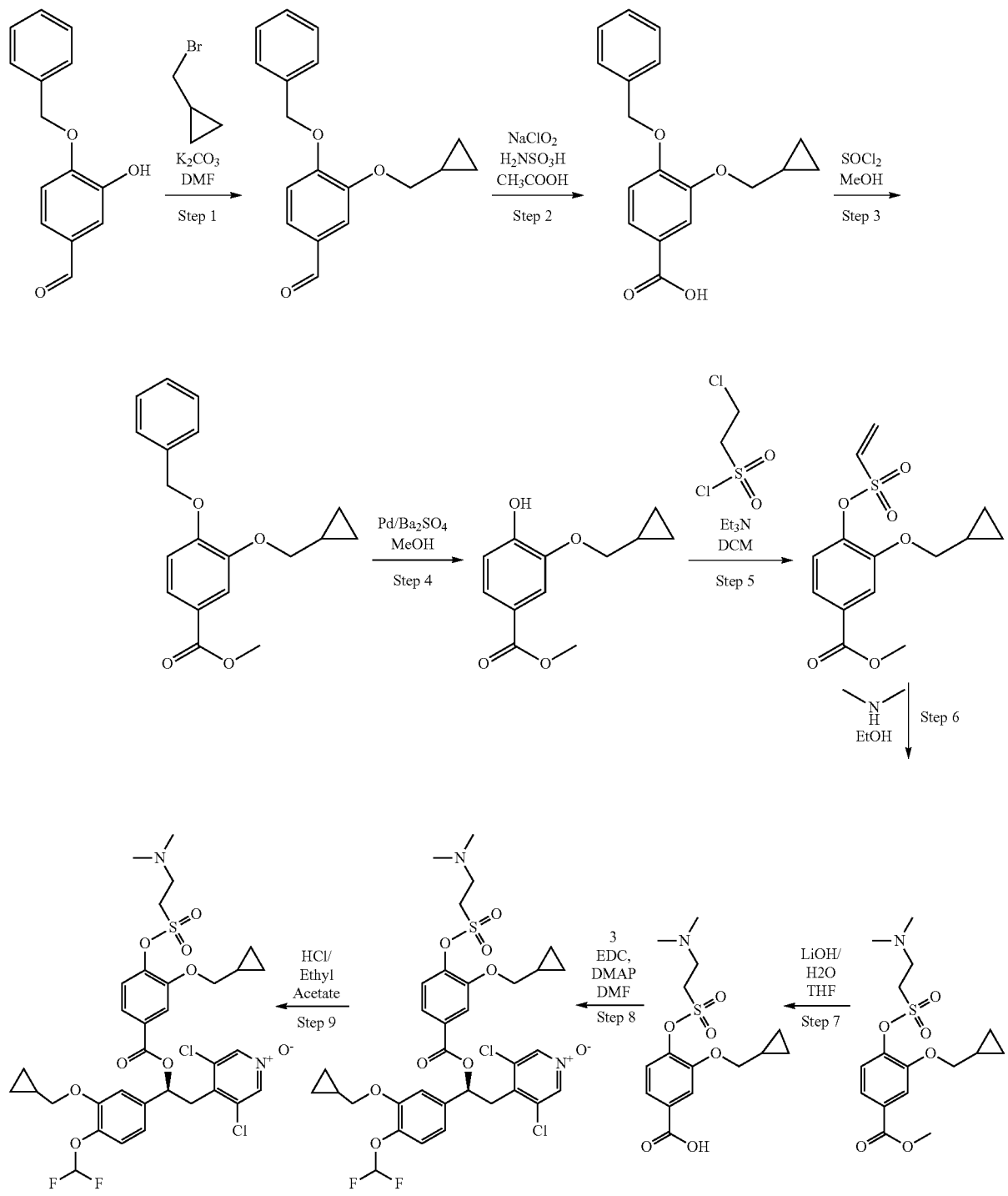
111

Step 1: Synthesis of 4-(benzyloxy)-3-(cyclopropylmethoxy)benzaldehyde (119)

4-(benzyloxy)-3-hydroxybenzaldehyde (640 mg, 2.8 mmol) was dissolved in DMF (5 ml), then $K_2CO_3$ (774 mg, 5.6 mmol) and (bromomethyl)cyclopropane (544 µl, 5.6 mmol) were added, and the mixture was stirred at 90° C. for 2 hours. The reaction was diluted with $Et_2O$ and the organic phase was washed with $NaHCO_3$ sat sol, water and brine, dried over $Na_2SO_4$ and evaporated under vacuum to give 750 mg of the desired product (yield 95%).

Step 2: Synthesis of 4-(benzyloxy)-3-(cyclopropylmethoxy)benzoic acid (118)

4-(benzyloxy)-3-(cyclopropylmethoxy)benzoic acid was obtained from compound 4-(benzyloxy)-3-(cyclopropylmethoxy)benzaldehyde following the procedure described in Example 11, Scheme 11, Step 2.

Step 3: Synthesis of methyl 4-(benzyloxy)-3-(cyclopropylmethoxy)benzoate (117)

4-(benzyloxy)-3-(cyclopropylmethoxy)benzoic acid (300 mg, 1 mmol) was dissolved in MeOH (6 ml), then thionyl chloride (109 µl, 1.5 mmol) was added, and the mixture was stirred at 70° C. for 2 hours. The solvent was removed, and the crude product was triturated in Petroleum Ether and filtered to give 200 mg of the desired product (Yield 64%).

Step 4: Synthesis of methyl 3-(cyclopropylmethoxy)-4-hydroxybenzoate (116)

Methyl 4-(benzyloxy)-3-(cyclopropylmethoxy)benzoate (200 mg, 0.64 mmol) was dissolved in MeOH, then $Pd/Ba_2SO_4$ 5% (136 mg, 0.064 mmol) was added, and the mixture was shaken on a PARR apparatus at 35 psi of hydrogen for 1 hour. The catalyst was filtered on a diatomaceous earth pad, and the solvent was evaporated under vacuum to give 130 mg of the desired product (Yield 91%).

Step 5: Synthesis of methyl 3-(cyclopropylmethoxy)-4-(vinylsulfonyloxy)benzoate (115)

Methyl 3-(cyclopropylmethoxy)-4-(vinylsulfonyloxy)benzoate was obtained from methyl 3-(cyclopropylmethoxy)-4-hydroxybenzoate following the procedure described in Example 11, Scheme 11, Step 6.

Step 6: Synthesis of methyl 3-(cyclopropylmethoxy)-4-(2-(dimethylamino)-ethylsulfonyloxy)benzoate (114)

Methyl 3-(cyclopropylmethoxy)-4-(2-(dimethylamino) ethylsulfonyloxy)benzoate was obtained from methyl 3-(cyclopropylmethoxy)-4-(vinylsulfonyloxy)benzoate following the procedure described in Example 11 Scheme 11, Step 7 using diethylamine instead of diethanolamine.

Step 7: Synthesis of 3-(cyclopropylmethoxy)-4-(2-(dimethylamino)ethylsulfonyloxy)-benzoic acid (113)

Methyl 3-(cyclopropylmethoxy)-4-(2-(dimethylamino) ethylsulfonyloxy)benzoate (190 mg, 0.53 mmol) was dissolved in THF (3 ml), then LiOH 1N (2 ml) was added, and the mixture was stirred at RT for 2 days. The reaction mixture was acidified to pH:7 by addition of HCl 1N and extracted with ethyl acetate. The organic phase was dried over $Na_2SO_4$ and evaporated under vacuum. The crude product was purified by semi-preparative HPLC to give 47 mg of the final product (Yield: 26%).

Step 8: Synthesis of (S)-3,5-dichloro-4-(2-(3-(cyclopropylmethoxy)-4-(2-(dimethylamino)ethylsulfonyloxy)benzoyloxy)-2-(3-(cyclopropylmethoxy)-4-(difluoromethoxy)phenyl)ethyl)pyridine 1-oxide (112)

The title compound was obtained from 3-(cyclopropylmethoxy)-4-(2-(dimethylamino)ethylsulfonyloxy)benzoic acid following the procedure described in Example 2, Step 1.

Step 9: Synthesis of (S)-3,5-dichloro-4-(2-(3-(cyclopropylmethoxy)-4-(2-(dimethylamino)ethylsulfonyloxy)benzoyloxy)-2-(3-(cyclopropylmethoxy)-4-(difluoromethoxy)phenyl)ethyl)pyridine 1-oxide hydrochloride (111)

(S)-3,5-dichloro-4-(2-(3-(cyclopropylmethoxy)-4-(2-(dimethylamino)-ethylsulfonyloxy)benzoyloxy)-2-(3-(cyclopropylmethoxy)-4-(difluoromethoxy)-phenyl)ethyl)pyridine 1-oxide (10 mg, 0.013 mmol) was dissolved in HCl/ethyl acetate solution (500 µl) and kept at RT for 2 hours then the solvent was removed. The crude product was dried in a vacuum oven, to give 10 mg of the final product.

MS/ESI$^+$ 745.2 [MH]$^+$ $^1$H NMR (400 MHz, acetone) δ ppm 13.29-13.80 (bs, 1 H), 8.29 (s, 2 H), 7.67-7.77 (m, 2 H), 7.57 (d, J=8.38 Hz, 1 H), 7.32 (d, J=1.76 Hz, 1 H), 7.13-7.25 (m, 2 H), 6.61 (t, 1H, $CHF_2$), 6.32 (dd, J=9.70, 4.41 Hz, 1 H), 4.26-4.42 (m, 2 H), 4.11 (d, J=7.06 Hz, 2 H), 3.99 (d, J=6.62 Hz, 2 H), 3.76 (dd, J=9.04, 5.07 Hz, 3 H), 3.44 (dd, J=14.11, 4.41 Hz, 1 H), 2.05-2.10 (m, 6 H), 1.39-1.53 (m, 1 H), 1.22-1.34 (m, 1 H), 0.63-0.73 (m, 2 H), 0.55-0.63 (m, 2 H), 0.44-0.52 (m, 2 H), 0.34-0.41 (m, 2 H).

The compound in Table 11 was prepared with analogous synthetic steps and procedures to that described in Example 13, Scheme 13, Steps 5-8 by reacting the appropriate precursors (commercially available or synthesized by a person skilled in the art) with suitable reagents. Specific variations in the experimentals or purification methods are indicated in the table.

TABLE 11

| Structure | Compound | Salt Name | NMR characterization and MS/ESI+ [MH]+ | Carboxylic acid | Synthetic Procedure |
|---|---|---|---|---|---|
| 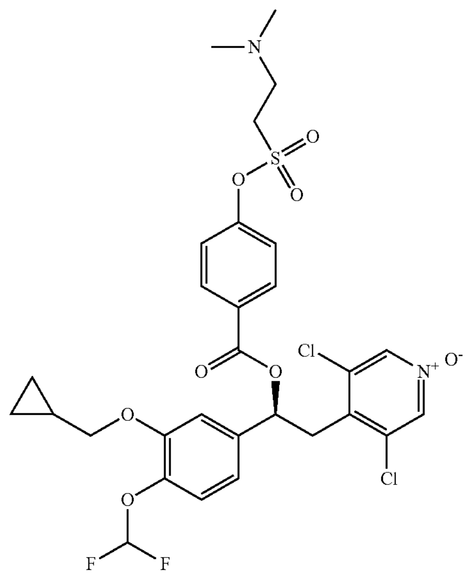 | 120 | Formate | 1H NMR (400 MHz, CHLOROFORM-d) δ ppm 8.16 (s, 2 H), 8.08 (d, J = 8.51 Hz, 2 H), 7.37 (d, J = 8.51 Hz, 2 H), 7.19 (d, J = 7.92 Hz, 1 H), 6.98-7.10 (m, 2 H), 6.63 (t, J = 75.00 Hz, 1 H), 6.27 (dd, J = 9.98, 4.11 Hz, 1 H), 3.90 (d, J = 6.75 Hz, 2 H), 3.70 (dd, J = 14.23, 10.12 Hz, 1 H), 3.41-3.51 (m, 2 H), 3.33 (dd, J = 14.23, 4.26 Hz, 1 H), 2.86-3.03 (m, 2 H), 2.31 (s, 6 H), 1.17-1.38 (m, 1 H), 0.60-0.72 (m, 2 H), 0.32-0.44 (m, 2 H). [MH]+ 675.5 |  | Step 7: Instead of ester hydrolysis, debenzylation with Pd/C 5% in MeOH was performed |

Example 14

Synthesis of 4-((S)-2-(4-((1s,4R)-4-aminocyclohexylcarbamoyl)-3-(cyclopropylmethoxy)benzoyloxy)-2-(3-(cyclopropylmethoxy)-4-(difluoromethoxy)phenyl)ethyl)-3,5-dichloropyridine 1-oxide hydrochloride (121)

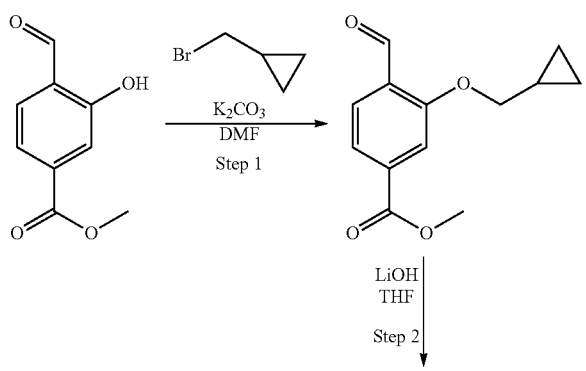

Scheme 14

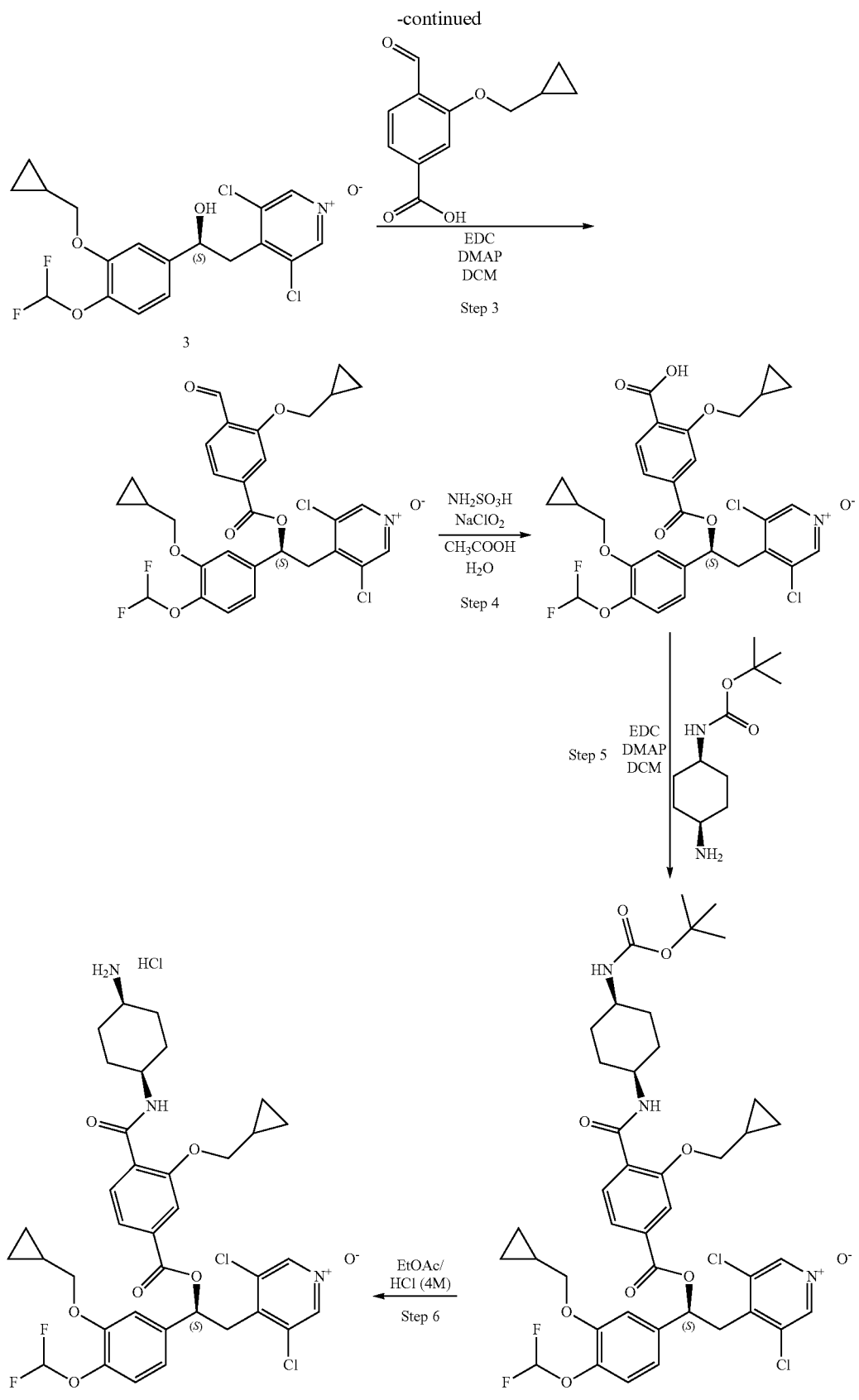

Step 1: Synthesis of methyl 3-(cyclopropylmethoxy)-4-formylbenzoate (125)

To a solution of methyl 4-formyl-3-hydroxybenzoate (50 mg, mmol) in DMF (1 ml), cyclopropylbromide (0.5 ml, mmol) and potassium carbonate (50 mg, mmol) were added at RT. The reaction was stirred at 60 degrees for 3 hours, then poured onto water and the aqueous phase extracted with AcOEt twice. The combined organic phases were dried over $Na_2SO_4$, and the solvent was removed under reduced pressure to yield 50 mg of the title compound (mmol, yield %), which was used for the next step without further purification. MS/ESI+ 180.04 [MH]+

Step 2: Synthesis of 3(cyclopropylmethoxy)-4-formylbenzoic acid (126)

To a solution of methyl 3-(cyclopropylmethoxy)-4-formylbenzoate (50 mg, mmol) in THF (2 ml) LiOH 1M (1 ml) was added and the mixture stirred at RT overnight. HCl 1M was added to precipitate the product that was filtered to give the desired compound (50 mg, mmol), that was used for the next step without further purification. MS/ESI+ 234.09 [MH]+

Step 3: Synthesis of (S)-3,5-dichloro-4-(2-(3-(cyclopropylmethoxy)-4-(difluoromethoxy)-phenyl)-2-(3-(cyclopropylmethoxy)-4-formylbenzoyloxy)ethyl) pyridine 1-oxide (124)

Compound 3 (200.0 mg, 0.48 mmol) and 3(cyclopropylmethoxy)-4-formylbenzoic acid (200.0 mg, 0.9 mmol) were dissolved in DCM (20 ml) after that DMAP (100.0 mg, 0.82 mmol) and EDC-HCl (200 mg, 1.04 mmol) were added. The reaction was stirred at RT for 3 hours and then it was diluted with water (50 ml) and extracted with DCM (50 ml). The organic phase was washed with HCl 1N and with $K_2CO_3$ sat. sol. The resulting organic extract was dried over $Na_2SO_4$, and the solvent was removed under reduced pressure to yield 200 mg of the title compound (yield=67.5%) as yellow oil. MS/ESI+ 622.44 [MH]+

$^1$H NMR (400 MHz, CHLOROFORM-d) δ ppm 10.59 (s, 1 H), 8.15 (s, 2 H), 7.84-7.96 (m, 1 H), 7.65-7.73 (m, 1 H), 7.55-7.59 (m, 1 H), 7.15-7.23 (m, 1 H), 6.96-7.12 (m, 2 H), 6.41-6.63-6.85 (t, 1 H, $CHF_2$), 6.20-6.34 (m, 1 H), 3.85-4.12 (m, 4 H), 3.59-3.76 (m, 1 H), 3.26-3.40 (m, 1 H), 1.21-1.41 (m, 2 H), 0.52-0.77 (m, 4 H), 0.29-0.46 (m, 4 H).

Step 4: Synthesis of (S)-4-(2-(4-carboxy-3-(cyclopropylmethoxy)benzoyloxy)-2-(3-(cyclopropylmethoxy)-4-(difluoromethoxy)phenyl)ethyl)-3,5-dichloropyridine 1-oxide (123)

(S)-3,5-dichloro-4-(2-(3-(cyclopropylmethoxy)-4-(difluoromethoxy)phenyl)-2-(3-(cyclopropylmethoxy)-4-formylbenzoyloxy)ethyl) pyridine 1-oxide (200.0 mg, 0.32 mmol) was dissolved in acetic acid (4 mL) and cooled down to 0° C. (ice/water bath). Sulfamic acid (46.8 mg, 0.48 mmol) was added followed by drop-wise addition of sodium chlorite (34.9 mg, 0.386 mmol) pre-dissolved in water (0.5 mL). The reaction was stirred at RT for 3 hours. Water was added and the aqueous phase was extracted with ethyl acetate. Solvent was removed under reduced pressure and the oil residue was recrystallized from 2-propanol/heptane (10:90) solvent system at −20° C. The precipitate was filtered, dried in a vacuum oven at 40° C. to give the title compound as white solid (67 mg; yield 32.7%). MS/ESI+ 638.44 [MH]+

Step 5: Synthesis of (S)-4-(2-(4-(4-(tert-butoxycarbonylamino) cyclohexylcarbamoyl)-3-(cyclopropylmethoxy)benzoyloxy)-2-(3-(cyclopropylmethoxy)-4-(difluoromethoxy) phenyl) ethyl)-3,5-dichloropyridine 1-oxide (122)

(S)-4-(2-(4-carboxy-3-(cyclopropylmethoxy)benzoyloxy)-2-(3-(cyclopropylmethoxy)-4-(difluoromethoxy)phenyl)ethyl)-3,5-dichloropyridine 1-oxide (20 mg; 0. 0.031 mmol) was dissolved in DMF (1.0 ml), and (S)-1-(tert-butoxycarbonyl)pyrrolidine-2-carboxylic acid (20.0 mg, 0.093 mmol) was added followed by EDC (20.0 mg, 0.104 mmol) and DMAP (10.0 mg, 0.082 mmol). The solution was stirred at RT for 6 hours. After that time, the reaction was diluted with 15 ml of HCl 1M and extracted with AcOEt (15 ml). The organic phase was extracted with HCl 1M (15 ml; ×3) and with $K_2CO_3$ conc. (3×15 ml). The resulting organic extract was dried over $Na_2SO_4$ and the solvent removed under reduced pressure. The crude oil residue was purified by preparative HPLC to obtain 20.0 mg of the title compound 76% (yield).

Step 6: Synthesis of 4-((S)-2-(4-((1s,4R)-4-aminocyclohexylcarbamoyl)-3-(cyclopropylmethoxy)benzoyloxy)-2-(3-(cyclopropylmethoxy)-4-(difluoromethoxy) phenyl)ethyl)-3,5-dichloropyridine 1-oxide hydrochloride (121)

(S)-4-(2-(4-(4-(tert-butoxycarbonylamino) cyclohexylcarbamoyl)-3-(cyclopropylmethoxy)benzoyloxy-2-(3-(cyclopropylmethoxy)-4-(difluoromethoxy) phenyl) ethyl)-3,5-dichloropyridine 1-oxide (20 mg; 0.024 mmol) was dissolved in HCl/AcOEt 4M (0.3 ml) and stirred for 30 minutes at RT. After that time HCl 1M (5 ml) was added and the reaction mixture was extracted with AcOEt (5 ml). The resulting organic extract was dried over $Na_2SO_4$ and the solvent removed under reduced pressure to yield the desired product (15 mg; yield 85%). MS/ESI+ 733.88 [MH]+

$^1$H NMR (400 MHz, acetone) δ ppm 8.28 (s, 2 H), 8.12-8.22 (m, 1 H), 7.65-7.78 (m, 2H), 7.29-7.39 (m, 1 H), 7.15-7.26 (m, 2 H), 6.90 (t, J=75.00 Hz, 1 H), 6.30-6.41 (m, 1 H), 4.11-4.36 (m, 3 H), 3.92-4.06 (m, 2 H), 3.65-3.83 (m, 1 H), 3.38-3.51 (m, 1 H), 2.16-2.28 (m, 3 H), 1.63-1.99 (m, 6 H), 1.17-1.39 (m, 2 H), 0.50-0.78 (m, 6 H), 0.27-0.43 (m, 2 H).

The compounds listed in Table 12 were prepared with analogous synthetic steps and procedures to that described in Example 14 Scheme 14, Steps 1-5 by reacting the appropriate precursors (commercially available or synthesized by a person skilled in the art) with suitable reagents. Salification step (Step 6) was performed only when salification is reported.

TABLE 12

| Structure | Compound | Salt Name | MS/ESI+ [MH]+ | NMR characterization | Amine/Alcohol | Carboxylic acid |
|---|---|---|---|---|---|---|
| 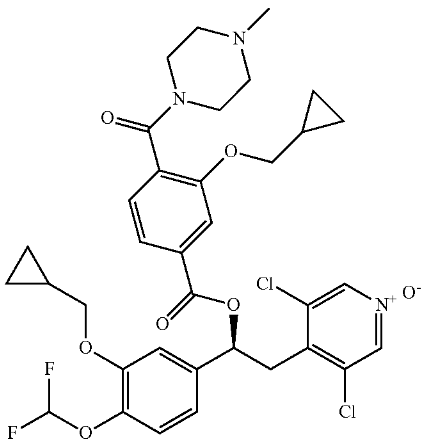 | 127 | Hydrochloride | 719.81 | 1H NMR (400 MHz, DMSO-d6) δ ppm 10.45-10.72 (bs, 1 H), 8.57 (s, 2 H), 7.65 (d, J = 6.62 Hz, 1 H), 7.53 (m, 1 H), 7.39 (m, 1 H), 7.15-7.30 (m, 2 H), 7.02-7.13 (m, 2 H), 6.19 (d, J = 5.29 Hz, 1 H), 3.82-4.11 (m, 4 H), 3.40-3.60 (m, 5H), 3.14-3.35 (m, 5 H), 2.75 (s, 3 H), 1.21 (m, 2 H), 0.48-0.72 (m, 4 H), 0.35 (m, 4 H) | | |
| 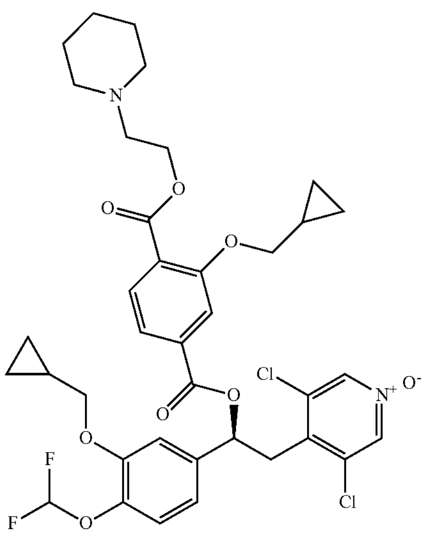 | 128 | Hydrochloride | 748.88 | 1H NMR (400 MHz, acetone) δ ppm 12.87-13.18 (m, 1 H), 8.27 (s, 2 H), 7.53-7.90 (m, 3 H), 7.15-7.50 (m, 3 H), 6.91 (t, J = 75.00 Hz, 1 H), 6.25-6.43 (m, 1 H), 4.32-4.53 (m, 2 H), 3.89-4.23 (m, 4 H), 3.70-3.83 (m, 1 H), 3.36-3.59 (m, 3 H), 3.05-3.26 (m, 2 H), 2.81-2.97 (m, 2 H), 2.33-2.54 (m, 2 H), 1.74-1.87 (m, 2 H), 1.54-1.71 (m, 2 H), 1.30 (m, 2 H), 0.54-0.73 (m, 4 H), 0.32-0.50 (m, 4 H). | | |

TABLE 12-continued

| Structure | Compound | Salt Name | MS/ESI+ [MH]+ | NMR characterization | Amine/Alcohol | Carboxylic acid |
|---|---|---|---|---|---|---|
| 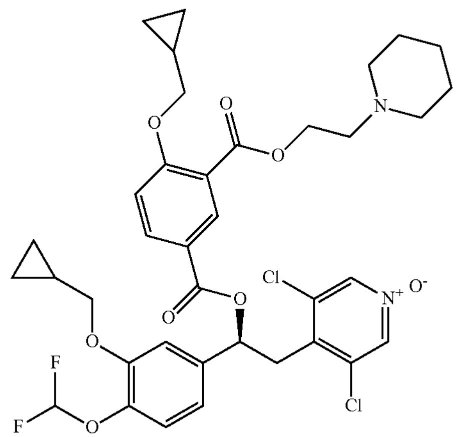 | 129 | No Salt | 749.1 | 1H NMR (400 MHz, DMSO-d6) δ ppm 8.55 (s, 2 H), 8.18-8.32 (m, 1 H), 7.99-8.15 (m, 1 H), 7.14-7.33 (m, 3 H), 7.03-7.13 (m, 2 H), 6.10-6.25 (m, 1 H), 4.26-4.48 (m, 2 H), 3.83-4.10 (m, 4 H), 3.51-3.69 (m, 1 H), 3.30-3.45 (m, 1 H), 2.56-2.84 (m, 6 H), 1.30-1.67 (m, 6 H), 1.15-1.30 (m, 2 H), 0.56 (m, 4 H), 0.36 (m, 4 H) | | |
| 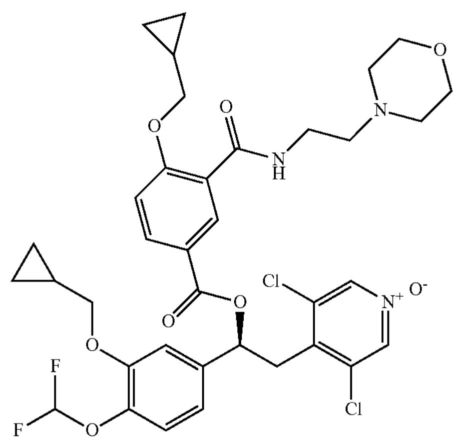 | 130 | No Salt | 750.61 | 1H NMR (400 MHz, DMSO-d6) δ ppm 8.54 (s, 2 H), 8.44 (s, 1 H), 8.27 (m, 1 H), 8.03 (d, J = 7.94 Hz, 1 H), 7.14-7.32 (m, 3 H), 7.00-7.12 (m, 2 H), 6.12-6.24 (m, 1 H), 4.10 (d, J = 7.06 Hz, 2 H), 3.92 (d, J = 4.41 Hz, 2 H), 3.50-3.68 (m, 5 H), 3.44 (d, J = 5.73 Hz, 3 H), 2.45 (m, 2 H), 2.41 (m, 4 H), 1.29-1.46 (m, 1 H), 1.10-1.27 (m, 1 H), 0.58 (dd, J = 17.20, 7.50 Hz, 4 H), 0.25-0.47 (m, 4 H) | | |

TABLE 12-continued
| Structure | Compound | Salt Name | MS/ESI+ [MH]+ | NMR characterization | Amine/Alcohol | Carboxylic acid |
|---|---|---|---|---|---|---|
| 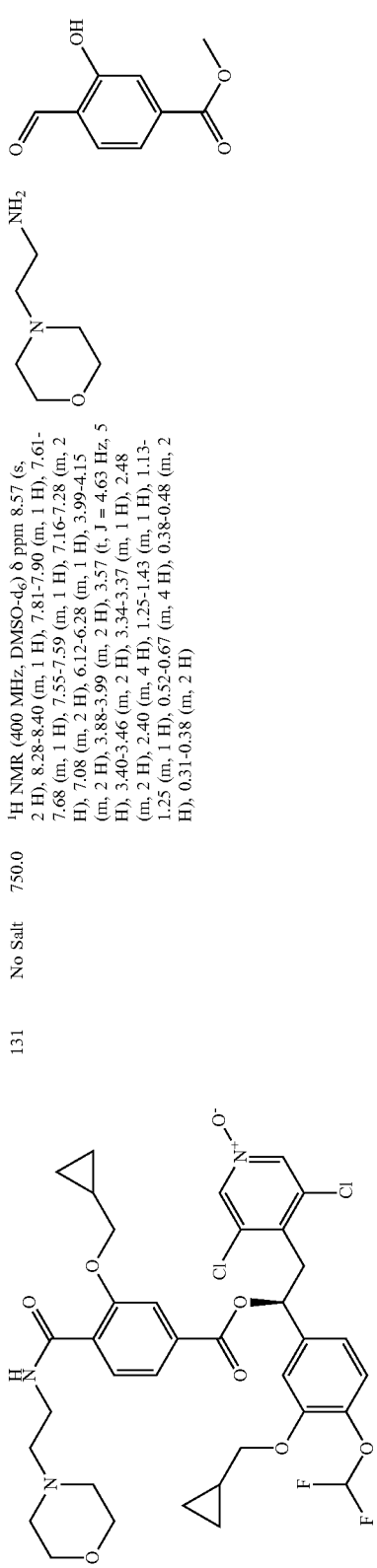 | 131 | No Salt | 750.0 | 1H NMR (400 MHz, DMSO-d6) δ ppm 8.57 (s, 2 H), 8.28-8.40 (m, 1 H), 7.81-7.90 (m, 1 H), 7.61-7.68 (m, 1 H), 7.55-7.59 (m, 1 H), 7.16-7.28 (m, 2 H), 7.08 (m, 2 H), 6.12-6.28 (m, 1 H), 3.99-4.15 (m, 2 H), 3.88-3.99 (m, 2 H), 3.57 (t, J = 4.63 Hz, 5 H), 3.40-3.46 (m, 2 H), 3.34-3.37 (m, 1 H), 2.48 (m, 2 H), 2.40 (m, 4 H), 1.25-1.43 (m, 1 H), 1.13-1.25 (m, 1 H), 0.52-0.67 (m, 4 H), 0.38-0.48 (m, 2 H), 0.31-0.38 (m, 2 H) | 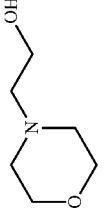 |  |
| 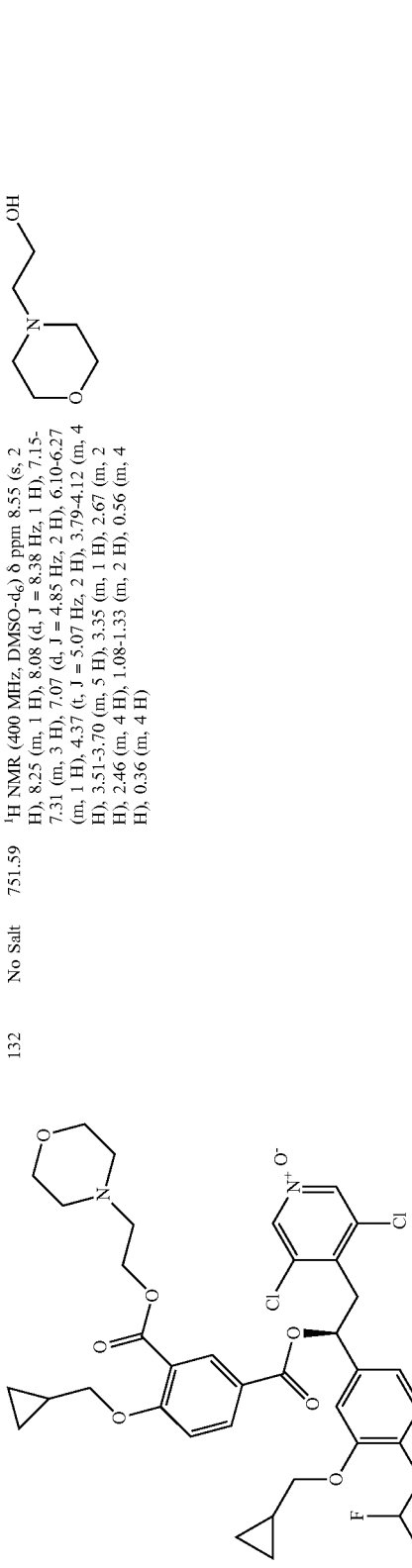 | 132 | No Salt | 751.59 | 1H NMR (400 MHz, DMSO-d6) δ ppm 8.55 (s, 2 H), 8.25 (m, 1 H), 8.08 (d, J = 8.38 Hz, 1 H), 7.15-7.31 (m, 3 H), 7.07 (d, J = 4.85 Hz, 2 H), 6.10-6.27 (m, 1 H), 4.37 (t, J = 5.07 Hz, 2 H), 3.79-4.12 (m, 4 H), 3.51-3.70 (m, 5 H), 3.35 (m, 1 H), 2.67 (m, 2 H), 2.46 (m, 4 H), 1.08-1.33 (m, 2 H), 0.56 (m, 4 H), 0.36 (m, 4 H) | 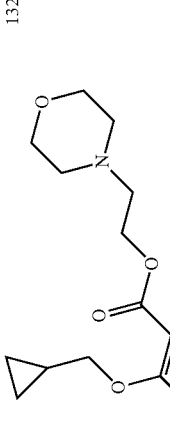 | 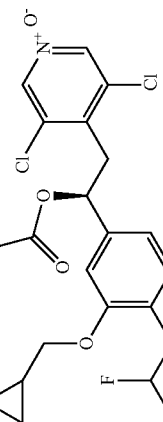 |

Example 15

Synthesis of (S)-3,5-dichloro-4-(2-(3-(cyclopropylmethoxy)-4-(difluoromethoxy)phenyl)-2-(4-methoxy-3-(N-(2-morpholinoethyl)sulfamoyl)benzoyloxy)ethyl)pyridine 1-oxide (133)

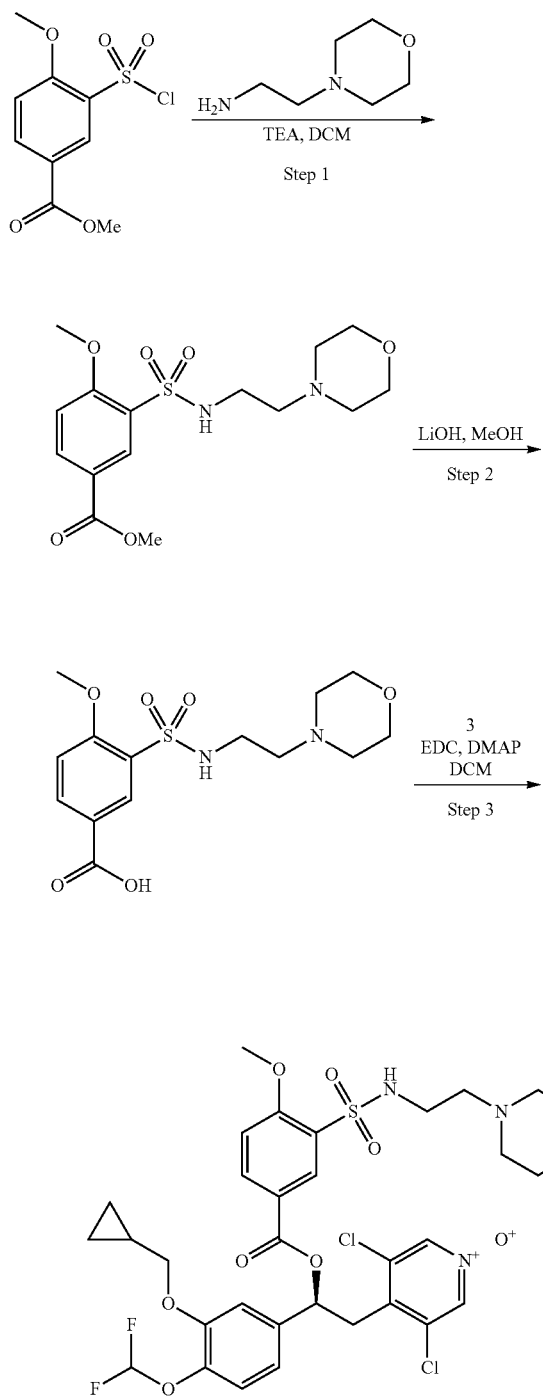

Step 1: Synthesis of methyl 4-methoxy-3-(N-(2-morpholinoethyl)sulfamoyl)benzoate (134)

To a stirred solution of methyl 3-(chlorosulfonyl)-4-methoxybenzoate (400 mg, 1.511 mmol) and TEA (0.421 ml, 3.02 mmol) in DCM (7 ml), 2-morpholinoethanamine (236 mg, 1.813 mmol) was added portionwise. The mixture was stirred at RT for 2 hours. The reaction mixture was diluted with DCM, washed with 0.5 M HCl, brine, dried over $Na_2SO_4$ and evaporated under reduced pressure. The desired product was obtained as a solid (540 mg, 100% yield) and was used in the following reaction without further purification.

MS/ESI$^+$ 359 [MH]$^+$

Step 2: Synthesis of 4-methoxy-3-(N-(2-morpholinoethyl)sulfamoyl)benzoic acid (135)

To stirred solution of methyl 4-methoxy-3-(N-(2-morpholinoethyl)sulfamoyl)-benzoate (540 mg, 1.507 mmol) in MeOH (10 ml), a 1 M solution of lithium hydroxide (5 ml, 5.00 mmol) was added dropwise. The mixture was stirred at RT for 4 hours, then the mixture was cooled at 0° C. (ice-water bath) and 6 M HCl was added dropwise until pH 4-5. A white solid precipitated and was collected by filtration. The desired product was obtained as a solid (480 mg, 93% yield) and used in the following reaction without further purification.

MS/ESI$^+$ 345 [MH]$^+$

Step 3: Synthesis of (S)-3,5-dichloro-4-(2-(3-(cyclopropylmethoxy)-4-(difluoromethoxy)phenyl)-2-(4-methoxy-3-(N-(2-morpholinoethyl)sulfamoyl) benzoyloxy)ethyl)pyridine 1-oxide (133)

4-Methoxy-3-(N-(2-morpholinoethyl)sulfamoyl)benzoic acid (146 mg, 0.424 mmol), was suspended in anhydrous DCM (10 ml) under $N_2$ atmosphere; DMAP (24.86 mg, 0.203 mmol) and EDC (156 mg, 0.814 mmol) were sequentially added. The mixture was stirred at RT for 1 hour. Compound 3 (171 mg, 0.407 mmol) was added in one portion to the mixture and the reaction was stirred overnight at RT. The mixture was concentrated under reduced pressure and purified by flash chromatography on silica gel (DCM:Acetone 1:1) affording 212 mg of the desired product as a white solid. A second flash chromatography on silica gel (DCM:MeOH 10:0.5) was necessary and the desired product was obtained (170 mg, 56% yield). MS/ESI$^+$ 746.23 [MH]$^+$. $[\alpha]_D^{20}$=-42.95, (c=0.50, DCM).

1H NMR (300 MHz, DMSO-d6) δ ppm 8.53 (s, 2 H) 8.33 (d, 1 H) 8.18 (dd, 1 H) 7.36 (d, 1 H) 7.13-7.25 (m, 3 H) 7.03-7.11 (m, 1 H) 7.07 (t, 1 H) 6.20 (dd, 1 H) 4.00 (s, 3 H) 3.86-3.98 (m, 2 H) 3.63 (dd, 1 H) 3.38-3.45 (m, 4 H) 3.31-3.38 (m, 1 H) 2.93 (dd, 2 H) 2.26 (t, 2 H) 2.14-2.21 (m, 4 H) 1.16-1.28 (m, 1 H) 0.51-0.62 (m, 2 H) 0.30-0.40 (m, 2 H)

The compound of Table 13 was prepared with analogous synthetic steps and procedures to that described in Example 15, Scheme 15, by reacting the appropriate precursors (commercially available or synthesized by a person skilled in the art) with suitable reagents. Specific variations in the experimentals or purification methods are indicated in the table.

TABLE 13

| Structure | Comp. | Salt Name | NMR characterization | MS/ESI+ [MH]+ | Amine |
|---|---|---|---|---|---|
| (structure shown) | 136 | No Salt | ¹H NMR (300 MHz, DMSO-d$_6$) δ ppm 8.53 (s, 2 H), 8.33 (d, 1 H), 8.17 (dd, 1 H), 7.36 (d, 1 H), 7.23 (d, 1 H), 7.21 (d, 1 H), 7.11 (t, 1 H), 7.07 (dd, 1 H), 7.07 (t, 1 H), 6.19 (dd, 1 H), 4.00 (s, 3 H), 3.94 (dd, 2 H), 3.63 (dd, 1 H), 3.34 (dd, 1 H), 2.92 (q, 2 H), 2.23 (t, 2 H), 2.13 (br. s., 4 H), 2.17 (br. s., 4 H), 2.04 (s, 3 H), 1.19-1.27 (m, 1 H), 0.51-0.62 (m, 2 H), 0.31-0.40 (m, 2 H) | 759.38 | (structure shown) |

Example 16

Synthesis of (S)-3,5-dichloro-4-(2-(3-(cyclopropylmethoxy)-4-(difluoromethoxy)phenyl)-2-(4-(N-(2-(dimethylamino)ethyl)sulfamoyl)benzoyloxy)-ethyl)pyridine 1-oxide (Compound 137)

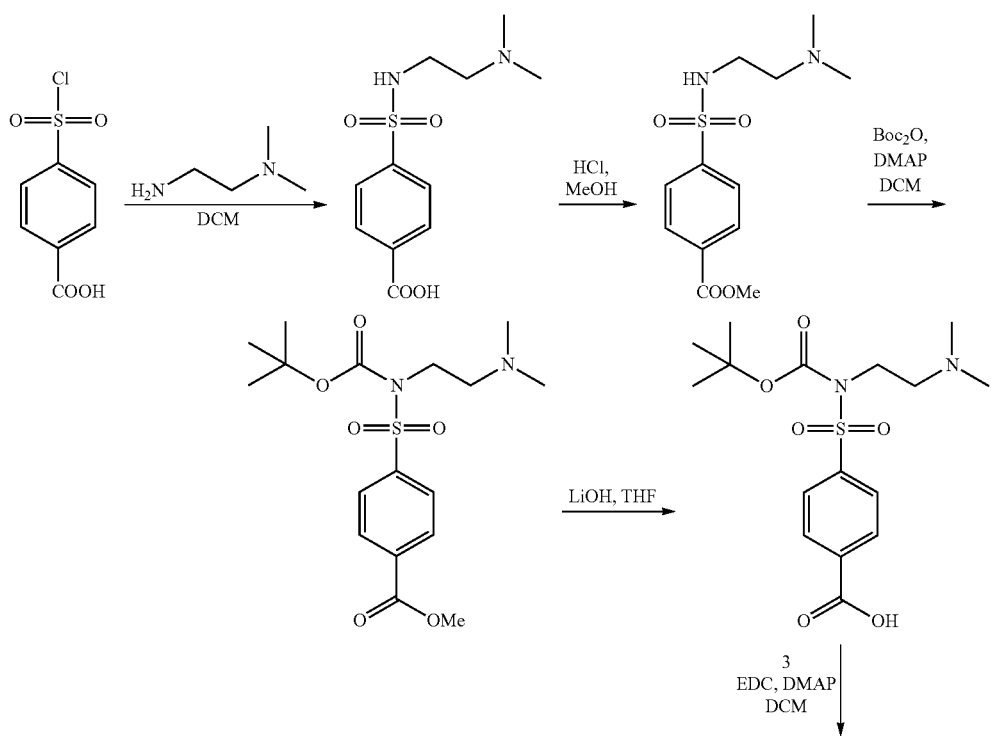

Scheme 16

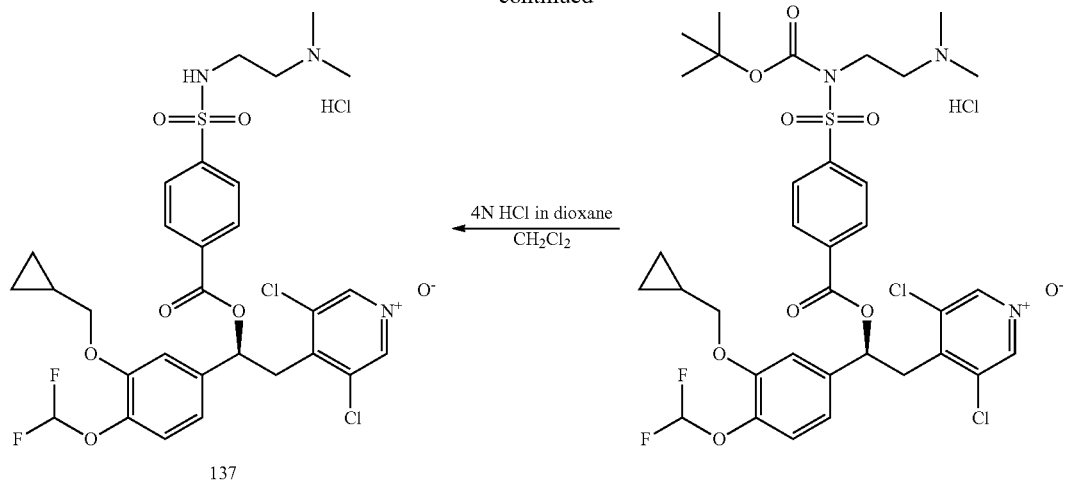

Step 1: Synthesis of 4-(N-(2-(dimethylamino)ethyl) sulfamoyl)benzoic acid (142)

4-(Chlorosulfonyl)benzoic acid (500 mg, 2.266 mmol) was dissolved in DCM (50 ml). N1,N1-dimethylethane-1,2-diamine (999 mg, 11.33 mmol) was added and the resulting solution was stirred at room temperature for 24 hours. Note: the solution became red. HCl (4M solution in dioxane, 10 ml) was added in order to obtain complete salification of the product and of excess N1,N1-dimethylethane-1,2-diamine. The solvent was evaporated and the crude product (1.7 g) was used in the following reaction without further purification.

Step 2: Synthesis of methyl 4-(N-(2-(dimethylamino)ethyl)sulfamoyl)benzoate (141)

Crude 4-(N-(2-(dimethylamino)ethyl)sulfamoyl)benzoic acid (1.7 g, 2.497 mmol) was dissolved in MeOH (100 ml); hydrogen chloride, 4M solution in dioxane (5 ml, 20.00 mmol) was added and the resulting mixture was stirred at room temperature for 24 hours. The reaction mixture was evaporated to dryness, then partitioned between EtOAc (100 ml) and aqueous NaHCO$_3$ (5% w/w, 100 ml). The organic layer was dried over Na$_2$SO$_4$ and evaporated to dryness to give the desired product as a white solid (610 mg, 2.130 mmol, 85% yield, MS/ESI$^+$ 287 [MH]$^+$) and used in the following reaction without further purification.

Step 3: Synthesis of methyl 4-(N-(tert-butoxycarbonyl)-N-(2-(dimethylamino)ethyl)-sulfamoyl)benzoate (140)

Methyl 4-(N-(2-(dimethylamino)ethyl)sulfamoyl)benzoate (610 mg, 2.130 mmol) was dissolved in DCM (50 ml). Boc$_2$O (0.495 ml, 2.130 mmol) and DMAP (260 mg, 2.130 mmol) were added and the mixture was stirred at room temperature for 24 hours. The reaction mixture was washed with 1N HCl (2×20 ml). The organic layer was dried over Na$_2$SO$_4$ and evaporated to dryness. The crude desired product was obtained (780 mg, 2.018 mmol, 95% yield, MS/ESI$^+$ 387 [MH]$^+$) and used in the following reaction without further purification.

Step 4: Synthesis of 4-(N-(tert-butoxycarbonyl)-N-(2-(dimethylamino)ethyl)sulfamoyl)-benzoic acid (139)

Methyl 4-(N-(tert-butoxycarbonyl)-N-(2-(dimethylamino)ethyl)sulfamoyl)-benzoate (0.78 g, 2.018 mmol) was dissolved in tetrahydrofuran (15 ml). LiOH, 1N solution (2.220 ml, 2.220 mmol) was added and the mixture was stirred at room temperature for 24 hours. The reaction mixture was diluted with EtOAc (60 ml), 1N HCl was added and the phases were separated. The organic layer was dried over Na$_2$SO$_4$ and evaporated to dryness to yield the crude desired product (220 mg, 0.591 mmol, 29.3% yield, MS/ESI$^+$ 373 [MH]$^+$) which was used in the following reaction without further purification.

Step 5: Synthesis of (S)-4-(2-(4-(N-(tert-butoxycarbonyl)-N-(2-(dimethylamino)ethyl)-sulfamoyl)benzoyloxy)-2-(3-(cyclopropylmethoxy)-4-(difluoromethoxy)phenyl)ethyl)-3,5-dichloropyridine 1-oxide (138)

Compound 3 (200 mg, 0.476 mmol) was dissolved in DCM (20 ml). DMAP (29.1 mg, 0.238 mmol), EDC (182 mg, 0.952 mmol) and 4-(N-(tert-butoxycarbonyl)-N-(2-(dimethylamino)ethyl)sulfamoyl)benzoic acid (220 mg, 0.591 mmol) were added, and the resulting mixture was stirred at room temperature for 24 hours. The reaction mixture was washed with aq. sat. NaHCO$_3$ solution (30 ml) and 1N HCl (2×30 ml); the organic layer was dried over Na$_2$SO$_4$ and evaporated to dryness. The crude desired product (290 mg, 0.374 mmol, 79% yield, MS/ESI$^+$ 774.3 [MH]$^+$) was used in the following reaction without further purification.

Step 6: Synthesis of (S)-3,5-dichloro-4-(2-(3-(cyclopropylmethoxy)-4-(difluoromethoxy)phenyl)-2-(4-(N-(2-(dimethylamino)ethyl)sulfamoyl)-benzoyloxy)ethyl)pyridine 1-oxide (137)

(S)-4-(2-(4-(N-(tert-butoxycarbonyl)-N-(2-(dimethylamino)ethyl)sulfamoyl)-benzoyloxy)-2-(3-(cyclopropylmethoxy)-4-(difluoromethoxy)phenyl)ethyl)-3,5-dichloropyridine 1-oxide (290 mg, 0.374 mmol) was dissolved in DCM (20 ml). 4N HCl solution in dioxane (3 ml, 12.00 mmol) was added and the resulting mixture was stirred at room temperature for 24 hours. The reaction mixture was evaporated to dryness, dissolved in DCM (30 ml) and washed with 5% aq. NaHCO$_3$ solution (30 ml). The organic layer was dried over Na$_2$SO$_4$ and evaporated to dryness. The crude product was purified by flash chromatography on silica gel (eluent: DCM:EtOAc=from 8:2 to 7:3) to yield 120 mg of the desired product as a colorless oil. The oil was dissolved in DCM (20 ml) and 4N HCl solution in dioxane (0.5 ml) was added; the resulting solution was evaporated to dryness to obtain the desired product as hydrochloride salt (102 mg, 0.143 mmol, 38.3% yield, MS/ESI$^+$ 673.87 [MH]$^+$, [$\alpha_D$]=−54.9, c=0.51, DCM).

Example 17

Synthesis of (S)-3,5-dichloro-4-(2-(3-(cyclopropylmethoxy)-4-(difluoromethoxy)phenyl)-2-(3-(methylsulfonamidomethyl)-4-(2-morpholinoethoxy)benzoyloxy)ethyl)pyridine 1-oxide (Compound 143)

Scheme 17
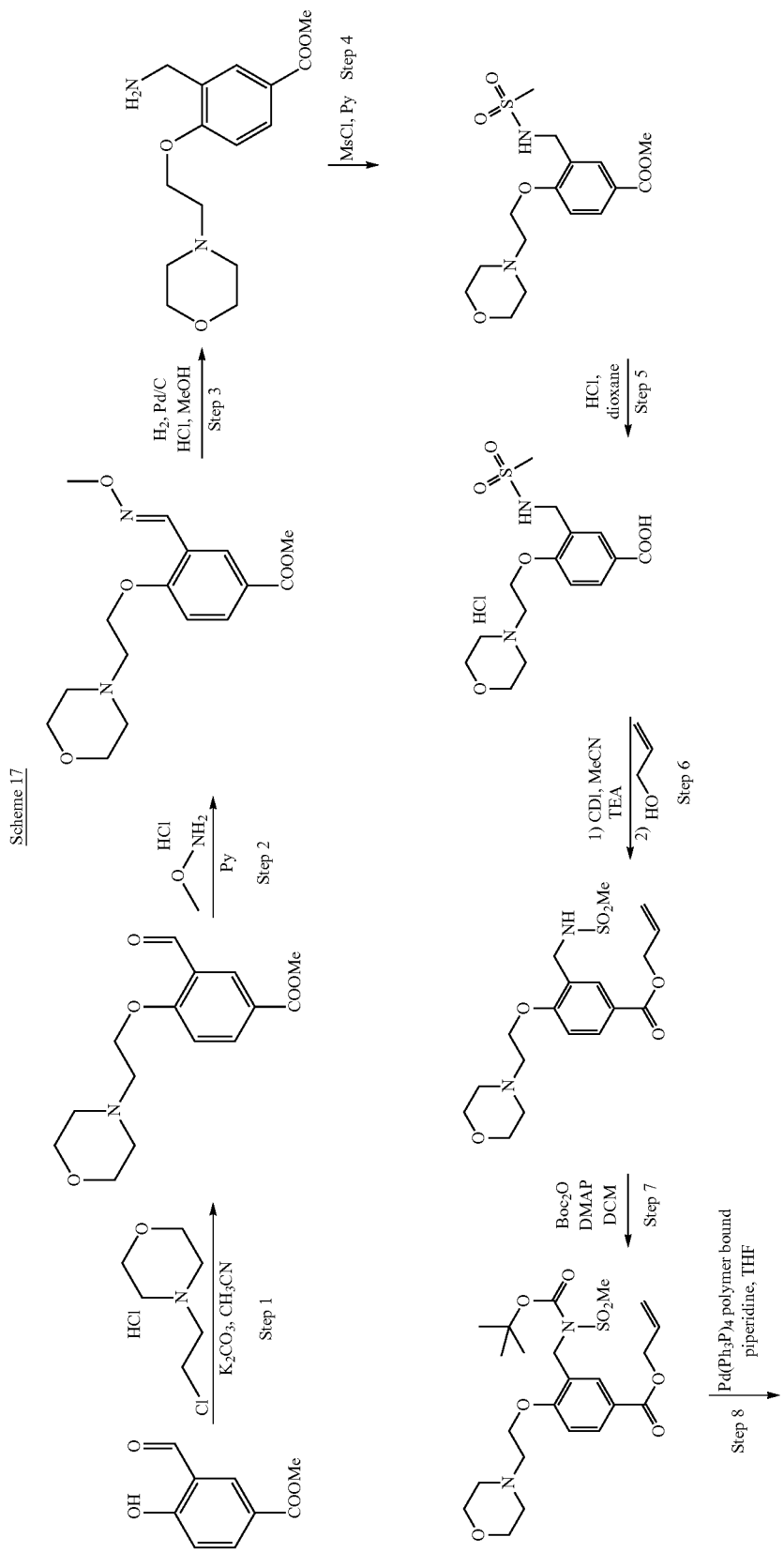

-continued
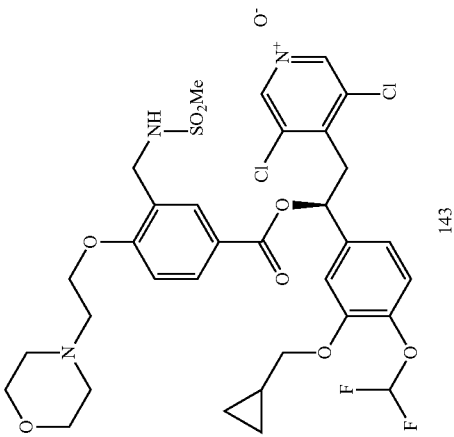
143
HCl
dioxane
Step 10
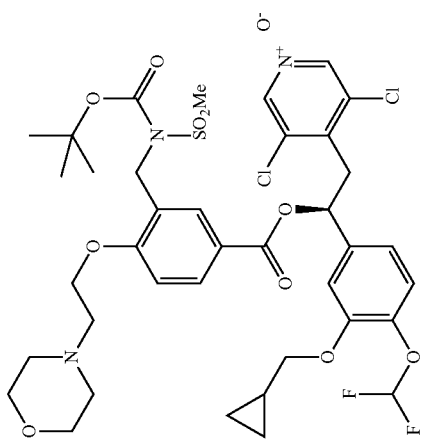
EDC, DMAP
DCM
Step 9
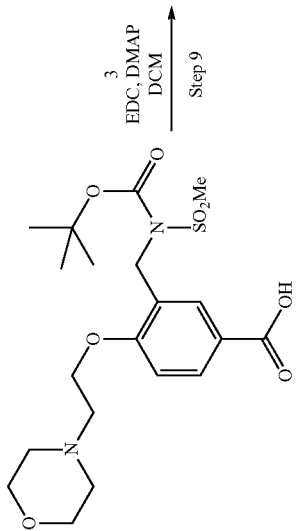

Step 1: Synthesis of methyl
3-formyl-4-(2-morpholinoethoxy)benzoate (152)

A mixture of methyl 3-formyl-4-hydroxybenzoate (0.800 g, 4.44 mmol), 4-(2-chloroethyl)morpholine hydrochloride (1.653 g, 8.88 mmol) and K$_2$CO$_3$ (1.227 g, 8.88 mmol) in CH$_3$CN (5 ml) was heated under MW irradiation at 100° C. for 2 hours. The mixture was portioned between ethyl acetate and water. The organic phase was dried over Na$_2$SO$_4$, the solvent was removed and the crude was purified by flash chromatography on silica gel (DCM:MeOH=99:1 to 97:3) to give methyl 3-formyl-4-(2-morpholinoethoxy)benzoate as a pale yellow solid (1.177 g, 90% yield).
MS/ESI$^+$ 294.2 [MH]$^+$ Step 2: Synthesis of (E)-methyl 3-((methoxyimino)
methyl)-4-(2-morpholinoethoxy)-benzoate (151)

A solution of methyl 3-formyl-4-(2-morpholinoethoxy)benzoate (0.450 g, 1.534 mmol) and O-methylhydroxylamine hydrochloride (0.141 g, 1.688 mmol) in pyridine (15 ml) was heated at 60° C. for 1 hour. The solvent was removed and the crude was portioned between ethyl acetate and 5% NaHCO$_3$. The organic phase was dried over Na$_2$SO$_4$, the solvent was removed and the crude (E)-methyl 3-((methoxyimino)methyl)-4-(2-morpholinoethoxy)benzoate was obtained as a white solid (0.492 g, 99% yield) and used in the next step without further purification. MS/ESI$^+$ 323.2 [MH]$^+$ Step 3: Synthesis of methyl
3-(aminomethyl)-4-(2-morpholinoethoxy)benzoate
(150)

A mixture of (E)-methyl 3-((methoxyimino)methyl)-4-(2-morpholinoethoxy)-benzoate (0.492 g, 1.526 mmol), 10% Pd/C (0.050 g, 0.047 mmol) and conc. HCl (0.093 ml, 3.05 mmol) in MeOH (30 ml) was hydrogenated in a Parr apparatus at 35 psi for 48 hours. Pd/C (0.030 g, 0.028 mmol) and HCl (0.023 ml, 0.763 mmol) were added, and the mixture was hydrogenated at 38 psi for additional 24 hours. The catalyst was filtered off, and the residue was portioned between ethyl acetate and 5% NaHCO$_3$. The aqueous phase was extracted twice with DCM and some MeOH, the combined organic layers were dried over Na$_2$SO$_4$ and the solvent was removed. Methyl 3-(aminomethyl)-4-(2-morpholinoethoxy)benzoate was obtained as a colorless oil (0.405 g, 90% yield) and used in the next step without further purification. MS/ESI$^+$ 295.2, 278.2 [MH]$^+$ Step 4: Synthesis of methyl 3-(methylsulfonamidomethyl)-4-(2-morpholinoethoxy)-benzoate
(149)

A mixture of methyl 3-(aminomethyl)-4-(2-morpholinoethoxy)benzoate (0.405 g, 1.376 mmol) in pyridine (15 ml) was cooled to 0° C. and methanesulfonyl chloride (0.118 ml, 1.514 mmol) was added. The mixture was warmed to RT and stirred for 48 hours. The solvent was removed and the crude was portioned between ethyl acetate and 5% NaHCO$_3$. The organic phase was dried over Na$_2$SO$_4$ and the solvent was evaporated. The crude was purified by flash chromatography on silica gel cartridge (DCM:MeOH=99:1) to give methyl 3-(methylsulfonamidomethyl)-4-(2-morpholinoethoxy)benzoate as a white solid (0.233 g, 45.5% yield).
MS/ESI$^+$ 373.2 [MH]$^+$ Step 5: Synthesis of 3-(methylsulfonamidomethyl)-
4-(2-morpholinoethoxy)benzoic acid hydrochloride
(148)

A solution of methyl 3-(methylsulfonamidomethyl)-4-(2-morpholinoethoxy)-benzoate (0.233 g, 0.626 mmol) and 6N HCl (2.61 ml, 15.64 mmol) in dioxane was heated at 70° C. for 36 hours. The solvent was removed and the residue was dried under vacuum to give 3-(methylsulfonamidomethyl)-4-(2-morpholinoethoxy)benzoic acid hydrochloride as an off-white solid (0.245 g, 99% yield) that was used in the next step without further purification. MS/ESI$^+$ 359.2 [MH]$^+$ Step 6: Synthesis of allyl 3-(methylsulfonamidomethyl)-4-(2-morpholinoethoxy)benzoate (147)

A mixture of 3-(methylsulfonamidomethyl)-4-(2-morpholinoethoxy)benzoic acid hydrochloride (0.245 g, 0.620 mmol), CDI (0.121 g, 0.745 mmol) and TEA (0.086 ml, 0.620 mmol) in acetonitrile (30 ml) was heated to 70° C. for 3 hours. The solvent was removed and the crude was dissolved in prop-2-en-1-ol (10 ml, 146 mmol) and heated to 70° C. for 2 hours then at RT over week-end. The mixture was diluted with ethyl acetate and washed with sat. NH$_4$Cl (×4) and with 5% NaHCO$_3$. The organic phase was dried over Na$_2$SO$_4$ and the solvent was removed. The crude was purified by SCX cartridge (DCM:MeOH=1:1; MeOH:conc. NH$_3$=90:10). Allyl 3-(methylsulfonamidomethyl)-4-(2-morpholinoethoxy)benzoate was obtained as a white solid (0.215 g, 87% yield) and was used in the next step without further purification.
MS/ESI$^+$ 399.2 [MH]$^+$ Step 7: Synthesis of allyl 3-((N-(tert-butoxycarbonyl)methylsulfonamido)methyl)-4-(2-morpholinoethoxy)benzoate (146)

A solution of allyl 3-(methylsulfonamidomethyl)-4-(2-morpholinoethoxy)-benzoate (0.215 g, 0.540 mmol), di-tert-butyl dicarbonate (0.130 g, 0.594 mmol) and DMAP (0.073 g, 0.594 mmol) in DCM (20 ml) was stirred at RT for 1 hour. The mixture was washed with 0.5 N HCl and 5% NaHCO$_3$. The organic layer was dried Na$_2$SO$_4$ and the solvent was removed. The crude allyl 3-((N-(tert-butoxycarbonyl)-methylsulfonamido)methyl)-4-(2-morpholinoethoxy)benzoate obtained as a colorless amorphous solid (0.251 g, 93% yield, was used in the next step without further purification. MS/ESI$^+$ 499.3 [MH]$^+$ Step 8: Synthesis of 3-((N-(tert-butoxycarbonyl)
methylsulfonamido)methyl)-4-(2-morpholinoethoxy)
benzoic acid (145)

A mixture of allyl 3-((N-(tert-butoxycarbonyl)methylsulfonamido)methyl)-4-(2-morpholinoethoxy)benzoate (0.251 g, 0.503 mmol), tetrakis(triphenylphospine)palladium polymer bound (loading 0.5-0.9 mmol/g) (0.700 g, 0.503 mmol) and piperidine (0.050 ml, 0.503 mmol) in THF was heated to 50° C. for 48 hours. The mixture was portioned between sat. NH$_4$Cl and ethyl acetate and the aqueous phase were extracted several times with ethyl acetate. The combined organic layers were washed with 5% NaHCO$_3$. The basic aqueous phase was acidified with 1N HCl (pH=5) and extracted with ethyl acetate. The organic layer was dried over Na2SO4 and the solvent was removed. 3-((N-(tert-butoxycarbonyl)methylsulfonamido)methyl)-4-(2-morpholinoethoxy)benzoic acid was obtained as a pale yellow amorphous solid (0.116 g 50.3% yield) and was used in the next step without further purification. MS/ESI$^+$ 459.3, 359.3 [MH]$^+$ Step 9: Synthesis of (S)-4-(2-(3-((N-(tert-butoxycarbonyl)methylsulfonamido)methyl)-4-(2-morpholinoethoxy)benzoyloxy)-2-(3-(cyclopropylmethoxy)-
4-(difluoromethoxy)phenyl)ethyl)-3,5-
dichloropyridine 1-oxide (144)

A mixture of 3-((N-(tert-butoxycarbonyl)methylsulfonamido)methyl)-4-(2-morpholinoethoxy)benzoic acid (0.116 g, 0.253 mmol), compound 3 (0.097 g, 0.230 mmol), EDC (0.132 g, 0.690 mmol) and DMAP (0.014 g, 0.115 mmol) in DCM was stirred at RT over week-end. The mixture was diluted with DCM and washed twice with 1N HCl and with 5% NaHCO₃. The organic phase was dried over Na₂SO₄ and the solvent was removed. The residue was purified by filtration on SCX cartridge (DCM:MeOH=1:1; MeOH:

The compound of Table 14 was prepared with analogous synthetic steps and procedures to those described in Example 17, Scheme 17, by reacting the appropriate precursors (commercially available or synthesized by a person skilled in the art) with suitable reagents. Specific variations in the experimentals or purification methods are indicated in the table.

TABLE 14

| Structure | Comp. | Salt Name | NMR characterization | MS/ESI⁺ [MH]⁺ | Carboxylic acid |
|---|---|---|---|---|---|
| (structure shown) | 153 | Hydrochloride | ¹H NMR (300 MHz, DMSO-d6) δ ppm 8.56 (s, 2 H), 7.62 (dd, 1 H), 7.44-7.55 (m, 2 H), 7.35 (t, 1 H), 7.24 (d, 1 H), 7.21 (d, 1 H), 7.09 (dd, 1 H), 7.06 (t, 1 H), 6.21 (dd, 1 H), 4.15-4.27 (m, 4 H), 3.94 (d, 2 H), 3.62 (dd, 1 H), 3.55-3.61 (m, 4 H), 3.35 (dd, 1 H), 2.89 (s, 3 H), 2.76 (t, 2 H), 2.41-2.48 (m, 4 H), 1.10-1.21 (m, 1 H), 0.49-0.64 (m, 2 H), 0.24-0.43 (m, 2 H) | 760.38 | (structure shown) |

NH₄OH=90:10). The basic fraction was portioned between ethyl acetate and water and the organic phase was washed with brine and dried over Na₂SO₄. The solvent was removed and (S)-4-(2-(3-((N-(tert-butoxycarbonyl)-methylsulfonamido)methyl)-4-(2-morpholinoethoxy)benzoyloxy)-2-(3-(cyclopropylmethoxy)-4-(difluoromethoxy)phenyl)ethyl)-3,5-dichloropyridine 1-oxide was obtained as a colorless amorphous solid (0.108 g, 54.6% yield) and used in the next step without further purification. MS/ESI⁺ 860.6 [MH]⁺

Step 10: Synthesis of (S)-3,5-dichloro-4-(2-(3-(cyclopropylmethoxy)-4-(difluoromethoxy)phenyl)-2-(3-(methylsulfonamidomethyl)-4-(2-morpholinoethoxy)benzoyloxy)ethyl)pyridine 1-oxide (143)

To a solution of (S)-4-(2-(3-((N-(tert-butoxycarbonyl)methylsulfonamido)-methyl)-4-(2-morpholinoethoxy)benzoyloxy)-2-(3-(cyclopropylmethoxy)-4-(difluoromethoxy)phenyl)ethyl)-3,5-dichloropyridine 1-oxide (0.108 g, 0.125 mmol) in DCM (10 ml), HCl 4M in dioxane (2 ml, 8.00 mmol) was added, and the mixture was stirred at RT overnight. The mixture was portioned between DCM and 5% NaHCO₃ and the organic phase was dried over Na₂SO₄. The solvent was removed and the crude was purified by filtration on silica gel cartridge (DCM:MeOH=99:1 to 98:2) to give (S)-3,5-dichloro-4-(2-(3-(cyclopropylmethoxy)-4-(difluoromethoxy)phenyl)-2-(3-(methylsulfonamidomethyl)-4-(2-morpholinoethoxy)benzoyloxy)ethyl)pyridine 1-oxide as a colorless amorphous solid (0.056 g, 59.0% yield). MS/ESI⁺ 760.04 [MH]⁺. [α]$_D^{20}$=−38.18 (c=0.44, MeOH).

¹H NMR (300 MHz, DMSO-d6) δ ppm 8.53 (s, 2 H), 8.00 (d, 1 H), 7.93 (dd, 1 H), 7.31 (t, 1 H), 7.21 (d, 1 H), 7.20 (d, 1 H), 7.15 (d, 1 H), 7.08 (dd, 1 H), 7.06 (t, 1 H), 6.21 (dd, 1 H), 4.24 (t, 2 H), 4.16 (d, 2 H), 3.93 (d, 2 H), 3.53-3.66 (m, 5 H), 3.34 (dd, 1 H), 2.88 (s, 3 H), 2.74-2.81 (m, 2 H), 2.53-2.61 (m, 4 H), 1.10-1.22 (m, 1 H), 0.45-0.63 (m, 2 H), 0.28-0.45 (m, 2 H)

Example 18

Synthesis of ((S)-3,5-dichloro-4-(2-(3-(cyclopropylmethoxy)-4-(difluoromethoxy)phenyl)-2-((4-methoxy-3-(N-(2-morpholinoethyl)methylsulfonamido) phenoxy)carbonyloxy)ethyl)pyridine 1-oxide (154)

Scheme 18

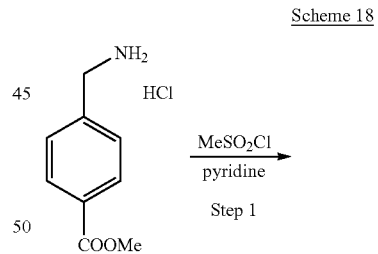

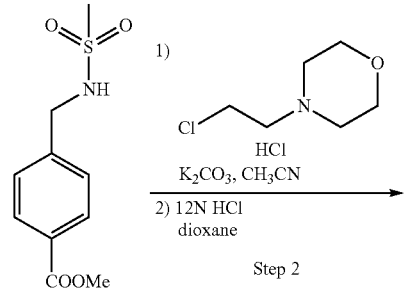

Step 1

Step 2

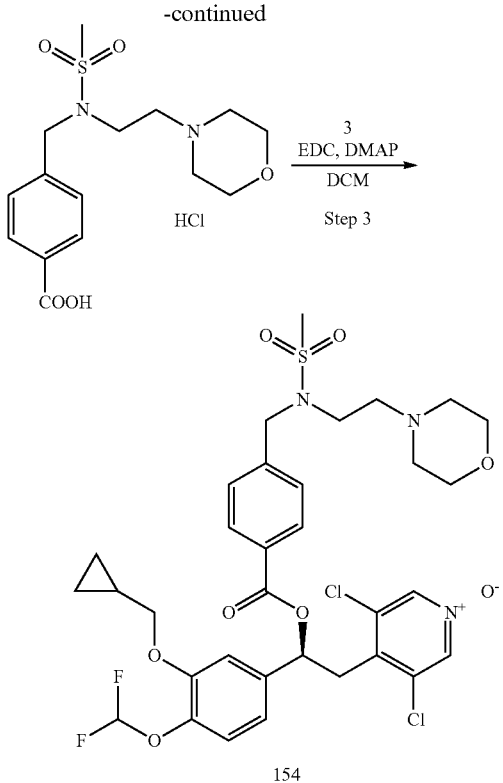

Step 1: Synthesis of methyl 4-(methylsulfonamidomethyl)benzoate (156)

To a solution of methyl 4-(aminomethyl)benzoate hydrochloride (2 g, 9.92 mmol) in pyridine (90 ml), methanesulfonyl chloride (1.183 ml, 14.88 mmol) was added, and the mixture was stirred at RT for 3 hours. The solvent was evaporated, the residue was partitioned between ethyl acetate (100 ml) and 1N HCl (100 ml) and the aqueous layer was extracted with ethyl acetate (3×100 ml). The combined organic layers were dried over $Na_2SO_4$ and the solvent was removed affording crude methyl 4-(methylsulfonamidomethyl)benzoate as a pale yellow solid (2.8 g) that was used for the next step without any additional purification. MS/ESI$^+$ 244.1 [MH]$^+$

Step 2: Synthesis of 4-(2-(N-(4-carboxybenzyl)methylsulfonamido)ethyl)morpholin-4-ium chloride (155)

To a solution of methyl 4-(methylsulfonamidomethyl)benzoate (theoric 9.92 mmol) in $CH_3CN$ (100 ml), 4-(2-chloroethyl)morpholine hydrochloride (2.75 g, 14.80 mmol) and $K_2CO_3$ (2.045 g, 14.80 mmol) were added and the mixture refluxed for 3 hours. The solid was filtered off, the solvent was evaporated and the resulting yellow oil was dissolved in dioxane (50 ml). Aqueous 12N HCl (50 ml, 600 mmol) was added and the mixture was heated to 70° C. for 3 hours. The solvent was removed under vacuum and the resulting crude was purified by trituration with $CH_3CN$ recovering 4-(2-(N-(4-carboxybenzyl)methylsulfonamido)ethyl)morpholin-4-ium chloride as a white solid (2.4 g, 64% yield over 3 steps). MS/ESI$^+$ 739.0 [MH]$^+$

Step 3: Synthesis of (S)-3,5-dichloro-4-(2-(3-(cyclopropylmethoxy)-4-(difluoromethoxy)phenyl)-2-(4-((N-(2-morpholinoethyl)methylsulfonamido)methyl)benzoyloxy)ethyl)pyridine 1-oxide (154)

To a solution of 4-(2-(N-(4-carboxybenzyl)methylsulfonamido)ethyl)morpholin-4-ium chloride (1.0 g, 2.64 mmol) in DCM (35 ml), compound 3 (1.109 g, 2.64 mmol), EDC (1.518 g, 7.92 mmol) and DMAP (0.161 g, 1.320 mmol) were added, and the mixture was stirred at RT for 3 hours. Ethanol (50 ml) was added to the reaction mixture and the precipitate was collected by filtration recovering 1.3 g of desired compound. This product was furthermore purified by flash chromatography on silica gel column (DCM/MeOH=9:1) affording (S)-3,5-dichloro-4-(2-(3-(cyclopropylmethoxy)-4-(difluoromethoxy)phenyl)-2-(4-((N-(2-morpholinoethyl)methylsulfonamido)methyl)benzoyloxy)ethyl)pyridine 1-oxide as a white solid (1.100 g, 56% yield). MS/ESI$^+$ 744.41 [MH]$^+$. $[\alpha]_D^{20}$=−35.96 (c=0.5, DCM).

$^1$H NMR (300 MHz, DMSO-d$_6$) δ ppm 8.54 (s, 2 H), 7.96-8.04 (m, 2 H), 7.43-7.58 (m, 2 H), 7.22 (d, 1 H), 7.20 (d, 1 H), 7.09 (dd, 1 H), 7.06 (t, 1 H), 6.22 (dd, 1 H), 4.46 (s, 2 H), 3.93 (d, 2 H), 3.62 (dd, 1 H), 3.44-3.53 (m, 4 H), 3.35 (dd, 1 H), 3.24 (t, 2 H), 3.08 (s, 3 H), 2.33 (t, 2 H), 2.21-2.30 (m, 4 H), 1.01-1.32 (m, 1 H), 0.48-0.66 (m, 2 H), 0.25-0.48 (m, 2 H)

Example 19

Synthesis of (S)-3,5-dichloro-4-(2-(3-(cyclopropylmethoxy)-4-((N-(2-morpholinoethyl)methylsulfonamido)methyl)benzoyloxy)-2-(3-(cyclopropylmethoxy)-4-(difluoromethoxy)phenyl)ethyl)pyridine 1-oxide (157)

Scheme 19

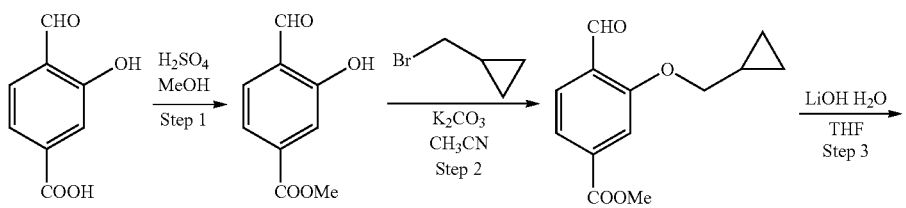

-continued

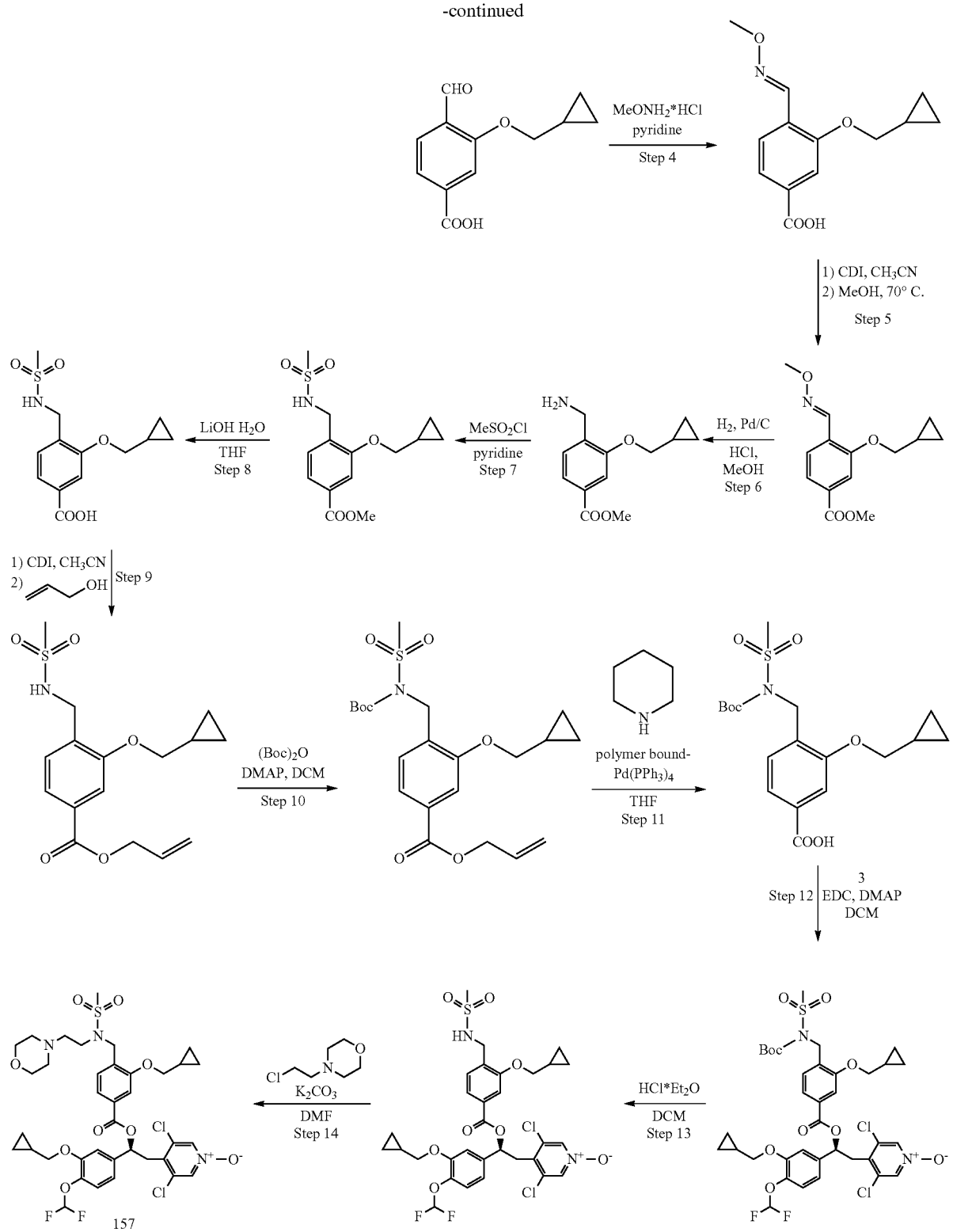

Step 1: Synthesis of methyl 4-formyl-3-hydroxybenzoate (170)

4-Formyl-3-hydroxybenzoic acid (1 g, 6.02 mmol) was suspended in MeOH (50 ml). Sulfuric acid (few drops) was added and the resulting mixture was heated to 60° C. for 6 hours. The reaction mixture was diluted with ethyl acetate (150 ml) and washed with brine (2×100 ml). The organic layer was dried over Na$_2$SO$_4$ and evaporated to dryness affording methyl 4-formyl-3-hydroxybenzoate (0.970 g, 5.38 mmol, 89% yield). The compound was used in the next step without further purification. MS/ESI$^+$ 181.1 [MH]$^+$

Step 2: Synthesis of methyl 3-(cyclopropylmethoxy)-4-formylbenzoate (169)

Methyl 4-formyl-3-hydroxybenzoate (0.97 g, 5.38 mmol) was dissolved in acetonitrile (30 ml). Potassium carbonate (1.488 g, 10.77 mmol) and (bromomethyl)cyclopropane (0.945 g, 7.00 mmol) were added, and the mixture was heated to 60° C. under vigorous stirring for 30 hours. The reaction mixture was poured in water (100 ml), acidified with aq. 36% HCl (pH=1) and then extracted with ethyl acetate (2×100 ml). The organic phase was dried over $Na_2SO_4$ and evaporated to dryness. The crude methyl 3-(cyclopropylmethoxy)-4-formylbenzoate (1.100 g, 87% yield) was employed in the next step without further purification. MS/ESI$^+$ 235.1 [MH]$^+$

Step 3: Synthesis of 3-(cyclopropylmethoxy)-4-formylbenzoic acid (168)

Methyl 3-(cyclopropylmethoxy)-4-formylbenzoate (1.1 g, 4.70 mmol) was dissolved in THF (60 ml) and lithium hydroxide 1N solution in water (5.64 ml, 5.64 mmol) was added. The mixture was stirred at RT for 3 days and then diluted with ethyl acetate (100 ml) and washed with aq. 1N HCl (50 ml). The organic layer was dried over $Na_2SO_4$ and evaporated to dryness affording 3-(cyclopropylmethoxy)-4-formylbenzoic acid (0.940 g, 91% yield). This intermediate was employed in the next step without further purification. MS/ESI$^+$ 221.1 [MH]$^+$

Step 4: Synthesis of (Z)-3-(cyclopropylmethoxy)-4-((methoxyimino)methyl)benzoic acid (167)

A solution of 3-(cyclopropylmethoxy)-4-formylbenzoic acid (0.560 g, 2.54 mmol) and O-methylhydroxylamine hydrochloride (0.234 g, 2.80 mmol) in pyridine (12 ml) was heated to 60° C. for 1 hour. The solvent was removed and the crude was dissolved in ethyl acetate and washed with aq. 1N HCl and brine. The organic layer was dried over sodium sulfate, the solvent was evaporated and (Z)-3-(cyclopropylmethoxy)-4-((methoxyimino)methyl)benzoic acid was obtained as a white solid (0.620 g, 98% yield). This product was used for the next step without any further purification. MS/ESI$^+$ 272.3 [MNa]$^+$

Step 5: Synthesis of (Z)-methyl 3-(cyclopropylmethoxy)-4-((methoxyimino)methyl)benzoate (166)

A solution of (Z)-3-(cyclopropylmethoxy)-4-((methoxyimino)methyl)benzoic acid (0.620 g, 2.487 mmol) and CDI (0.444 g, 2.74 mmol) in acetonitrile (40 ml) was heated to 70° C. for 3 hours left at RT overnight and then heated to 70° C. for 1 additional hour. The solvent was removed and the crude was dissolved in MeOH (30 ml) and heated to 70° C. for 1.5 hours. The solvent was removed and the crude was dissolved in ethyl acetate and washed twice with aq. 1N HCl and with brine. The organic layer was dried over sodium sulfate and evaporated to dryness affording (Z)-methyl 3-(cyclopropylmethoxy)-4-((methoxyimino) methyl)benzoate as a yellow oil (0.635 g, 97% yield). MS/ESI$^+$ 264.1 [MH]$^+$

Step 6: Synthesis of methyl 4-(aminomethyl)-3-(cyclopropylmethoxy)benzoate (165)

(Z)-Methyl 3-(cyclopropylmethoxy)-4-((methoxyimino) methyl)benzoate (0.635 g, 2.412 mmol) was dissolved in MeOH until complete dissolution and 10% Pd/C (0.070 g, 0.066 mmol) was added followed by 37% aqueous HCl (0.297 ml, 3.62 mmol). The mixture was hydrogenated at 35 psi overnight in a Parr apparatus. The catalyst was filtered off, the filtrate was evaporated to dryness and the residue was portioned between ethyl acetate and aq. $NaHCO_3$ sat. sol. The organic layer was washed with brine, dried over $Na_2SO_4$ and the solvent was removed. Methyl 4-(aminomethyl)-3-(cyclopropylmethoxy)benzoate was obtained as a pale yellow amorphous solid (0.530 g, 93% yield). This intermediate was used without any further purification. MS/ESI$^+$ 236.2 [MH]$^+$

Step 7: Synthesis of methyl 3-(cyclopropylmethoxy)-4-(methylsulfonamidomethyl)benzoate (164)

A solution of methyl 4-(aminomethyl)-3-(cyclopropylmethoxy)benzoate (0.530 g, 2.253 mmol) in pyridine (20 ml) was cooled to 0° C. and methanesulfonyl chloride (0.193 ml, 2.478 mmol) was added. The mixture was allowed to warm to RT and stirred for 3 hours. A new portion of methanesulfonyl chloride (0.088 ml, 1.127 mmol) was added over 2 hours, and the mixture was stirred at RT overnight. The solvent was removed and the crude was portioned between ethyl acetate and aq. 1N HCl. The organic phase was washed with aq. 5% $NaHCO_3$ and dried over $Na_2SO_4$. The solvent was evaporated to dryness and the crude was purified by filtration on silica gel cartridge (petroleum ether:ethyl acetate=70:30 to 60:40) affording methyl 3-(cyclopropylmethoxy)-4-(methylsulfonamidomethyl)benzoate as a pale yellow solid (0.435 g, 61.6% yield). MS/ESI$^+$ 336.3 [MNa]$^+$

Step 8: Synthesis of 3-(cyclopropylmethoxy)-4-(methylsulfonamidomethyl)benzoic acid (163)

To a solution of methyl 3-(cyclopropylmethoxy)-4-(methylsulfonamidomethyl)-benzoate (0.435 g, 1.388 mmol) in THF (20 ml), LiOH, 1N aqueous solution (1.527 ml, 1.527 mmol), was added and the mixture was stirred at RT overnight. A second portion of LiOH, 1N aqueous solution, (1.388 ml, 1.388 mmol) was added and the mixture was stirred at RT for additional 24 hours. The reaction mixture was acidified with aq. 1N HCl and extracted with ethyl acetate. The organic layer was washed with brine and dried over $Na_2SO_4$; the solvent was removed under vacuum affording crude 3-(cyclopropylmethoxy)-4-(methylsulfonamidomethyl)benzoic acid as a pale yellow solid (0.400 g, 96% yield). This intermediate was used without any further purification.

MS/ESI$^+$ 322.2 [MNa]$^+$

Step 9: Synthesis of allyl 3-(cyclopropylmethoxy)-4-(methylsulfonamidomethyl)benzoate (162)

A mixture of 3-(cyclopropylmethoxy)-4-(methylsulfonamidomethyl)benzoic acid (0.350 g, 1.169 mmol) and CDI (0.209 g, 1.286 mmol) in acetonitrile (35 ml) was heated to 70° C. for 3 hours. The solvent was removed under vacuum; the residue was dissolved in allyl alcohol (10 ml, 147 mmol), heated to 70° C. for 30 minutes and left at RT overnight. The reaction mixture was partitioned between ethyl acetate and aq. $NH_4Cl$ sat. sol. The organic phase was dried over $Na_2SO_4$, the solvent was removed and the crude was purified by filtration on silica gel cartridge (petroleum ether:ethyl acetate=70:30) affording allyl 3-(cyclopropylmethoxy)-4-(methylsulfonamidomethyl)benzoate as a white solid (0.320 g, 81% yield). MS/ESI$^+$ 340.2 [MH]$^+$

Step 10: Synthesis of allyl 4-((N-(tert-butoxycarbonyl)methylsulfonamido)methyl)-3-(cyclopropylmethoxy)benzoate (161)

A solution of allyl 3-(cyclopropylmethoxy)-4-(methylsulfonamidomethyl)-benzoate (0.320 g, 0.943 mmol), di-tert-butyl dicarbonate (0.226 g, 1.037 mmol) and DMAP (0.115 g, 0.943 mmol) in DCM (30 ml) was stirred at RT for 1 hour. The reaction mixture was washed with aq. 1N HCl and brine; the organic phase was dried over $Na_2SO_4$ and the solvent was removed under vacuum affording allyl 4-((N-(tert-butoxycarbonyl)methylsulfonamido) methyl)-3-(cyclopropylmethoxy)benzoate as a colorless amorphous solid (0.385 g, 93% yield). This product was employed in the next step without further purification. MS/ESI$^+$ 462.2 [MNa]$^+$

Step 11: Synthesis of 4-((N-(tert-butoxycarbonyl)methylsulfonamido)methyl)-3-(cyclopropylmethoxy)benzoic acid (160)

A mixture of allyl 4-(N-(tert-butoxycarbonyl)methylsulfonamido)methyl)-3-(cyclopropylmethoxy)benzoate (0.385 g, 0.876 mmol), piperidine (0.087 ml, 0.876 mmol) and polymer bound tetrakis(triphenylphosphine)palladium (loading 0.5-0.9 mmol/g, 1 g, 0.876 mmol) in THF (70 ml) was heated to 50° C. for 24 hours. A second portion of polymer bound tetrakis(triphenylphosphine)palladium (loading 0.5-0.9 mmol/g, 0.300 g, 0.263 mmol) and piperidine (0.030 ml, 0.303 mmol) was added and the mixture was heated to 50° C. for additional 24 hours. The polymer was filtered off and washed with ethyl acetate. The filtrate was washed with aq. NH$_4$Cl sat. sol.; the organic layer was dried over Na$_2$SO$_4$ and the solvent was removed. Crude 4-((N-(tert-butoxycarbonyl)-methylsulfonamido)methyl)-3-(cyclopropylmethoxy)benzoic acid, obtained as a dark yellow solid (0.350 g, 100% yield) was used without any further purification. MS/ESI$^+$422.2 [MNa]$^+$

Step 12: Synthesis of (S)-4-(2-(4-((N-(tert-butoxycarbonyl)methylsulfonamido)methyl)-3-(cyclopropylmethoxy)benzoyloxy)-2-(3-(cyclopropylmethoxy)-4-(difluoromethoxy) phenyl)ethyl)-3,5-dichloropyridine 1-oxide (159)

A mixture of 4-((N-(tert-butoxycarbonyl)methylsulfonamido)methyl)-3-(cyclopropylmethoxy)benzoic acid (0.350 g, 0.876 mmol), EDC (0.420 g, 2.190 mmol), DMAP (0.045 g, 0.365 mmol) and (S)-3,5-dichloro-4-(2-(3-(cyclopropylmethoxy)-4-(difluoromethoxy)phenyl)-2-hydroxyethyl) pyridine 1-oxide compound 3 (0.307 g, 0.730 mmol) in DCM (30 ml) was stirred at RT overnight. The reaction mixture was diluted with DCM and washed with aq. 5% NaHCO$_3$, aq. 1N HCl and brine. The organic layer was dried over Na$_2$SO$_4$, the solvent was removed under vacuum and the residue was purified by flash chromatography on silica gel cartridge (DCM:ethyl acetate=80:20 to 70:30) affording (S)-4-(2-(4-((N-(tert-butoxycarbonyl)methylsulfonamido)methyl)-3-(cyclopropylmethoxy)benzoyloxy)-2-(3-(cyclopropylmethoxy)-4-(difluoromethoxy)phenyl)ethyl)-3,5-dichloropyridine 1-oxide as a white amorphous solid (0.305 g, 52.1% yield). MS/ESI$^+$ 801.3 [MH]$^+$

Step 13: Synthesis of (S)-3,5-dichloro-4-(2-(3-(cyclopropylmethoxy)-4-(difluoromethoxy)phenyl)-2-(3-(cyclopropylmethoxy)-4-(methylsulfonamidomethyl)benzoyloxy)ethyl)pyridine 1-oxide (158)

A mixture of (S)-4-(2-(4-((N-(tert-butoxycarbonyl)methylsulfonamido)methyl)-3-(cyclopropylmethoxy)benzoyloxy)-2-(3-(cyclopropylmethoxy)-4-(difluoromethoxy)phenyl)ethyl)-3,5-dichloropyridine 1-oxide (0.305 g, 0.380 mmol) and HCl 4M in Et$_2$O (3 ml, 12.00 mmol) in DCM (25 ml) was stirred at RT overnight. The volatiles were removed under vacuum and the crude was purified by trituration with EtOH to give (S)-3,5-dichloro-4-(2-(3-(cyclopropylmethoxy)-4-(difluoromethoxy)phenyl)-2-(3-(cyclopropylmethoxy)-4-(methyl sulfonamidomethyl)benzoyloxy)ethyl) pyridine 1-oxide as a white solid (0.207 g, 78% yield). MS/ESI$^+$ 700.96 [MH]$^+$. $[\alpha]_D^{20}$=−35.81, c=0.54, MeOH

Step 14: Synthesis of (S)-3,5-dichloro-4-(2-(3-(cyclopropylmethoxy)-4-((N-(2-morpholinoethyl)methylsulfonamido)methyl)benzoyloxy)-2-(3-(cyclopropylmethoxy)-4-(difluoromethoxy)phenyl)ethyl) pyridine 1-oxide (157)

(S)-3,5-dichloro-4-(2-(3-(cyclopropylmethoxy)-4-(difluoromethoxy)phenyl)-2-(3-(cyclopropylmethoxy)-4-(methylsulfonamidomethyl)benzoyloxy)ethyl)pyridine 1-oxide (100 mg, 0.24 mmol), was dissolved in DMF (1 ml). 4-(2 chloroethyl) morpholine (64 mg, 0.43 mmol) and K2CO3 (30 mg, 0.21 mmol) were added, and the mixture was stirred at 60° C. for 4 hours. The reaction was diluted with water, and extracted with ethyl acetate. The organic phase was dried over Na2SO4 and evaporated under vacuum. The crude product was purified by semi-preparative HPLC to yield 8.1 mg of the final compound. MS/ESI$^+$ 814.2 [MH]$^+$ $^1$H NMR (400 MHz, acetone) δ ppm 13.65-13.95 (bs, 1 H), 8.30 (s, 2 H), 7.66-7.75 (m, 1 H), 7.53-7.65 (m, 2 H), 7.30-7.36 (m, 1 H), 7.15-7.25 (m, 2 H), 6.90 (t, J=75.00 Hz, 1 H), 6.27-6.42 (m, 1 H), 4.48 (s, 2 H), 3.99 (d, J=6.62 Hz, 10 H), 3.69-3.82 (m, 1 H), 3.29-3.47 (m, 3 H), 3.03-3.27 (m, 4 H), 2.97 (s, 3 H), 1.35-1.50 (m, 1 H), 0.79-1.00 (m, 1 H), 0.54-0.71 (m, 4 H), 0.32-0.52 (m, 4 H).

Example 20

Synthesis of (S)-1-(3-(cyclopropylmethoxy)-4-(difluoromethoxy)phenyl)-2-(3,5-dichloropyridin-4-yl)ethyl 3-(cyclopropylmethoxy)-4-(2-(dimethylamino)-ethylsulfonamido)benzoate (171)

Scheme 20

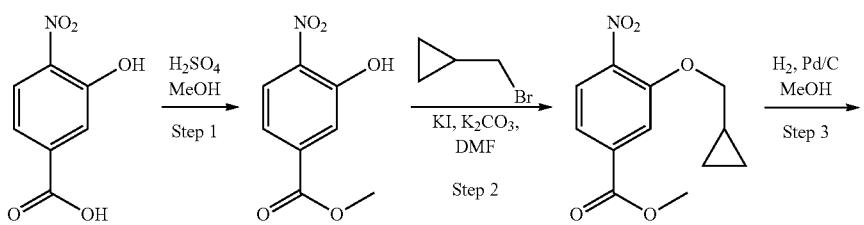

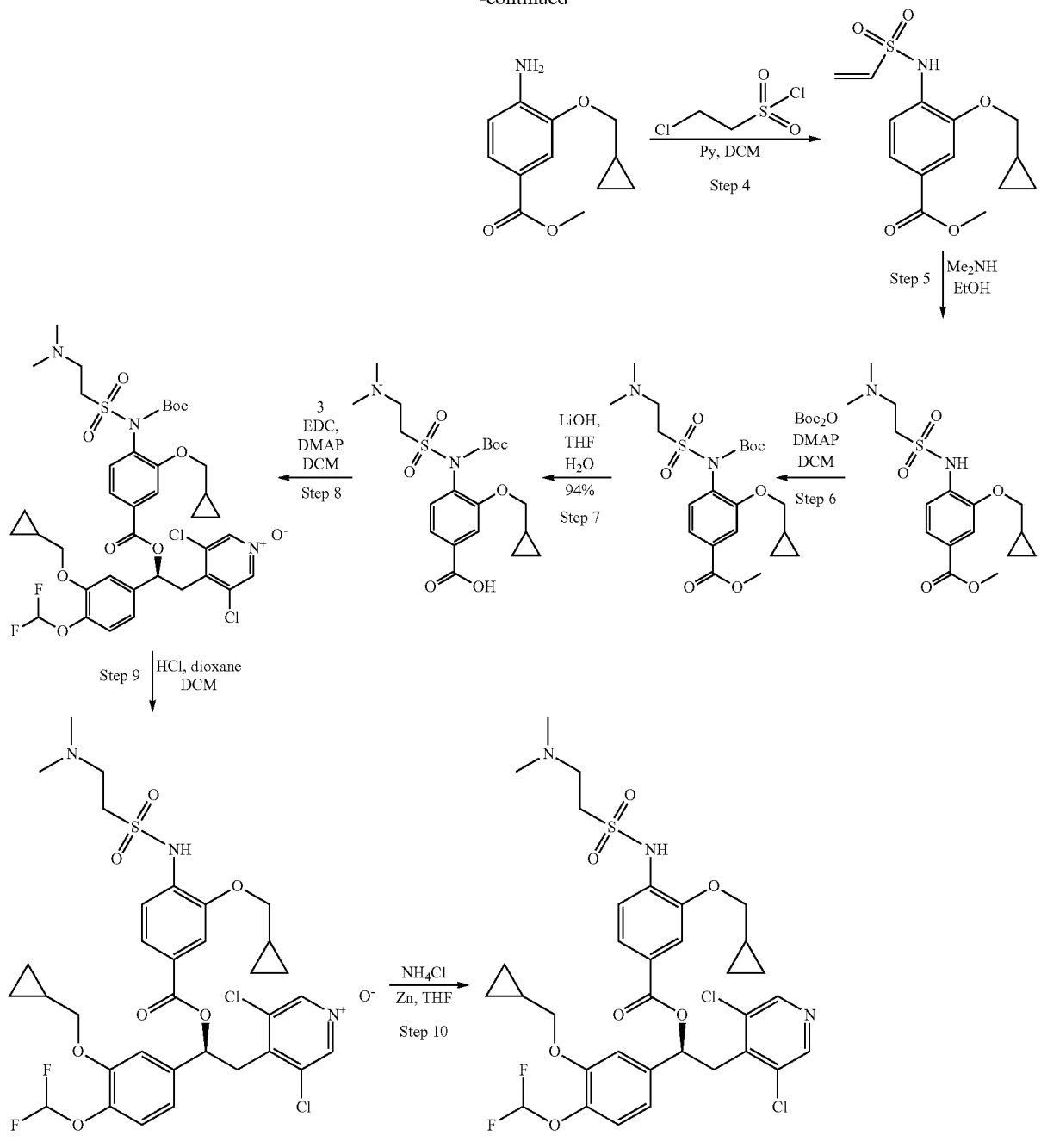

Step 1: Synthesis of methyl 3-hydroxy-4-nitrobenzoate (180).

3-Hydroxy-4-nitrobenzoic acid (5.17 g, 28.2 mmol) was dissolved in methanol (100 ml, 2466 mmol) to give a suspension and then $H_2SO_4$ 50% in water (0.25 ml, 2.345 mmol) was added. The reaction mixture was stirred at 60° C. for 6 days, then the solvent was evaporated and the yellow residue was dissolved in AcOEt and water. The aqueous phase was extracted with AcOEt and the organic phase was dried over $Na_2SO_4$ and concentrated to give the desired product as a yellow solid. (5.53 g, 99% yield).

Step 2: Synthesis of methyl 3-(cyclopropylmethoxy)-4-nitrobenzoate (179)

Methyl 3-hydroxy-4-nitrobenzoate (5.53 g, 28.1 mmol) was dissolved in dry DMF (65 ml) under $N_2$ atmosphere. Potassium iodide (1.397 g, 8.42 mmol), potassium carbonate (12.79 g, 93 mmol) and then (bromomethyl)cyclopropane (5.44 ml, 56.1 mmol) were added. The reaction mixture was vigorously stirred at 50° C. overnight. The solvent was evaporated and the residue was treated with AcOEt and water. The aqueous phase was extracted with AcOEt and the combined organic layer was dried over $Na_2SO_4$ and concentrated to give the desired product as a yellow solid (7 g, 100% yield). MS/ESI+ 252 [MH]+

Step 3: Synthesis of methyl 4-amino-3-(cyclopropylmethoxy)benzoate (178)

A mixture of methyl 3-(cyclopropylmethoxy)-4-nitrobenzoate (0.890 g, 3.54 mmol) and 10% Pd/C (0.80 g, 7.52 mmol) in MeOH (80 ml) was hydrogenated in a Parr apparatus at 15 psi for 2 hours. The catalyst was filtered off and the solvent was removed. The crude methyl 4-amino-3-(cyclopropylmethoxy)benzoate was obtained as a pale yellow solid (0.760 g, 97% yield) and used in the next step without further purification. MS/ESI+ 222.3 [MH]+

Step 4: Synthesis of f methyl 3-(cyclopropylmethoxy)-4-(vinylsulfonamido)benzoate (177)

A solution of methyl 4-amino-3-(cyclopropylmethoxy) benzoate (0.760 g, 3.43 mmol) and pyridine (3.33 ml, 41.2 mmol) in DCM (60 ml) was cooled to 0° C. and 2-chloroethanesulfonyl chloride (0.431 ml, 4.12 mmol) was added dropwise. The mixture was warmed to RT and stirred for 1 hour. The mixture was diluted with DCM and washed with 1N HCl and brine. The organic phase was dried over $Na_2SO_4$ and the solvent was removed. The crude was purified by filtration on silica gel cartridge (petroleum ether:ethyl acetate=90:10 to 70:30) to give methyl 3-(cyclopropylmethoxy)-4-(vinylsulfonamido)benzoate as a pale orange solid (0.788 g, 73.7% yield). MS/ESI+ 334.2 [MNa]+

Step 5: Synthesis of methyl 3-(cyclopropylmethoxy)-4-(2-(dimethylamino)-ethylsulfonamido) benzoate (176)

To a solution of methyl 3-(cyclopropylmethoxy)-4-(vinylsulfonamido)benzoate (0.788 g, 2.53 mmol) in EtOH (30 ml), dimethylamine (0.678 ml, 3.80 mmol) 5.6 M in EtOH was added and the mixture was stirred at RT for 1 hour. The solvent was removed and the crude methyl 3-(cyclopropylmethoxy)-4-(2-(dimethylamino)ethylsulfonamido)-benzoate was obtained as a yellow oil (0.902 g, 100% yield) and used in the next step without further purification. MS/ESI+ 357.4 [MH]+

Step 6: Synthesis of methyl 4-(N-(tert-butoxycarbonyl)-2-(dimethylamino)-ethylsulfonamido)-3-(cyclopropylmethoxy)benzoate (175)

A solution of methyl 3-(cyclopropylmethoxy)-4-(2-(dimethylamino)-ethylsulfonamido)benzoate (0.902 g, 2.53 mmol), $Boc_2O$ (0.552 g, 2.53 mmol) and DMAP (0.309 g, 2.53 mmol) in DCM (40 ml) was stirred at RT for 1 hour. The mixture was washed with water and brine, the organic phase was dried over $Na_2SO_4$ and the solvent was removed. The crude product (1.15 g, 100% yield) as used in the next step, without further purification. MS/ESI+ 457.3 [MH]+

Step 7: Synthesis of 4-(N-(tert-butoxycarbonyl)-2-(dimethylamino)ethylsulfonamido)-3-(cyclopropylmethoxy)benzoic acid (174)

A mixture of methyl 4-(N-(tert-butoxycarbonyl)-2-(dimethylamino)-ethylsulfonamido)-3-(cyclopropylmethoxy) benzoate (1.155 g, 2.53 mmol) and 1N LiOH (3.79 ml, 3.79 mmol) in $H_2O$ was stirred at RT for 24 hours. The mixture was diluted with ethyl acetate and water and 1N HCl was added until pH 5. The phases were separated and the organic layer was washed with brine and dried over $Na_2SO_4$. The solvent was removed and the desired product was obtained as a pale orange amorphous solid (0.660 g, 1.491 mmol, 59.0% yield). The pH of the aqueous phase was adjusted to 6 and it was extracted with ethyl acetate. The organic phase was dried over $Na_2SO_4$ and the solvent was removed. The desired product was obtained as a colorless amorphous solid (0.394 g, 35.2% yield). Total amount of (1.05 g, 94% yield) was used in the next step without further purification. MS/ESI+ 443.3 [MH]+

Step 8: Synthesis of (S)-4-(2-(4-(N-(tert-butoxycarbonyl)-2-(dimethylamino)-ethylsulfonamido)-3-(cyclopropylmethoxy)benzoyloxy)-2-(3-(cyclopropylmethoxy)-4-(difluoromethoxy)phenyl)ethyl)-3,5-dichloropyridine 1-oxide (173)

A solution of 4-(N-(tert-butoxycarbonyl)-2-(dimethylamino)ethylsulfonamido)-3-(cyclopropylmethoxy)benzoic acid (0.411 g, 0.928 mmol), EDC (0.411 g, 2.142 mmol), DMAP (0.044 g, 0.357 mmol) and compound 3 (0.300 g, 0.714 mmol) in DCM (30 ml) was stirred at RT for 24 hours. The mixture was washed with 5% $NaHCO_3$ and brine; the organic layer was dried over $Na_2SO_4$ and the solvent was removed. The crude was purified by flash chromatography on silica gel cartridge (DCM:MeOH=99:1 to 98:2) to give (S)-4-(2-(4-(N-(tert-butoxycarbonyl)-2-(dimethylamino) ethylsulfonamido)-3-(cyclopropylmethoxy)benzoyloxy)-2-(3-(cyclopropylmethoxy)-4-(difluoromethoxy)phenyl) ethyl)-3,5-dichloropyridine 1-oxide as a pale yellow amorphous solid (0.455 g, 75% yield). MS/ESI+ 844.4 [MH]+

Step 9: Synthesis of (S)-3,5-dichloro-4-(2-(3-(cyclopropylmethoxy)-4-(2-(dimethylamino)ethylsulfonamido)benzoyloxy)-2-(3-(cyclopropylmethoxy)-4-(difluoromethoxy)phenyl)ethyl)pyridine 1-oxide (172)

A solution of (S)-4-(2-(4-(N-(tert-butoxycarbonyl)-2-(dimethylamino)-ethylsulfonamido)-3-(cyclopropylmethoxy) benzoyloxy)-2-(3-(cyclopropylmethoxy)-4-(difluoromethoxy)phenyl)ethyl)-3,5-dichloropyridine 1-oxide (0.455 g, 0.539 mmol) and 4 M HCl (4 ml, 16.00 mmol) in dioxane in DCM (25 ml) was stirred at RT overnight. The solvent was removed and the crude was dissolved in ethyl acetate and washed with sat. $NaHCO_3$ and brine. The organic phase was dried over $Na_2SO_4$, the solvent was removed and the crude was filtered on SCX cartridge (DCM:MeOH=1:1; aq. $NH_3$:MeOH=1:9). The basic phase was portioned between ethyl acetate and brine, and the aqueous phase was extracted with ethyl acetate. The combined organic layers were dried over $Na_2SO_4$ and the solvent was removed. (S)-3,5-dichloro-4-(2-(3-(cyclopropylmethoxy)-4-(2-(dimethylamino)ethylsulfonamido)benzoyloxy)-2-(3-(cyclopropylmethoxy)-4-(difluoromethoxy)phenyl)ethyl)pyridine1-oxide was obtained as a pale yellow amorphous solid (0.321 g, 80% yield). MS/ESI+ 744.02 [MH]+. $[\alpha]_D^{20}$=−33.81 (c=0.53, MeOH)

$^1$H NMR (300 MHz, DMSO-d6) δ ppm 10.49 (br. s., 1 H), 9.69 (s, 1 H), 8.56 (s, 2 H), 7.59 (dd, 1 H), 7.52 (d, 1 H), 7.43 (d, 1 H), 7.22 (d, 1 H), 7.21 (d, 1 H), 7.07 (dd, 1 H), 7.06 (t, 1 H), 6.19 (dd, 1 H), 3.97 (d, 2 H), 3.93 (d, 2 H), 3.73-3.80 (m, 2 H), 3.62 (dd, 1 H), 3.45-3.56 (m, 2 H), 3.26-3.41 (m, 1 H), 2.80 (d, 6 H), 1.28-1.41 (m, 1 H), 1.15-1.27 (m, 1 H), 0.60-0.69 (m, 2 H), 0.51-0.60 (m, 2 H), 0.39-0.47 (m, 2 H), 0.24-0.38 (m, 2 H)

Step 10: Synthesis of (S)-1-(3-(cyclopropylmethoxy)-4-(difluoromethoxy)phenyl)-2-(3,5-dichloropyridin-4-yl)ethyl 3-(cyclopropylmethoxy)-4-(2-(dimethylamino)-ethylsulfonamido)benzoate (171)

To a solution of (S)-3,5-dichloro-4-(2-(3-(cyclopropylmethoxy)-4-(2-(dimethylamino)ethylsulfonamido)benzoyloxy)-2-(3-(cyclopropylmethoxy)-4-(difluoromethoxy)phenyl)ethyl)pyridine 1-oxide (0.321 g, 0.431 mmol) in THF (25 ml), a solution of ammonium chloride (0.922 g, 17.24 mmol) in water (5 ml) was added followed by zinc powder (1.409 g, 21.55 mmol). The mixture was stirred at RT for 30 minutes then was filtered through a celite pad and the filtrate was diluted with ethyl acetate and washed with brine. The organic layer was dried over $Na_2SO_4$ and the solvent was removed. The crude was purified by filtration on silica gel cartridge (DCM:MeOH=99:1). (S)-1-(3-(cyclopropylmethoxy)-4-(difluoromethoxy)phenyl)-2-(3,5-dichloropyridin-4-yl)ethyl 3-(cyclopropylmethoxy)-4-(2-(dimethylamino)-ethylsulfonamido)benzoate was obtained as a pale yellow amorphous solid (0.250 g, 80% yield). MS/ESI$^+$ 727.95 [MH]$^+$. $[\alpha]_D^{20}$=−26.87, c=0.55, MeOH.

$^1$H NMR (300 MHz, DMSO-d6) δ 9.99 (br. s., 1 H), 9.71 (br. s., 1 H), 8.61 (s, 2 H), 7.57 (dd, 1 H), 7.49 (d, 1 H), 7.42 (d, 1 H), 7.22 (d, 0 H), 7.21 (d, 1 H), 7.08 (dd, 1 H), 7.07 (t, 1 H), 6.26 (dd, 1 H), 3.83-4.01 (m, 4 H), 3.65-3.79 (m, 3 H), 3.38-3.57 (m, 3 H), 2.79 (s, 5 H), 1.25-1.39 (m, 1 H), 1.06-1.27 (m, 2 H), 0.49-0.70 (m, 4 H), 0.22-0.48 (m, 4 H)

Example 21

Synthesis of (S)-3,5-dichloro-4-(2-(3-(cyclopropylmethoxy)-4-(difluoromethoxy)phenyl)-2-(4-(2-(dimethylamino)ethylsulfonamido)benzoyloxy)ethyl)pyridine 1-oxide hydrochloride (Compound 181)

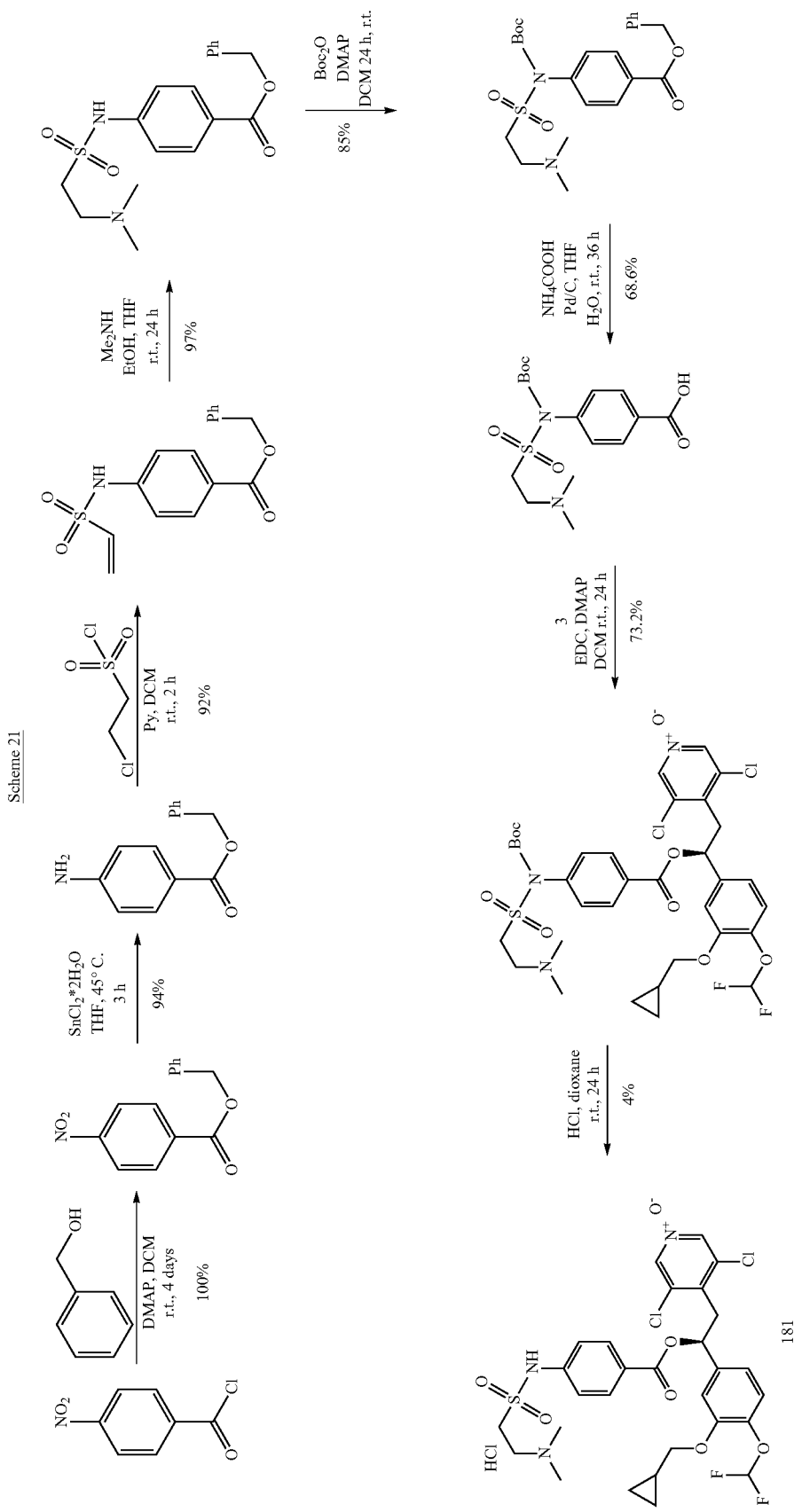
Scheme 21

Step 1: Synthesis of benzyl 4-nitrobenzoate (188)

4-Nitrobenzoyl chloride (1 g, 5.39 mmol) was dissolved in dry DCM (30 ml), under $N_2$ atmosphere; DMAP (0.329 g, 2.69 mmol) and benzyl alcohol (0.616 ml, 5.93 mmol) were added and the reaction was stirred at room temperature for 4 days. $NaHCO_3$ s.s. and DCM were added to the reaction mixture; the aqueous phase was extracted twice with DCM, the organic layers were washed with 1N HCl, dried over sodium sulfate and evaporated to dryness to give the desired product (1.5 g, 5.83 mmol, 100% yield, UPLC-MS purity: 100%,

Step 2: Synthesis of benzyl 4-aminobenzoate (187)

Benzyl 4-nitrobenzoate (1.5 g, 5.83 mmol) was dissolved in THF (40 ml), $SnCl_2$ dihydrate (5.92 g, 26.2 mmol) was added and the mixture was stirred at 45° C. for 3 hours. $NaHCO_3$ s.s. and EtOAc were added to the reaction mixture that was filtered on a celite pad. The solution was separated and the aqueous phase was extracted with EtOAc. The combined organic layers were dried over sodium sulfate and the solvent was evaporated. The desired product was obtained as a pale yellow solid (1.25 g, 5.50 mmol, 94% yield, MS/ESI$^+$ 228.1 [MH]$^+$) and used in the following step without further purification.

Step 3: Synthesis of benzyl 4-(vinylsulfonamido)benzoate (186)

Benzyl 4-aminobenzoate (620 mg, 2.73 mmol) was dissolved in DCM (20 ml). Pyridine (1 ml, 12.36 mmol) was added, then 2-chloroethanesulfonyl chloride (0.371 ml, 3.55 mmol) and the resulting mixture was stirred at room temperature for 2 hours. The reaction mixture was diluted with DCM (20 ml) and washed with 1N HCl (2×50 ml). The organic layer was dried over $Na_2SO_4$ and evaporated to dryness. The crude desired product (0.8 g, 2.52 mmol, 92% yield) was used in the following step without further purification.

Step 4: Synthesis of benzyl 4-(2-(dimethylamino)ethylsulfonamido)benzoate (185)

Benzyl 4-(vinylsulfonamido)benzoate (800 mg, 2.52 mmol) was dissolved in THF (30 ml). Dimethylamine, 5.6M in EtOH (0.585 ml, 3.28 mmol) was added and the mixture was stirred at room temperature overnight. Excess reagents and solvents were removed under reduced pressure to yield the crude desired product (0.89 g, 2.45 mmol, 97% yield, MS/ESI$^+$ 363 [MH]$^+$) that was used in the following step without further purification.

Step 5: Synthesis of benzyl 4-(N-(tert-butoxycarbonyl)-2-(dimethylamino)-ethylsulfonamido)benzoate (184)

Benzyl 4-(2-(dimethylamino)ethylsulfonamido)benzoate (890 mg, 2.456 mmol) was dissolved in DCM (40 ml). DMAP (300 mg, 2.456 mmol) and di-tert-butyl dicarbonate (536 mg, 2.456 mmol) were added and the resulting mixture was stirred at room temperature for 24 hours. The reaction mixture was washed with 1N HCl (2×20 ml), the organic layer was dried over $Na_2SO_4$ and evaporated to dryness. The crude desired product (0.96 g, 2.075 mmol, 85% yield) was used in the following step without further purification.

Step 6: Synthesis of 4-(N-(tert-butoxycarbonyl)-2-(dimethylamino)-ethylsulfonamido)benzoic acid (183)

Benzyl 4-(N-(tert-butoxycarbonyl)-2-(dimethylamino)ethylsulfonamido)benzoate (0.96 g, 2.075 mmol) was dissolved in tetrahydrofuran (40 ml). Ammonium formate (1.7 g, 27.0 mmol), water (20.0 ml) and Pd/C, 10% w/w (0.200 g, 0.188 mmol) were added and the mixture was stirred at room temperature for 36 hours. The reaction mixture was then filtered on celite pad, diluted with EtOAc (100 ml) and washed with water (2×80 ml). The organic layer was dried over $Na_2SO_4$ and evaporated to dryness. The crude desired product (0.53 g, 1.423 mmol, 68.6% yield) was used in the following step without further purification.

Step 7: Synthesis of (S)-4-(2-(4-(N-(tert-butoxycarbonyl)-2-(dimethylamino)-ethylsulfonamido)benzoyloxy)-2-(3-(cyclopropylmethoxy)-4-(difluoromethoxy)-phenyl)ethyl)-3,5-dichloropyridine 1-oxide (182)

Compound 3 (200 mg, 0.476 mmol) was dissolved in DCM (20 ml). DMAP (29.1 mg, 0.238 mmol), EDC (182 mg, 0.952 mmol) and 4-(N-(tert-butoxycarbonyl)-2-(dimethylamino)ethylsulfonamido)benzoic acid (266 mg, 0.714 mmol) were added and the resulting mixture was stirred at room temperature for 24 hours. The reaction mixture was washed with aq. sat. $NaHCO_3$ solution (30 ml) and 1N HCl (2×30 ml); the organic layer was dried over $Na_2SO_4$ and evaporated to dryness. The crude desired product (0.27 g, 0.349 mmol, 73.2% yield) was used in the following step without further purification.

Step 8: Synthesis of (S)-3,5-dichloro-4-(2-(3-(cyclopropylmethoxy)-4-(difluoromethoxy)phenyl)-2-(4-(2-(dimethylamino)ethylsulfonamido)benzoyloxy)ethyl) pyridine 1-oxide hydrochloride (181)

(S)-4-(2-(4-(N-(tert-butoxycarbonyl)-2-(dimethylamino)ethylsulfonamido)-benzoyloxy)-2-(3-(cyclopropylmethoxy)-4-(difluoromethoxy)phenyl)ethyl)-3,5-dichloropyridine 1-oxide (270 mg, 0.349 mmol) was dissolved in DCM (20 ml). 4N HCl solution in dioxane (3 ml, 12.00 mmol) was added and the resulting mixture was stirred at room temperature for 24 hours. The reaction mixture was evaporated to dryness, redissolved in DCM (30 ml) and washed with 5% aq. $NaHCO_3$ solution (30 ml). The organic layer was dried over $Na_2SO_4$ and evaporated to dryness. The crude product was purified by flash chromatography on silica gel (eluent: DCM:EtOAc=from 8:2 to 7:3) to yield 80 mg of the desired product in mixture with the corresponding alcohol derivative. Other attempts of purification by crystallization and SCX cartridge failed. The product was finally purified by preparative HPLC (Method 1). The HPLC fractions (20 ml, solvent: $H_2O+CH_3CN+0.1\%$ TFA) were diluted with brine (20 ml) and DCM (40 ml). The organic layer was dried over $Na_2SO_4$ and evaporated to dryness. The oil so obtained was dissolved in DCM (50 ml) and 4N HCl solution in dioxane (0.1 ml) was added; the resulting solution was evaporated to dryness to obtain the desired product as hydrochloride salt (10 mg, 0.014 mmol, 4.0% yield, MS/ESI$^+$ 673.79 [MH]$^+$).

1H NMR (300 MHz, DMSO-d6) δ ppm 10.75 (s, 1 H), 9.98 (br. s., 1 H), 8.56 (s, 2 H), 7.87-8.05 (m, 2 H), 7.25-7.41 (m, 2 H), 7.21 (d, 1 H), 7.21 (d, 1 H), 7.08 (dd, 1 H), 7.06 (t, 1 H), 6.20 (dd, 1 H), 3.93 (d, 2 H), 3.70-3.81 (m, 1 H), 3.58-3.66 (m, 1 H), 3.40-3.53 (m, 4 H), 2.79 (s, 6 H), 1.09-1.32 (m, 1 H), 0.47-0.65 (m, 2 H), 0.16-0.46 (m, 2 H)

Example 22

Synthesis of (S)-3,5-dichloro-4-(2-(3-(cyclopropylmethoxy)-4-(difluoromethoxy)phenyl)-2-(4-methoxy-3-(2-morpholinoethylsulfonamido)-benzoyloxy)ethyl)pyridine 1-oxide (Compound 189)

Step 1: Synthesis of (S)-3,5-dichloro-4-(2-(3-(cyclopropylmethoxy)-4-(difluoromethoxy)-phenyl)-2-(4-methoxy-3-nitrobenzoyloxy)ethyl)pyridine 1-oxide (192)

4-Methoxy-3-nitrobenzoic acid (244 mg, 1.237 mmol), DMAP (76 mg, 0.619 mmol), EDC (474 mg, 2.475 mmol), compound 3 (520 mg, 1.237 mmol) were dissolved in DCM (60 ml) and the resulting mixture was stirred at room temperature for 1 hour. The mixture was washed with 1N HCl (2×60 ml) and aq. sat. NaHCO$_3$ solution (1×60 ml). The organic phase was dried over Na$_2$SO$_4$ and evaporated to

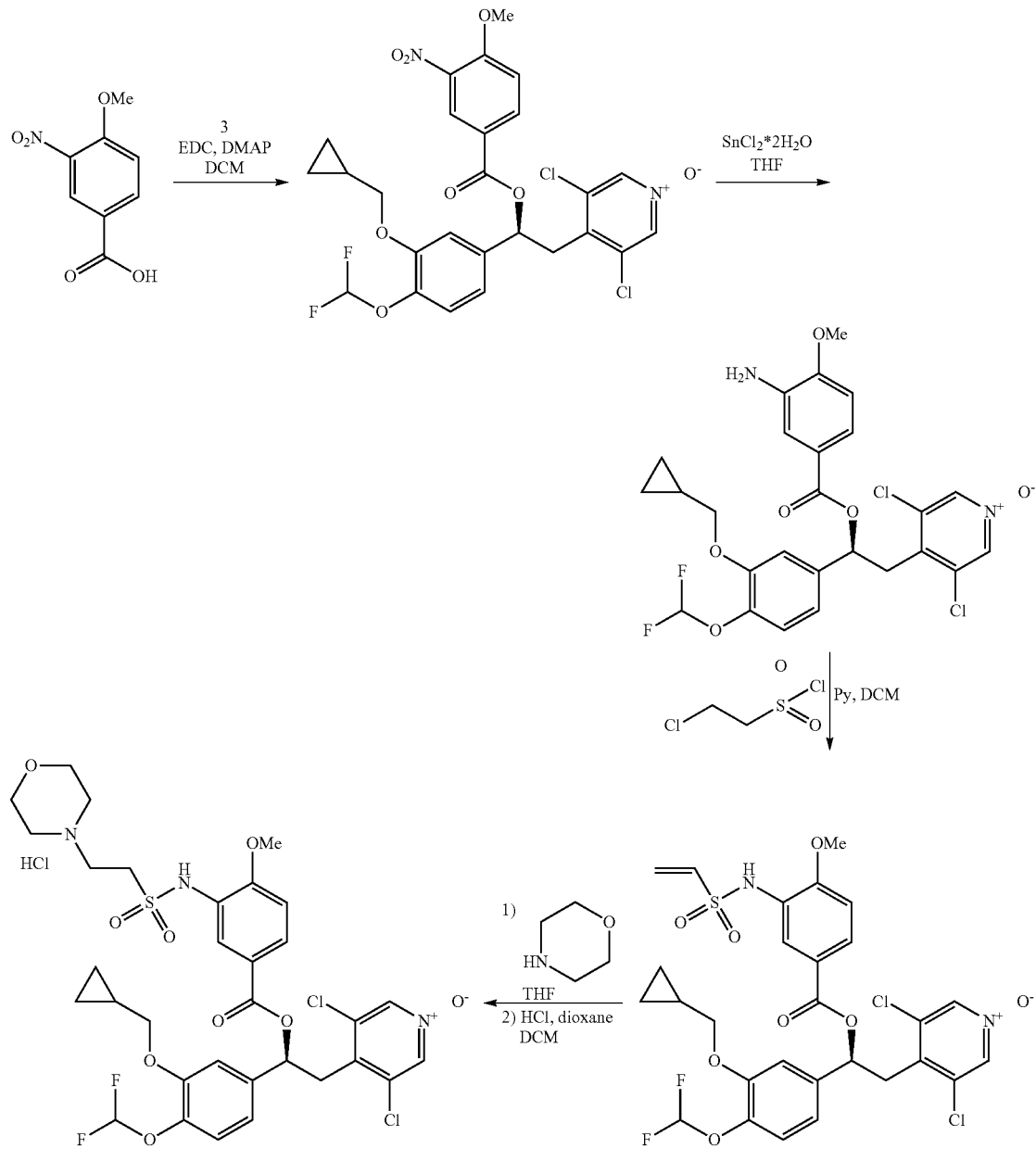

Scheme 22 dryness. The crude desired product (0.71 g, 1.185 mmol, 96% yield) was used in the next step without further purification.

Step 2: Synthesis of (S)-4-(2-(3-amino-4-methoxybenzoyloxy)-2-(3-(cyclopropylmethoxy)-4-(difluoromethoxy)phenyl)ethyl)-3,5-dichloropyridine 1-oxide (191)

(S)-3,5-dichloro-4-(2-(3-(cyclopropylmethoxy)-4-(difluoromethoxy)phenyl)-2-(4-methoxy-3-nitrobenzoyloxy)ethyl)pyridine 1-oxide (710 mg, 1.185 mmol) was dissolved in tetrahydrofuran (100 ml). SnCl$_2$ dihydrate (1336 mg, 5.92 mmol) was added and the resulting mixture was stirred at 40° C. for 24 hours. The reaction mixture was diluted with aqueous 5% NaHCO$_3$ (300 ml) and EtOAc (400 ml): a thick emulsion was obtained. The emulsion was filtered over celite pad, thus obtaining two clear phases. The organic layer was dried over Na$_2$SO$_4$ and evaporated to dryness. The crude was purified by flash chromatography on silica gel (eluent: from DCM:EtOAc=8:2 to pure EtOAc, then EtOAc: MeOH=95:5) to yield the desired product (180 mg, 0.316 mmol, 26.7% yield, MS/ESI$^+$ 569 [MH]$^+$).

Step 3: Synthesis of (S)-3,5-dichloro-4-(2-(3-(cyclopropylmethoxy)-4-(difluoromethoxy)phenyl)-2-(4-methoxy-3-(vinylsulfonamido)benzoyloxy)ethyl)pyridine 1-oxide (190)

(S)-4-(2-(3-amino-4-methoxybenzoyloxy)-2-(3-(cyclopropylmethoxy)-4-(difluoromethoxy)phenyl)ethyl)-3,5-dichloropyridine 1-oxide (180 mg, 0.316 mmol) was dissolved in DCM (50 ml). Pyridine (0.077 ml, 0.948 mmol) and 2-chloroethanesulfonyl chloride (61.8 mg, 0.379 mmol) were added and the mixture was stirred at room temperature for 24 hours. The reaction mixture was diluted with DCM (50 ml) and washed with 1N HCl (2×50 ml). The organic layer was dried over Na$_2$SO$_4$ and evaporated to dryness to yield the crude desired product (199 mg, 0.302 mmol, 95% yield) that was used in the next step without further purification.

Step 8: Synthesis of (S)-3,5-dichloro-4-(2-(3-(cyclopropylmethoxy)-4-(difluoromethoxy)-phenyl)-2-(4-methoxy-3-(2-morpholinoethylsulfonamido)benzoyloxy)ethyl)pyridine 1-oxide (189)

(S)-3,5-dichloro-4-(2-(3-(cyclopropylmethoxy)-4-(difluoromethoxy)phenyl)-2-(4-methoxy-3-(vinylsulfonamido)benzoyloxy)ethyl)pyridine 1-oxide (199 mg, 0.302 mmol) was dissolved in THF (30 ml). Morpholine (26.30, 0.302 mmol) was added and the mixture was stirred at room temperature for 24 hours. The reaction mixture was poured in water (50 ml) and extracted with EtOAc (2×50 ml). The organic layer was dried over Na$_2$SO$_4$ and evaporated to dryness. The crude was purified by flash chromatography on silica gel cartridge (eluent: DCM:EtOAc=from 8:2 to 1:1, then pure EtOAc) to give 80 mg of the desired product as a brownish oil. Further purification was performed by preparative LC-MS. The eluted fractions were collected and evaporated to dryness; the residue was dissolved in DCM (10 ml) and treated with 4N HCl in dioxane (100 μl); the solution was evaporated to dryness to obtain the desired product as hydrochloride salt, as a white amorphous solid (30 mg, 0.038 mmol, 12.7% yield, MS/ESI$^+$ 746.1 [MH]$^+$, [$\alpha_D$]=−38.8, c=0.36, DCM).

$^1$H NMR (300 MHz, DMSO-d$_6$) d ppm 10.51 (s, 1 H), 9.65 (br. s., 1 H), 8.55 (s, 2 H), 7.91 (dd, 1 H), 7.88 (d, 1 H), 7.18-7.26 (m, 3 H), 7.06 (dd, 1 H), 7.07 (t, 1 H), 6.19 (dd, 1 H), 3.95 (s, 3 H), 3.89-3.94 (m, 4 H), 3.41-3.81 (m, 10 H), 3.00-3.27 (m, 2 H), 1.15-1.28 (m, 1 H), 0.51-0.64 (m, 2 H), 0.26-0.41 (m, 2 H)

Example 23

Synthesis of 3,5-dichloro-4-((S)-2-(3-(cyclopropylmethoxy)-4-(difluoromethoxy)phenyl)-2-(3-(3-((2S, 5R)-2,5-dimethylpiperazin-1-yl)-3-oxopropanamido)-4-methoxybenzoyloxy)ethyl)pyridine 1-oxide (193)

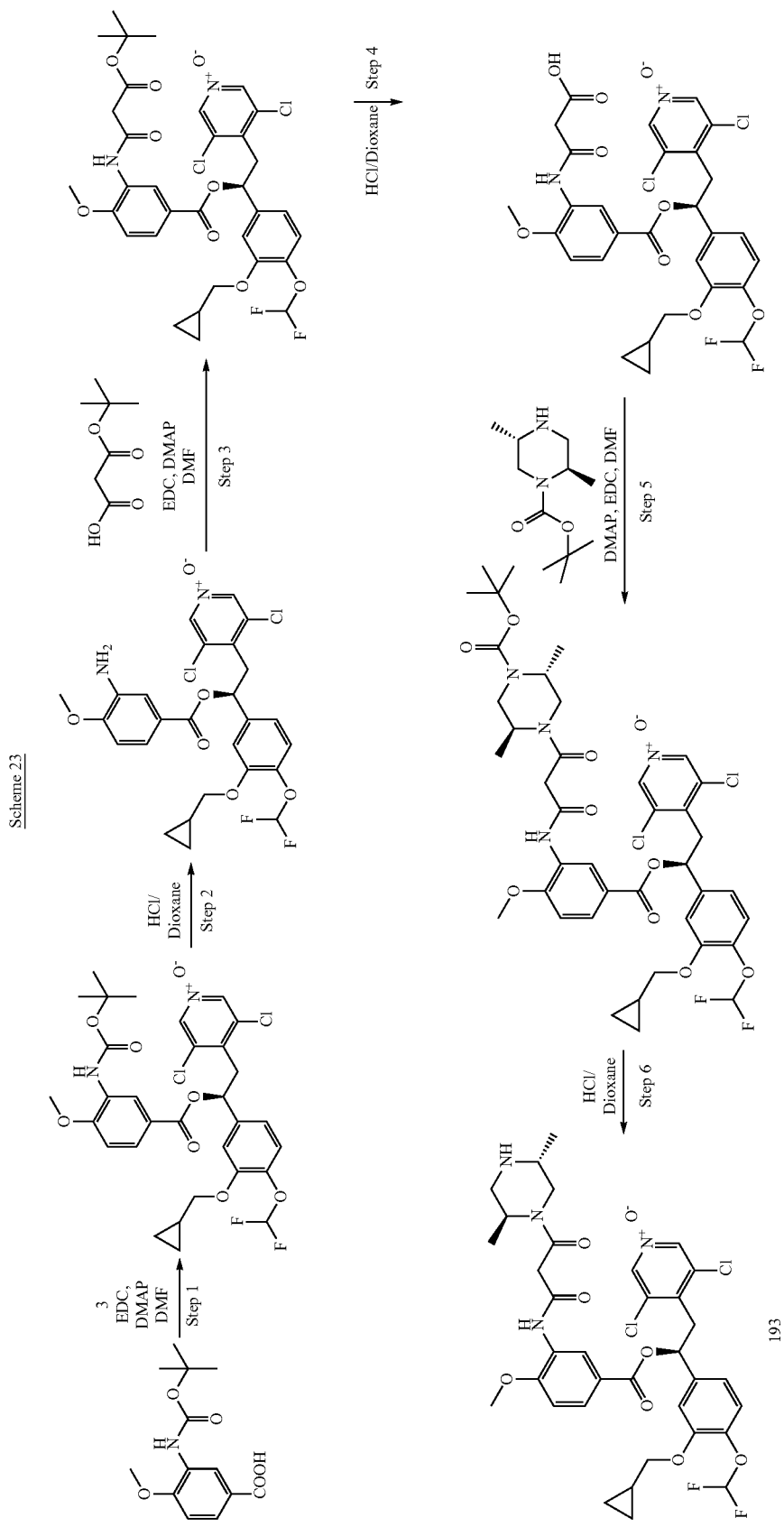

Step 1: Synthesis of (S)-4-(2-(3-(tert-butoxycarbonylamino)-4-methoxybenzoyloxy)-2-(3-(cyclopropylmethoxy)-4-(difluoromethoxy)phenyl)ethyl)-3,5-dichloropyridine 1-oxide (198)

Compound 3 (500 mg, 1.2 mmol) and 3-(tert-butoxycarbonylamino)-4-methoxybenzoic acid (481 mg, 1.8 mmol) were dissolved in DMF (5 ml). DMAP (176 mg, 1.44 mmol) and EDC (690 mg, 3.6 mmol) were added, and the mixture was stirred at RT over night. The reaction was diluted with water and extracted with ethyl acetate. The organic phase was washed with HCl 1N (2×), NaHCO$_3$ saturated solution and brine, dried over Na$_2$SO$_4$ and evaporated under vacuum to yield 650 mg of crude, that was used for the next step without any further purification.

Step 2: Synthesis of (S)-4-(2-(3-amino-4-methoxybenzoyloxy)-2-(3-(cyclopropylmethoxy)-4-(difluoromethoxy)phenyl)ethyl)-3,5-dichloropyridine 1-oxide (197)

(S)-4-(2-(3-(tert-butoxycarbonylamino)-4-methoxybenzoyloxy)-2-(3-(cyclopropylmethoxy)-4-(difluoromethoxy)phenyl)ethyl)-3,5-dichloropyridine 1-oxide (650 mg, 0.97 mmol) was dissolved in HCl/Dioxane 4M (5 ml), and the mixture was stirred at RT over night. The reaction was diluted with NaHCO$_3$ sat. sol. and then extracted with ethyl acetate. The organic phase was washed with water, dried over Na$_2$SO$_4$ and evaporated under vacuum to yield 600 mg of crude that was used for the next step without any further purification.

Step 3: Synthesis of (S)-4-(2-(3-(3-tert-butoxy-3-oxopropanamido)-4-methoxybenzoyloxy)-2-(3-(cyclopropylmethoxy)-4-(difluoromethoxy)phenyl)ethyl)-3,5-dichloropyridine 1-oxide (196)

(S)-4-(2-(3-amino-4-methoxybenzoyloxy)-2-(3-(cyclopropylmethoxy)-4-(difluoromethoxy)phenyl)ethyl)-3,5-dichloropyridine 1-oxide (100 mg, 0.17 mmol) and 3-tert-butoxy-3-oxopropanoic acid (31 µl, 0.2 mmol) were dissolved in DMF (1.5 ml). DMAP (24 mg, 0.2 mmol) and EDC (65 mg, 0.34 mmol) were added, and the mixture was stirred at RT for 2 hours. The reaction was quenched with water, and the product was extracted with ethyl acetate. The organic phase was washed with HCl 1N (2×), NaHCO$_3$ saturated solution and brine, dried over Na$_2$SO$_4$ and evaporated under vacuum to yield 150 mg of crude that was used for the next step without any further purification.

Step 4: Synthesis of (S)-4-(2-(3-(2-carboxyacetamido)-4-methoxybenzoyloxy)-2-(3-(cyclopropylmethoxy)-4-(difluoromethoxy)phenyl)ethyl)-3,5-dichloropyridine 1-oxide (195)

(S)-4-(2-(3-(3-tert-butoxy-3-oxopropanamido)-4-methoxybenzoyloxy)-2-(3-(cyclopropylmethoxy)-4-(difluoromethoxy)phenyl)ethyl)-3,5-dichloropyridine 1-oxide (150 mg, crude) was dissolved in HCl/Dioxane 4M (1.5 ml), and the mixture was stirred at RT for 6 hours. The reaction was diluted with water and then extracted with ethyl acetate. The organic phase was dried over Na$_2$SO$_4$ and evaporated under vacuum to yield 140 mg of crude that was used for the next step without any further purification.

Step 5: Synthesis of 4-((S)-2-(3-(3-((2S,5R)-4-(tert-butoxycarbonyl)-2,5-dimethylpiperazin-1-yl)-3-oxopropanamido)-4-methoxybenzoyloxy)-2-(3-(cyclopropylmethoxy)-4-(difluoromethoxy)phenyl)ethyl)-3,5-dichloropyridine 1-oxide (194)

(S)-4-(2-(3-(2-carboxyacetamido)-4-methoxybenzoyloxy)-2-(3-(cyclopropylmethoxy)-4-(difluoromethoxy)phenyl)ethyl)-3,5-dichloropyridine 1-oxide (40 mg, 0.06 mmol) and (2R,5S)-tert-butyl 2,5-dimethylpiperazine-1-carboxylate (26 mg, 0.12 mmol) were dissolved in DMF (2 ml), then DMAP (15 mg, 0.12 mmol) and EDC (34 mg, 0.18 mmol) were added, and the mixture was stirred at RT for 2 hours. The reaction was diluted with water and then extracted with ethyl acetate. The organic phase dried over Na$_2$SO$_4$ and evaporated under vacuum to yield 50 mg of crude that was used for the next step without any further purification.

Step 6: Synthesis of 3,5-dichloro-4-((S)-2-(3-(cyclopropylmethoxy)-4-(difluoromethoxy)-phenyl)-2-(3-(3-((2S,5R)-2,5-dimethylpiperazin-1-yl)-3-oxopropanamido)-4-methoxybenzoyloxy)ethyl)pyridine 1-oxide (193)

4-((S)-2-(3-(3-((2S,5R)-4-(tert-butoxycarbonyl)-2,5-dimethylpiperazin-1-yl)-3-oxopropanamido)-4-methoxybenzoyloxy)-2-(3-(cyclopropylmethoxy)-4-(difluoromethoxy)phenyl)ethyl)-3,5-dichloropyridine 1-oxide (50 mg, crude) was dissolved in HCl/Dioxane 4M (1.5 ml), and the mixture was stirred at RT for 5 hours. The solvent was evaporated under vacuum, and the crude was purified by preparative HPLC (Method 2) to yield 20 mg of the final product.

$^1$H NMR (400 MHz, acetone) δ ppm 10.18-10.46 (bs, 1 H), 9.16 (d, J=1.76 Hz, 1 H), 8.24 (s, 2 H), 7.79 (dd, J=8.82, 2.21 Hz, 1 H), 7.31 (m, 1 H), 7.17-7.25 (m, 1 H), 7.07-7.15 (m, 2 H), 6.91 (t, J=75.00 Hz, 1 H), 6.19-6.44 (m, 1 H), 3.92-4.06 (m, 5 H), 3.66-3.75 (m, 1 H), 3.48-3.62 (m, 2 H), 3.41 (dd, J=14.11, 4.41 Hz, 1 H), 3.19 (m, 6 H), 1.21-1.43 (m, 6 H), 1.14 (d, J=9.26 Hz, 1 H), 0.60 (dd, J=8.16, 1.54 Hz, 2 H), 0.40 (d, J=4.41 Hz, 2 H).

MS/ESI$^+$ 727.95 [MH]$^+$: 751.4

The compound listed in Table 15 was prepared with analogous synthetic steps and procedures to those described in Example 23, Scheme 23, Step 1-3, 6 by reacting the appropriate precursors (commercially available or synthesized by a person skilled in the art) with suitable reagents. Specific variations in the experimentals or purification methods are indicated in the table.

TABLE 15

| Structure | Comp. | Salt Name | NMR characterization | MS/ESI+ [MH]+ | Experimental procedure | Carboxylic acid |
|---|---|---|---|---|---|---|
| 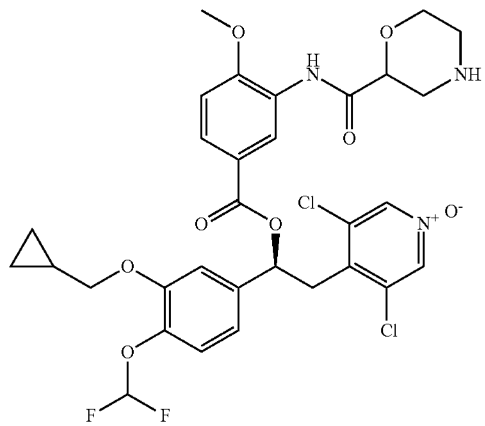 | 199 | No Salt | 1H NMR (400 MHz, acetone) δ ppm 9.17 (m, 1 H), 8.89-8.99 (bs, 1 H), 8.24 (s, 2 H), 7.76-7.87 (m, 1 H), 7.33 (m, 1 H), 7.08-7.25 (m, 3 H), 6.91 (t, J = 75.00 Hz, 1 H), 6.28-6.39 (m, 1 H), 3.94-4.11 (m, 7 H), 3.64-3.76 (m, 2 H), 3.38-3.47 (m, 1 H), 3.22-3.35 (m, 1 H), 2.60-2.74 (m, 4 H), 1.25-1.35 (m, 1 H), 0.60 (dd, J = 7.94, 1.76 Hz, 2 H), 0.40 (d, J = 4.41 Hz, 2 H) | 682.5 | Step 3: reaction was performed using CDI (1.2 eq) in DCM | |

Example 24

Synthesis of 3,5-dichloro-4-((S)-2-(3-(cyclopropyl-methoxy)-4-(difluoromethoxy)phenyl)-2-(3-(2-((2S,5R)-2,5-dimethylpiperazin-1-yl)acetamido)-4-methoxybenzoyloxy)ethyl)pyridine 1-oxide (Compound 200)

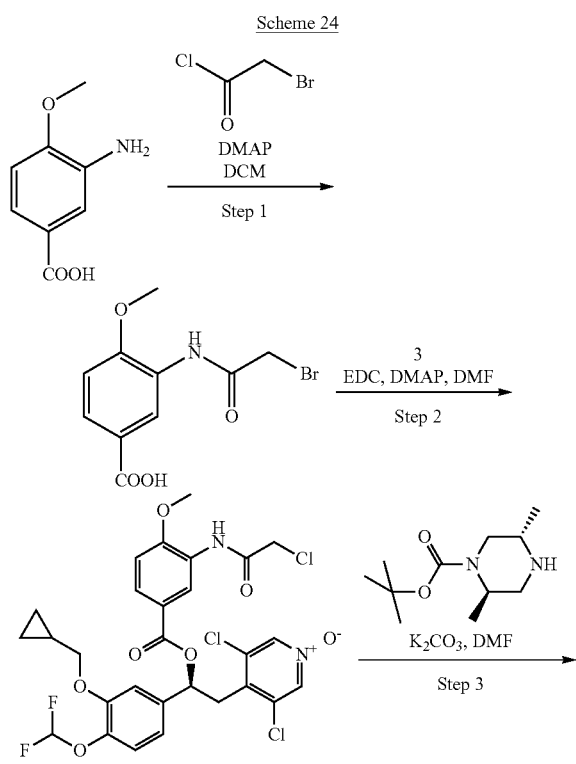

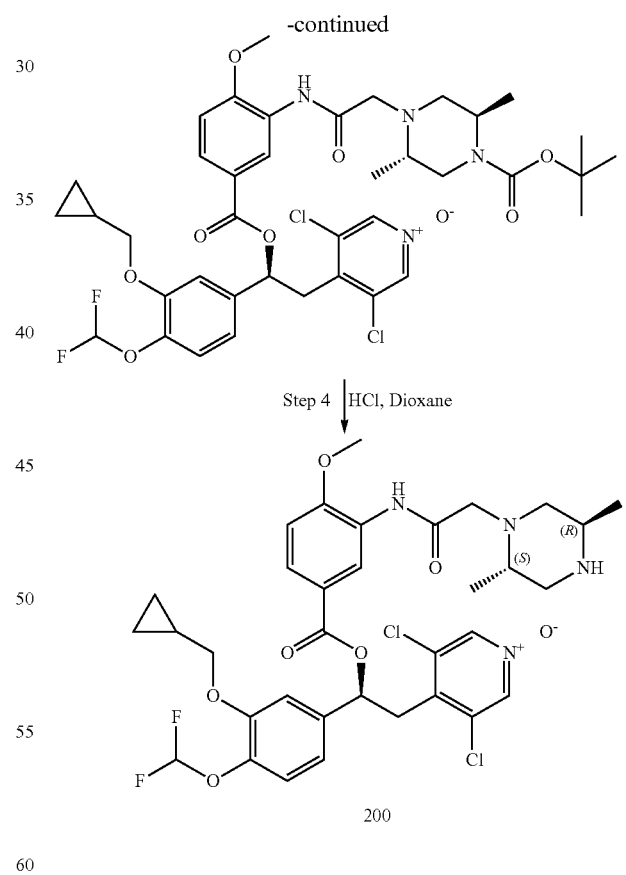

Step 1: Synthesis of 3-(2-bromoacetamido)-4-methoxybenzoic acid (203)

3-amino-4-methoxybenzoic acid (300 g, 1.8 mmol) was dissolved in DCM (10 ml). DMAP (440 mg, 3.6 mmol) was added, and 2-bromoacetyl chloride (225 μl, 2.7 mmol) was slowly added dropwise to the mixture. The reaction was stirred at RT for 1 hour, then was diluted with DCM and washed with HCl 1N (×2). The organic phase was dried over Na₂SO₄ and evaporated under vacuum, to yield 300 mg of crude that was used for the next step without any further purification. (yield: 58%)

Step 2: Synthesis of (S)-3,5-dichloro-4-(2-(3-(2-chloroacetamido)-4-methoxybenzoyloxy)-2-(3-(cyclopropylmethoxy)-4-(difluoromethoxy)phenyl) ethyl) pyridine 1-oxide (202)

(S)-3,5-dichloro-4-(2-(3-(cyclopropylmethoxy)-4-(difluoromethoxy)phenyl)-2-(hydroxyethyl)pyridine 1-oxide, compound 3 (200 mg, 0.5 mmol) and 3-(2-bromoacetamido)-4-methoxybenzoic acid (288 mg, 1 mmol) were dissolved in DMF (5 ml), then EDC (288 mg, 1.5 mmol) and DMAP (122 mg, 1 mmol) were added. The mixture was stirred at RT overnight, then quenched by adding water and extracted with AcOEt. The organic phase was washed with HCl 1N (2×), NaHCO₃ saturated solution and brine, dried over Na₂SO₄ and evaporated under vacuum to yield 140 mg of crude, that was used for the next step without any further purification.

Step 3: Synthesis of 4-((S)-2-(3-(2-((2S,5R)-4-(tert-butoxycarbonyl)-2,5-dimethylpiperazin-1-yl)acetamido)-4-methoxybenzoyloxy)-2-(3-(cyclopropylmethoxy)-4-(difluoromethoxy)phenyl)ethyl)-3,5-dichloropyridine 1-oxide (201)

(S)-3,5-dichloro-4-(2-(3-(2-chloroacetamido)-4-methoxybenzoyloxy)-2-(3(cyclopropylmethoxy)-4-(difluoromethoxy)phenyl)ethyl)pyridine 1-oxide (30 mg, 0.05 mmol) was dissolved in DMF (1.5 ml), then (2R,5S)-tert-butyl 2,5-dimethylpiperazine-1-carboxylate (32 mg, 0.15 mmol) and K₂CO₃ (14 mg, 0.1 mmol) were added, and the mixture was stirred at RT over night. The reaction was diluted with water and then extracted with ethyl acetate. The organic phase was washed with water, dried over Na₂SO₄ and evaporated to dryness, to yield 40 mg of crude that was used for the next step without any further purification.

Step 4: Synthesis of 3,5-dichloro-4-((S)-2-(3-(cyclopropylmethoxy)-4-(difluoromethoxy)phenyl)-2-(3-(2-((2S,5R)-2,5-dimethylpiperazin-1-yl)acetamido)-4-methoxybenzoyloxy)ethyl)pyridine 1-oxide (200)

4-((S)-2-(3-(2-((2S,5R)-4-(tert-butoxycarbonyl)-2,5-dimethylpiperazin-1-yl)acetamido)-4-methoxybenzoyloxy)-2-(3-(cyclopropylmethoxy)-4-(difluoromethoxy)-phenyl)ethyl)-3,5-dichloropyridine 1-oxide (40 mg, 0.05 mmol) was dissolved in HCl/Dioxane 4M (1.5 ml) and the mixture was stirred at RT for 5 hours, then it was evaporated under vacuum and purified by semi-preparative HPLC to yield 25 mg of the final compound (Yield: 69%). MS/ESI⁺ 723.4 [MH]⁺

¹H NMR (400 MHz, acetone) δ ppm 9.00-9.27 (m, 1 H), 8.25 (s, 2 H), 8.14 (s, 1 H), 7.63-7.86 (m, 1 H), 7.33 (d, J=1.76 Hz, 1 H), 7.00-7.27 (m, 3 H), 6.91 (t, J=75.00 Hz, 1 H), 6.26-6.39 (m, 1 H), 4.06 (s, 2 H), 3.82-4.03 (m, 3 H), 3.66-3.77 (m, 1 H), 3.28-3.51 (m, 3 H), 2.88-3.00 (m, 2 H), 2.80-2.87 (m, 1 H), 2.35-2.47 (m, 1 H), 2.09 (m, 3 H), 1.19-1.36 (m, 1 H), 0.98-1.05 (m, 3 H), 0.60 (dd, J=8.16, 1.54 Hz, 2 H), 0.32-0.46 (m, 2 H).

The compounds listed in Table 16 were prepared with analogous synthetic steps and procedures to those described in Example 24, Scheme 24, Step 1-4 by reacting the appropriate precursors (commercially available or synthesized by a person skilled in the art) with suitable reagents. Specific variations in the experimentals or purification methods are indicated in the table.

TABLE 16

| Structure | Comp. | Salt Name | NMR characterization | MS/ESI⁺ [MH]⁺ | Amine |
|---|---|---|---|---|---|
| (structure shown) | 204 | No salt | ¹H NMR (400 MHz, acetone) δ ppm 9.75-9.95 (bs, 1 H), 9.15 (d, J = 2.20 Hz, 1 H), 8.24 (s, 2 H), 7.74-7.86 (m, 1 H), 7.33 (d, J = 1.76 Hz, 1 H), 7.12-7.23 (m, 3 H), 7.00 (t, J = 75.00 Hz, 1 H), 6.27-6.40 (m, 1 H), 4.07 (s, 3 H), 4.01 (dd, J = 6.62, 4.85 Hz, 2 H), 3.66-3.80 (m, 5 H), 3.36-3.49 (m, 1 H), 3.17 (d, J = 1.76 Hz, 2 H), 2.56-2.68 (m, 4 H), 1.22-1.35 (m, 1 H), 0.60 (dd, J = 7.94, 1.76 Hz, 2 H), 0.35-0.46 (m, 2 H). | 696 | (morpholine structure) |

TABLE 16-continued

| Structure | Comp. | Salt Name | NMR characterization | MS/ESI+ [MH]+ | Amine |
|---|---|---|---|---|---|
| 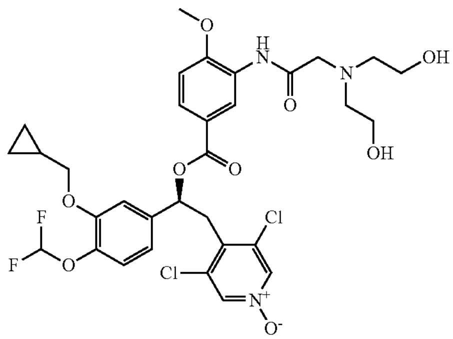 [SMILES: COc1ccc(C(=O)O[C@@H](Cc2c(Cl)c[n+]([O-])cc2Cl)c2ccc(OC(F)F)c(OCC3CC3)c2)cc1NC(=O)CN(CCO)CCO] | 205 | No Salt | ¹H NMR (400 MHz, acetone) δ ppm 9.74-9.95 (bs, 1 H), 8.91-9.17 (bs, 1 H), 8.11-8.36 (m, 2 H), 7.78 (m, 1 H), 7.31 (d, J = 1.76 Hz, 2 H), 7.17-7.22 (m, 1 H), 7.07-7.17 (m, 2 H), 6.91 (t, 1 H, CHF₂), 6.29-6.38 (m, 1 H), 3.94-4.08 (m, 5 H), 3.78-3.92 (m, 4 H), 3.70 (dd, J = 14.11, 9.26 Hz, 2 H), 3.38-3.49 (m, 2 H), 3.27-3.37 (m, 2 H), 2.94-2.80 (m, 2 H), 1.19-1.35 (m, 1 H), 0.49-0.69 (m, 2 H), 0.31-0.47 (m, 2 H). | 714.3 | HN(CH₂CH₂OH)₂ |
| 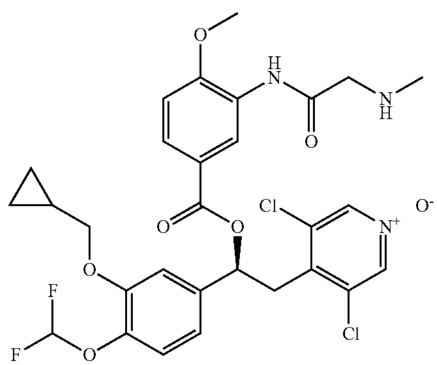 | 206 | No Salt | ¹H NMR (400 MHz, acetone) δ ppm 8.32 (s, 2H), 8.11-8.20 (m, 1 H), 7.71-7.85 (m, 1 H), 7.05-7.26 (m, 4 H), 6.90 (t, 1 H, CHF₂), 6.22-6.39 (m, 1 H), 3.91-4.06 (m, 3 H), 3.88 (s, 3 H), 3.61-3.79 (m, 1 H), 3.35-3.47 (m, 1 H), 3.31 (s, 2 H), 2.41 (s, 3 H), 1.27 (m, 1 H), 1.14 (m, 1 H), 0.51-0.66 (m, 2 H), 0.31-0.45 (m, 2 H). | 640.3 | NH₂Me |

Example 25

Synthesis of (S)-3,5-dichloro-4-(2-(3-(cyclopropyl-methoxy)-4-(difluoromethoxy) phenyl)-2-(3-(methylsulfonyloxy)-4-(2morpholinoethoxy)-benzoyloxy)ethyl)pyridine 1-oxide hydrochloride (Compound 207)

Scheme 25

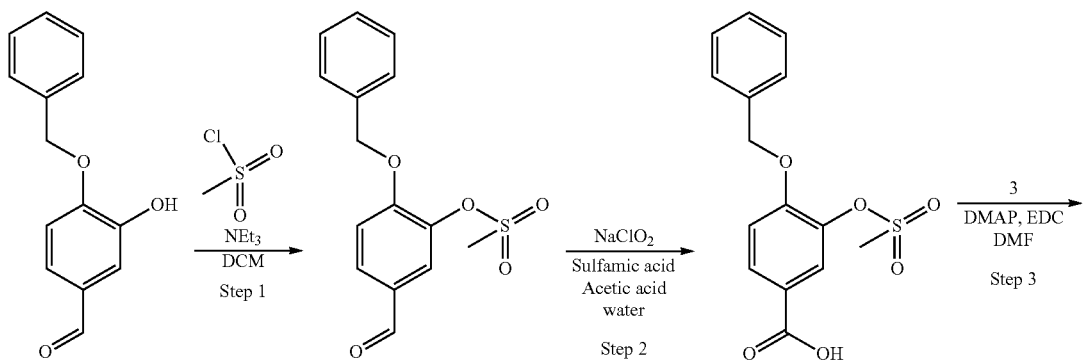

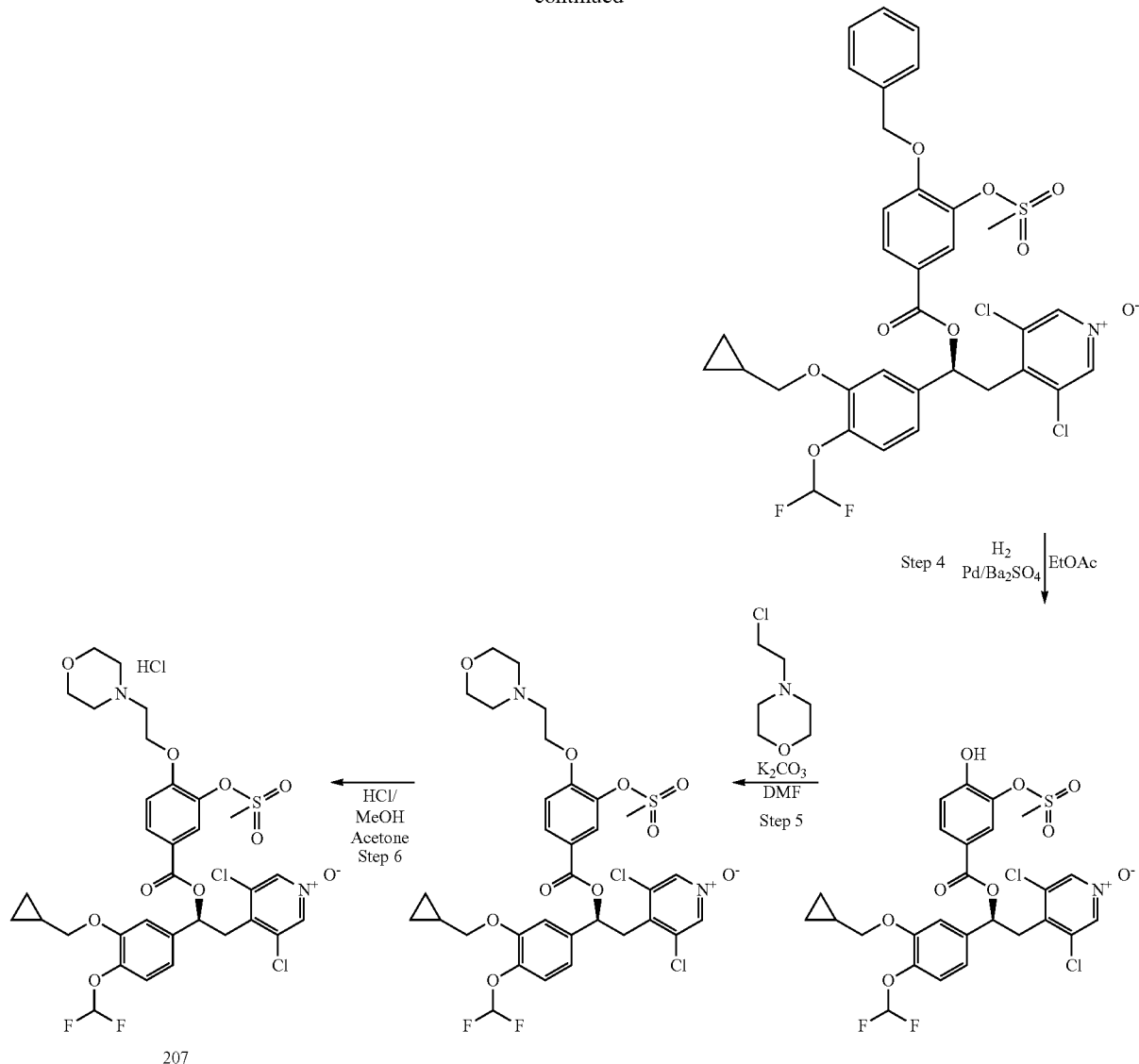

Step 1: Synthesis of 2-(benzyloxy)-5-formylphenyl methanesulfonate (212)

Title compound was obtained from 4-(benzyloxy)-3-hydroxybenzaldehyde following the procedure described in Example 13, Step 5 using methylsulfonyl chloride instead of 2-chloroethansulfonyl chloride.

Step 2: Synthesis of 4-(benzyloxy)-3-(methylsulfonyloxy)benzoic acid (211)

Title compound was obtained from 2-(benzyloxy)-5-formylphenyl methanesulfonate following the procedure described in Example 13, Step 2.

Step 3: Synthesis of (S)-4-(2-(4-(benzyloxy)-3-(methylsulfonyloxy)benzoyloxy)-2-(3-(cyclopropylmethoxy)-4-(difluoromethoxy)phenyl)ethyl)-3,5-dichloropyridine 1-oxide (210)

Compound 3 (1.5 g, 3.6 mmol) and 4-(benzyloxy)-3-(methylsulfonyloxy)benzoic acid (1.5 g, 4.7 mmol) were dissolved in DMF (10 ml), then EDC (2.1 g, 10.8 mmol) and DMAP (484 mg, 4 mmol) were added. The mixture was stirred at RT for 2 hours, then quenched by adding water. The precipitate was filtered and then dissolved in AcOEt. The organic phase was washed with HCl 1N (2×), NaHCO$_3$ saturated solution (2×) and brine, dried over Na$_2$SO$_4$ and evaporated under vacuum. The crude was crystallized from EtOH to yield 1.8 g of the desired compound (Yield: 69%).

MS/ESI$^+$ 724.55 [MH]$^+$ $^1$H NMR (400 MHz, CHLOROFORM-d) δ ppm 8.16 (s, 2 H), 8.01 (d, J=1.96 Hz, 1 H), 7.93 (dd, J=8.61, 1.96 Hz, 1 H), 7.34-7.49 (m, 5 H), 7.18 (d, J=8.61 Hz, 1 H), 7.10 (d, J=9.00 Hz, 1 H), 6.98-7.06 (m, 2 H), 6.38-6.63-6.85 (t, 1 H, CHF$_2$), 6.24 (dd, J=9.98, 4.11 Hz, 1 H), 5.20 (s, 2 H), 3.91 (dd, J=6.85, 4.89 Hz, 2 H), 3.69 (dd, J=14.09, 10.17 Hz, 1 H), 3.31 (dd, J=14.09, 4.30 Hz, 1 H), 3.10 (s, 3 H), 1.28 (d, J=7.04 Hz, 1 H), 0.59-0.73 (m, 2 H), 0.34-0.45 (m, 2 H).

Step 4: Synthesis of (S)-3,5-dichloro-4-(2-(3-(cyclopropylmethoxy)-4-(difluoromethoxy)phenyl)-2-(4-hydroxy-3-(methylsulfonyloxy)benzoyloxy)ethyl)pyridine 1-oxide (209)

(S)-4-(2-(4-(benzyloxy)-3-(methylsulfonyloxy)benzoyloxy)-2-(3-(cyclopropylmethoxy)-4-(difluoromethoxy)phenyl)ethyl)-3,5-dichloropyridine 1-oxide (1.8 g, 2.5 mmol) was dissolved in ethyl acetate (50 ml), and 5% Pd/Ba$_2$SO$_4$ (5.85 g, 2.75 mmol) was added and the mixture was hydrogenated in a Parr apparatus (H$_2$: 30 psi) for 1 hour. The catalyst was filtered over a celite pad, and the solvent was evaporated under vacuum, to yield 1.5 g of crude that was used for the next step without any further purification.

MS/ESI$^+$ 634.43 [MH]$^+$ $^1$H NMR (400 MHz, acetone) δ ppm 10.08 (bs, 1 H0, 8.19 (s, 2 H), 8.01 (d, J=2.20 Hz, 1 H), 7.90 (dd, J=8.38, 1.76 Hz, 1 H), 7.30 (d, J=1.76 Hz, 1 H), 7.13-7.23 (m, 3 H), 6.91 (t, J=75.00 Hz, 1 H), 6.31 (dd, J=9.70, 4.41 Hz, 1 H), 3.91-4.03 (m, 2 H), 3.74 (dd, J=14.11, 9.70 Hz, 1 H), 3.43 (dd, J=14.11, 4.41 Hz, 1 H), 3.34 (s, 3 H), 1.22-1.36 (m, 1H), 0.52-0.66 (m, 2 H), 0.31-0.45 (m, 2 H).

Step 5: Synthesis of (S)-3,5-dichloro-4-(2-(3-(cyclopropylmethoxy)-4-(difluoromethoxy)-phenyl)-2-(3-(methylsulfonyloxy)-4-(2morpholinoethoxy)benzoyloxy)ethyl)pyridine 1-oxide (208)

(S)-3,5-dichloro-4-(2-(3-(cyclopropylmethoxy)-4-(difluoromethoxy)phenyl)-2-(4-hydroxy-3-(methylsulfonyloxy)benzoyloxy)ethyl)pyridine 1-oxide (1.5 g, 2.4 mmol) was dissolved in DMF (10 ml), then 4-(2-chloroethyl)morpholine (1.1 g, 7.2 mmol) and K$_2$CO$_3$ (431 mg, 3.12 mmol) were added and the mixture was stirred at 40° C. for 4 hours. The reaction was quenched with water, and the precipitate was filtered and dissolved in Ethyl Acetate (50 ml). The organic phase was washed with HCl 1N (4.8 ml, 4.8 mmol), water (50 ml), NaHCO$_3$ saturated solution (50 ml) and NaCl saturated solution, dried over Na$_2$SO$_4$ and evaporated under vacuum to yield 1.8 g of crude that was used for the next step without any further purification.

Step 6: Synthesis of (S)-3,5-dichloro-4-(2-(3-(cyclopropylmethoxy)-4-(difluoromethoxy)-phenyl)-2-(3-(methylsulfonyloxy)-4-(2morpholinoethoxy)benzoyloxy)ethyl)pyridine 1-oxide hydrochloride (207)

(S)-3,5-dichloro-4-(2-(3-(cyclopropylmethoxy)-4-(difluoromethoxy)phenyl)-2-(3-(methylsulfonyloxy)-4-(2morpholinoethoxy)benzoyloxy)ethyl)pyridine 1-oxide was dissolved in Acetone, and HCl/MeOH 7M (343 μl, 2.5 mmol) was added. The solvent was evaporated and the salt obtained was dissolved in CHCl$_3$ and dropped in Et$_2$O (200 ml). The precipitate was filtered to yield 1.4 g of the final compound (Yield: 78%).

MS/ESI$^+$ 747.3 [MH]$^+$ $^1$H NMR (400 MHz, acetone) δ ppm 13.86-14.37 (bs, 1 H), 8.25 (s, 2 H), 8.06 (dd, J=8.60, 1.98 Hz, 1 H), 8.01 (d, J=2.21 Hz, 1 H), 7.41 (d, J=8.82 Hz, 1 H), 7.32 (d, J=1.76 Hz, 1 H), 7.13-7.24 (m, 2 H), 6.91 (t, J=75.00 Hz, 1 H), 6.32 (dd, J=9.70, 4.41 Hz, 1 H), 4.89 (t, J=4.63 Hz, 2 H), 4.15 (d, J=11.91 Hz, 2 H), 3.88-4.05 (m, 4 H), 3.52-3.82 (m, 5 H), 3.36-3.49 (m, 4 H), 3.30 (d, J=9.26 Hz, 2 H), 1.27 (m, 1 H), 0.60 (dd, J=7.94, 1.32 Hz, 2 H), 0.29-0.47 (m, 2 H).

The compound listed in Table 17 was prepared with analogous synthetic steps and procedures to that described in Example 25, Scheme 25, Steps 1-5 by reacting the appropriate precursors (commercially available or synthesized by a person skilled in the art) with suitable reagents. Specific variations in the experimentals or purification methods are indicated in the table.

TABLE 17

| Structure | Compound | Salt Name | Name | NMR characterization and MS/ESI+ [MH]+ | Alkylating agent | Alcohol |
|---|---|---|---|---|---|---|
| [structure shown] | 213 | No salt | | ¹H NMR (400 MHz, acetone) δ ppm 8.63 (d, J = 3.97 Hz, 2 H), 8.25 (s, 2 H), 7.97-8.08 (m, 2 H), 7.55 (d, J = 5.29 Hz, 2 H), 7.28-7.40 (m, 2 H), 7.12-7.24 (m, 2 H), 6.70-6.90-7.11 (t, 1 H, CHF₂), 6.31 (dd, J = 9.70, 4.41 Hz, 1 H), 5.45 (s, 2 H), 3.89-4.06 (m, 2 H), 3.75 (dd, J = 14.11, 9.70 Hz, 1 H), 3.43 (dd, J = 14.33, 4.63 Hz, 1 H), 3.35 (s, 3 H), 1.23-1.38 (m, 1 H), 0.51-0.66 (m, 2 H), 0.38 (q, J = 4.85 Hz, 2 H). [MH]+ 725.541 | [structure shown] | [structure shown] |

TABLE 17-continued

| Compound | Salt Name | NMR characterization and MS/ESI+ [MH]+ | Alkylating agent | Alcohol |
|---|---|---|---|---|
| 214 | Methane-sulfonate | 1H NMR (400 MHz, DMSO-d6) δ ppm 9.67-9.93 (bs, 1 H), 8.59 (s, 2 H), 7.92-8.03 (m, 1 H), 7.80-7.91 (m, 1 H), 7.35-7.49 (m, 1 H), 7.15-7.30 (m, 2 H), 7.02-7.13 (m, 2 H), 6.11-6.39 (m, 1 H), 4.42-4.63 (m, 2 H), 3.80-4.08 (m, 4 H), 3.59-3.77 (m, 5 H), 3.53 (d, J = 11.91 Hz, 2 H), 3.36-3.48 (m, 6 H), 2.27 (s, 3 H), 1.11-1.28 (m, 1 H), 0.47-0.63 (m, 2 H), 0.22-0.40 (m, 2 H) [MH]+ 730.99 | | |

Example 26

Synthesis of (S)-3,5-dichloro-4-(2-(3-(cyclopropyl-methoxy)-4-(difluoromethoxy)phenyl)-2-(4-methoxy-3-(2-(4-methylpiperazin-1-yl) ethylsulfonamido)benzoyloxy)ethyl)pyridine 1-oxide (215)

Scheme 26
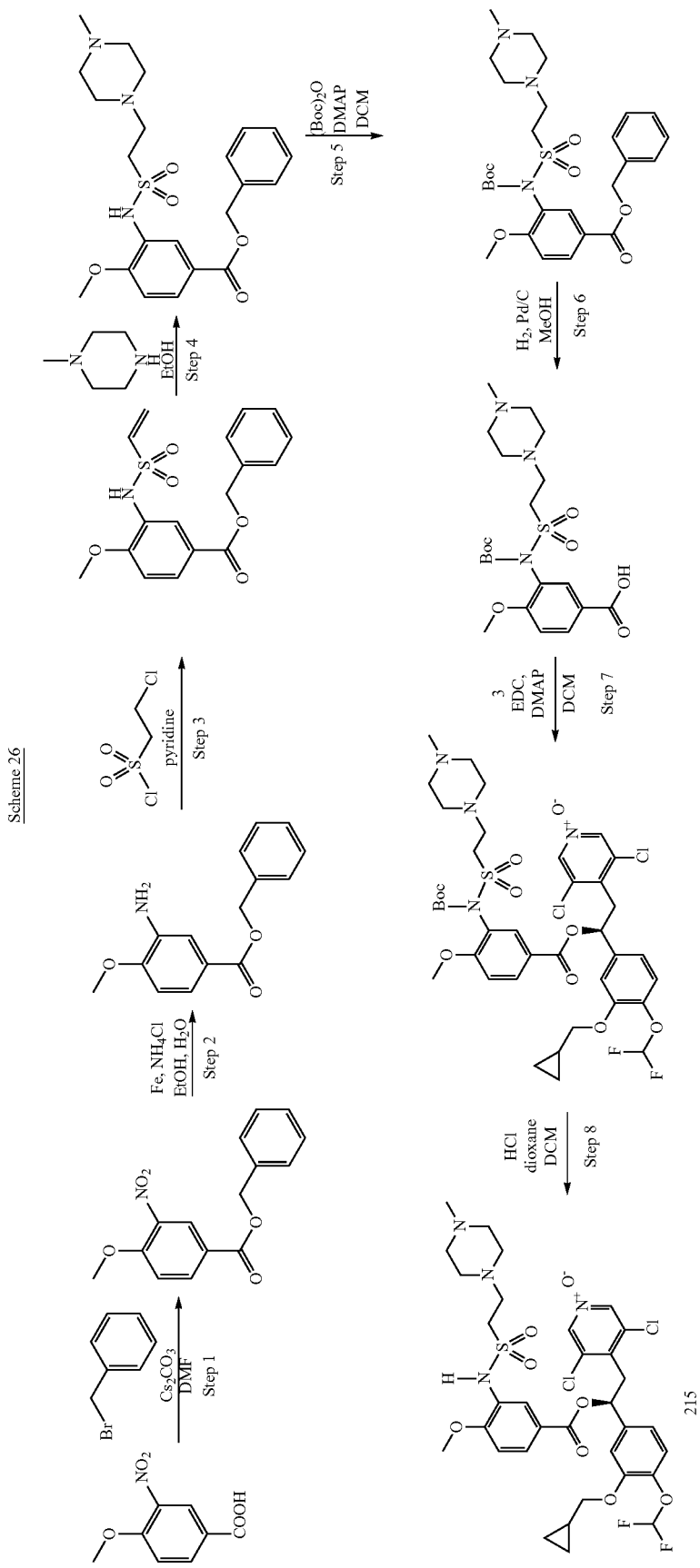

Step 1: Synthesis of benzyl 4-methoxy-3-nitrobenzoate (222)

To a solution of 4-methoxy-3-nitrobenzoic acid (1 g, 5.07 mmol) in dry DMF (50 ml), cesium carbonate (0.992 g, 3.04 mmol) was added and the mixture was stirred at RT for 1 hour. Benzyl bromide (0.724 ml, 6.09 mmol) was added and the reaction was stirred at RT for 2 hours. Additional cesium carbonate (0.413 g, 1.268 mmol) and benzyl bromide (0.302 ml, 2.54 mmol) were added stirring at the same temperature for 6 hours. The mixture was acidified with aq. 1M HCl and extracted twice with ethyl acetate. The combined organic layers were washed with brine, dried over $Na_2SO_4$ and evaporated to dryness. The crude was purified by flash chromatography on silica gel column (petroleum ether:ethyl acetate=95:5 to 80:20) affording benzyl 4-methoxy-3-nitrobenzoate as a white solid (1.450 g, 5.05 mmol, 100% yield).

Step 2: Synthesis of benzyl 3-amino-4-methoxybenzoate (221)

To a suspension of benzyl 4-methoxy-3-nitrobenzoate (1.450 g, 5.05 mmol) in ethanol (38 ml) and water (16 ml), ammonium chloride (0.189 g, 3.534 mmol) was added followed by iron powder (1.693 g, 30.29 mmol). The reaction was heated to 80° C. for 2.5 hours. The mixture was filtered and the filtrate was evaporated to dryness. The residue was dissolved in ethyl acetate and washed with water and brine; the organic phase was dried over $Na_2SO_4$ and the solvent was removed under vacuum affording benzyl 3-amino-4-fluorobenzoate as a yellow oil (1.0837 g, 83.3% yield). This product was used without any further purification. MS/ESI$^+$ 258.0 [MH]$^+$

Step 3: Synthesis of benzyl 4-methoxy-3-(vinylsulfonamido)benzoate (220)

A solution of benzyl 3-amino-4-methoxybenzoate (1.0837 g, 4.21 mmol) and pyridine (4.09 ml, 50.5 mmol) in DCM (55 ml) was cooled to 0° C. 2-Chloroethanesulfonyl chloride (0.528 ml, 5.05 mmol) was added and the reaction was stirred under nitrogen atmosphere at RT overnight. A second portion of 2-chloroethanesulfonyl chloride (0.220 ml, 2.106 mmol) was added and the mixture was stirred at the same temperature for additional 4 hours. The mixture was washed with aq. 1N HCl and brine; the organic phase was dried over $Na_2SO_4$ and evaporated to dryness.

The crude was purified by flash chromatography on silica gel column (petroleum ether:ethyl acetate=7:3) affording benzyl 4-methoxy-3-(vinylsulfonamido)benzoate as a pale yellow oil (1.1423 g, 78% yield). MS/ESI$^+$ 348.0 [MH]$^+$

Step 4: Synthesis of benzyl 4-methoxy-3-(2-(4-methylpiperazin-1-yl)ethylsulfonamido)benzoate (219)

To a solution of benzyl 4-methoxy-3-(vinylsulfonamido)benzoate (1.1423 g, 3.29 mmol) in ethanol (40 ml), N-methylpiperazine (0.548 ml, 4.93 mmol) was added and the mixture was stirred at RT overnight. The solvent was removed under vacuum and the residue was dissolved in ethyl acetate and washed with aq. $NaHCO_3$ and brine; the organic phase was dried over $Na_2SO_4$, the solvent was evaporated and the crude was purified by flash chromatography on silica gel column (DCM:MeOH=95:5) affording benzyl 4-methoxy-3-(2-(4-methylpiperazin-1-yl)ethylsulfonamido)benzoate as a yellow oil (1.38 g, 94% yield). MS/ESI$^+$ 448.1 [MH]$^+$

Step 5: Synthesis of benzyl 3-(N-(tert-butoxycarbonyl)-2-(4-methylpiperazin-1-yl)ethylsulfonamido)-4-methoxybenzoate (218)

To a solution of benzyl 4-methoxy-3-(2-(4-methylpiperazin-1-yl)ethylsulfonamido)benzoate (1.38 g, 3.08 mmol) in DCM (30 ml), DMAP (0.414 g, 3.39 mmol) and di-tert-butyl dicarbonate (0.740 g, 3.39 mmol) were added, and the mixture was stirred at RT for 4 hours. Additional DMAP (0.828 g, 6.79 mmol) and di-tert-butyl dicarbonate (1.48 g, 6.78 mmol) were added and stirring continued 24 hours at the same temperature. The mixture was washed with water, aq. 5% $NaHCO_3$ and brine; the organic phase was dried over $Na_2SO_4$ and evaporated to dryness affording benzyl 3-(N-(tert-butoxycarbonyl)-2-(4-methylpiperazin-1-yl)ethylsulfonamido)-4-methoxybenzoate as a white solid (1.680 g, 99% yield). This crude was used without any further purification. MS/ESI$^+$ 548.2 [MH]$^+$

Step 6: Synthesis of 3-(N-(tert-butoxycarbonyl)-2-(4-methylpiperazin-1-yl)ethylsulfonamido)-4-methoxybenzoic acid (217)

A mixture of benzyl 3-(N-(tert-butoxycarbonyl)-2-(4-methylpiperazin-1-yl)ethylsulfonamido)-4-methoxybenzoate (1.680 g, 3.07 mmol) and a catalytic amount of 10% Pd/C (suspended in 3 ml of water) in MeOH (25 ml) was hydrogenated in a Parr apparatus at 30 psi for 5 hours. The catalyst was filtered off and the solvent was evaporated to dryness affording 3-(N-(tert-butoxycarbonyl)-2-(4-methylpiperazin-1-yl)ethylsulfonamido)-4-methoxybenzoic acid as a yellow solid (1.400 g, 100% yield). This product was used for the next step without purification. MS/ESI$^+$ 458.1 [MH]$^+$

Step 7: Synthesis of (S)-4-(2-(3-(N-(tert-butoxycarbonyl)-2-(4-methylpiperazin-1-yl)ethylsulfonamido)-4-methoxybenzoyloxy)-2-(3-(cyclopropylmethoxy)-4-(difluoromethoxy)phenyl)ethyl)-3,5-dichloropyridine 1-oxide (216)

A mixture of 3-(N-(tert-butoxycarbonyl)-2-(4-methylpiperazin-1-yl)ethylsulfonamido)-4-methoxybenzoic acid (0.4 g, 0.874 mmol), compound 3 (0.334 g, 0.795 mmol), EDC (0.457 g, 2.384 mmol) and DMAP (0.146 g, 1.192 mmol) in DCM (30 ml) was stirred at RT for 4 hours The mixture was washed with water, aq. $NaHCO_3$ and brine; the organic phase was dried over $Na_2SO_4$ and the solvent was removed under vacuum. The residue was purified by flash chromatography on silica gel column (DCM:MeOH=98:2) affording (S)-4-(2-(3-(N-(tert-butoxycarbonyl)-2-(4-methylpiperazin-1-yl)ethylsulfonamido)-4-methoxybenzoyloxy)-2-(3-(cyclopropylmethoxy)-4-(difluoromethoxy)phenyl)ethyl)-3,5-dichloropyridine 1-oxide as a white solid (0.261 g, 38.2% yield). MS/ESI$^+$ 859.3 [MH]$^+$

Step 8: Synthesis of (S)-3,5-dichloro-4-(2-(3-(cyclopropylmethoxy)-4-(difluoromethoxy)phenyl)-2-(4-methoxy-3-(2-(4-methylpiperazin-1-yl)ethylsulfonamido)benzoyloxy)ethyl)pyridine 1-oxide (215)

To a solution of (S)-4-(2-(3-(N-(tert-butoxycarbonyl)-2-(4-methylpiperazin-1-yl)ethylsulfonamido)-4-methoxybenzoyloxy)-2-(3-(cyclopropylmethoxy)-4-(difluoromethoxy)phenyl)ethyl)-3,5-dichloropyridine 1-oxide (0.261 g, 0.304 mmol) in DCM (20 ml), 4M HCl in dioxane (1.518 ml, 6.07 mmol) was added and the reaction was stirred at RT overnight. The volatiles were removed under vacuum and the residue was treated with aq. $NaHCO_3$ and extracted twice with ethyl acetate. The combined organic layers were washed with brine, dried over $Na_2SO_3$ and evaporated to dryness. The crude was purified by flash chromatography on silica gel column (DCM:MeOH=98:2 to 90:10) affording (S)-3,5-dichloro-4-(2-(3-(cyclopropylmethoxy)-4-(difluoromethoxy)phenyl)-2-(4-methoxy-3-(2-(4-methylpiperazin-1-yl)ethylsulfonamido)benzoyloxy)ethyl)pyridine 1-oxide as an off-white foam (0.0703 g, 30.5% yield). MS/ESI+ 759.41 [MH]+. $[\alpha]_D^{20}$=−54.06 (c=0.33, MeOH)

$^1$H NMR (300 MHz, DMSO-d$_6$) δ ppm 9.14 (br. s., 1 H), 8.53 (s, 2 H), 7.96 (d, 1 H), 7.82 (dd, 1 H), 7.14-7.24 (m, 3 H), 7.00-7.08 (m, 1 H), 7.06 (t, 1 H), 6.20 (dd, 1 H), 3.92-4.00 (m, 2 H), 3.91 (s, 3 H), 3.59 (dd, 1 H), 3.33 (dd, 1 H), 3.19-3.27 (m, 2 H), 2.67-2.78 (m, 2 H), 2.30-2.43 (m, 4 H), 2.17-2.30 (m, 4 H), 2.11 (s, 3 H), 1.09-1.30 (m, 1 H), 0.50-0.65 (m, 2 H), 0.26-0.46 (m, 2 H)

The compounds listed in Table 18 were prepared with analogous synthetic steps and procedures to those described in Example 26 by reacting the appropriate precursors (commercially available or synthesized by a person skilled in the art) with suitable reagents. Specific variations in the experimentals or purification methods are indicated in the table.

TABLE 18

| Structure | Comp. | Salt Name | NMR characterization | MS/ESI+ [MH]+ | Amine | Carboxylic acid |
|---|---|---|---|---|---|---|
| 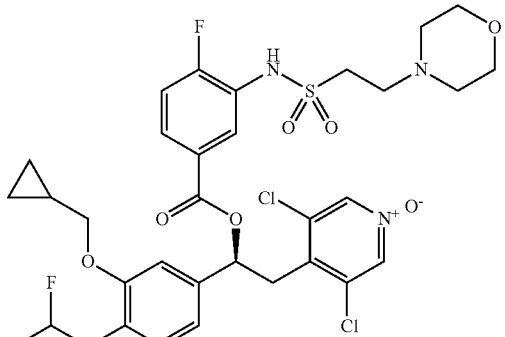 | 223 | No salt | $^1$H NMR (300 MHz, DMSO-d$_6$) δ ppm 9.93 (br. s., 1 H), 8.53 (s, 2 H), 8.08 (dd, 1 H), 7.84 (ddd, 1 H), 7.44 (dd, 1 H), 7.17-7.23 (m, 2 H), 7.06 (dd, 1 H), 7.07 (t, 1 H), 6.21 (dd, 1 H), 3.93 (d, 2 H), 3.61 (dd, 1 H), 3.43-3.51 (m, 4 H), 3.31-3.40 (m, 3 H), 2.67-2.82 (m, 2 H), 2.31-2.39 (m, 4 H), 1.06-1.33 (m, 1 H), 0.50-0.63 (m, 2 H), 0.28-0.39 (m, 2 H) | 734.46 | 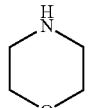 | 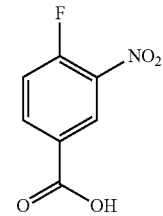 [SMILES: O=C(O)c1ccc(F)c([N+](=O)[O-])c1] |
| 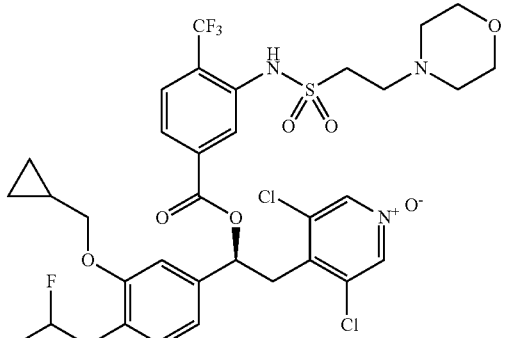 | 224 | No salt | $^1$H NMR (300 MHz, DMSO-d$_6$) δ ppm 8.54 (s, 2 H), 8.12 (s, 1 H), 7.78 (br. s., 1 H), 7.14-7.27 (m, 3 H), 6.94-7.14 (m, 2 H), 7.07 (t, 1 H), 6.20-6.25 (m, 1 H), 3.94 (d, 2 H), 3.64 (d, 2 H), 3.51-3.58 (m, 5 H), 3.35-3.43 (m, 4 H), 2.86 (t, 3 H), 1.18-1.25 (m, 1 H), 0.57 (dd, 2 H), 0.36 (d, 2 H) | 784.13 | 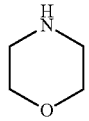 | 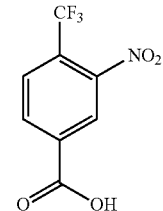 [SMILES: O=C(O)c1ccc(C(F)(F)F)c([N+](=O)[O-])c1] |

Example 27

Synthesis of S)-3,5-dichloro-4-(2-(3-(cyclopropylmethoxy)-4-(difluoromethoxy)phenyl)-2-(3-(2-hydroxyethoxy)-4-(N-(2-morpholinoethyl) methylsulfonamido)benzoyloxy)ethyl)pyridine 1-oxide (Compound 225)

Scheme 27
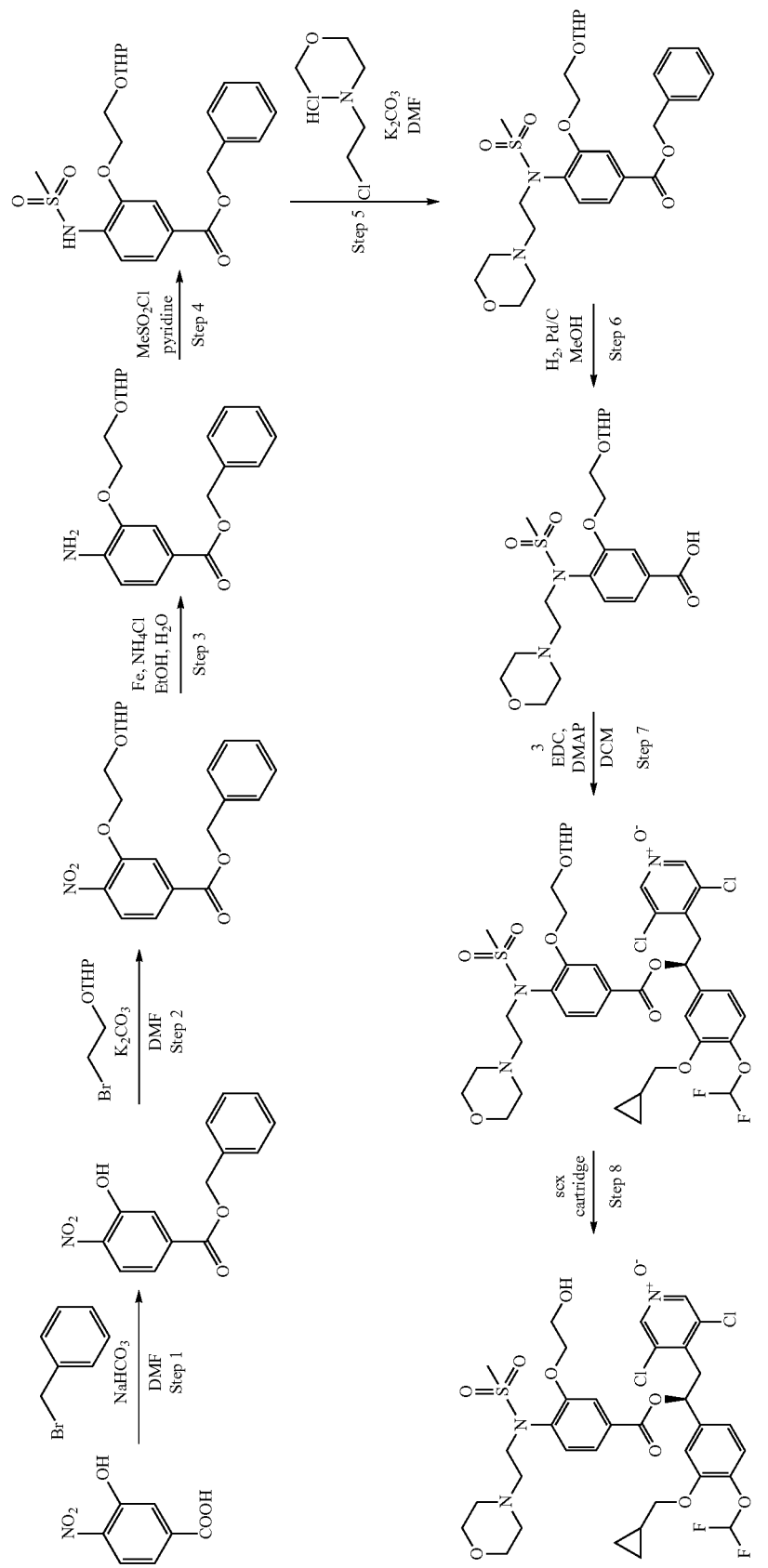

Step 1: Synthesis of benzyl 3-hydroxy-4-nitrobenzoate (232)

To a solution of 3-hydroxy-4-nitrobenzoic acid (1.1 g, 5.976 mmol) in dry DMF (55 ml), sodium bicarbonate (0.606 g, 7.205 mmol) was added and the mixture was stirred at RT for 45 minutes. Benzyl bromide (0.857 ml, 7.22205 mmol) was added and the reaction was heated to 50° C. for 5 hours. A second portion of sodium bicarbonate (0.115 g, 1.365 mmol) and benzyl bromide (0.162 ml, 1.365 mmol) was added and the reaction was heated to 50° C. for 1 additional hour and left at RT overnight. Aq. 1N HCl was added and the mixture was extracted twice with ethyl acetate. The combined organic layers were washed with brine, dried over $Na_2SO_4$ and evaporated to dryness. The crude was purified by flash chromatography on silica gel column (petroleum ether:ethyl acetate=98:2) affording benzyl 3-hydroxy-4-nitrobenzoate as a yellow solid (1.600 g, 100% yield).

Step 2: Synthesis of benzyl 4-nitro-3-(2-(tetrahydro-2H-pyran-2-yloxy)ethoxy)benzoate (231)

To a solution of benzyl 3-hydroxy-4-nitrobenzoate (1.6 g, 5.86 mmol) in dry DMF (50 ml), 2-(2-bromoethoxy)tetrahydro-2H-pyran (1.238 ml, 8.20 mmol) and $K_2CO_3$ (1.133 g, 8.20 mmol) were added and the reaction was heated to 100° C. for 48 hours. A second portion of 2-(2-bromoethoxy)tetrahydro-2H-pyran (0.442 ml, 2.93 mmol) and $K_2CO_3$ (0.405 g, 2.93 mmol) was added and the mixture was stirred at 100° C. for additional 6 hours The reaction mixture was diluted with 1N HCl and extracted several times with ethyl acetate. The combined organic layers were washed with brine, dried over $Na_2SO_4$ and evaporated to dryness. The residue was purified by flash chromatography on silica gel column (petroleum ether:ethyl acetate=95:5 to 90:10) affording benzyl 4-nitro-3-(2-(tetrahydro-2H-pyran-2-yloxy)ethoxy)benzoate as a yellow oil (0.7884 g, 33.5% yield). MS/ESI$^+$ 424.0 [MNa]$^+$

Step 3: Synthesis of benzyl 4-amino-3-(2-(tetrahydro-2H-pyran-2-yloxy)ethoxy)benzoate (230)

To a suspension of benzyl 4-nitro-3-(2-(tetrahydro-2H-pyran-2-yloxy)ethoxy)benzoate (0.707 g, 1.761 mmol) in ethanol (15 ml) and water (7 ml), ammonium chloride (0.066 g, 1.233 mmol) was added followed by iron powder (0.590 g, 10.57 mmol). The resulting mixture was heated to 80° C. for 2 hours, cooled to RT and filtered. The filtrate was evaporated to dryness and the residue was dissolved in ethyl acetate and washed with water and brine. The organic phase was dried over $Na_2SO_4$ and the solvent was removed under vacuum affording benzyl 4-amino-3-(2-(tetrahydro-2H-pyran-2-yloxy)ethoxy)benzoate as a yellow oil (0.652 g, 100% yield). This product was used without any further purification. MS/ESI$^+$ 372.1 [MNa]$^+$

Step 4: Synthesis of benzyl 4-(methylsulfonamido)-3-(2-(tetrahydro-2H-pyran-2-yloxy)ethoxy)benzoate (229)

A solution of benzyl 4-amino-3-(2-(tetrahydro-2H-pyran-2-yloxy)ethoxy)benzoate (0.652 g, 1.755 mmol) in pyridine (20 ml) was cooled to 0° C. and methanesulfonyl chloride (0.150 ml, 1.931 mmol) was added. The reaction was stirred at RT overnight and heated to 50° C. for 2 hours. After cooling to RT, additional methanesulfonyl chloride (0.232 ml, 2.984 mmol) was added over 24 hours. The solvent was removed under vacuum and the residue was dissolved in ethyl acetate and washed with aq. 1N HCl and then with brine. The organic layer was dried over $Na_2SO_4$ and evaporated to dryness. The crude was purified by flash chromatography on silica gel column (petroleum ether:ethyl acetate=75:25) affording benzyl 4-(methylsulfonamido)-3-(2-(tetrahydro-2H-pyran-2-yloxy)ethoxy)benzoate as a yellow oil (0.720 g, 91% yield). MS/ESI$^+$ 472.0 [MNa]$^+$

Step 5: Synthesis of benzyl 4-(N-(2-morpholinoethyl)methylsulfonamido)-3-(2-(tetrahydro-2H-pyran-2-yloxy)ethoxy)benzoate (228)

To a solution of benzyl 4-(methylsulfonamido)-3-(2-(tetrahydro-2H-pyran-2-yloxy)ethoxy)benzoate (0.720 g, 1.602 mmol) in DMF (25 ml), $K_2CO_3$ (0.531 g, 3.84 mmol) and 4-(2-chloroethyl)morpholine hydrochloride (0.358 g, 1.922 mmol) were added. The reaction mixture was heated to 70° C. for 5 hours and to 80° C. for 1 hour. The mixture was partitioned between ethyl acetate and water; the organic phase was washed with brine, dried over $Na_2SO_3$ and evaporated to dryness. The crude was purified by flash chromatography on silica gel column (100% ethyl acetate) affording benzyl 4-(N-(2-morpholinoethyl)methylsulfonamido)-3-(2-(tetrahydro-2H-pyran-2-yloxy)ethoxy)benzoate as a yellow oil (0.680 g, 75% yield). MS/ESI$^+$ 563.2 [MH]$^+$

Step 6: Synthesis of 4-(N-(2-morpholinoethyl)methylsulfonamido)-3-(2-(tetrahydro-2H-pyran-2-yloxy)ethoxy)benzoic acid (227)

A mixture of benzyl 4-(N-(2-morpholinoethyl)methylsulfonamido)-3-(2-(tetrahydro-2H-pyran-2-yloxy)ethoxy)benzoate (0.680 g, 1.209 mmol) and a suspension in water (2 ml) of 10% w/w Pd/C (0.643 g, 0.604 mmol) in methanol (15 ml) was hydrogenated in a Parr apparatus at 30 psi for 3.5 hours. The catalyst was filtered off and the filtrate was evaporated to dryness affording 4-(N-(2-morpholinoethyl)-methylsulfonamido)-3-(2-(tetrahydro-2H-pyran-2-yloxy)ethoxy)benzoic acid as a pale red oil (0.428 g, 74.9% yield). This product was used without any further purification. MS/ESI$^+$ 473.1 [MH]$^+$

Step 7: Synthesis of 3,5-dichloro-4-((2S)-2-(3-(cyclopropylmethoxy)-4-(difluoromethoxy)phenyl)-2-(4-(N-(2-morpholinoethyl)methylsulfonamido)-3-(2-(tetrahydro-2H-pyran-2-yloxy)ethoxy)benzoyloxy)ethyl)pyridine 1-oxide (226)

A mixture of 4-(N-(2-morpholinoethyl)methylsulfonamido)-3-(2-(tetrahydro-2H-pyran-2-yloxy)ethoxy)benzoic acid (0.428 g, 0.906 mmol), (S)-3,5-dichloro-4-(2-(3-(cyclopropylmethoxy)-4-(difluoromethoxy)phenyl)-2-hydroxyethyl)pyridine 1-oxide (0.346 g, 0.823 mmol), EDC (0.474 g, 2.470 mmol) and DMAP (0.151 g, 1.235 mmol) in DCM (20 ml) was stirred at RT for 4 hours. The reaction mixture was washed with aq. $NH_4Cl$ sat. sol., aq. $NaHCO_3$ and brine; the organic phase was dried over $Na_2SO_4$ and the solvent was removed under vacuum. This crude was filtered through a silica gel cartridge (DCM:MeOH=99:1) affording the title compound as a white foam (0.566 g, 79% yield). MS/ESI$^+$ 874.2 [MH]$^+$

Step 8: Synthesis of (S)-3,5-dichloro-4-(2-(3-(cyclopropylmethoxy)-4-(difluoromethoxy)phenyl)-2-(3-(2-hydroxyethoxy)-4-(N-(2-morpholinoethyl)methylsulfonamido)benzoyloxy)ethyl)pyridine 1-oxide (225)

3,5-Dichloro-4-((2S)-2-(3-(cyclopropylmethoxy)-4-(difluoromethoxy)phenyl)-2-(4-(N-(2-morpholinoethyl)methylsulfonamido)-3-(2-(tetrahydro-2H-pyran-2-yloxy)ethoxy) benzoyloxy) ethyl)pyridine 1-oxide (0.250 g, 0.286 mmol) was loaded on a scx cartridge eluting first with DCM:MeOH=1:1 and then with MeOH:aq. 32% NH$_4$OH=9:1. The volatiles were removed under vacuum and the residue was purified by flash chromatography on silica gel column (DCM:MeOH=99:1 to 95:5) affording (S)-3,5-dichloro-4-(2-(3-(cyclopropylmethoxy)-4-(difluoromethoxy)phenyl)-2-(3-(2-hydroxyethoxy)-4-(N-(2-morpholinoethyl)methyl sulfonamido)benzoyloxy)ethyl)pyridine 1-oxide as a white foam (0.113 g, 50.0% yield).MS/ESI$^+$ 790.53 [MH]$^+$. [α]$_D^{20}$=−44.63, c=0.32, MeOH $^1$H NMR (300 MHz, DMSO-d$_6$) δ ppm 8.56 (s, 2 H), 7.58 (d, 1 H), 7.58 (dd, 1 H), 7.40 (d, 1 H), 7.24 (d, 1 H), 7.20 (d, 1 H), 7.09 (dd, 1 H), 7.06 (t, 1 H), 6.19 (dd, 1 H), 4.88 (t, 1 H), 4.05-4.26 (m, 2 H), 3.94 (d, 2 H), 3.79 (q, 2 H), 3.69 (t, 2 H), 3.64 (dd, 1 H), 3.39-3.46 (m, 4 H), 3.35 (dd, 1 H), 3.08 (s, 3 H), 2.32 (t, 2 H), 2.16-2.29 (m, 4 H), 1.10-1.32 (m, 1 H), 0.48-0.66 (m, 2 H), 0.23-0.46 (m, 2 H)

Example 28

Synthesis of (S)-3,5-dichloro-4-(2-(3-(cyclopropylmethoxy)-4-(difluoromethoxy)phenyl)-2-(3-(methylsulfonyloxy)-4-(morpholinomethyl)-benzoyloxy)ethyl)pyridine 1-oxide (Compound 233)

Scheme 28

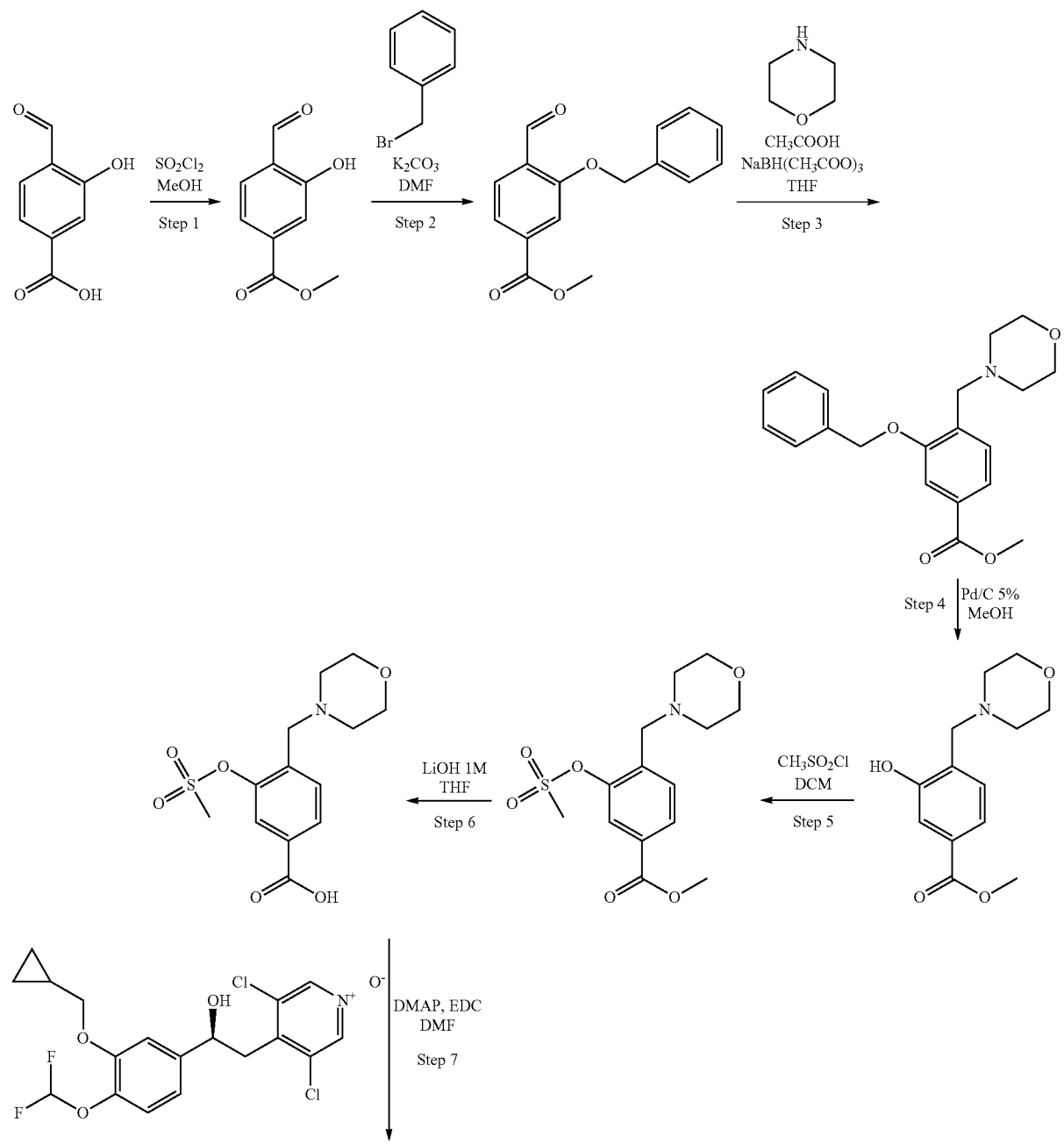

-continued

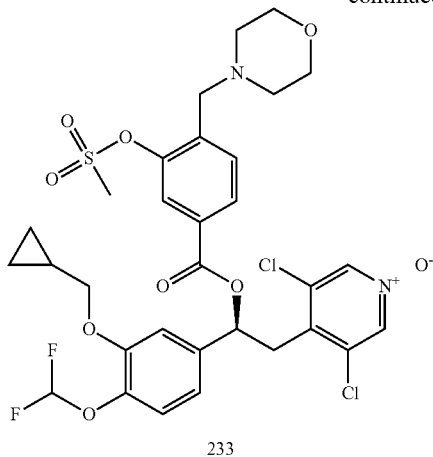

233

Step 1: Synthesis of methyl 4-formyl-3-hydroxybenzoate (239)

4-Formyl-3-hydroxybenzoic acid (1.2 g, 7.22 mmol) was dissolved in MeOH (10 ml). SOCl2 (1.054 ml, 14.45 mmol) was added, and the reaction was stirred at 60° C. for 3 hours to achieve completion. The reaction mixture was concentrated, and the crude was triturated in Hexane and filtered to give methyl 4-formyl-3-hydroxybenzoate (1.3 g, 7.22 mmol, 100% yield). MS/ESI⁺ 181.04 [MH]⁺

Step 2: Synthesis of methyl 3-(benzyloxy)-4-formylbenzoate (238)

Methyl 4-formyl-3-hydroxybenzoate (312 mg, 1.732 mmol) was dissolved in DMF (3 ml). (Bromomethyl)benzene (592 mg, 3.46 mmol) and K2CO3 (359 mg, 2.60 mmol) were added, and the reaction was stirred at RT for 3 days to achieve completion. The reaction mixture was diluted with water and the precipitate was filtered, dissolved in Ethyl Acetate and washed with water (2×). The organic phase was dried over Na2SO4 and concentrated under vacuum to give methyl 3-(benzyloxy)-4-formylbenzoate (423 mg, 1.565 mmol, 90% yield). MS/ESI⁺ 271.09 [MH]⁺

Step 3: Synthesis of methyl 3-(benzyloxy)-4-(morpholinomethyl)benzoate (237)

Methyl 3-(benzyloxy)-4-formylbenzoate (423 mg, 1.565 mmol) was dissolved in THF dry (3.5 ml). Morpholine (205 mg, 2.348 mmol) and acetic acid (141 mg, 2.348 mmol) were added, and the mixture was stirred at RT for 30'. Sodium triacetoxyhydroborate (498 mg, 2.348 mmol) was added, and the mixture was stirred at RT for 2 hours to achieve completion. The reaction mixture was diluted with Water and extracted with ethyl acetate. The organic phase was washed with NaHCO3 sat. sol., water and brine, dried over Na2SO4 and concentrated under vacuum to give methyl 3-(benzyloxy)-4-(morpholinomethyl)benzoate (491 mg, 1.438 mmol, 92% yield). MS/ESI⁺342.17 [MH]⁺

Step 4: Synthesis of methyl 3-hydroxy-4-(morpholinomethyl)benzoate (236)

Methyl 3-(benzyloxy)-4-(morpholinomethyl)benzoate (491 mg, 1.438 mmol) was dissolved in MeOH (20 ml) and then Pd/C 5% (306 mg, 2.88 mmol) was added. The solution was shaken under hydrogen atmosphere (35 psi) on a Parr apparatus for 1 hour. The catalyst was filtered off and the solvent removed under vacuum to give methyl 3-hydroxy-4-(morpholinomethyl)benzoate (317 mg, 1.262 mmol, 88% yield). MS/ESI⁺252.12 [MH]⁺

Step 5: Synthesis of methyl 3-(methylsulfonyloxy)-4-(morpholinomethyl)benzoate (235)

Methyl 3-hydroxy-4-(morpholinomethyl)benzoate (317 mg, 1.262 mmol) was dissolved in DCM (10 ml). Methanesulfonyl chloride (217 mg, 1.892 mmol) and TEA (191 mg, 1.892 mmol) were added, and the reaction was stirred at RT for 1 hour to achieve completion. The reaction mixture was diluted with DCM and extracted with water (2×), brine, dried over Na2SO4 and concentrated under vacuum to give methyl 3-(methylsulfonyloxy)-4-(morpholinomethyl)benzoate (420 mg, 1.275 mmol, 101% yield).
MS/ESI⁺ 330.10 [MH]⁺

Step 6: Synthesis of 3-(methylsulfonyloxy)-4-(morpholinomethyl)benzoic acid (234)

Methyl 3-(methylsulfonyloxy)-4-(morpholinomethyl)benzoate (420 mg, 1.275 mmol) was dissolved in THF (6 ml). LiOH 1M (2.5 ml, 1.275 mmol) was added, and the reaction was stirred at RT overnight to achieve completion. The reaction mixture was diluted with HCl 1N until neutralisation and concentrated under vacuum to give 3-(methylsulfonyloxy)-4-(morpholinomethyl)benzoic acid (400 mg, 1.268 mmol, 99% yield). MS/ESI⁺ 316.08 [MH]⁺

Step 7: Synthesis of (S)-3,5-dichloro-4-(2-(3-(cyclopropylmethoxy)-4-(difluoromethoxy)-phenyl)-2-(3-(methylsulfonyloxy)-4-(morpholinomethyl)benzoyloxy)ethyl)pyridine 1-oxide (233)

(S)-3,5-dichloro-4-(2-(3-(cyclopropylmethoxy)-4-(difluoromethoxy)phenyl)-2-hydroxyethyl)pyridine 1-oxide (60 mg, 0.143 mmol), 3-(methylsulfonyloxy)-4-(morpholinomethyl)benzoic acid (400 mg, 1.268 mmol), N,N-dimethylpyridin-4-amine (20.93 mg, 0.171 mmol) and N1-((ethylimino)methylene)-N3,N3-dimethylpropane-1,3-diamine hydrochloride (219 mg, 1.142 mmol) were dissolved in DMF (2 ml). The reaction was stirred at RT for 3 days to achieve completion. The reaction mixture was diluted with Water and extracted with AcOEt. The organic phase was washed with water, dried over Na2SO4 and concentrated under vacuum. The crude was purified by preparative HPLC to give (S)-3,5-dichloro-4-(2-(3-(cyclopropylmethoxy)-4-(difluoromethoxy)phenyl)-2-(3-(methylsulfonyloxy)-4-(morpholinomethyl)benzoyloxy)ethyl)pyridine 1-oxide (30 mg, 0.042 mmol, 29.3% yield). MS/ESI$^+$ 716.9 [MH]$^+$ $^1$H NMR (400 MHz, DMSO-d$_6$) δ ppm 8.56 (s, 2 H), 7.94-8.01 (m, 1 H), 7.90-7.92 (m, 1 H), 7.63-7.78 (m, 1 H), 7.18-7.24 (m, 2 H), 7.02-7.11 (m, 2 H), 6.07-6.26 (m, 1 H), 3.86-3.98 (m, 2 H), 3.47-3.69 (m, 11 H), 2.35-2.42 (m, 4 H), 1.13-1.27 (m, 1 H), 0.50-0.63 (m, 2 H), 0.30-0.41 (m, 2 H).

The compounds listed in Table 19 were prepared with analogous synthetic steps and procedures to that described in Example 28, Scheme 28, Step 2-7, reacting the appropriate precursors (commercially available or synthesized by a person skilled in the art) with suitable reagents. Specific variations in the experimentals or purification methods are indicated in the table.

TABLE 19

| STRUCTURE | Comp. | Salt Name | NMR characterization and MS/ESI+ [MH]+ | Experimental Procedure | Carboxylic acid | Sulfonyl chloride |
|---|---|---|---|---|---|---|
| 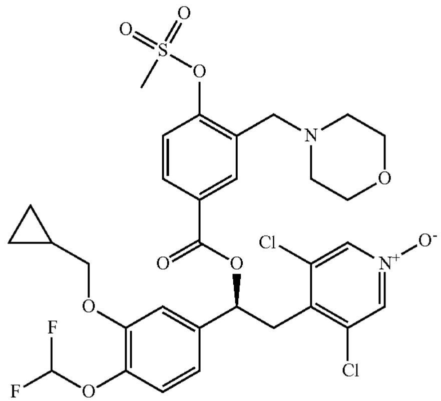 [SMILES: CS(=O)(=O)Oc1ccc(C(=O)O[C@@H](Cc2c(Cl)c[n+]([O-])cc2Cl)c2ccc(OC(F)F)c(OCC3CC3)c2)cc1CN1CCOCC1] | 240 | Formate | 1H NMR (400 MHz, DMSO-d6) δ ppm 8.56 (s, 2 H), 8.08-8.17 (m, 1 H), 7.92-8.03 (m, 1 H), 7.47-7.57 (m, 1 H), 7.22 (m, 2 H), 7.07 (m, 2 H), 6.09-6.26 (m, 1 H), 3.87-4.00 (m, 2 H), 3.52-3.71 (m, 10 H), 3.35-3.40 (m, 1 H), 2.39 (m, 4 H), 1.16-1.28 (m, 1 H), 0.50-0.61 (m, 2 H), 0.27-0.40 (m, 2 H) [MH]+ 717.2 | | | |
| 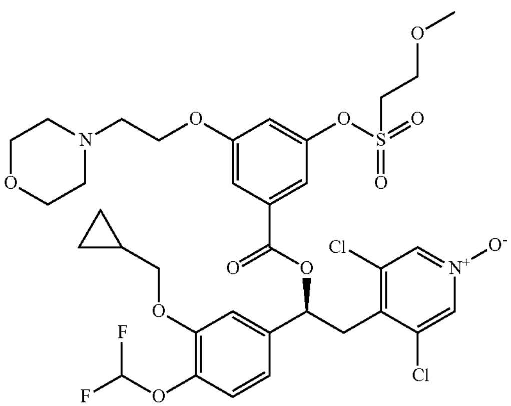 [SMILES: COCCS(=O)(=O)Oc1cc(OCCN2CCOCC2)cc(C(=O)O[C@@H](Cc2c(Cl)c[n+]([O-])cc2Cl)c2ccc(OC(F)F)c(OCC3CC3)c2)c1] | 241 | No Salt | 1H NMR (400 MHz, DMSO-d6) δ ppm 8.56 (s, 2 H), 7.42-7.51 (m, 2 H), 7.16-7.28 (m, 3 H), 7.03-7.11 (m, 2 H), 6.10-6.24 (m, 1 H), 4.11-4.25 (m, 2 H), 3.89-3.97 (m, 2 H), 3.83-3.88 (m, 2 H), 3.76-3.82 (m, 2 H), 3.57 (m, 5 H), 3.35-3.38 (m, 1 H), 3.29 (s, 3 H), 2.64-2.76 (m, 2 H), 2.43-2.48 (m, 4 H), 1.16-1.27 (m, 1 H), 0.51-0.62 (m, 2 H), 0.28-0.42 (m, 2 H) [MH]+ 791.0 | Step 3: Instead of reductive amination, alkylation with (1.2 eq.), K2CO3 (1.3 eq.) in DMF (10 vv) was performed. | | |

Example 29

Synthesis of (S)-3,5-dichloro-4-(2-(3-(cyclopropylmethoxy)-4-(difluoromethoxy)phenyl)-2-(4-((4-hydroxypiperidin-1-yl)methyl)benzoyloxy)ethyl) pyridine 1-oxide (Compound 242)

Scheme 29

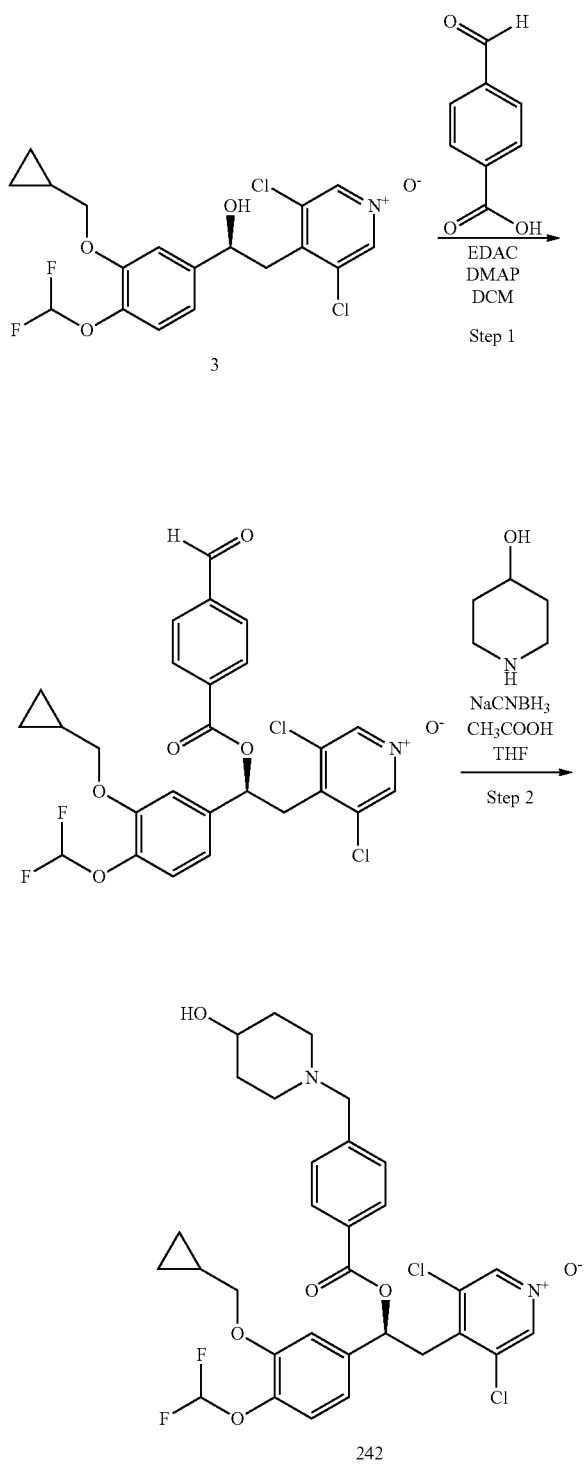

Step 1: Synthesis of (S)-3,5-dichloro-4-(2-(3-(cyclopropylmethoxy)-4-(difluoromethoxy)phenyl)-2-(4-formylbenzoyloxy)ethyl)pyridine 1-oxide (243)

EDC (593 mg, 3.09 mmol) was added to a solution of compound 3 (1 g, 2.38 mmol), 2-(3-(4-nitrobenzyl)-2,4,5-trioxoimidazolidin-1-yl)acetic acid (464 mg, 3.09 mmol) and DMAP (87 mg, 0.714 mmol) in CH$_2$Cl$_2$ (10 mL) at RT under nitrogen atmosphere. The mixture was stirred at RT overnight. The mixture was then diluted with CH$_2$Cl$_2$ and washed with NaHCO$_3$ saturated solution, HCl 0.1 N and brine. The organic phase was dried over Na$_2$SO$_4$ and the solvent was evaporated. (S)-3,5-dichloro-4-(2-(3-(cyclopropylmethoxy)-4-(difluoromethoxy)phenyl)-2-(4-formylbenzoyloxy)ethyl)pyridine 1-oxide was obtained as a pale yellow amorphous solid (1.24 g, 94% yield).

Step 2: Synthesis of (S)-3,5-dichloro-4-(2-(3-(cyclopropylmethoxy)-4-(difluoromethoxy)phenyl)-2-(4-((4-hydroxypiperidin-1-yl)methyl)benzoyloxy) ethyl) pyridine 1-oxide (242)

A solution of (S)-3,5-dichloro-4-(2-(3-(cyclopropylmethoxy)-4-(difluoromethoxy)phenyl)-2-(4-formylbenzoyloxy)ethyl)pyridine 1-oxide (250 mg, 0.452 mmol) and piperidin-4-ol (55 mg, 0.543 mmol) in dry THF (12 ml), under argon atmosphere, was stirred for 15 minutes at RT. Then NaCNBH$_3$ (71.9 mg, 0.34 mmol) and CH$_3$COOH (13 µl, 0.27 mmol) were added and the mixture stirred at RT for 24 hours. The solvent was removed and the crude was dissolved in ethyl acetate and washed with sat. NaHCO$_3$ and brine. The organic phase was dried over Na$_2$SO$_4$ and the solvent was removed. (S)-3,5-dichloro-4-(2-(3-(cyclopropylmethoxy)-4-(difluoromethoxy)phenyl)-2-(4-((4-hydroxypiperidin-1-yl)methyl)benzoyloxy)ethyl)pyridine 1-oxide was obtained as a yellow amorphous solid (122 mg, 0.191 mmol), which was purified by preparative HPLC to give 47 mg of the title compound as a white solid (32% yield). MS/ESI$^+$ 637.49 [MH]$^+$ $^1$H NMR (400 MHz, DMSO-d$_6$) δ ppm 8.56 (s, 2 H), 7.94 (d, J=7.83 Hz, 2 H), 7.43 (d, J=7.83 Hz, 2 H), 7.16-7.27 (m, 2 H), 7.08 (d, J=10.27 Hz, 2 H), 6.12-6.25 (m, 1 H), 4.53 (d, J=2.69 Hz, 1 H), 3.92 (d, J=6.85 Hz, 2 H), 3.55-3.70 (m, 1 H), 3.40-3.50 (m, 3 H), 2.63 (d, J=10.52 Hz, 2 H), 2.04 (m, 2 H), 1.68 (m, 2 H), 1.39 (m, 2 H), 1.11-1.27 (m, 1 H), 0.55 (d, J=6.85 Hz, 2 H), 0.34 (d, J=3.42 Hz, 2 H).

The compounds listed in Table 20 were prepared with analogous synthetic steps and procedures to those described in Example 29 reacting the appropriate precursors (commercially available or synthesized by a person skilled in the art) with suitable reagents. Specific variations in the experimentals or purification methods are indicated in the table.

TABLE 20
| Comp. | Salt Name | NMR characterization | Amine | MS/ESI+ [MH]+ |
|---|---|---|---|---|
| 244 | No salt | 1H NMR (400 MHz, DMSO-d6) δ ppm 8.56 (s) 7.94 (d, J = 8.31 Hz) 7.44 (d, J = 8.31 Hz) 7.25 (s) 7.17-7.23 (m) 7.05-7.11 (m) 6.88 (s) 6.19 (dd, J = 9.42, 4.28 Hz) 4.24-4.58 (m) 3.92 (d, J = 7.09 Hz) 3.56-3.67 (m) 3.51 (s) 3.10-3.38 (m) 2.75 (s) 1.92 (t, J = 11.62 Hz) 1.61 (d, J = 10.76 Hz) 1.32 (dd, J = 9.17, 5.26 Hz) 1.05-1.27 (m) 0.49-0.61 (m) 0.28-0.40 (m) | 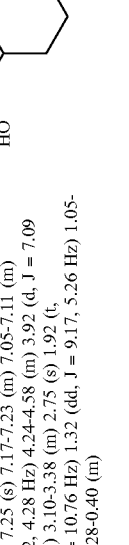 | 651.53 |
| 245 | No salt | 1H NMR (400 MHz, DMSO-d6) δ ppm 8.56 (s) 7.94 (d, J = 8.31 Hz) 7.44 (d, J = 8.31 Hz) 7.25 (s) 7.17-7.23 (m) 7.05-7.11 (m) 6.88 (s) 6.19 (dd, J = 9.42, 4.28 Hz) 4.24-4.58 (m) 3.92 (d, J = 7.09 Hz) 3.56-3.67 (m) 3.51 (s) 3.10-3.38 (m) 2.75 (s) 1.92 (t, J = 11.62 Hz) 1.61 (d, J = 10.76 Hz) 1.32 (dd, J = 9.17, 5.26 Hz) 1.05-1.27 (m) 0.49-0.61 (m) 0.28-0.40 (m) | 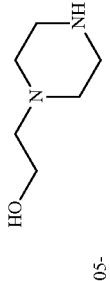 | 666.54 |
STRUCTURE

TABLE 20-continued

| Comp. | Salt Name | NMR characterization | Amine | MS/ESI+ [MH]+ |
|---|---|---|---|---|
| 246 | No Salt | 1H NMR (400 MHz, DMSO-d6) δ ppm 8.55 (s) 7.82-7.93 (m) 7.41-7.61 (m) 7.17-7.28 (m) 7.04-7.12 (m) 6.88 (s) 6.20 (dd, J = 9.66, 4.28 Hz) 4.45-4.65 (m) 3.92 (dd, J = 6.85, 1.47 Hz) 3.62 (dd, J = 14.31, 9.66 Hz) 3.15-3.54 (m) 2.56-2.71 (m) 2.05 (t, J = 10.03 Hz) 1.70 (d, J = 9.78 Hz) 1.32-1.46 (m) 1.15-1.26 (m) 0.50-0.61 (m) 0.30-0.39 (m) | 4-hydroxypiperidine | 637.49 |
| 247 | No Salt | 1H NMR (400 MHz, DMSO-d6) δ ppm 8.55 (s) 7.84-7.93 (m) 7.57 (d, J = 7.83 Hz) 7.43-7.51 (m) 7.16-7.27 (m) 7.03-7.12 (m) 6.88 (s) 6.20 (dd, J = 9.54, 4.40 Hz) 4.31-4.49 (m) 3.88-3.97 (m) 3.62 (dd, J = 14.18, 9.78 Hz) 3.50 (s) 3.18-3.45 (m) 2.72-2.83 (m) 1.84-1.98 (m) 1.62 (d, J = 11.00 Hz) 1.34 (br. s.) 1.04-1.27 (m) 0.47-0.61 (m) 0.30-0.38 (m) | 4-(hydroxymethyl)piperidine | 651.53 |
| 248 | No Salt | 1H NMR (400 MHz, DMSO-d6) δ ppm 8.55 (s) 7.80-7.97 (m) 7.57 (d, J = 7.58 Hz) 7.44-7.51 (m) 7.25 (s) 7.17-7.23 (m) 7.03-7.11 (m) 6.88 (s) 6.20 (dd, J = 9.54, 4.40 Hz) 4.12-4.61 (m) 3.92 (d, J = 6.85 Hz) 3.62 (dd, J = 14.06, 9.66 Hz) 3.45-3.54 (m) 3.34 (dd, J = 14.18, 4.40 Hz) 2.38 (t, J = 6.36 Hz) 1.13-1.27 (m) 0.51-0.60 (m) 0.28-0.39 (m) | 1-(2-hydroxyethyl)piperazine | 666.54 |

TABLE 20-continued

| STRUCTURE | Comp. | Salt Name | NMR characterization | Amine | MS/ESI+ [MH]+ |
|---|---|---|---|---|---|
| (structure 249) | 249 | No Salt | 1H NMR (400 MHz, DMSO-d6) □ ppm 8.56 (s, 2 H), 8.16 (s, 2 H), 7.74 (d, J = 7.50 Hz, 1 H), 7.46 (d, J = 7.06 Hz, 1 H), 7.16-7.35 (m, 2 H), 7.07 (m, 2 H), 6.88 (t, J = 7.50 Hz, 1 H), 6.21 (dd, J = 8.38, 4.41 Hz, 1 H), 3.78-4.10 (m, 8 H), 3.58 (dd, J = 13.89, 9.48 Hz, 1 H), 3.16-3.30 (m, 1 H), 2.64 (t, J = 10.14 Hz, 1 H), 1.79 (d, J = 12.35 Hz, 2 H), 1.08-1.43 (m, 3 H), 0.56 (d, J = 7.06 Hz, 2 H), 0.35 (d, J = 3.53 Hz, 2 H) | (4-aminotetrahydropyran) | 652.8 |
| (structure 250) | 250 | No Salt | 1H NMR (400 MHz, DMSO-d6) □ ppm 10.14 (bs, 1 H), 8.55 (s, 2 H), 7.80 (d, J = 1.76 Hz, 1 H), 7.42 (dd, J = 8.38, 1.76 Hz, 1 H), 7.17-7.30 (m, 2 H), 7.03-7.11 (m, 2 H), 6.85-6.94 (m, 1 H), 6.14-6.26 (m, 1 H), 4.57 (m, 1 H), 3.92 (dd, J = 6.84, 2.87 Hz, 2 H), 3.55-3.72 (m, 3 H), 3.45 (m, 3 H), 2.66 (d, J = 10.58 Hz, 2 H), 1.71 (d, J = 11.91 Hz, 2 H), 1.39 (d, J = 9.26 Hz, 2 H), 1.10-1.30 (m, 1 H), 0.50-0.65 (m, 2 H), 0.35 (m, 2 H) | (4-hydroxypiperidine) | 652.9 |

Example 30

Synthesis of (S)-3,5-dichloro-4-(2-(3-(cyclopropyl-
methoxy)-4-(difluoromethoxy)phenyl)-2-(2-
methoxy-5-((N-(2-morpholinoethyl)-methylsulfona-
mido)methyl)benzoyloxy)ethyl)pyridine 1-oxide
(251)

Scheme 30
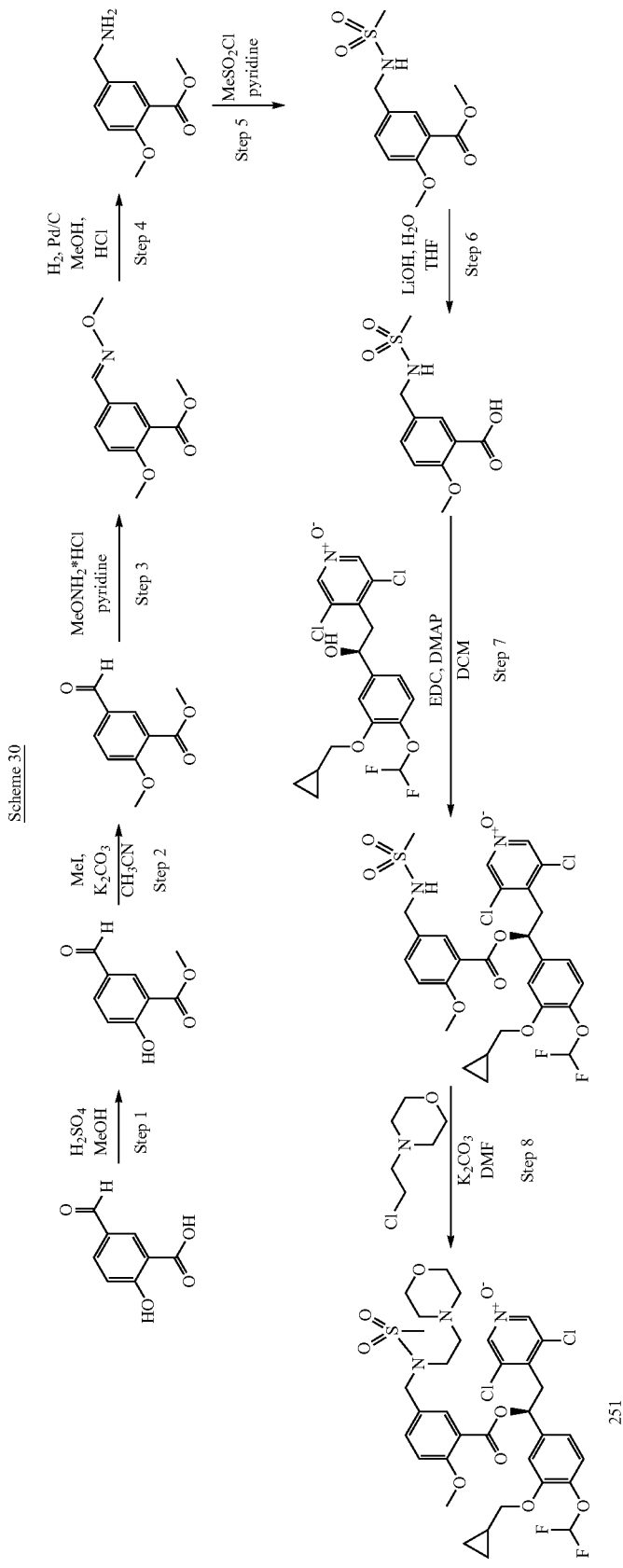

Step 1: Synthesis of methyl 5-formyl-2-hydroxybenzoate (258)

A solution of 5-formyl-2-hydroxybenzoic acid (1.6 g, 9.63 mmol) and a catalytic amount of conc. $H_2SO_4$ in MeOH (100 ml) was heated to reflux for 48 hours. The mixture was portioned between EtOAc and aq. 5% $NaHCO_3$; the organic phase was dried over sodium sulfate and the solvent was removed yielding methyl 5-formyl-2-hydroxybenzoate (1.66 g, 9.21 mmol, 96% yield, MS/ESI$^+$ 180.9 [MH]$^+$). This product was used without purification.

Step 2: Synthesis of methyl 5-formyl-2-methoxybenzoate (257)

A mixture of methyl 5-formyl-2-hydroxybenzoate (0.500 g, 2.78 mmol), potassium carbonate (0.767 g, 5.55 mmol) and iodomethane (0.208 ml, 3.33 mmol) in acetonitrile (20 ml) was stirred at RT for 1 hour. Additional iodomethane (0.312 ml, 4.99 mmol) was added and the reaction was heated under microwave irradiation at 100° C. for 1 hour and then for further 30 minutes. The mixture was portioned between EtOAc and 1N HCl and the organic phase was washed with 1N NaOH and brine. The organic layer was dried over sodium sulfate and the solvent was removed yielding methyl 5-formyl-2-methoxybenzoate (0.352 g, 1.813 mmol, 65% yield, MS/ESI$^+$ 194.9 [MH]$^+$) which was used without purification.

Step 3: Synthesis of (E)-methyl 2-methoxy-5-((methoxyimino)methyl)benzoate (256)

A solution of methyl 5-formyl-2-methoxybenzoate (0.352 g, 1.813 mmol) and O-methylhydroxylamine hydrochloride (0.167 g, 1.994 mmol) in pyridine (20 ml) was heated at 60° C. for 2 hours. The solvent was removed under vacuum and the crude was partitioned between EtOAc and 1N HCl. The organic phase was washed with brine and dried over sodium sulfate; the solvent was removed affording (E)-methyl 2-methoxy-5-((methoxyimino)methyl)benzoate (0.395 g, 1.770 mmol, 98% yield, MS/ESI$^+$ 224.0 [MH]$^+$). The crude was used without purification.

Step 4: Synthesis of methyl 5-(aminomethyl)-2-methoxybenzoate (255)

A mixture of (E)-methyl 2-methoxy-5-((methoxyimino)methyl)benzoate (0.395 g, 1.770 mmol), 10% Pd/C (a catalytic amount) and conc. HCl (0.108 ml, 1.740 mmol) in MeOH (50 ml) was hydrogenated in a Parr apparatus at 35 psi for 40 hours. The catalyst was filtered off, the filtrate was evaporated to dryness and the residue was purified by filtration on scx cartridge (DCM:MeOH=1:1; aq. conc. $NH_4OH$:MeOH=1:9). The basic fractions were evaporated to afford methyl 5-(aminomethyl)-2-methoxybenzoate (0.271 g, 1.388 mmol, 78% yield).

Step 5: Synthesis of methyl 2-methoxy-5-(methylsulfonamidomethyl)benzoate (254)

To a solution of methyl 5-(aminomethyl)-2-methoxybenzoate (0.271 g, 1.388 mmol) and pyridine (1.123 ml, 13.88 mmol) in DCM (30 ml), methanesulfonyl chloride (0.162 ml, 2.082 mmol) was added drop-wise and the mixture was stirred at RT for 2 hours. Additional methanesulfonyl chloride (0.216 ml, 2.776 mmol) was added over 22 hours stirring at the same temperature. The mixture was diluted with DCM and washed with 2N HCl and water; the organic layer was dried over sodium sulfate and the solvent was removed. The crude was purified by filtration through a silica gel cartridge (DCM:EtOAc=90:10) to afford methyl 2-methoxy-5-(methylsulfonamidomethyl)benzoate (0.304 g, 1.112 mmol, 80% yield, MS/ESI$^+$ 274.0 [MH]$^+$).

Step 6: Synthesis of 2-methoxy-5-(methylsulfonamidomethyl)benzoic acid (253)

To a solution of methyl 2-methoxy-5-(methylsulfonamidomethyl)benzoate (0.304 g, 1.112 mmol) in THF (15 ml), aqueous 1N LiOH (1.335 ml, 1.335 mmol) was added and the mixture was stirred at RT overnight. Additional 1N LiOH (0.700 ml, 0.700 mmol) was added and the reaction was stirred at the same temperature for further 8 hours. The mixture was portioned between EtOAc and 1N HCl; the organic layer was dried over sodium sulfate and the solvent was removed yielding 2-methoxy-5-(methylsulfonamidomethyl)benzoic acid (0.170 g, 0.656 mmol, 59% yield, MS/ESI$^±$259.9 [MH]$^+$).

Step 7: Synthesis of (S)-3,5-dichloro-4-(2-(3-(cyclopropylmethoxy)-4-(difluoromethoxy)-phenyl)-2-(2-methoxy-5-(methylsulfonamidomethyl)benzoyloxy)ethyl)pyridine 1-oxide (252)

To a mixture of (S)-3,5-dichloro-4-(2-(3-(cyclopropylmethoxy)-4-(difluoromethoxy)phenyl)-2-hydroxyethyl)pyridine 1-oxide (0.230 g, 0.546 mmol), EDC (0.282 g, 1.476 mmol) and DMAP (0.160 g, 1.311 mmol) in DCM (20 ml), 2-methoxy-5-(methylsulfonamidomethyl)benzoic acid (0.170 g, 0.656 mmol) was added and the reaction was stirred at RT for 1 hour. The mixture was washed with 1N HCl and aq. 5% $NaHCO_3$; the organic phase was dried over sodium sulfate, the solvent was removed and the crude was purified by preparative HPLC (Method 3) affording (S)-3,5-dichloro-4-(2-(3-(cyclopropylmethoxy)-4-(difluoromethoxy)phenyl)-2-(2-methoxy-5-(methylsulfonamidomethyl)benzoyloxy)ethyl)pyridine 1-oxide (0.145 g, 0.219 mmol, 40% yield, MS/ESI$^+$ 661.26 [MH]$^+$, $[\alpha_D]$=−27.80, c=0.49, MeOH).

$^1$H NMR (300 MHz, DMSO-d$_6$) δ ppm 8.55 (s, 2 H), 7.65 (d, 1 H), 7.48-7.56 (m, 2 H), 7.21 (d, 1 H), 7.18 (d, 1 H), 7.14 (d, 1 H), 7.06 (dd, 1 H), 7.07 (t, 1 H), 6.19 (dd, 1 H), 4.12 (s, 2 H), 3.94 (dd, 1 H), 3.90 (dd, 1 H), 3.79 (s, 3 H), 3.52 (dd, 1 H), 3.32 (dd, 1 H), 2.86 (s, 3 H), 1.09-1.33 (m, 1 H), 0.49-0.66 (m, 2 H), 0.27-0.43 (m, 2 H)

Step 8: Synthesis of (S)-3,5-dichloro-4-(2-(3-(cyclopropylmethoxy)-4-(difluoromethoxy)phenyl)-2-(2-methoxy-5-((N-(2-morpholinoethyl)-methylsulfonamido)methyl)benzoyloxy)ethyl)pyridine 1-oxide (251)

To a solution of (S)-3,5-dichloro-4-(2-(3-(cyclopropylmethoxy)-4-(difluoromethoxy)phenyl)-2-(2-methoxy-5-(methylsulfonamidomethyl)-benzoyloxy)ethyl)pyridine 1-oxide (40 mg, 0.06 mmol) in DMF (2 ml), $K_2CO_3$ (17 mg, 0.12 mmol) and 4-(2-chloroethyl)morpholine (18 mg, 0.12 mmol) were added. The reaction mixture was heated to 45° C. for 4 hours and to 60° C. for 2 hours. The mixture was partitioned between ethyl acetate and water; the organic phase was washed with brine, dried over $Na_2SO_3$ and evaporated to dryness. The crude was purified by preparative HPLC (Method 2) affording the desired product (15 mg, 32% yield). MS/ESI+ 773.8 [MH]+.
$^1$H NMR (400 MHz, DMSO-d$_6$) δ ppm 8.56 (s, 2 H), 7.70 (m, 1 H), 7.55 (d, J=8.38 Hz, 1 H), 6.98-7.32 (m, 5 H), 6.18 (d, J=3.97 Hz, 1 H), 4.32 (s, 2 H), 3.91 (t, J=6.39 Hz, 2 H), 3.79 (s, 3 H), 3.28 (m, 5 H), 3.48 (m, 1 H), 3.19 (m, 2 H), 3.06 (s, 3 H), 2.20-2.35 (m, 6 H), 1.21 (m, 1 H), 0.56 (d, J=7.06 Hz, 2 H), 0.35 (d, J=3.53 Hz, 2 H).
Example 31
Synthesis of (S)-3,5-dichloro-4-(2-(3-(cyclopropyl-methoxy)-4-(difluoromethoxy)phenyl)-2-(4-methoxy-3-(N-(2-(4-methylpiperazin-1-yl)-2-oxo-ethyl) methylsulfonamido)benzoyloxy)ethyl) pyridine 1-oxide (Compound 259)
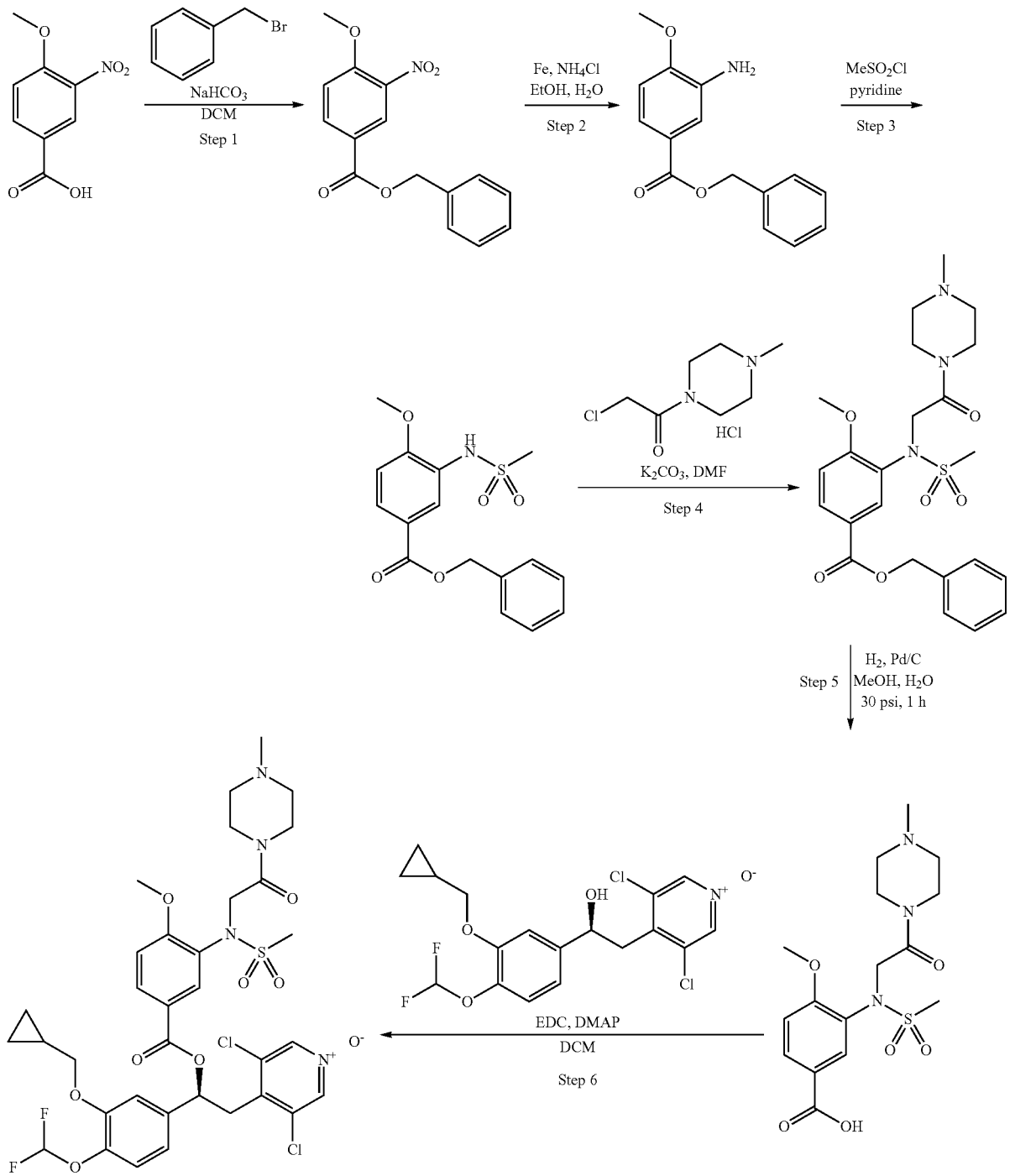
Scheme 31

Step 1: Synthesis of benzyl 4-methoxy-3-nitrobenzoate (264)

To a solution of 4-methoxy-3-nitrobenzoic acid (1 g, 5.07 mmol) in dry DMF (50 ml), sodium bicarbonate (0.511 g, 6.09 mmol) and benzyl bromide (0.724 ml, 6.09 mmol) were added and the reaction was stirred at 50° C. for 4 hours The mixture was treated with 1N HCl and extracted twice with AcOEt; the combined organic layers were washed with brine, dried over $Na_2SO_4$ and evaporated to dryness. The crude was purified by flash chromatography on silica gel (petroleum ether/AcOEt=9/1) to afford benzyl 4-methoxy-3-nitrobenzoate (1.2539 g, 4.36 mmol, 86% yield, MS/ESI$^+$ 288.1 [MH]$^+$).

Step 2: Synthesis of benzyl 3-amino-4-methoxybenzoate (263)

To a suspension of benzyl 4-methoxy-3-nitrobenzoate (1.2539 g, 4.36 mmol) in EtOH (25 ml) and water (12 ml), ammonium chloride (0.163 g, 3.06 mmol) was added followed by iron powder (1.463 g, 26.2 mmol) and the reaction was heated at 80° C. for 2 hours. The insoluble was filtered off and the filtrate was evaporated to dryness. The residue was dissolved in EtOAc and washed with water and brine; the organic phase was dried over $Na_2SO_4$ and the solvent was removed affording benzyl 3-amino-4-methoxybenzoate (1.035 g, 4.02 mmol, 92% yield, MS/ESI$^+$ 257.9 [MH]$^+$). This product was used without any additional purification.

Step 3: Synthesis of benzyl 4-methoxy-3-(methylsulfonamido)benzoate (262)

To a solution of benzyl 3-amino-4-methoxybenzoate (1.035 g, 4.02 mmol) in pyridine (40 ml) cooled at 0° C., methanesulfonyl chloride (0.376 ml, 4.83 mmol) was added and the mixture was stirred at RT overnight. The solvent was evaporated and the residue was partitioned between EtOAc and 1N HCl; the organic phase was washed with brine and dried over $Na_2SO_4$. The solvent was removed under vacuum and the crude was purified by trituration with diethyl ether yielding benzyl 4-methoxy-3-(methyl-sulfonamido)benzoate (0.920 g, 2.74 mmol, 68.2% yield, MS/ESI$^+$ 336.0 [MH]$^+$).

Step 4: Synthesis of benzyl 4-methoxy-3-(N-(2-(4-methylpiperazin-1-yl)-2-oxoethyl)methylsulfonamido)benzoate (261)

A mixture of benzyl 4-methoxy-3-(methylsulfonamido)benzoate (0.500 g, 1.491 mmol), 2-chloro-1-(4-methylpiperazin-1-yl)ethanone hydrochloride (0.381 g, 1.789 mmol) and potassium carbonate (0.495 g, 3.58 mmol) in DMF (15 ml) was heated at 70° C. for 1 hour. The mixture was diluted with EtOAc and washed with water and several times with brine. The organic phase was dried over sodium sulfate, the solvent was removed and the crude was purified by flash chromatography on silica gel column (EtOAc:MeOH=90:10 to 80:20) affording benzyl 4-methoxy-3-(N-(2-(4-methylpiperazin-1-yl)-2-oxoethyl)methylsulfonamido)benzoate (0.561 g, 1.180 mmol, 79% yield, MS/ESI$^+$ 475.9 [MH]$^+$).

Step 5: Synthesis of 4-methoxy-3-(N-(2-(4-methylpiperazin-1-yl)-2-oxoethyl)-methylsulfonamido) benzoic acid (260)

Benzyl 4-methoxy-3-(N-(2-(4-methylpiperazin-1-yl)-2-oxoethyl)-methylsulfonamido)benzoate (0.555 g, 1.167 mmol) was dissolved in MeOH (22.200 ml) and 10% w/w Pd/C (0.248 g, 0.233 mmol) was added. The resulting mixture was hydrogenated in a Parr apparatus at 30 psi for 1 hour. The catalyst was filtered off and washed with MeOH, EtOAc and DCM. The combined filtrates were evaporated to dryness yielding 4-methoxy-3-(N-(2-(4-methylpiperazin-1-yl)-2-oxoethyl)methyl-sulfonamido)benzoic acid (0.339 g, 0.880 mmol, 75% yield, MS/ESI$^+$ 386.1 [MH]$^+$).

Step 5: Synthesis of (S)-3,5-dichloro-4-(2-(3-(cyclopropylmethoxy)-4-(difluoromethoxy)phenyl)-2-(4-methoxy-3-(N-(2-(4-methylpiperazin-1-yl)-2-oxoethyl) methylsulfonamido)benzoyloxy)ethyl) pyridine 1-oxide (259)

4-Methoxy-3-(N-(2-(4-methylpiperazin-1-yl)-2-oxoethyl)methylsulfonamido)-benzoic acid (0.200 g, 0.519 mmol) was suspended in dry DCM (3.459 ml) and, stirring at room temperature, (S)-3,5-dichloro-4-(2-(3-(cyclopropylmethoxy)-4-(difluoromethoxy)phenyl)-2-hydroxyethyl) pyridine 1-oxide (0.145 g, 0.346 mmol), EDC (0.199 g, 1.038 mmol) and DMAP (0.0423 g, 0.346 mmol) were sequentially added. The suspension was reacted for 24 hours at RT. The mixture was evaporated and the residue was purified by flash chromatography on silica gel SNAP column (DCM/MeOH=95/5 to 93/7) to afford (S)-3,5-dichloro-4-(2-(3-(cyclopropylmethoxy)-4-(difluoromethoxy)-phenyl)-2-(4-methoxy-3-(N-(2-(4-methylpiperazin-1-yl)-2-oxoethyl) methylsulfonamido)-benzoyloxy)ethyl)pyridine 1-oxide (197 mg, 0.250 mmol, 72.3% yield, MS/ESI$^+$ 787.24 [MH]$^+$, [$\alpha_D$]=−41.60, c=0.5, MeOH).

$^1$H NMR (300 MHz, DMSO-d$_6$) δ ppm 8.52 (s, 2 H), 8.15 (d, 1 H), 7.99 (dd, 1 H), 7.16-7.26 (m, 3 H), 7.06 (dd, 1 H), 7.06 (t, 1 H), 6.19 (dd, 1 H), 4.43 (s, 2 H), 3.94 (d, 2 H), 3.93 (s, 3 H), 3.62 (dd, 1 H), 3.33-3.45 (m, 4 H), 3.33 (dd, 1 H), 3.08 (s, 3 H), 2.20-2.36 (m, 4 H), 2.17 (s, 3 H), 1.07-1.39 (m, 1 H), 0.49-0.66 (m, 2 H), 0.22-0.46 (m, 2 H)

Example 32
Synthesis of (S)-3,5-dichloro-4-(2-(3-(cyclopropylmethoxy)-4-(difluoromethoxy)phenyl)-2-(3-(N-(2-morpholinoethyl)methylsulfonamido)-4-(trifluoromethoxy)benzoyloxy)ethyl)pyridine 1-oxide (Compound 265)
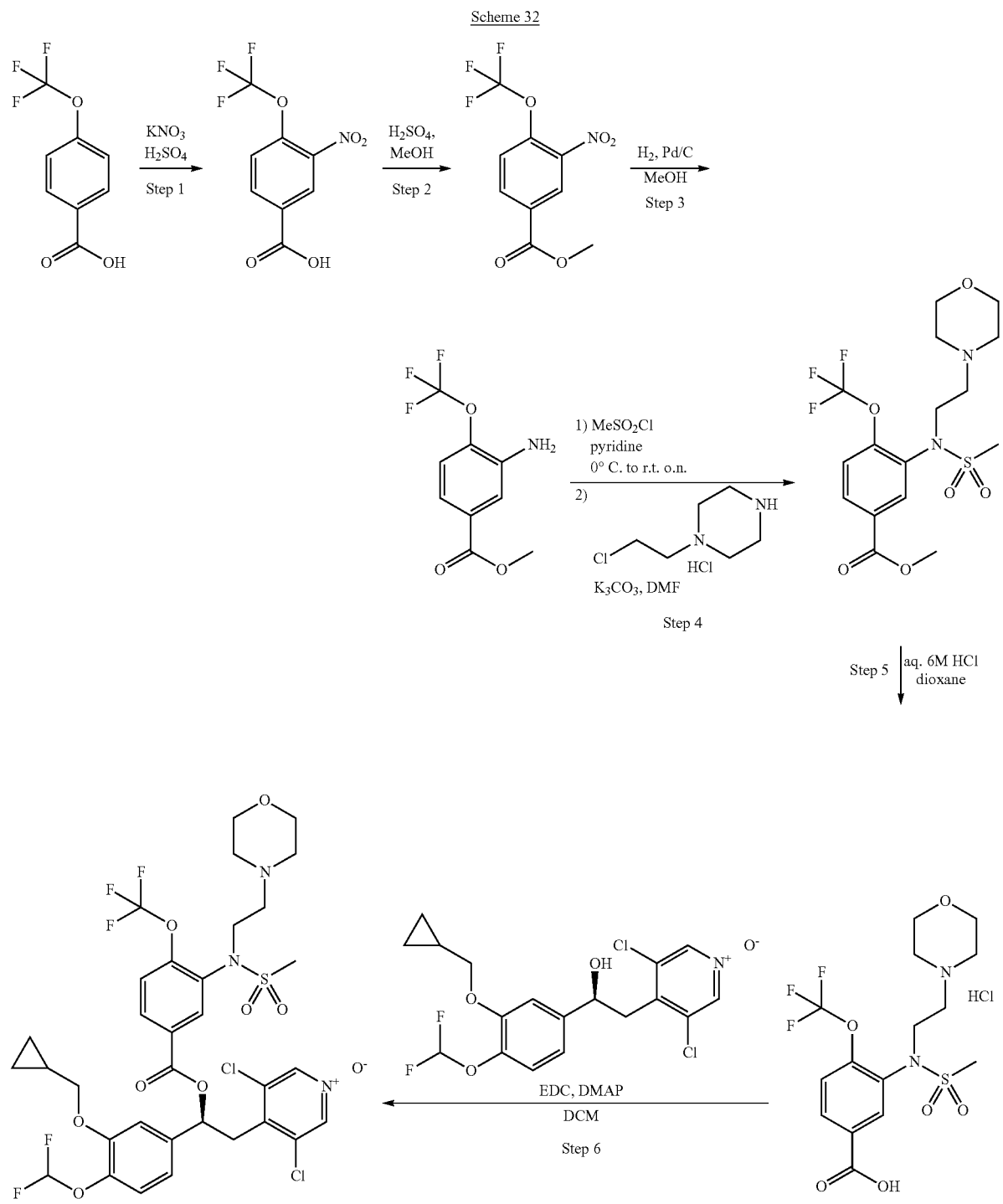

Step 1: Synthesis of 3-nitro-4-(trifluoromethoxy)benzoic acid (270)

To a solution of 4-(trifluoromethoxy)benzoic acid (900 mg, 4.37 mmol) in conc. $H_2SO_4$ (9 ml) cooled at 0° C., a solution of potassium nitrate (486 mg, 4.80 mmol) in conc. $H_2SO_4$ (4.5 ml) was added, and the reaction was stirred at the same temperature for 2 hours. The mixture was treated with $H_2O$ (50 ml) and extracted with EtOAc (150 ml). The organic phase was washed with brine (2×100 ml), dried over $Na_2SO_4$ and evaporated to dryness affording 3-nitro-4-(trifluoromethoxy)benzoic acid (2) (1.05 g, 4.18 mmol, 96% yield, MS/ESI$^+$ 252.1 [MH]$^+$). This product was used without purification.

Step 2: Synthesis of methyl 3-nitro-4-(trifluoromethoxy)benzoate (269)

To a solution of 3-nitro-4-(trifluoromethoxy)benzoic acid (1.05 g, 4.18 mmol) in MeOH (40 ml), conc. $H_2SO_4$ (0.446 ml) was added, and the resulting mixture was heated to reflux overnight. The solvent was removed under vacuum and aqueous sat. $NaHCO_3$ (60 ml) was added to the residue. The mixture was extracted with EtOAc (2×100 ml) and the combined organic layers were dried over $Na_2SO_4$, filtered and evaporated to afford methyl 3-nitro-4-(trifluoromethoxy)benzoate (1.05 g, 3.96 mmol, 95% yield, MS/ESI$^+$ 265.9 [MH]$^+$).

Step 3: Synthesis of methyl 3-amino-4-(trifluoromethoxy)benzoate (268)

To a solution of ethyl 3-nitro-4-(trifluoromethoxy)benzoate (1.0 g, 3.77 mmol) in MeOH (20 ml), a catalytic amount of Pd/C (10% w/w) was added, and the mixture was hydrogenated in a Parr apparatus at 20 psi for 2 hours. The catalyst was filtered off and the filtrate was evaporated to dryness yielding methyl 3-amino-4-(trifluoromethoxy)-benzoate (730 mg, 3.10 mmol, 82% yield, MS/ESI$^+$ 235.9 [MH]$^+$).

Step 4: Synthesis of methyl 3-(N-(2-morpholinoethyl)methylsulfonamido)-4-(trifluoromethoxy)benzoate (267)

To a solution of methyl 3-amino-4-(trifluoromethoxy) benzoate (730 mg, 3.10 mmol) in dry pyridine (8 ml) cooled at 0° C., methanesulfonyl chloride (0.721 ml, 9.31 mmol) was added, and the mixture was left to warm to RT and stirred overnight. The solvent was removed under vacuum and the residue was treated with aqueous sat. $NaHCO_3$ (50 ml) and extracted with EtOAc (2×150 ml). The combined organic layers were dried over $Na_2SO_4$, filtered and evaporated under reduced pressure. The residue was triturated with $Et_2O$ (20 ml) to give 1.00 g of crude. 500 mg of this crude were dissolved in dry DMF (10 ml), 4-(2-chloroethyl) morpholine hydrochloride (401 mg, 2.156 mmol) was added followed by $K_2CO_3$ (496 mg, 3.59 mmol), and the reaction mixture was heated at 100° C. overnight. The solvent was removed under vacuum and the residue was partitioned between EtOAc and water; the organic phase was washed with brine and dried over sodium sulfate. The solvent was removed and the crude was purified by flash chromatography on silica gel (DCM:EtOAc=90:10 to 100% EtOAc) affording methyl 3-(N-(2-morpholinoethyl)methylsulfonamido)-4-(trifluoromethoxy)-benzoate (600 mg, 1.407 mmol, 91% yield over 50% starting material, MS/ESI$^+$ 426.9 [MH]$^+$).

Step 5: Synthesis of 3-(N-(2-morpholinoethyl)methylsulfonamido)-4-(trifluoromethoxy)benzoic acid hydrochloride (266)

To a solution of methyl 3-(N-(2-morpholinoethyl)methylsulfonamido)-4-(trifluoromethoxy)benzoate (600 mg, 1.407 mmol) in dioxane (10 ml), aqueous 6M HCl (2.814 ml, 16.89 mmol) was added, and the mixture was heated at 100° C. for 4 hours. The volatiles were removed under vacuum to obtain 3-(N-(2-morpholinoethyl)-methylsulfonamido)-4-(trifluoromethoxy)benzoic acid hydrochloride (600 mg, 1.337 mmol, 95% yield, MS/ESI$^+$ 412.9 [MH]$^+$).

Step 4: Synthesis of (S)-3,5-dichloro-4-(2-(3-(cyclopropylmethoxy)-4-(difluoromethoxy)phenyl)-2-(3-(N-(2-morpholinoethyl)methylsulfonamido)-4-(trifluoromethoxy)benzoyloxy)ethyl)pyridine 1-oxide (265)

A mixture of 3-(N-(2-morpholinoethyl)methylsulfonamido)-4-(trifluoromethoxy)benzoic acid (236 mg, 0.571 mmol), (S)-3,5-dichloro-4-(2-(3-(cyclopropylmethoxy)-4-(difluoromethoxy)phenyl)-2-hydroxyethyl)pyridine 1-oxide (200 mg, 0.476 mmol), EDC (128 mg, 0.666 mmol), and DMAP (116 mg, 0.952 mmol) in dry DCM (10 ml) was stirred at RT for 3 days. The reaction mixture was treated with 1M HCl and extracted twice with DCM. The combined organic layers were washed with brine, dried over $Na_2SO_4$, filtered and evaporated. The crude was purified by flash chromatography on silica gel (DCM/MeOH=98/2 to 90/10). A further purification by flash chromatography on silica gel cartridge (DCM/MeOH 99/1) was required to afford (S)-3,5-dichloro-4-(2-(3-(cyclopropylmethoxy)-4-(difluoromethoxy)phenyl)-2-(3-(N-(2-morpholinoethyl)methylsulfonamido)-4-(trifluoromethoxy)benzoyloxy)ethyl)pyridine 1-oxide (28 mg, 0.034 mmol, 7.22% yield, MS/ESI$^+$ 814.06 [MH]$^+$, $[\alpha_D]$=−20.55, c=0.510, DCM).

$^1$H NMR (300 MHz, DMSO-d$_6$) δ ppm 8.54 (s, 2 H), 8.11 (d, 1 H), 8.11 (dd, 1 H), 7.55-7.66 (m, 1 H), 7.23 (d, 1 H), 7.20 (d, 1H), 7.09 (dd, 1 H), 7.06 (t, 1 H), 6.20 (dd, 1H), 3.83-4.03 (m, 2 H), 3.55-3.80 (m, 3 H), 3.31-3.42 (m, 5 H), 3.15 (s, 3 H), 2.09-2.46 (m, 6 H), 1.06-1.38 (m, 1 H), 0.45-0.69 (m, 2 H), 0.21-0.45 (m, 2 H)

Example 33
Synthesis of (S)-3,5-dichloro-4-(2-(3-(cyclopropyl-methoxy)-4-(difluoromethoxy)phenyl)-2-(3-(N-(2-(4-methylpiperazin-1-yl)ethyl)methylsulfonamido)-4-(trifluoromethyl)benzoyloxy)ethyl)pyridine 1-oxide (Compound 271)
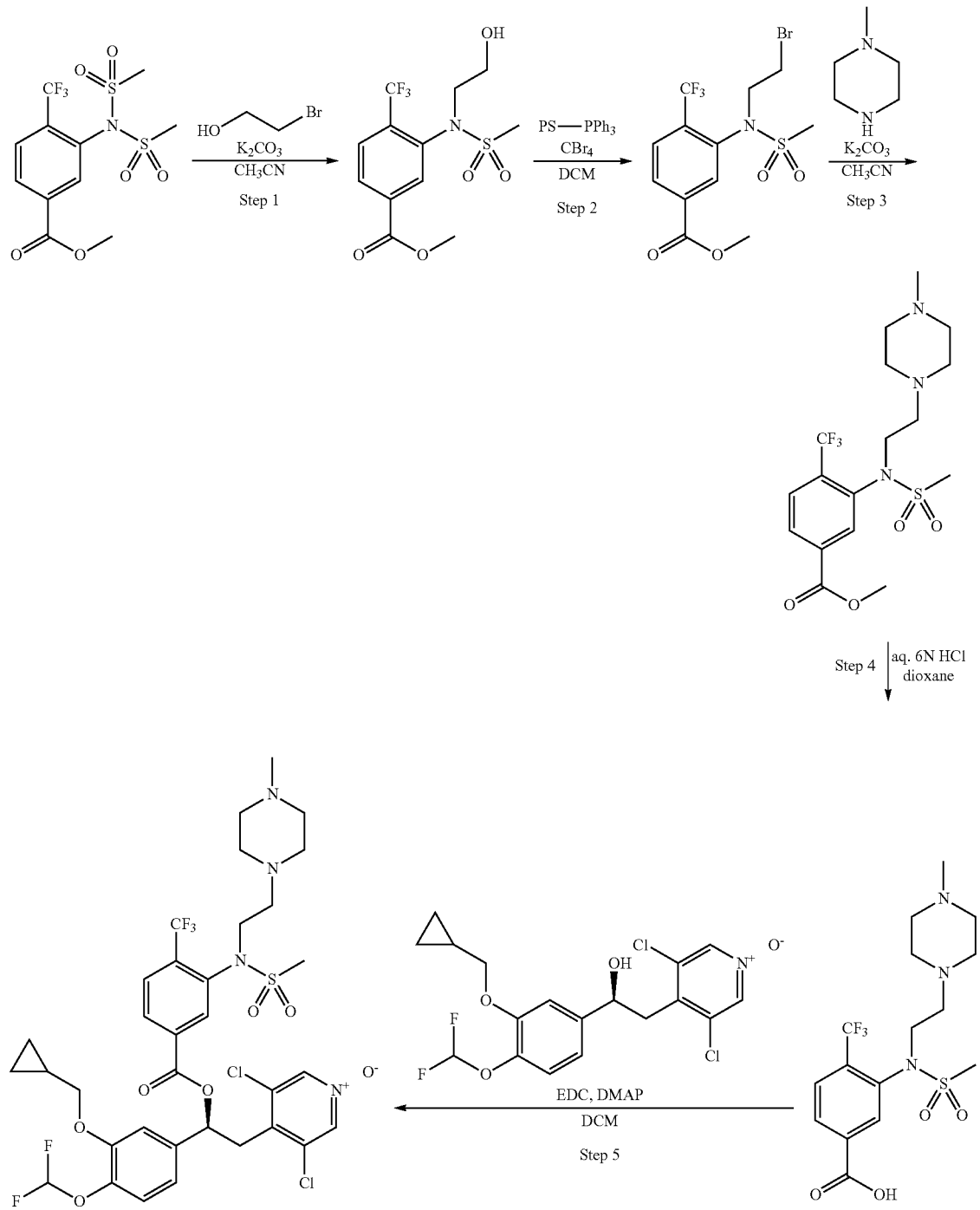

Step 1: Synthesis of methyl 3-(N-(2-hydroxyethyl) methylsulfonamido)-4-(trifluoromethyl)benzoate (275)

A mixture of methyl 3-(N-(methylsulfonyl)methylsulfonamido)-4-(trifluoromethyl)benzoate (1.12 g, 2.98 mmol), 2-bromoethanol (0.847 ml, 11.94 mmol) and $K_2CO_3$ (825 mg, 5.97 mmol) in $CH_3CN$ (20 ml) was split in two vials and heated under microwave irradiation at 110° C. for 2 hours. The solvent was removed under reduced pressure and the residue was purified by flash chromatography on silica gel (petroleum ether/EtOAc=80/20) to give methyl 3-(N-(2-hydroxyethyl)methyl-sulfonamido)-4-(trifluoromethyl)benzoate (700 mg, 2.051 mmol, 69% yield, MS/ESI$^+$342.0 [MH]$^+$).

Step 2: Synthesis of methyl 3-(N-(2-bromoethyl) methylsulfonamido)-4-(trifluoromethyl)benzoate (274)

A suspension of PS-PPh$_3$ (loading: 1.88 mmol/g, 2.3 g, 1.324 mmol) in dry DCM (40 ml) was stirred for 30 minutes at RT; CBr$_4$ (874 mg, 2.64 mmol) and methyl 3-(N-(2-hydroxyethyl)methylsulfonamido)-4-(trifluoromethyl)benzoate (500 mg, 1.465 mmol) were added, and the resulting mixture was stirred at RT for 1.5 hours. The resin was filtered off and the filtrate was evaporated to dryness affording methyl 3-(N-(2-bromoethyl)methylsulfonamido)-4-(trifluoromethyl)benzoate (590 mg, 1.460 mmol, quantitative yield, MS/ESI$^+$ 403.8-405.7 [MH]$^+$). This intermediate was used without any additional purification.

Step 3: Synthesis of methyl 3-(N-(2-(4-methylpiperazin-1-yl)ethyl)methylsulfonamido)-4-(trifluoromethyl)benzoate (273)

A mixture of methyl 3-(N-(2-bromoethyl)methylsulfonamido)-4-(trifluoromethyl)benzoate (780 mg, 1.930 mmol), $K_2CO_3$ (400 mg, 2.89 mmol) and 1-methylpiperazine (0.536 ml, 4.82 mmol) in $CH_3CN$ (40 ml) was split in two vials and heated under MW irradiation at 130° C. for 1 hour. The solvent was removed under reduced pressure, and the residue was mixed with the crude obtained performing the same reaction on 58 mg (0.143 mmol) of starting compound. The combined crudes were purified by flash chromatography on silica gel (DMC/MeOH=97/3 to 95/5) to afford methyl 3-(N-(2-(4-methylpiperazin-1-yl)ethyl)methylsulfonamido)-4-(trifluoromethyl)benzoate (600 mg, 1.418 mmol, 47% yield, MS/ESI$^+$ 424.0 [MH]$^+$).

Step 4: Synthesis of 3-(N-(2-(4-methylpiperazin-1-yl)ethyl)methylsulfonamido)-4-(trifluoromethyl) benzoic acid (272)

To a solution of methyl 3-(N-(2-(4-methylpiperazin-1-yl)ethyl)methyl-sulfonamido)-4-(trifluoromethyl)benzoate (460 mg, 1.086 mmol) in dioxane (11 ml), aqueous 6N HCl (2.173 ml, 13.04 mmol) was added, and reaction mixture was heated at 100° C. for 2 hours. The volatiles were removed under vacuum to afford 3-(N-(2-(4-methylpiperazin-1-yl)ethyl)methylsulfonamido)-4-(trifluoromethyl) benzoic acid hydrochloride (440 mg, 0.988 mmol, 92% yield, MS/ESI$^+$ 409.8 [MH]$^+$).

Step 5: Synthesis of (S)-3,5-dichloro-4-(2-(3-(cyclopropylmethoxy)-4-(difluoromethoxy)phenyl)-2-(3-(N-(2-(4-methylpiperazin-1-yl)ethyl)methylsulfonamido)-4-(trifluoromethyl)benzoyloxy)ethyl) pyridine 1-oxide (271)

A mixture of 3-(N-(2-(4-methylpiperazin-1-yl)ethyl) methylsulfonamido)-4-(trifluoromethyl)benzoic acid hydrochloride (234 mg, 0.525 mmol), (S)-3,5-dichloro-4-(2-(3-(cyclopropylmethoxy)-4-(difluoromethoxy)phenyl)-2-hydroxyethyl)pyridine 1-oxide (200 mg, 0.476 mmol), EDC (128 mg, 0.666 mmol) and DMAP (116 mg, 0.952 mmol) in dry DCM (8 ml) was stirred at RT overnight. The reaction mixture was treated with 1M HCl and the aqueous phase was extracted twice with DCM. The combined organic layers were washed with brine, dried over $Na_2SO_4$, filtered and evaporated. The crude was purified by flash chromatography on silica gel (DCM/MeOH=97/3 to 90/10) to afford (S)-3,5-dichloro-4-(2-(3-(cyclopropylmethoxy)-4-(difluoromethoxy)phenyl)-2-(3-(N-(2-(4-methylpiperazin-1-yl) ethyl)methylsulfonamido)-4-(trifluoromethyl)-benzoyloxy) ethyl)pyridine 1-oxide (186 mg, 0.229 mmol, 48.2% yield, MS/ESI$^+$ 811.19 [MH]$^+$, $[\alpha_D]$=−19.36, c=0.500, DCM).

$^1$H NMR (300 MHz, DMSO-d$_6$) δ ppm 8.54 and 8.55 (s, 2 H), 8.17 (d, 1 H), 8.10 (s, 1 H), 7.96 (dd, 1 H), 7.18-7.27 (m, 2 H), 7.06-7.13 (m, 1 H), 7.06 and 7.07 (t, 1 H), 6.10-6.32 (m, 1 H), 3.92 (t, 2 H), 3.75-4.07 (m, 1 H), 3.45-3.75 (m, 2 H), 3.37 (dt, 1 H), 3.19 (s, 3 H), 2.30-2.43 (m, 4 H), 2.06-2.24 (m, 4 H), 1.92-2.05 (m, 2 H), 1.98 and 2.00 (s, 3 H), 1.14-1.32 (m, 1 H), 0.44-0.70 (m, 2 H), 0.12-0.44 (m, 2 H)

Example 34

Synthesis of (S)-3,5-dichloro-4-(2-(3-(cyclopropylmethoxy)-4-(difluoromethoxy)phenyl)-2-(5-(N-(2-morpholinoethyl)methylsulfonamido)-2-(trifluoromethyl)benzoyloxy)ethyl)pyridine 1-oxide 2,2,2-trifluoroacetatic acid salt (Compound 276)

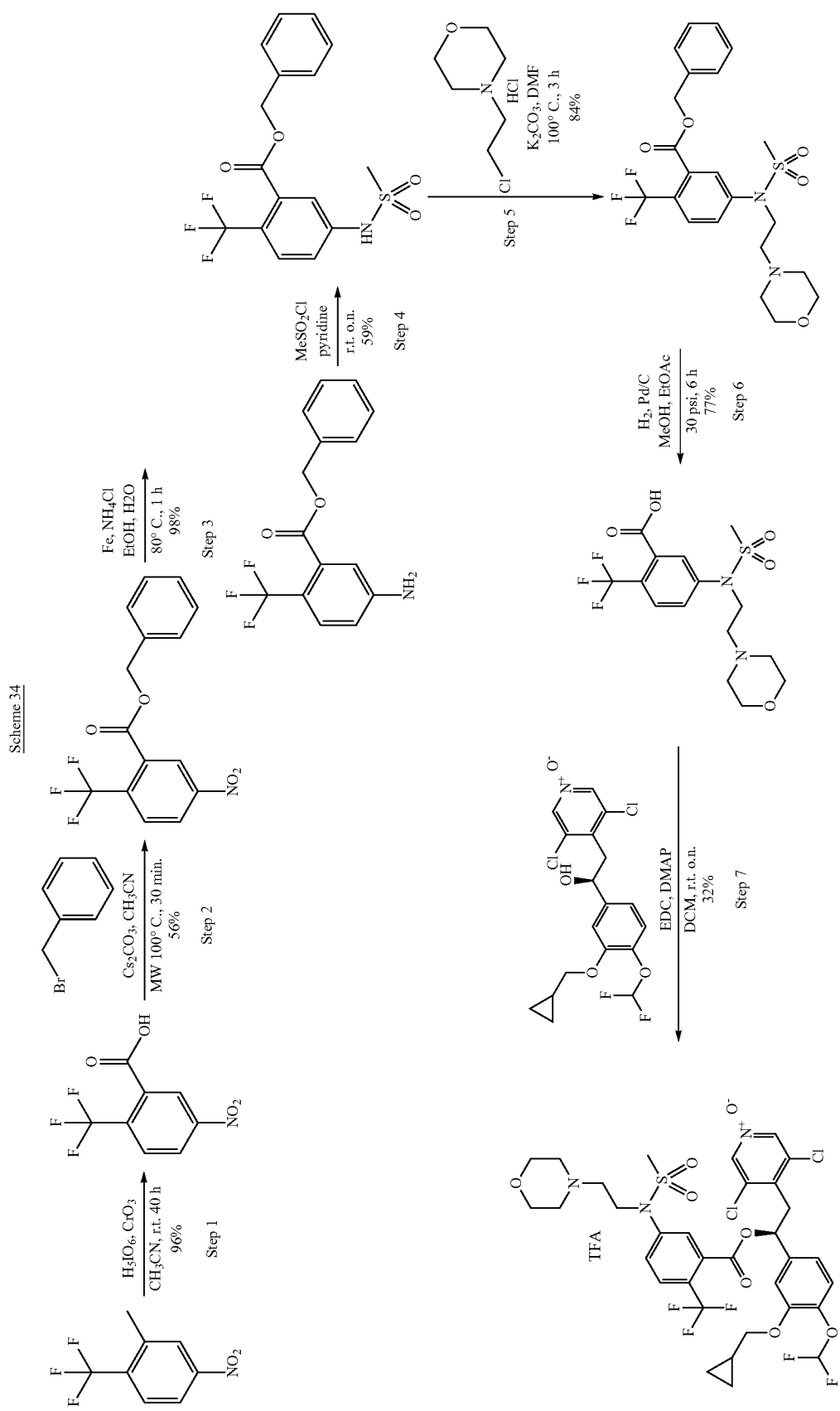

Step 1: Synthesis of 5-nitro-2-(trifluoromethyl)benzoic acid (282)

To a solution of 2-methyl-4-nitro-1-(trifluoromethyl)benzene (1 g, 4.87 mmol) in $CH_3CN$ (30 ml), $H_5IO_6$ (5.56 g, 24.37 mmol) and $CrO_3$ (0.126 ml, 3.40 mmol) were added, and the reaction mixture was stirred at RT for 2 hours. Additional $CrO_3$ (0.0722 ml, 1.950 mmol) was added, and the mixture was stirred at RT overnight. iPrOH (150 ml) was added to the reaction mixture, and the suspension turned into green. The precipitate was filtered off and the filtrate was evaporated to dryness; the solid residue was triturated with AcOEt (40 ml) and filtered to afford 5-nitro-2-(trifluoromethyl)-benzoic acid (1.1 g, 4.68 mmol, 96% yield).

Step 2: Synthesis of benzyl 5-nitro-2-(trifluoromethyl)benzoate (281)

To a solution of 5-nitro-2-(trifluoromethyl)benzoic acid (1.0 g, 4.25 mmol) and benzyl bromide (0.506 ml, 4.25 mmol) in $CH_3CN$ (8 ml), $Cs_2CO_3$ (416 mg, 1.276 mmol) was added, and the resulting mixture was heated at 100° C. under MW irradiation for 30 minutes. The reaction mixture was concentrated under vacuum and the residue was partitioned between water and EtOAc. The organic phase was dried over $Na_2SO_4$, the solvent was removed under reduced pressure, and the crude was purified by flash chromatography on silica gel (petroleum ether/DCM=95/5) to afford benzyl 5-nitro-2-(trifluoromethyl)benzoate (770 mg, 2.367 mmol, 56% yield).

Step 3: Synthesis of benzyl 5-amino-2-(trifluoromethyl)benzoate (280)

To a suspension of benzyl 5-nitro-2-(trifluoromethyl)benzoate (770 mg, 2.367 mmol) in ethanol (8 ml) and water (4 ml), ammonium chloride (253 mg, 4.73 mmol) was added in one portion. The mixture was heated at 80° C., iron powder (793 mg, 14.20 mmol) was added and the reaction was stirred at the same temperature for 1 hour. The mixture was filtered through a celite pad and the filtrate was evaporated to dryness. The residue was dissolved in EtOAc and washed with water and brine; the organic phase was dried over $Na_2SO_4$ and the solvent was removed affording benzyl 5-amino-2-(trifluoromethyl)benzoate (688 mg, 2.330 mmol, 98% yield, MS/ESI$^+$ 296.0 [MH]$^+$). This intermediate was used without purification.

Step 4: Synthesis of benzyl 5-(methylsulfonamido)-2-(trifluoromethyl)benzoate (279)

To a solution of benzyl 5-amino-2-(trifluoromethyl)benzoate (688 mg, 2.330 mmol) in dry pyridine (6 ml) cooled at 0° C., methanesulfonyl chloride (0.198 ml, 2.56 mmol) was added drop wise and the reaction mixture was stirred at RT overnight. The volatiles were removed under vacuum and the residue was treated with aqueous sat. $NaHCO_3$ and extracted twice with EtOAc; the combined organic layers were dried over Na2SO4, the solvent was removed and crude was purified by trituration with $Et_2O$ (100 ml) to yield benzyl 5-(methylsulfonamido)-2-(trifluoromethyl)benzoate (510 mg, 1.366 mmol, 59% yield).

Step 5: Synthesis of benzyl 5-(N-(2-morpholinoethyl)methylsulfonamido)-2-(trifluoromethyl)benzoate (278)

Benzyl 5-(methylsulfonamido)-2-(trifluoromethyl)benzoate (510 mg, 1.366 mmol) was dissolved in dry DMF (6 ml) and 4-(2-chloroethyl)morpholine hydrochloride (381 mg, 2.049 mmol) was added followed by $K_2CO_3$ (529 mg, 3.82 mmol). The reaction was heated at 100° C. for 3 hours. The mixture was portioned between ethyl acetate and water; the organic layer was washed several times with brine and dried over sodium sulfate. The solvent was removed under reduced pressure and the crude was purified by flash chromatography on silica gel (EtOAc/petroleum ether=80/20 to AcOEt) to give benzyl 5-(N-(2-morpholinoethyl)methylsulfonamido)-2-(trifluoromethyl)benzoate (560 mg, 1.151 mmol, 84% yield, MS/ESI$^+$ 487.1 [MH]$^+$).

Step 6: Synthesis of 5-(N-(2-morpholinoethyl)methylsulfonamido)-2-(trifluoromethyl)benzoic acid (277)

A mixture of benzyl 5-(N-(2-morpholinoethyl)methylsulfonamido)-2-(trifluoromethyl)benzoate (560 mg, 1.151 mmol) and a catalytic amount of 10% Pd/C in AcOEt (5 ml) and MeOH (15 ml) was hydrogenated in a Parr apparatus at 30 psi for 6 hours. The catalyst was filtered off, and the solvent was removed under vacuum; the crude residue was triturated with MeOH (5 ml) to afford after filtration 5-(N-(2-morpholinoethyl)methylsulfonamido)-2-(trifluoromethyl)benzoic acid (350 mg, 0.883 mmol, 77% yield, MS/ESI$^+$ 396.9 [MH]$^+$).

Step 5: Synthesis of (S)-3,5-dichloro-4-(2-(3-(cyclopropylmethoxy)-4-(difluoromethoxy)phenyl)-2-(5-(N-(2-morpholinoethyl)methylsulfonamido)-2-(trifluoromethyl)benzoyloxy)ethyl)pyridine 1-oxide, 2,2,2-trifluoroacetate salt (276)

A mixture of 5-(N-(2-morpholinoethyl)methylsulfonamido)-2-(trifluoromethyl)-benzoic acid (200 mg, 0.505 mmol), (S)-3,5-dichloro-4-(2-(3-(cyclopropylmethoxy)-4-(difluoromethoxy)phenyl)-2-hydroxyethyl)pyridine 1-oxide (177 mg, 0.420 mmol), EDC (121 mg, 0.631 mmol), and DMAP (128 mg, 1.051 mmol) in dry DCM was stirred at RT for 3 hours. Additional 5-(N-(2-morpholinoethyl)methylsulfonamido)-2-(trifluoromethyl)benzoic acid (7) (167 mg, 0.420 mmol), EDC (81 mg, 0.420 mmol) and DMAP (25.7 mg, 0.210 mmol) were added and the reaction was stirred at RT overnight. The mixture was washed with water and brine; the organic phase was dried over $Na_2SO_4$, filtered and evaporated. The crude was purified by flash chromatography on silica gel (DCM/MeOH=95/05) and then by a further chromatography on silica gel (DCM/AcOEt 60/40, then DCM/MeOH 90/10). The obtained product was triturated with EtOH (3 ml) and finally purified by preparative HPLC yielding (S)-3,5-dichloro-4-(2-(3-(cyclopropylmethoxy)-4-(difluoromethoxy)phenyl)-2-(5-(N-(2-morpholinoethyl)-methylsulfonamido)-2-(trifluoromethyl)benzoyloxy)ethyl) pyridine 1-oxide 2,2,2-trifluoroacetate salt (121 mg, 0.133 mmol, 31.6% yield, MS/ESI$^+$ 798.1 [MH]$^+$, [$\alpha_D$]=−2.513, c=0.390, DCM).

$^1$H NMR (300 MHz, DMSO-d$_6$+Na2CO3) d ppm 8.56 (s, 2 H), 7.91 (d, 1 H), 7.83 (dd, 1 H), 7.78 (d, 1 H), 7.21 (d, 1 H), 7.17 (d, 1 H), 7.03 (dd, 1 H), 7.09 (t, 1 H), 6.20 (dd, 1 H), 3.94 (dd, 1 H), 3.87 (dd, 1 H), 3.85 (t, 2 H), 3.60 (dd, 1 H), 3.36-3.47 (m, 4 H), 3.40 (dd, 1 H), 3.13 (s, 3 H), 2.39 (t, 2 H), 2.18-2.32 (m, 4 H), 1.12-1.31 (m, 1 H), 0.48-0.69 (m, 2 H), 0.25-0.48 (m, 2 H)

Example 35

Synthesis of (S)-3,5-dichloro-4-(2-(4-(cyclopropyl-methoxy)-3-((2-(4-hydroxypiperidin-1-yl)acetoxy)methyl)benzoyloxy)-2-(3-(cyclopropylmethoxy)-4-(difluoromethoxy)phenyl) (Compound 283)

Scheme 35

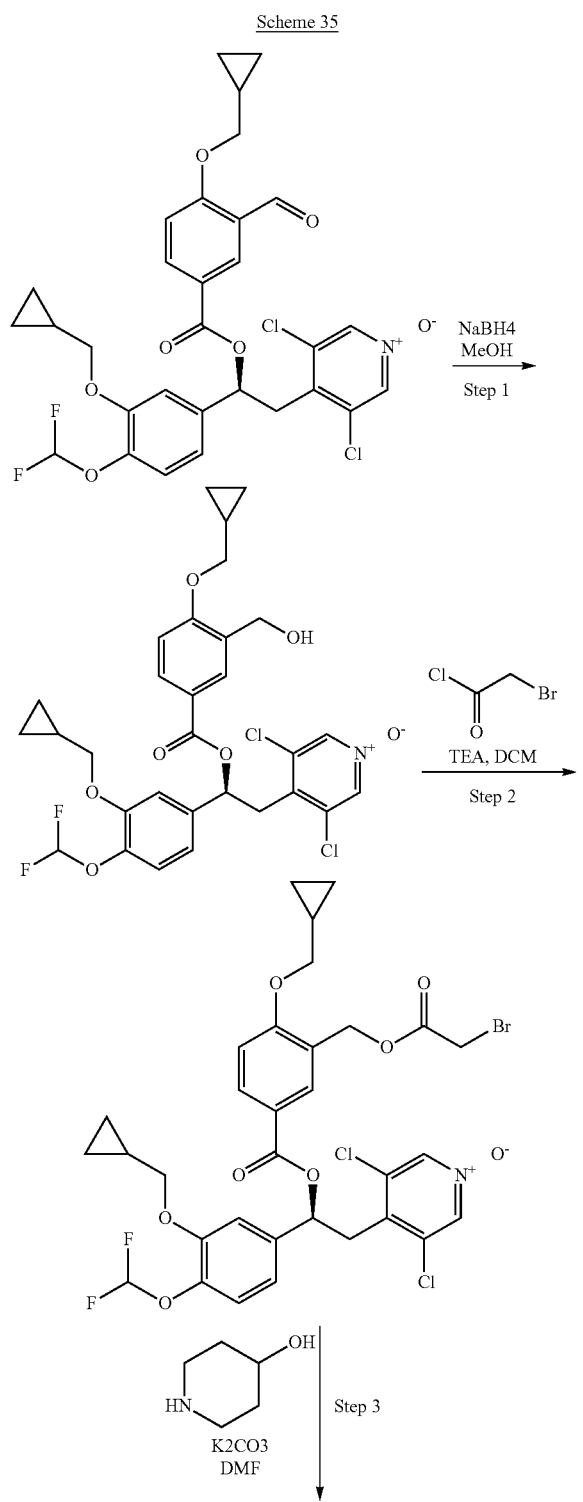

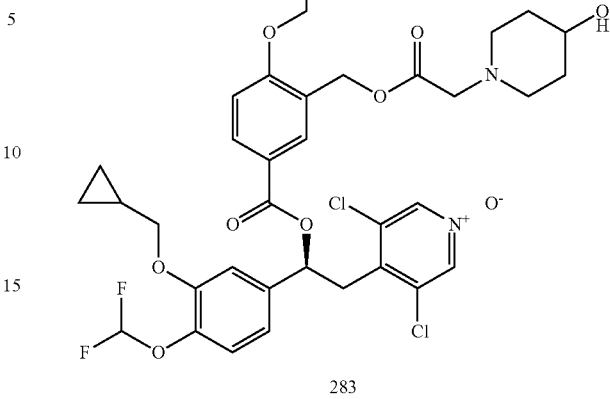

Step 1: Synthesis of (S)-3,5-dichloro-4-(2-(4-(cyclopropylmethoxy)-3-(hydroxymethyl)-benzoyloxy)-2-(3-(cyclopropylmethoxy)-4-(difluoromethoxy)phenyl)ethyl)pyridine 1-oxide (285)

(S)-3,5-dichloro-4-(2-(4-(cyclopropylmethoxy)-3-formylbenzoyloxy)-2-(3-(cyclopropylmethoxy)-4-(difluoromethoxy)phenyl)ethyl)pyridine 1-oxide (100 mg, 0.161 mmol), obtained as reported in Example 14, Scheme 14 step 1-3, was dissolved in MeOH (2 ml). NaBH4 (18.2 mg, 0.482 mmol) was added, and the mixture was stirred at RT for 2 hours. The reaction was diluted with HCl 1M and extracted with ethyl acetate. The organic phase was washed with HCl 1N and brine, dried over Na2SO4 and concentrated under vacuum to give (S)-3,5-dichloro-4-(2-(4-(cyclopropylmethoxy)-3-(hydroxymethyl)benzoyloxy)-2-(3-(cyclopropylmethoxy)-4-(difluoromethoxy)phenyl)-ethyl)pyridine 1-oxide (90 mg, 0.144 mmol, 90% yield). MS/ESI$^+$ 624.5 [MH]$^+$ Step 2: Synthesis of (S)-4-(2-(3-((2-bromoacetoxy)methyl)-4-(cyclopropylmethoxy)-benzoyloxy)-2-(3-(cyclopropylmethoxy)-4-(difluoromethoxy)phenyl)ethyl)-3,5-dichloropyridine 1-oxide (284)

(S)-3,5-dichloro-4-(2-(4-(cyclopropylmethoxy)-3-(hydroxymethyl)benzoyloxy)-2-(3-(cyclopropylmethoxy)-4-(difluoromethoxy)phenyl)ethyl)pyridine 1-oxide (50 mg, 0.080 mmol) was dissolved in DCM (1.5 ml). 2-Bromoacetyl chloride (16.38 mg, 0.104 mmol) and TEA (0.044 ml, 0.317 mmol) were added, and the mixture was stirred at RT for 1.5 hours until completion. The reaction mixture was diluted with HCl 1N, and extracted with DMC. The organic phase was washed with HCl 1N, NaHCO3 5% and brine, dried over Na2SO4 and concentrated under vacuum to give (S)-4-(2-(3-((2-bromoacetoxy)methyl)-4-(cyclopropylmethoxy)benzoyloxy)-2-(3-(cyclopropylmethoxy)-4-(difluoromethoxy)phenyl)ethyl)-3,5-dichloropyridine 1-oxide (50 mg, 0.067 mmol, 84% yield). MS/ESI$^+$ 746.39 [MH]$^+$ Step 3: Synthesis of (S)-3,5-dichloro-4-(2-(4-(cyclopropylmethoxy)-3-((2-(4-hydroxypiperidin-1-yl)acetoxy)methyl)benzoyloxy)-2-(3-(cyclopropylmethoxy)-4-(difluoromethoxy)phenyl)ethyl)pyridine 1-oxide (283)

(S)-4-(2-(3-((2-bromoacetoxy)methyl)-4-(cyclopropylmethoxy)benzoyloxy)-2-(3-(cyclopropylmethoxy)-4-(difluoromethoxy)phenyl)ethyl)-3,5-dichloropyridine 1-oxide (50 mg, 0.067 mmol) was dissolved in DMF. Piperidin-4-ol (20.35 mg, 0.201 mmol) and K2CO3 (11.12 mg, 0.080 mmol) were added, and the reaction was stirred at RT for 2 hours to achieve completion. The reaction mixture was diluted with water and extracted with ethyl acetate. The organic phase was dried over $Na_2SO_4$ and concentrated under vacuum. The crude was purified by preparative HPLC to give (S)-3,5-dichloro-4-(2-(4-(cyclopropylmethoxy)-3-((2-(4-hydroxypiperidin-1-yl)acetoxy)methyl)benzoyloxy)-2-(3-(cyclopropylmethoxy)-4-(difluoromethoxy)phenyl)ethyl)pyridine 1-oxide (18 mg, 0.024 mmol, 35.0% yield). MS/ESI$^+$ 764.9 [MH]$^+$ $^1$H NMR (400 MHz, DMSO-$d_6$) δ ppm 8.55 (s, 2 H), 7.93 (m, 2 H), 6.96-7.31 (m, 5 H), 6.03-6.28 (m, 1 H), 5.12 (s, 2 H), 4.52 (bs, 1 H), 3.85-4.08 (m, 4 H), 3.51-3.66 (m, 1 H), 3.41-3.50 (m, 2 H), 3.23 (m, 2 H), 2.71 (d, J=11.03 Hz, 2 H), 2.23 (m, 2 H), 1.67 (d, J=10.14 Hz, 2 H), 1.36 (d, J=9.70 Hz, 2 H), 1.23 (m, 2 H), 0.56 (m, 4 H), 0.35 (m, 4 H).

The compound listed in Table 21 was prepared with analogous synthetic steps and procedures to that described in Example 35 reacting the appropriate precursors (commercially available or synthesized by a person skilled in the art) with suitable reagents. Specific variations in the experimentals or purification methods are indicated in the table.

TABLE 21

| STRUCTURE | Comp. | Salt Name | NMR characterization | MS/ESI$^+$ [MH]$^+$ | Acyl chloride | Amine |
|---|---|---|---|---|---|---|
| 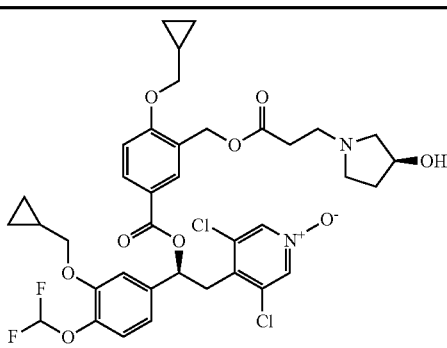 | 286 | No salt | $^1$H NMR (400 MHz, DMSO-$d_6$) δ ppm 8.55 (s, 2 H), 7.86-8.00 (m, 2 H), 7.01-7.27 (m, 5 H), 6.19 (d, J = 5.29 Hz, 1 H), 5.11 (s, 2 H), 4.67 (s, 1 H), 4.13 (m, 1 H), 3.87-4.04 (m, 4 H), 3.48-3.70 (m, 2 H), 2.61-2.77 (m, 3 H), 2.44 (d, J = 6.17 Hz, 4 H), 2.29 (d, J = 6.62 Hz, 1 H), 1.91 (dd, J = 13.01, 6.84 Hz, 1 H), 1.49 (d, J = 3.97 Hz, 1 H), 1.13-1.28 (m, 2 H), 0.57 (d, J = 6.17 Hz, 4 H), 0.35 (m, 4 H) | 764.9 | 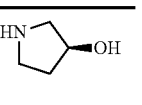 | 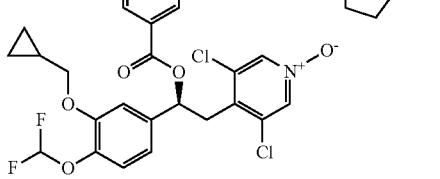 |

Example 36

Synthesis of (S)-3,5-dichloro-4-(2-(3-(cyclopropylmethoxy)-4-(difluoromethoxy)phenyl)-2-(3-hydroxy-5-(N-(2-morpholinoethyl)-methylsulfonamido)benzoyloxy)ethyl)pyridine 1-oxide (Compound 287)

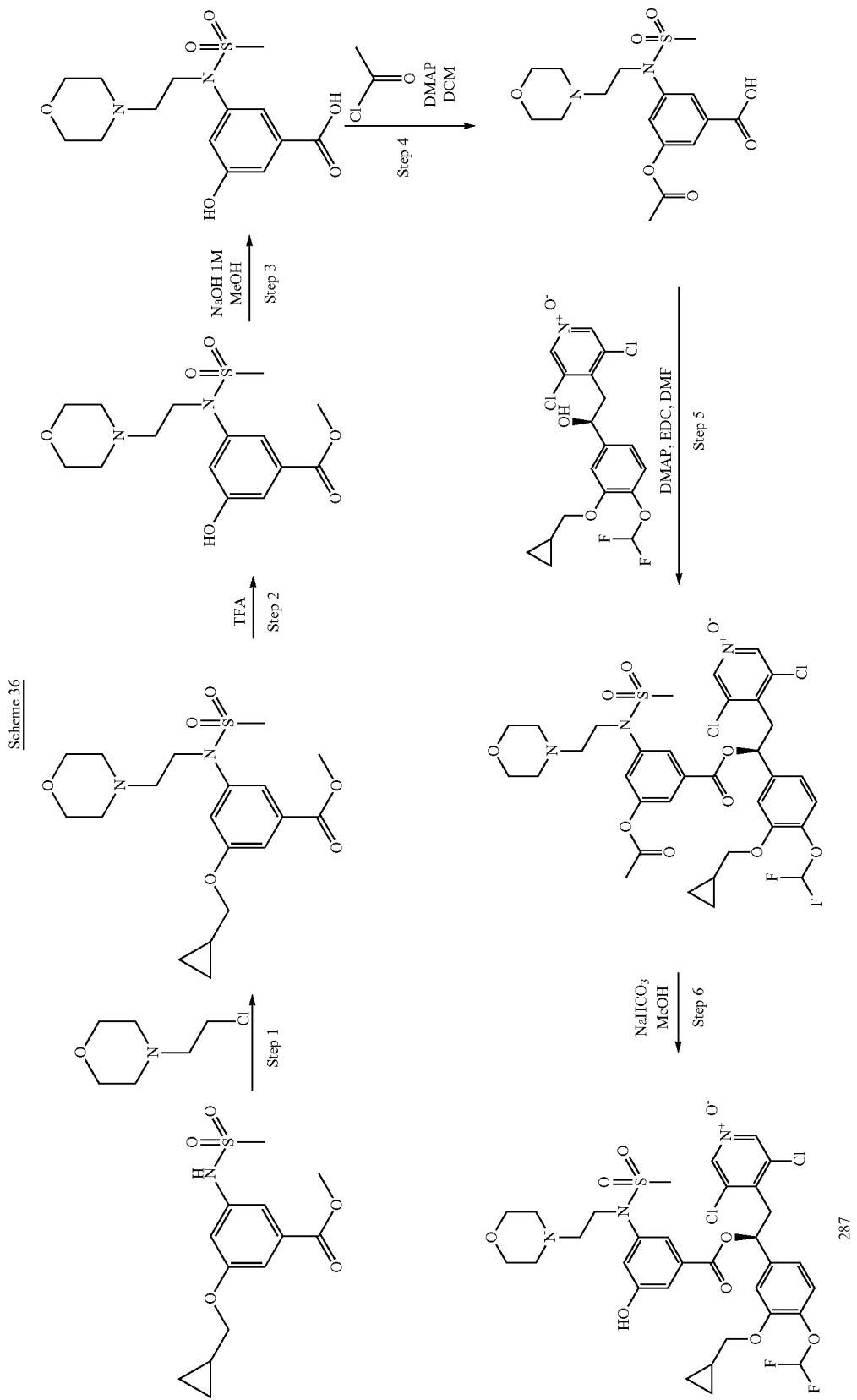

Step 1: Synthesis of Methyl 3-(cyclopropylmethoxy)-5-(N-(2-morpholinoethyl)-methylsulfonamido)benzoate (292)

Methyl 3-(cyclopropylmethoxy)-5-(methylsulfonamido)benzoate (202 mg, 0.675 mmol) (obtained following the same procedure described in WO2010/089107 (which is incorporated herein by reference in its entirety), Scheme 2, Example 18, step 1-4, starting from 3-hydroxy-5-nitrobenzoic acid methyl ester), was reacted as described in Example 5, Scheme 5, Step 3, to give the desired product (152 mg, 0.368 mmol, 55% yield). MS/ESI$^+$ 299.08 [MH]$^+$.

Step 2: Synthesis of methyl 3-hydroxy-5-(N-(2-morpholinoethyl)methyl-sulfonamido)benzoate (291)

Methyl 3-(cyclopropylmethoxy)-5-(N-(2-morpholinoethyl)methylsulfonamido)-benzoate (50 mg, 0.121 mmol) was dissolved in TFA (1.5 ml, 19.47 mmol). The reaction was stirred at RT for 4 hours to achieve completion. The solvent is concentrated under vacuum to give methyl 3-hydroxy-5-(N-(2-morpholinoethyl)methylsulfonamido)benzoate (40 mg, 0.112 mmol, 92% yield). MS/ESI$^+$ 359.12 [MH]$^+$

Step 3: Synthesis of 3-hydroxy-5-(N-(2-morpholinoethyl)methylsulfonamido)benzoic acid (290)

Methyl 3-hydroxy-5-(N-(2-morpholinoethyl)methylsulfonamido)benzoate (40 mg, 0.112 mmol) was dissolved in MeOH (1.5 ml). NaOH 1M (500 microl) was added, and the reaction was stirred at 50° C. for 2 hours to achieve completion. The reaction mixture was neutralized with HCl 1N and concentrated to give 3-hydroxy-5-(N-(2-morpholinoethyl)methylsulfonamido)benzoic acid (60 mg, 0.174 mmol, 156% yield). MS/ESI$^+$ 345.11 [MH]$^+$

Step 4: Synthesis of 3-acetoxy-5-(N-(2-morpholinoethyl)methylsulfonamido)benzoic acid (289)

3-hydroxy-5-(N-(2-morpholinoethyl)methylsulfonamido)benzoic acid (200 μl, 0.764 mmol) was dissolved in DCM (2 ml). Acetyl chloride (60 mg, 0.764 mmol) and DMAP (100 mg, 0.819 mmol) were added. The reaction was stirred at RT for 2 hours to achieve completion. The reaction mixture was concentrated, and the crude was triturated in hexane, filtered and dried in the vacuum oven to give 3-acetoxy-5-(N-(2-morpholinoethyl)methylsulfonamido)benzoic acid (60 mg, 0.155 mmol, 20.31% yield). MS/ESI$^+$ 387.42 [MH]$^+$

Step 5: Synthesis of (S)-4-(2-(3-acetoxy-5-(N-(2-morpholinoethyl)methylsulfonamido)-benzoyloxy)-2-(3-(cyclopropylmethoxy)-4-(difluoromethoxy)phenyl)ethyl)-3,5-dichloropyridine 1-oxide (288)

(S)-3,5-dichloro-4-(2-(3-(cyclopropylmethoxy)-4-(difluoromethoxy)phenyl)-2-hydroxyethyl)pyridine 1-oxide (20 mg, 0.048 mmol), 3-acetoxy-5-(N-(2-morpholinoethyl)methylsulfonamido)benzoic acid (60 mg, 0.155 mmol), DMAP (20 mg, 0.164 mmol), and EDC (100 mg, 0.522 mmol) were dissolved in DMF (1.5 ml). The reaction was stirred at 40° C. for 8 hours to achieve completion. The reaction mixture was diluted with water and the precipitate was dissolved in ethyl acetate. The organic phase was dried over Na2SO4 and concentrated under vacuum to give (S)-4-(2-(3-acetoxy-5-(N-(2-morpholinoethyl)methylsulfonamido)benzoyloxy)-2-(3-(cyclopropylmethoxy)-4-(difluoromethoxy)phenyl)ethyl)-3,5-dichloropyridine 1-oxide (30 mg, 0.038 mmol, 80% yield). MS/ESI$^+$ 788.64 [MH]$^+$

Step 6: Synthesis of (S)-3,5-dichloro-4-(2-(3-(cyclopropylmethoxy)-4-(difluoromethoxy)phenyl)-2-(3-hydroxy-5-(N-(2-morpholinoethyl)methyl-sulfonamido)benzoyloxy)ethyl)pyridine 1-oxide (287)

(S)-4-(2-(3-acetoxy-5-(N-(2-morpholinoethyl)methylsulfonamido)benzoyloxy)-2-(3-(cyclopropylmethoxy)-4-(difluoromethoxy)phenyl)ethyl)-3,5-dichloropyridine 1-oxide was dissolved in MeOH (1.5 ml). Sodium bicarbonate sat. sol. (500 μl) was added, and the reaction was stirred at RT for 2 hours to achieve completion. The reaction mixture was diluted with water, extracted with ethyl acetate and concentrated under vacuum. The crude was purified by preparative HPLC to give (S)-3,5-dichloro-4-(2-(3-(cyclopropylmethoxy)-4-(difluoromethoxy)phenyl)-2-(3-hydroxy-5-(N-(2-morpholinoethyl)methylsulfonamido)benzoyloxy)ethyl)pyridine 1-oxide (10 mg, 0.013 mmol). MS/ESI$^+$ 745.8 [MH]$^+$ $^1$H NMR (400 MHz, DMSO-d$_6$) δ ppm 10.03-10.22 (s, 1 H), 8.43-8.69 (s, 2 H), 7.38-7.45 (m, 1 H), 7.31-7.38 (m, 1 H), 7.16-7.28 (m, 2 H), 7.00-7.12 (m, 3 H), 6.05-6.25 (m, 1 H), 3.84-3.97 (m, 2 H), 3.66-3.78 (m, 2 H), 3.55-3.65 (m, 1 H), 3.47 (m, 5 H), 3.02 (s, 3 H), 2.23-2.38 (m, 6 H), 1.08-1.33 (m, 1 H), 0.49-0.67 (m, 2 H), 0.24-0.45 (m, 2 H).

Example 37

Synthesis of (S)-3,5-dichloro-4-(2-(3-(cyclopropylmethoxy)-4-(difluoromethoxy)phenyl)-2-(4-(methylthio)-3-(N-(2-morpholinoethyl)methyl-sulfonamido)benzoyloxy)ethyl)pyridine 1-oxide (Compound 293)

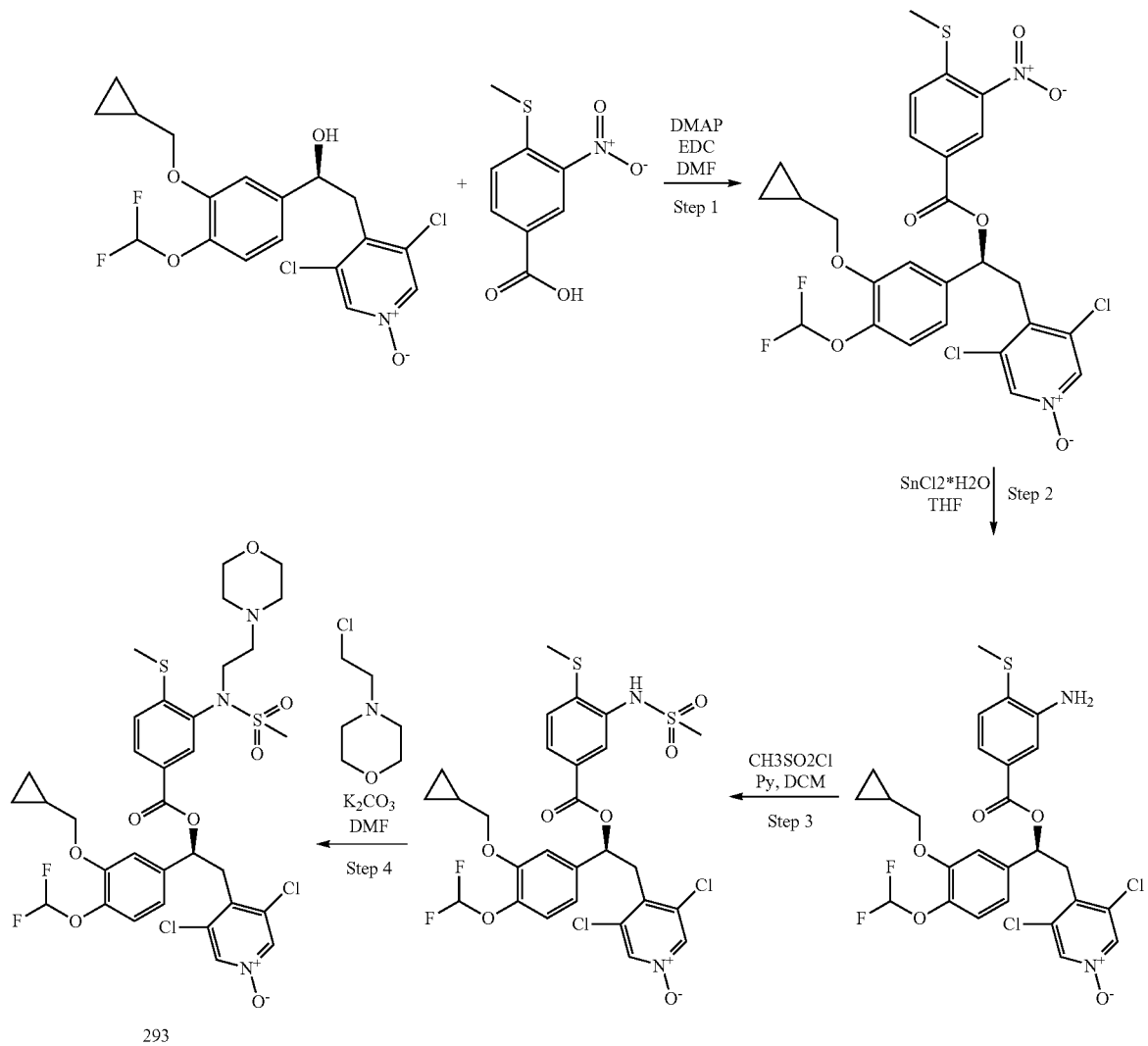

Scheme 37

Step 1: Synthesis of (S)-3,5-dichloro-4-(2-(3-(cyclopropylmethoxy)-4-(difluoromethoxy)-phenyl)-2-(4-(methylthio)-3-nitrobenzoyloxy)ethyl)pyridine 1-oxide (296)

(S)-3,5-dichloro-4-(2-(3-(cyclopropylmethoxy)-4-(difluoromethoxy)phenyl)-2-hydroxyethyl)pyridine 1-oxide (240 mg, 0.571 mmol), N,N-dimethylpyridin-4-amine (84 mg, 0.685 mmol), N1-((ethylimino)methylene)-N3,N3-dimethylpropane-1,3-diamine hydrochloride (328 mg, 1.713 mmol) were dissolved in DMF (2 ml). The reaction was stirred at RT overnight. The reaction mixture was diluted with HCl 1N, and the precipitate was filtered, washed with HCl 1N, dissolved in ethyl acetate and extracted with HCl 1N, NaHCO3 5% and brine. The organic phase was dried over Na2SO4 and concentrated under vacuum to give (S)-3,5-dichloro-4-(2-(3-(cyclopropylmethoxy)-4-(difluoromethoxy)phenyl)-2-(4-(methylthio)-3-nitrobenzoyloxy)ethyl)pyridine 1-oxide (300 mg, 0.487 mmol, 85% yield). MS/ESI+ 615.43 [MH]+

Step 2: Synthesis of (S)-4-(2-(3-amino-4-(methylthio)benzoyloxy)-2-(3-(cyclopropylmethoxy)-4-(difluoromethoxy)phenyl)ethyl)-3,5-dichloropyridine 1-oxide (295)

(S)-3,5-dichloro-4-(2-(3-(cyclopropylmethoxy)-4-(difluoromethoxy)phenyl)-2-(4-(methylthio)-3-nitrobenzoyloxy)ethyl)pyridine 1-oxide (320 mg, 0.520 mmol) was dissolved in THF (5 ml). Tin(II) chloride dihydrate (587 mg, 2.60 mmol) was added, and the mixture was stirred at RT overnight. The solvent was concentrated under vacuum and the crude was dissolved in ethyl acetate and washed with HCl 1N, brine, dried over Na2SO4 and concentrated under vacuum. 20 mg of crude were purified by preparative HPLC to give (S)-4-(2-(3-amino-4-(methylthio)benzoyloxy)-2-(3-(cyclopropylmethoxy)-4-(difluoromethoxy)phenyl)ethyl)-3,5-dichloropyridine 1-oxide (10 mg, 0.017 mmol, 3.29% yield). MS/ESI⁺ 584.8 [MH]⁺

¹H NMR (400 MHz, DMSO-d₆) δ ppm 8.57 (s, 2 H), 7.27-7.31 (m, 1 H), 7.19 (m, 4 H), 7.01-7.10 (m, 2 H), 6.06-6.27 (m, 1 H), 5.29 (s, 2 H), 3.91 (d, J=7.06 Hz, 2 H), 3.51-3.64 (m, 1 H), 3.29 (m, 1 H), 2.43 (s, 3 H), 1.12-1.30 (m, 1 H), 0.48-0.62 (m, 2 H), 0.26-0.41 (m, 2 H)

Step 3: Synthesis of (S)-3,5-dichloro-4-(2-(3-(cyclopropylmethoxy)-4-(difluoromethoxy)-phenyl)-2-(3-(methylsulfonamido)-4-(methylthio)benzoyloxy)-ethyl)pyridine 1-oxide (294)

(S)-4-(2-(3-amino-4-(methylthio)benzoyloxy)-2-(3-(cyclopropylmethoxy)-4-(difluoromethoxy)phenyl)ethyl)-3,5-dichloropyridine 1-oxide (200 mg, 0.342 mmol) was dissolved in DCM (3 ml). Methanesulfonyl chloride (0.053 ml, 0.683 mmol) and pyridine (0.028 ml, 0.342 mmol) were added, and the reaction was stirred at RT for 8 hours to achieve completion. The reaction mixture was washed with HCl 1N and brine, dried over Na₂SO₄ and concentrated under vacuum. 30 mg of crude were purified by preparative HPLC to give (S)-3,5-dichloro-4-(2-(3-(cyclopropylmethoxy)-4-(difluoromethoxy)-phenyl)-2-(3-(methylsulfonamido)-4-(methylthio)benzoyloxy)ethyl)pyridine 1-oxide (20 mg, 0.030 mmol, 8.82% yield). MS/ESI⁺ 663.0 [MH]⁺

¹H NMR (400 MHz, DMSO-d₆) δ ppm 9.32-9.56 (bs, 1 H), 8.55 (s, 2 H), 7.83-7.93 (m, 1 H), 7.76-7.82 (m, 1 H), 7.33-7.44 (m, 1 H), 7.17-7.24 (m, 2 H), 7.00-7.10 (m, 2 H), 6.12-6.27 (m, 1 H), 3.85-3.97 (m, 2 H), 3.52-3.66 (m, 1 H), 3.36-3.42 (m, 1 H), 3.01 (s, 3 H), 2.49 (s, 3 H), 1.18-1.27 (m, 1 H), 0.50-0.61 (m, 2 H), 0.31-0.40 (m, 2 H).

Step 4: Synthesis of (S)-3,5-dichloro-4-(2-(3-(cyclopropylmethoxy)-4-(difluoromethoxy)-phenyl)-2-(4-(methylthio)-3-(N-(2-morpholinoethyl)methylsulfonamido)benzoyloxy)-ethyl)pyridine 1-oxide (293)

(S)-3,5-dichloro-4-(2-(3-(cyclopropylmethoxy)-4-(difluoromethoxy)phenyl)-2-(3-(methylsulfonamido)-4-(methylthio)benzoyloxy)ethyl)pyridine 1-oxide (50 mg, 0.075 mmol) was dissolved in DMF. 4-(2-Chloroethyl)morpholine (56.4 mg, 0.377 mmol) and K₂CO₃ (20.83 mg, 0.151 mmol) were added, and the reaction is stirred at 45° C. for 6 hours to achieve completion. The reaction mixture was diluted with water and extracted with AcOEt. The organic phase was dried over Na₂SO₄ and concentrated under vacuum. The crude was purified by preparative HPLC to give (S)-3,5-dichloro-4-(2-(3-(cyclopropylmethoxy)-4-(difluoromethoxy)phenyl)-2-(4-(methylthio)-3-(N-(2-morpholinoethyl)methylsulfonamido)benzoyloxy)ethyl)pyridine 1-oxide (30 mg, 0.039 mmol, 51.3% yield). MS/ESI⁺ 776.3 [MH]⁺

¹H NMR (400 MHz, DMSO-d₆) δ ppm 8.55 (d, J=10.14 Hz, 2 H), 7.92-8.00 (m, 1 H), 7.87 (t, J=2.21 Hz, 1 H), 7.37-7.45 (m, 1 H), 7.21 (d, J=7.94 Hz, 2 H), 7.07 (m, 2 H), 6.13-6.24 (m, 1 H), 3.93 (d, J=7.06 Hz, 2 H), 3.70-3.84 (m, 1 H), 3.48-3.67 (m, 2 H), 3.39 (d, J=4.41 Hz, 4 H), 3.18 (m, 1 H), 3.18 (s, 3 H), 2.50 (s, 3 H), 2.07-2.45 (m, 6 H), 1.14-1.29 (m, 1 H), 0.50-0.63 (m, 2 H), 0.27-0.42 (m, 2 H).

The compound listed in Table 22 was prepared with analogous synthetic steps and procedures to that described in Example 37 by reacting the appropriate precursors (commercially available or synthesized by a person skilled in the art) with suitable reagents.

TABLE 22

| STRUCTURE | Comp. | Salt Name | NMR characterization | MS/ESI⁺ [MH]⁺ | Carboxylic acid |
|---|---|---|---|---|---|
| (structure shown) | 297 | No Salt | 1H NMR (400 MHz, DMSO-d₆) δ ppm 8.57 (s) 7.86 (s) 7.28 (s) 7.19 (dd, J = 11.86, 5.01 Hz) 7.10 (s) 7.07 (d, J = 1.96 Hz) 6.91 (s) 6.16-6.25 (m) 3.81-3.96 (m) 3.54-3.64 (m) 3.35-3.42 (m) 3.13 (s) 2.37 (t, J = 6.24 Hz) 2.26 (d, J = 4.16 Hz) 1.23 (br. s.) 0.56 (dd, J = 7.95, 1.83 Hz) 0.27-0.38 (m)). | 798.60 | (structure shown) |

Pharmacological Activity of the Compounds of the Invention:

In Vitro Determination of PDE4 Inhibitory Activity in the Cell Free Assay:

PDE4 activity was determined in U937 human monocytic supernatants cells lysate. Cells were cultured, harvested and supernatant fraction prepared essentially as described in Torphy T J et al., J. Pharmacol. Exp. Ther. 1992; 263:1195-1205, which is incorporated herein by reference in its entirety. U937 cells (Cell Bank, Interlab Cell Line Collection, ICLC HTL94002) were grown at 37° C., 5% $CO_2$ in RPMI 1640 with GlutaMAX™-I medium supplemented with 10% fetal bovine serum and 100 μg/ml Pen-strep (Gibco).

Cells were harvested and washed twice by centrifugation (150×g, 8 min) in cold PBS. Washed cells were resuspended in cold Krebs-Ringer-Henseleit buffer at a final concentration $20\times10^6$ cells/ml and sonicated. After centrifugation at 15000×g for 20 minutes the supernatants were pooled, divided in aliquots and stored at −80° C.

PDE4 activity was determined in cells supernatants by assaying cAMP disappearance from the incubation mixtures.

The concentration of the test compounds ranged between $10^{-12}$ M and $10^{-6}$M. Reactions were stopped by enzyme heat inactivation (2.5 minutes at 100° C.) and residual cAMP content was determined using the 'LANCE cAMP Assay' from PerkinElmer following the providers instructions.

The results of the tested compounds, representatives of the invention, expressed as mean of the nM concentration of the test compound producing 50% inhibition of cAMP disappearance ($IC_{50}$), are <1 nM.

Percentage of inhibition of PDE4 activity was calculated, assuming cAMP disappearance in the absence of inhibitors as 100% and cAMP disappearance in heat inactivated samples as 0%.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound represented by formula (I):

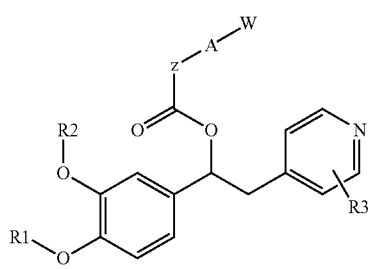

(I)

wherein:
R1 and R2 are different or the same and are independently hydrogen, methyl, ethyl, difluoromethyl, cyclopropylmethyl, cyclopropyl;

$R_3$ is one are more substituents selected from the group consisting of $CF_3$, fluorine, and chlorine;

Z is a group $(CH_2)_m$ wherein m=0;

A is a phenyl ring, which is optionally substituted by one or more substituents $R_4$, which may be the same or different and are:

$(C_1-C_2)$ alkyl optionally substituted by one or more $(C_3-C_7)$ cycloalkyl or $(C_3-C_7)$ heterocycloalkyl groups;

trifluoromethyl;

methylthio;

fluoro;

chloro; or $OR_7$, wherein $R_7$ is H; $(C_1-C_4)$ alkyl optionally substituted by a radical selected from the group consisting of OH, cyclopropyl, 4-moprpholinyl, 1-piperidinyl, 4-piperidinyl, 4-pyridinyl, and phenyl; trifluoromethyl or difluoromethyl; and W is:

—$NR_9SO_2R_{10}$, wherein $R_9$ is:

$(C_1-C_{10})$ alkyl optionally substituted by $(C_3-C_7)$ cycloalkyl, $(C_3-C_7)$ heterocycloalkyl, or $(C_3-C_7)$ heterocycloalkylcarbonyl, wherein any ring in said $(C_3-C_7)$ cycloalkyl, $(C_3-C_7)$ heterocycloalkyl or $(C_3-C_7)$ heterocycloalkylcarbonyl may be optionally substituted by one or more $(C_1-C_4)$ alkyl or OH groups; or $R_{11}R_{12}N$-$(C_1-C_{10})$alkylene wherein $R_{11}$ and $R_{12}$ are each independently H or $(C_1-C_6)$ alkyl optionally substituted by OH; and $R_{10}$ is:

$(C_1-C_4)$ alkyl optionally substituted by $(C_3-C_7)$ cycloalkyl;

$(C_3-C_7)$cycloalkyl; or phenyl, each of which may be optionally substituted with one or more halogen atoms or $(C_1-C_4)$ alkyl group;

or an N-oxide on the pyridine ring in formula (I), or pharmaceutically acceptable salt thereof.

2. A compound, N-oxide, or pharmaceutically acceptable salt according to claim 1, which is an N-oxide on the pyridine ring, represented by formula (Ia):

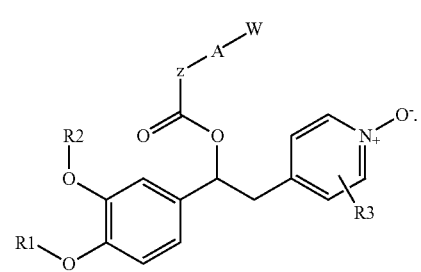

(Ia)

3. A compound, N-oxide, or pharmaceutically acceptable salt according to claim 1, which has the absolute configuration of carbon (1) shown in formula (I)':

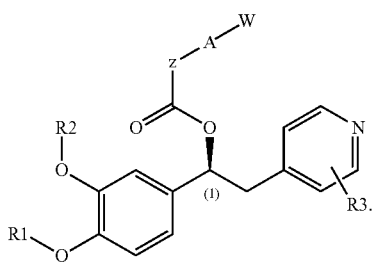

(I)'

4. A compound, N-oxide, or pharmaceutically acceptable salt according to claim 1, wherein W is —NR$_9$SO$_2$R$_{10}$, wherein R$_9$ is:
(C$_1$-C$_{10}$) alkyl optionally substituted by (C$_3$-C$_7$) cycloalkyl, (C$_3$-C$_7$) heterocycloalkyl, or (C$_3$-C$_7$) heterocycloalkylcarbonyl, wherein any ring in said (C$_3$-C$_7$) cycloalkyl, (C$_3$-C$_7$) heterocycloalkyl, or (C$_3$-C$_7$) heterocycloalkylcarbonyl may be optionally substituted by one or more (C$_1$-C$_4$) alkyl or OH groups; or R$_{11}$R$_{12}$N-(C$_1$-C$_{10}$)alkylene, wherein R$_{11}$ and R$_{12}$ are each independently H or (C$_1$-C$_6$) alkyl which may optionally be substituted by OH; and R$_{10}$ is (C$_1$-C$_4$) alkyl optionally substituted by (C$_3$-C$_7$) cycloalkyl, (C$_3$-C$_7$) cycloalkyl, or phenyl, any of which may be optionally substituted with one or more halogen atoms or (C$_1$-C$_4$) alkyl groups.

5. A compound, N-oxide, or pharmaceutically acceptable salt according to claim 1, wherein R$_9$ is (C$_1$-C$_4$) alkyl optionally substituted by 4-morpholinyl, 1-piperidinyl, 1-pyrrolidinyl, piperazinyl, 1,2-thiazolidin-3-yl, or piperazin-1-ylcarbonyl wherein any of said morpholinyl, 1-piperidinyl, 1-pyrrolidinyl, piperazinyl, 1,2-thiazolidin-3-yl, or piperazin-1-yl rings may optionally substituted by one or more methyl, ethyl or OH groups.

6. A pharmaceutical composition, comprising a compound, N-oxide, or pharmaceutically acceptable salt according to claim 1, and one or more pharmaceutically acceptable carriers and/or excipients.

7. A method for the treatment of asthma or COPD, comprising administering an effective amount of a compound, N-oxide, or pharmaceutically acceptable salt according to claim 1 to a subject in need thereof.

8. A method for the treatment of asthma, comprising administering an effective amount of a compound, N-oxide, or pharmaceutically acceptable salt according to claim 1 to a subject in need thereof.

9. A method for the treatment of COPD, comprising administering an effective amount of a compound, N-oxide, or pharmaceutically acceptable salt according to claim 1 to a subject in need thereof.

10. A method for the treatment of asthma, comprising administering an effective amount of a compound, N-oxide, or pharmaceutically acceptable salt according to claim 2 to a subject in need thereof.

11. A method for the treatment of COPD, comprising administering an effective amount of a compound, N-oxide, or pharmaceutically acceptable salt according to claim 2 to a subject in need thereof.

12. A method for the treatment of asthma, comprising administering an effective amount of a compound, N-oxide, or pharmaceutically acceptable salt according to claim 3 to a subject in need thereof.

13. A method for the treatment of COPD, comprising administering an effective amount of a compound, N-oxide, or pharmaceutically acceptable salt according to claim 3 to a subject in need thereof.

14. A method for the treatment of asthma, comprising administering an effective amount of a compound, N-oxide, or pharmaceutically acceptable salt according to claim 4 to a subject in need thereof.

15. A method for the treatment of COPD, comprising administering an effective amount of a compound, N-oxide, or pharmaceutically acceptable salt according to claim 4 to subject in need thereof.

16. A method for the treatment of asthma, comprising administering an effective amount of the pharmaceutical composition according to claim 6 to a subject in need thereof.

17. A method for the treatment of COPD, comprising administering an effective amount of the pharmaceutical composition according to claim 6 to a subject in need thereof.

18. A method for the treatment of asthma, comprising administering an effective amount of a compound, N-oxide, or pharmaceutically acceptable salt according to claim 5 to a subject in need thereof.

19. A method for the treatment of COPD, comprising administering an effective amount of compound, N-oxide, or pharmaceutically acceptable salt according to claim 5 to a subject in need thereof.

20. A device, comprising a pharmaceutical composition according to claim 6.

21. A kit, comprising a pharmaceutical composition according to claim 6 and a device which is a single- or multi-dose dry powder inhaler, a metered dose inhaler, or a soft mist nebulizer.

\* \* \* \* \*